(12) United States Patent
Blackwell et al.

(10) Patent No.: US 8,815,943 B2
(45) Date of Patent: Aug. 26, 2014

(54) MODULATION OF BACTERIAL QUORUM SENSING WITH SYNTHETIC LIGANDS

(75) Inventors: Helen E. Blackwell, Madison, WI (US); Grant D. Geske, Madison, WI (US); Jennifer C. O'Neill, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/032,036

(22) Filed: Feb. 22, 2011

(65) Prior Publication Data

US 2011/0212860 A1   Sep. 1, 2011

Related U.S. Application Data

(62) Division of application No. 12/051,826, filed on Mar. 19, 2008, now Pat. No. 7,910,622.

(60) Provisional application No. 60/895,598, filed on Mar. 19, 2007, provisional application No. 60/912,345, filed on Apr. 17, 2007, provisional application No. 60/974,026, filed on Sep. 20, 2007.

(51) Int. Cl.
C07D 307/33 (2006.01)

(52) U.S. Cl.
CPC .................................. *C07D 307/33* (2013.01)
USPC ........................................ 514/472; 549/321

(58) Field of Classification Search
CPC ........................................................ C07D 307/33
USPC ........................................... 514/472; 549/321
See application file for complete search history.

(56) References Cited

U.S. PATENT DOCUMENTS

| | | | |
|---|---|---|---|
| 5,776,974 A | 7/1998 | Bycroft et al. | |
| 6,555,356 B2 | 4/2003 | Kjelleberg et al. | |
| 6,559,176 B1 | 5/2003 | Bassler et al. | |
| 6,756,404 B2 | 6/2004 | Livinghouse | |
| 6,780,890 B2 | 8/2004 | Bassler et al. | |
| 6,958,145 B2 | 10/2005 | Kumar et al. | |
| 7,026,353 B2 | 4/2006 | Kjelleberg et al. | |
| 7,074,776 B2 | 7/2006 | Cooper et al. | |
| 7,078,435 B2 | 7/2006 | Livinghouse | |
| 7,094,394 B2 | 8/2006 | Davies et al. | |
| 7,332,509 B2 | 2/2008 | Shaper et al. | |
| 7,335,779 B2 | 2/2008 | Ammendola | |
| 7,338,969 B2 | 3/2008 | Ammendola | |
| 7,642,285 B2 | 1/2010 | Blackwell et al. | |
| 7,737,164 B2 | 6/2010 | Blackwell et al. | |
| 7,910,622 B2 | 3/2011 | Blackwell et al. | |
| 2002/0037578 A1 | 3/2002 | Kjelleberg et al. | |
| 2002/0177715 A1 | 11/2002 | Pesci et al. | |
| 2003/0105143 A1 | 6/2003 | Ammendola et al. | |
| 2003/0125381 A1 | 7/2003 | England et al. | |
| 2003/0198692 A1 | 10/2003 | Holmstrom et al. | |
| 2003/0224032 A1 | 12/2003 | Read et al. | |
| 2004/0072898 A1 | 4/2004 | Kjelleberg et al. | |
| 2004/0110966 A1 | 6/2004 | Kumar et al. | |
| 2004/0115732 A1 | 6/2004 | Suga et al. |
| 2004/0147595 A1 | 7/2004 | Kjelleberg et al. |
| 2004/0180829 A1 | 9/2004 | Bassler et al. |
| 2004/0235914 A1 | 11/2004 | Ammendola et al. |
| 2005/0054722 A1 | 3/2005 | England et al. |
| 2005/0215772 A1 | 9/2005 | Kumar |
| 2006/0052425 A1 | 3/2006 | Handelsman et al. |
| 2006/0178430 A1 | 8/2006 | Blackwell et al. |
| 2007/0054883 A1 | 3/2007 | Cooper et al. |
| 2007/0093534 A1 | 4/2007 | Ammendola et al. |
| 2007/0128658 A1 | 6/2007 | Blackwell et al. |
| 2007/0155698 A1 | 7/2007 | Steinberg et al. |
| 2007/0184014 A1 | 8/2007 | Ammendola et al. |
| 2007/0196340 A1 | 8/2007 | Ammendola et al. |
| 2007/0197492 A1 | 8/2007 | Ammendola et al. |
| 2007/0203128 A1 | 8/2007 | Ammendola et al. |
| 2007/0208012 A1 | 9/2007 | Ammendola et al. |
| 2007/0264715 A1 | 11/2007 | Robinson et al. |
| 2008/0009528 A1 | 1/2008 | Blackwell et al. |
| 2008/0027115 A1 | 1/2008 | Suga et al. |
| 2008/0312319 A1 | 12/2008 | Blackwell et al. |
| 2009/0270423 A1 | 10/2009 | Blackwell et al. |
| 2010/0261763 A1 | 10/2010 | Blackwell et al. |
| 2010/0305182 A1 | 12/2010 | Blackwell et al. |
| 2011/0046195 A1 | 2/2011 | Blackwell et al. |
| 2011/0212860 A1 | 9/2011 | Blackwell et al. |

FOREIGN PATENT DOCUMENTS

| | | |
|---|---|---|
| JP | 49020492 | 5/1974 |
| JP | 2235850 | 9/1990 |
| JP | 3031245 | 2/1991 |
| JP | 4-279568 | 10/1992 |

(Continued)

OTHER PUBLICATIONS

Tesser et al. (Int J Peptide Protein Res, 8:559-563, 1976).*
Andrews, J.M. (2001) "Determination of Minimum Inhibitory Concentrations," *J. Antimicrob. Chemother.* 48(Supp. 1):5-16.
Barnick et al. (1979) "Convenient Direct Method for the Preparation of Keto-Acids," *Synthesis* 79:787-788.
Bassler et al. (1994) "Multiple Signaling Systems Controlling Expression of Luminescence in *Vibrio harveyi*: Sequence and Function of Genes Encoding a Second Sensory Pathway," *Mol. Microbiol.* 13(2):273-286.
Bassler et al. (Apr. 21, 2006) "Bacterially Speaking," *Cell* 125(2):237-246.

(Continued)

*Primary Examiner* — Bong-Sook Baek
(74) *Attorney, Agent, or Firm* — Lathrop & Gage LLP

(57) ABSTRACT

The present invention provides compounds and methods for modulation of the quorum sensing of bacteria. In an embodiment, the compounds of the present invention are able to act as replacements for naturally occurring bacterial quorum sensing ligands in a ligand-protein binding system; that is, they imitate the effect of natural ligands and produce an agonistic effect. In another embodiment, the compounds of the present invention are able to act in a manner which disturbs or inhibits the naturally occurring ligand-protein binding system in quorum sensing bacteria; that is, they produce an antagonistic effect. The compounds of the present invention comprise N-acylated-homoserine lactones (AHLs) comprised of a wide range of acyl groups.

2 Claims, 45 Drawing Sheets

(56) References Cited

FOREIGN PATENT DOCUMENTS

| | | |
|---|---|---|
| WO | WO 92/18614 | 10/1992 |
| WO | WO 96/29392 | 9/1996 |
| WO | WO 98/15532 | 4/1998 |
| WO | WO 99/27786 | 6/1999 |
| WO | WO 99/53915 | 10/1999 |
| WO | WO 01/43739 | 6/2001 |
| WO | WO 01/68090 | 9/2001 |
| WO | WO 01/68091 | 9/2001 |
| WO | WO 01/76594 | 10/2001 |
| WO | WO 01/85664 | 11/2001 |
| WO | WO 02/00639 | 1/2002 |
| WO | WO 02/18342 | 3/2002 |
| WO | WO 02/47681 | 6/2002 |
| WO | WO 02/102370 | 12/2002 |
| WO | WO 03/039529 | 5/2003 |
| WO | WO 03/106445 | 12/2003 |
| WO | WO 2004/016588 | 2/2004 |
| WO | WO 2006/079015 | 7/2006 |
| WO | WO 2006/084056 | 8/2006 |
| WO | WO 2006/125262 | 11/2006 |
| WO | WO 2008/016738 | 2/2008 |
| WO | WO 2008/116029 | 9/2008 |

OTHER PUBLICATIONS

Bassler et al. (Jun. 1997) "Cross-Species Induction of Luminescence in the Quorum-Sensing Bacterium *Vibrio harveyi*," *J. Bacteriol.* 179(12):4043-4045.

Bassler et al. (Aug. 1993) "Intercellular Signaling in *Vibrio harveyi*: Sequence and Function of Genes Regulating Expression of Luminescence," *Mol. Microbiol.* 9(4):773-786.

Bassler et al. (1995) "Intercellular Communication in Marine *Vibrio* Species: Density-Dependent Regulation of the Expression of Bioluminescence," In; *Two Component Signal Transduction*, Hoch et al eds., Am. Soc. Microbiol., Washington D.C., pp. 431-445.

Bauer et al. (1966) "Antibiotic Susceptibility Testing by a Standardized Single Disk Method," *Tech Bull. Reg. Med. Technologists* 36(3):49-52.

Behrendt et al. (1999) "Photomodulation of the Conformation of Cyclic Peptides with Azobenzene Moieties in the Peptide Backbone," *Angew Chem. Int. Ed. Engl.* 38:2771-2774.

Blackwell, H.E. (2006) "Hitting the SPOT: Small-Molecule Macroarrays Advance Combinatorial Synthesis," *Curr. Opin. Chem. Biol.* 10:203-212.

Blackwell, H.E. (2003) "Out of the Oil Bath and into the Oven—Microwave-Assisted Combinatorial Chemistry Heats up," *Org. Biomol. Chem.* 1:1251-1255.

Bottomley et al. (May 4, 2007) "Molecular Insights into Quorum Sensing in the Human Pathogen *Pseudomonas aeruginosa* from the Structure of the Virulence Regulator LasR Bound to Its Autoinducer," *J. Biol. Chem.* 282(18):13592-13600.

Bowden et al. (1990) "Structure-Activity Relations. Part 5. Antibacterial Activity of a Series of Substituted (E)-3-(4-Phenylbenzoyl)acrylic Acids, -Chalcones, -2-Hydroxychalcones and -α-Bromochalcones; Addition of Cyteine to Substitutes 3-Benzoylacrylic Acids and Related Compounds," *J. Chem. Res.* (S) 377.

Bowden et al. (1990) "Structure-Activity Relations. Part 5. Antibacterial Activity of a Series of Substituted (E)-3-(4-Phenylbenzoyl)acrylic Acids, -Chalcones, -2-Hydroxychalcones and -α-Bromochalcones; Addition of Cyteine to Substitutes 3-Benzoylacrylic Acids and Related Compounds," *J. Chem. Res.* (M) 2801-2830.

Bowden et al. (1979) "Structure-Activity Relations. Part 4. Reactivity and Anti-Bacterial Activity of 3-Aroylacrylic Acids and Their Methyl Esters," *J. Chem. Res.* (S) 8.

Bowman et al. (Apr. 2007) "Rapid Identification of Antibacterial Agents Effective Against *Staphylococcus aureus* Using Small-Molecule Macroarrays," *Chem. Biol.* 14:351-357.

Bowman et al. (2006) "Discovery of Fluorescent Cyanopyridine and Deazalumazine Dyes Using Small Molecule Macroarrays," *Org. Lett.* 8:1645-1648.

Bowman et al. (2004) "Microwave-Accelerated SPOT-Synthesis on Cellulose Supports," *Org. Lett.* 6(12):2019-2022.

Bowman et al. (2006) "Efficient Synthesis of Small Molecule Macroarrays: Optimization of the Macroarray Synthesis Platform and Examination of Microwave and Conventional Heating Methods," *Tetrahedron* 62:4715-4727.

Bundgaard, H.(1991) "Design and Application of Prodrugs," In; *A Textbook of Drug Design and Development*, Krosgaard-Larsen et al. Eds., Ch. 5, pp. 113-191.

Bundgaard, H. (1992) "(C) Means to Enhance Penetration: (1) Prodrugs as a Means to Improve the Delivery of Peptide Drugs," *Adv. Drug Deliv. Rev.* 8(1):1-38.

Carpino et al. (1972) "The 9-Fluorenylmethoxycarbonyl Amino-Protecting Group," *J. Org. Chem.* 37(22):3404-3409.

Castang et al. (Oct. 18, 2004) "*N*-Sulfonyl Homoserine Lactone as Antagonists of Bacterial Quorum Sensing," *Bioorg. Med. Chem. Lett.* 14(20):5145-5149.

Clark et al. (Jul. 1999) "Partial Agonists and G Protein-Coupled Receptor Desensitization," *Trends Pharmacol. Sci.* 20(7):279-286.

Davies et al. (Apr. 10, 1998) "The Involvement of Cell-to-Cell Signals in the Development of a Bacterial Biofilm," *Science* 280:295-298.

de Kievit et al. (Sep. 2000) "Bacterial Quorum Sensing in Pathogenic Relationships," *Infect. Immun.* 68(9):4839-4849.

de Kievit et al. (Apr. 2001) "Quorum-Sensing in *Pseudomonas aeruginosa* Biofilms: Their Role and Expression Patterns," *Appl. Environ. Microbiol.* 67(4):1865-1873.

Dobaria, A. V. et al. (2002) "Synthesis and antimicrobial screening of cyanopyridines," J. Indian Chem. Soc. 79:772-773.

Duffy et al. (2002) "Identification of a Pharmacophore for Thrombopoietic Activity of Small, Non-Peptidyl Molecules. 1. Discovery and Optimization of Salicylaldehyde Thiosemicarbazone Thrombopoietin Mimics," *J. Med. Chem.* 45(17):3573-3575.

Duffy et al. (2002) "Identification of a Pharmacophore for Thrombopoietic Activity of Small, Non-Peptidyl Molecules. 2. Rational Design of Naphtho[1,2-*d*]imidazole Thrombopoietin Mimics," *J. Med. Chem.* 45(17):3576-3578.

Eberhard et al. (Oct. 1986) "Analogs of the Autoinducer of Bioluminescence in *Vibrio fisher*," *Arch Microbiol.* 146(1):35-40.

Eberhand et al. (2000) "Chemical Synthesis of Bacterial Autoinducers and Analogs," *Methods Enzymol.* 305:301-315.

Elgamey et al. (1990) "Nitriles in Heterocyclic Synthesis: A Novel Route for the Synthesis of Naphthodipyrans, Pyridines 2*H*- and 2*H*-Pyrans" *Coll. Czech. Chem. Commun.* 55:524-534.

Flemming et al. (Nov. 13, 1995) "Chemical Reagents in Photoaffinity Labeling," *Tetrahedron* (46)51:12479-12520.

Fray et al. (1999) "Plants Genetically Modified to Produce *N*-acylhomoserine Lactones Communicate with Bacteria," *Nat. Biotechnol.* 17:1017-1020.

Frezza et al. (2006) "Synthesis and Biological Evaluation of Homoserine Lactone Derived Ureas as Antagonists of Bacterial Quorum Sensing," *Bioorg. Med. Chem.* 14:4781-4791.

Fuqua et al. (2002) "Listening in on Bacteria: Acyl-Homoserine Lactone Signaling," *Nat. Rev. Mol. Cell Biol.* 3:685-695.

Fuqua et al. (2001) "Regulation of Gene Expression by Cell-To-Cell Communication: Acyl-Homoserine Lactone Quorum Sensing," *Ann. Rv. Genet.* 35:439-468.

Gasperi et al. STN Abstract of Tetrahedron Letters 2003, 44(27), 4953-4956.

Geske et al. (2007) "*N*-Phenylacetanoyl-L-Homoserine Lactones Can Strongly Antagonize or Superagonize Quorum Sensing in *Vibrio fischeri*," *Chem. Biol.* 2(5):315-320.

Geske et al. (2005) "Small Molecule Inhibitors of Bacterial Quorum Sensing and Biofilm Formation," *J. Am. Chem. Soc.* 127:12762-12763.

Geske et al. (Jun. 2008) "Expanding Dialogues: From Natural Autoinducers to Non-Natural Analogues that Modulate Quorum Sensing In Gram-Negative Bacteria" *Chem. Soc. Rev.* 37:1432-1447.

(56) References Cited

OTHER PUBLICATIONS

Geske et al. (Jan. 2008) "Comparative Analyses of N-Acylated Homoserine Lactones Reveal Unique Structural Features that Dictate Their Ability to Activate or Inhibit Quorum Sensing," *ChemBioChem* 9: 389-400.
Geske et al. (Oct. 2007)"Modulation of Bacterial Quorum Sensing with Synthetic Ligands: Systematic Evaluation of N-Acylated Homoserine Lactones in Multiple Species and New Insights into Their Mechanisms of Action," *J. Am. Chem. Soc.* 129: 13613-13625.
Ghose et al. (1999) "A Knowledge-Based Approach in Designing Combinatorial or Medicinal Chemistry Libraries for Drug Discovery," *J. Combin. Chem.* 1:55-68.
Glansdorp et al. (2004) "Synthesis and Stability of Small Molecule Probes for *Pseudomonas aeruginosa* quorum Sensing Modulation," *Org. Biomol. Chem.* 2:3329-3336.
Gonzalez et al. (Dec. 2006) "Messing with Bacterial Quorum Sensing," *Microbiol. Mol. Biol. Rev.* 70(4):859-875.
Gorske et al. (2006) "Interception of Quorum Sensing in *Staphylococcus aureus*: A New Niche for Pepdtidomoetics," *Org. Biomol. Chem.* 4:1441-1445.
Gorske et al. (2005) "Expedient Synthesis and Design Strategies for New Peptoid Construction," *Org. Lett.* 7(8):1521-1524.
Goto et al. (2004) "Ph4Dock: Pharmacophore-Based Protein-Ligand Docking," *J. Med. Chem.* (27)47:6804-6811.
Greenberg et al. (1999) "Quorum Sensing in Gram-Negative Bacteria: An Important Signaling Mechanism in Symbiosis and Disease," In; *Microbial Ecology and Infectious Disease*, Rosenberg, E. Ed., American Society for Microbiology: Washington, D.C. pp. 112-122.
Hafez et al. (1992) "Nitriles in Heterocyclic Synthesis. Part III: New Sulpha Drugs Related to Cyanopyridine Derivatives," *J. Chem. Technol. Biotechnol.* 55:333-338.
Hall-Stoodley et al. (Feb. 2004) "Bacterial Biofilms: From the Natural Environment to Infectious Diseases," *Nat. Rev. Microbiol.* 2:95-108.
Hentzer et al. (2003) "Attenuation of *Pseudomonas aeruginosa* Virulence by Quorum Sensing Inhibitors," *EMBO J.* 22(15):3803-3815.
Ikeda et al. (2001) "The Synthesis of Optically Pure Enantiomers of N-Acyl-Homoserine Lactone Autoinducers and Their Analogues," *Chem. Lett.* 30(4):314-315.
International Search Report and Written Opinion, Corresponding to International Application No. PCT/US08/57562, Mailed Jul. 7, 2008.
International Search Report and Written Opinion, Corresponding to International Application No. PCT/US2006/003715, Mailed Apr. 17, 2007.
International Search Report and Written Opinion, Corresponding to International Application No. PCT/US2007/069069, Mailed Nov. 17, 2008.
Izawa et al. STN Abstract of JP 02235850 (1990).
Izawa et al. STN Abstract of JP 03031245 (1991).
Janssens et al. (Jan. 2007) "Synthesis of N-Acyl Homoserine Lactone Analogues Reveals Strong Activators of SdiA, the *Salmonella enterica* Serovar Typhimurium LuxR Homologue," *Appl. Environ. Microbiol.* 73(2):535-544.
Jensen et al. (2007) "Probing the Pharmacophore of Ginkgolides as Glycine Receptor Antagonists," *J. Med. Chem.* 50(7):1610-1617.
Jog et al. (Feb. 2006) "Stereoisomers of *P. aeruginosa* Autoinducer Analog to probe the Regulator Binding Site," *Chem. Biol.* 13:123-128.
Kappe, C.O. (2004) "Controlled Microwave Heating in Modern Organic Synthesis," *Angew Chem. Int. Ed.* 43:6250-6284.
Kappel et al. (2005) "A Convenient Orthogonally Cleavable Methionine Handle for Anchoring Amines to Polymeric Supports," *J. Comb. Chem.* 7:78-84.
Kline et al. (Dec. 20, 1999) "Novel Synthetic Analogs of the *Pseudomonas* Autoinducer," *Bioorg. Med. Chem. Lett.* 9(24):3447-3452.
Ko et al. (Jan. 15, 1998) "New Cleavage Approached to Combinatorial Synthesis of Homoserine Lactones," *Tetrahedron Lett.* 39(3-4):297-300.

Koch et al. (2005) "The LuxR Receptor: The Sites of Interaction with Quorum-Sensing Signals and Inhibitors," *Microbiology* 151:3589-3602.
Krohnke, F. (1976) "The Specific Synthesis of Pyridines and Oligopyridines," *Synthesis* :1-24.
Lee et al. (Jan. 2006) "Activity of Purified QscR, a *Pseudomonas aeruginosa* Orphan Quorum-Sensing Transcription Factor," *Mol. Microbiol.* 59(2):602-609.
Ley et al. (Aug. 2002) "New Tools and Concepts for Modern Organic Synthesis," *Nat. Rev. Drug. Discov.* 1(8):573-586.
Lin et al. (2005) "Small Molecule Macroarray Construction via Ugi Four-Component Reactions," *Org. Lett.* 7(20):4455-4458.
Lin et al. (2006) "Rapid Synthesis of Diketopiperazine Macroarrays via Ugi Four-Component Reactions on Planar Solid Supports," *Chem. Commun.* :2884-2886.
Lipinski et al. (2001) "Experimental and Computational Approaches to Estimate Solubility and Permeability in Drug Discovery and Development Settings," *Adv. Drug Del. Rev.* 46:3-26.
Lupp et al. (Oct. 2003) "The *Vibrio fischeri* Quorum-Sensing Systems ain and lux Sequentially Induce Luminescence Gene Expressions and are Important for Persistence in the Squid Host," *Mol. Microbiol.* 50(1):319-331.
Lyczak et al. (Apr. 2002) "Lung Infections Associated with Cystic Fibrosis," *Clin. Microbiol. Rev.* 15(2):194-222.
Lyon et al. (Nov. 2003) "Chemical Signaling Among Bacteria and Its Inhibition," *Chem. Biol.* 10(11):1007-1021.
Mäe et al. (2001) "Transgenic Plants Producing the Bacterial Pheromone N-Acyl-Homoserine Lactone Exhibit Enhanced Resistance to the Bacterial Phytopathogen *Erwinia carotovora*," *Mol. Plant Microbe Interact.* 14(9):1035-1042.
Marketon et al. "Quorum Sensing Controls Exopolysaccharide Production in *Sinorhizobium meliloti*," J. Bacteriology (2003), 185(1):325-331.
Marketon et al. STN Abstract of Journal of Bacteriology (2003), 185(1):325-331.
Martinelli et al. (Jul. 2, 2004) "Effects of Natural and Chemically Synthesized Furanones on Quorum Sensing in *Chromobacterium violaceum*," *BMC Microbiology* 4:25, 1-10.
Marzinzik et al. (1998) "Key Intermediates in Combinatorial Chemistry: Access to Various Heterocycles from $\alpha,\beta$-Unsaturated Ketones on the Solid Phase," *J. Org. Chem.* 63:723-727.
Mattmann et al. (May 15, 2008) "Synthetic Ligands that Activate and Inhibit a Quorum-Sensing Regulator in *Pseudomonas aeruginosa*," *Biorg. Med. Chem. Lett.* 18(10):3072-3075.
Matsui et al. (1992) "Synthesis and Characterization of Fluorescent 4,6-Disubstituted-3-cyano-2-methylpyridines," *J. Chem. Soc. Perk. Trans.* 2:201-206.
Mcclean et al. (1997) "Quorum Sensing and *Chromobacterium violaceum*: Exploitation of Violacein Production and Inhibition for the Detection of N-Acylhomoserine Lactones," *Microbiology* 143(12):3703-3711.
Meagher et al. (2006) "Refining the Multiple Protein Structure Pharmacophore Method: Consistency Across Three Independent HIV-1 Protease Models," *J. Med. Chem.* 49:3478-3484.
Miller et al. (1972) "Assay of $\beta$-Galactosidase," In; *Experiments in Molecular Genetics*, Cold Spring: pp. 352-355.
Misato et al. STN Abstract of JP 49020492 (1974).
Misra et al. (1971) "Studies in Potential Germicides: Part VII, Syntheses of Napthalene and Phenanthrene Analogues of Chalcones" 34:260-264.
Müh et al. (Nov. 2006) "Novel *Pseudomonas aeruginosa* Quorum-Sensing Inhibitors Identifies in a Ultra-High-Throughput Screen," *Antimicrob. Agents Chemother.* 50(11):3674-3679.
Müh et al. (Nov. 7, 2006) "A Structurally Unrelated Mimic of a *Pseudomonas aeruginosa* Acyl-Homoserine Lactone Quorum-Sensing Signal," *Proc. Nat. Acad. Sci. USA* 103(45):16948-16952.
Nakayama et al. (2004) "Photochemical Regulation of the Activity of an Endonuclease *Bam*H1 Using an Azobenzene Moiety Incorporated Site-Selectively into the Dimer Interface," *Chem. Commun.* :2386-2387.
Ni et al. (2004) "Recent Advances in Therapeutic Chalcones," *Exp. Opin. Ther. Patents* 14:1669-1691.

(56) References Cited

OTHER PUBLICATIONS

Nielsen et al. (2005) "Cationic Chalcone Antibiotics. Design, Synthesis, and Mechanism of Action," *J. Med. Chem.* 48:2667-2677.
Nielson et al. (2004) "Antibacterial Chalcones—Bioisosteric Replacement of the 4'-hydroxy Group," *Bioorg. Med. Chem.* 12:3047-3054.
Nielsen et al. (Apr. 1988) "Glycolamide Esters as Biolable Prodrugs of Carboxylic Acid Agents: Synthesis, Stability, Bioconversion, and Physiocochemical Properties," *J. Pharm. Sci.* 77(4):285-298.
Nogrady (1985) "Pro-Drugs and Soft Drugs," In; *Medicinal Chemistry A Biochemical Approach*, Oxford University press, New York, pp. 388-392.
Notati, R.E. (1985) "Theory and Practice of Prodrug Kinetics," *Methods Enzymol.* 112:309-396.
Passador et al. (Oct. 1996) "Functional Analysis of the *Pseudomonas aeruginosa* Autoinducer PAI," *J. Bacteriol.* 178(20):5995-6000.
Pearson et al. (Jan. 1994) "Structure of the Autoinducer Required for Expression of *Pseudomonas aeruginosa* Virulence Genes," *Proc. Natl. Acad. Sci. USA* 91:197-201.
Persson et al. (2005) "Rational Design and Synthesis of New Quorum-Sensing Inhibitors Derived from Acylated Homoserine Lactones and Natural Products from Garlic," *Org. Biomol. Chem.* 3:253-262.
Powers et al. (1998) "Automated Parallel Synthesis of Chalcone-Based Screening Libraries," *Tetrahedron* 54:4085-4096.
Rajvaidya et al. (2004) "Synthesis and Microbiological Activities of Some Pyrazoles and Cyanopyridines," *Indian J. Chem.* 43B:906-908.
Ramussen et al. (2006) "Quorum Sensing Inhibitors: A Bargain of Effects," *Microbiology* 152:895-904.
Rathke et al. (1985) Synthesis of β-Keto Acids and Methyls Ketones Using Bis(Trimethylsilyl) Malonate and Triethylamine in the Presence of Lithium or Magnesium Halides,: *Synth. Commun.* 15:1039-1049.
Reverchon et al. (Apr. 22, 2002) "New Synthetic Analogues of *N*-acyl Homoserine Lactones as Agonists or Antagonists of Transcriptional Regulators Involved in Bacterial Quorum Sensing," *Bioorg. Med. Chem. Lett.* 12(8):1153-1157.
Ruby, E.G. (1996) "Lessons from a Cooperative, Bacterial-Animal Association: The *Vibrio fischeri-Euprymna scolopes* Light Organ Symbiosis," *Ann. Rev. Microbiol.* 50:591-624.
Schaefer et al. (May 1996) "Quorum Sensing in *Vibrio fisheri*: Probing Autoinducer-LuxR Interactions with Autoinducer Analogs," *J. Bacteriol.* 178(10):2897-2901.
Schultz et al. (2003) "Mechanism and Dynamics of Azobenzene Photoisomerization," *J. Am. Chem. Soc.* 125(27):8098-8099.
Schuster et al. (Nov. 9, 2004) "Promoter Specificity in *Pseudomonas aeruginosa* Quorum Sensing Revealed by DNA Binding of Purified LasR," *Proc. Nat. Acad. Sci. USA* 101(45):15833-15839.
Smith et al. (Jan. 2003) "Induction and Inhibition of *Pseudomonas aerinosa* Quorum Sensing by Synthetic Autoinducer Analogs," *Chem. Biol.* 10(1):81-89.
Smith et al. (Jun. 2003) "Library Screening for Synthetic Agonist and Antagonist of a *Pseudomonas aeruginosa* Autoinducer," *Chem. Biol.* 10(6):563-571.
Smith et al. (Feb. 2003) "*P. aeruginosa* Quorum-Sensing Systems and Virulence," *Cur. Opin. Microbiol.* 6(1):56-60.
Stover et al. (Aug. 31, 2000) "Complete Genome Sequence of *Pseudomonas aeruginosa* PAO1, an Opportunistic Pathogen," *Nature* 406:959-964.
Stringer et al. (Jan. 29, 2007) "Rapid Identification of Antibacterial Agents Effective Against *Staphylococcus aureus* Using Small-Molecule Macroarrays," Abstract for Poster Presentation at the American Chemical Society Meeting held in Chicago IL (USA) Mar. 2007.

Stringer et al. (Mar. 28, 2007) "Rapid Identification of Antibacterial Agents Effective Against *Staphylococcus aureus* Using Small-Molecule Macroarrays," Poster Presentation at the American Chemical Society Meeting held in Chicago IL (USA) Mar. 25-Mar. 29, 2007.
Taha et al. (Nov. 2006) Discovery of Potent Inhibitor of Pseudomonal Quorum Sensing via Pharmacophore Modeling and in Silico Screening,: *Bioorg. Med. Chem. Lett.* 16(22):5902-5906.
Teplitski et al. (2000) "Plants Secrete Substances that Mimic Bacterial *N*-Acyl Homoserine Lactone Signal Activities and Affect Population Density-Dependent Behaviors in Associated Bacteria," *Mol. Plant-Microbe Interact.* 13(6):637-648.
Tsiodras et al. (Jul. 2001) "Linezolid Resistance in a Clinical Isolate of *Staphylococcus aureus,* " *Lancet* 358:207-208.
Tu et al. (2005) "An Efficient Improve for the Kröhnke Reaction: One-Pot Synthesis of 2,4,6-Triarylpyridines Using Raw Materials Under Microwave Irradiation," Chem. Lett. 34:732-733.
Urbanowski et al. (Feb. 2004) "Reversible Acyl-Homoserine Lactone Binding to Purified *Vibrio fischeri* LuxR Protein," *J. Bacteriol.* 186(3):631-637.
Van Delden et al. (1998) "Cell-to-Cell Signaling and *Pseudomonas aeruginosa* Infections," *Emerg. Infect. Dis.* 4(4):551-560.
Vannini et al. (2002) "The Crystal Structure of the Quorum Sensing Protein TraR Bound to Its Autoinducer and Target DNA," *EMBO J.* 21(17):4393-4401.
Visick et al. (Dec. 2006) "*Vibrio fischeri* and its Host: It Takes Two to Tango," *Curr. Opin. Microbiol.* 9(6):632-638.
von Bodman, B. (Jun. 1998) "A Negative Regulator Mediates Quorum-Sensing Control of Exopolysaccharide Production in *Pantoea stewartii* subsp. *Stewartii,"* *Proc. Nat. Acad. Sci. USA* 95:7687-7692.
Waters et al. (2005) "Quorum Sensing: Cell-to-Cell Communication in Bacteria," *Ann. Rev. Cell. Dev. Biol.* 21:319-346.
Welch et al. (2005) "Cell-Cell Communication in Gram-Negative Bacteria," *Molecular Biosystems* 1:196-202.
Whitehead et al. (Aug. 2001) "Quorum-Sensing in Gram-Negative Bacteria," *Microbiol. Rev.* 25(4):365-404.
Winans, S.C. (Oct. 1, 1998) "Command, Control and Communication in Bacterial Pathogenesis," *Trends Microbiol.* 6(10):382-383.
Yamaguchi et al. (1998) "A New Expedient Route to 2,6-Diaryl-3-cyano-4-(trifluoromethyl)pyridines" J. Het. Chem. 35:805-810.
Zhang et al. (Jun. 27, 2002) "Structure of a Bacterial Quorum-Sensing Transcription Factor Complexed with Pheromone and DNA," *Nature* 417:971-974.
Zhu et al. (Feb. 13, 2001) "The Quorum-Sensing Transcriptional Regulator TraR Requires its Cognate Signaling Ligand for Protein Folding, Protease Resistance, and Dimerization," *Proc. Nat. Acad. Sci. USA* 98(4):1507-1512.
Zhu et al. (Jul. 2000) "The Basis of Brown Gall Tumorigenesis," *J. Bacteriol.* 182(14):3885-3895.
Zhu et al. (2005) "Mechanistic Explanation for the Unique Pharmacologic Properties of Receptor Partial Agonists," *Biomed. Pharmacother.* 59:76-89.
Zhu et al. (Oct. 1998) "Analogs of the Autoinducer 3-Oxooctanoyl-Homoserine Lactone Strongly Inhibit Activity of the TraR Protein of *Agrobacterium tumerfaciens," J. Bacteriol.* 180(20):5398-5405.
Extended European Search Report dated Sep. 6, 2011 for corresponding European Patent Application No. 08732506.4.
Mattmann et al. (Available online Nov. 28, 2007) "Synthetic Ligands that Activate and Inhibit a Quorum-Sensing Regulator in *Pseudomonas aeruginosa" Biorg. Med. Chem. Lett.* 18: 3072-3075.
Persson, T., Givskov M., Nielsen, J (Dec. 2005) "Quorum sensing inhibition: targeting chemical communication in gram-negative bacteria," Curr Med Chem 12(26) 3103-3115.

\* cited by examiner

| A1: n = 1; C4 | A4: n = 7; C10 | A9: n = 5; C10 |
| A2: n = 3; C6 | A5: n = 9; C12 | A7: n = 9; C14 |
| A3: n = 5; C8 | A6: n = 13; C16 | |

C10: n = 1; C4   C14: n = 5; C8
C11: n = 2; C5   C15: n = 6; C9
C12: n = 3; C6   C16: n = 7; C10
C13: n = 4; C7   C17: n = 8; C11

PHL

| B3: X = H | B13: X = 4-I | B24: X = 4-CH₃ |
|---|---|---|
| B4: X = 4-F | B14: X = 3-I | B23: X = 4-CF₃ |
| B5: X = 3-F | B15: X = 2-I | B26: X = 4-NH₂ |
| B6: X = 2-F | B16: X = 4-NO₂ | B25: X = 4-NHBoc |
| B7: X = 4-Cl | B17: X = 3-NO₂ | B27: X = 4-OH |
| B8: X = 3-Cl | B18: X = 2-NO₂ | B28: X = 4-OMe |
| B9: X = 2-Cl | B19: X = F₅ | B29: X = 4-OEt |
| B10: X = 3-Br | B20: X = 4-N₃ | |
| B11: X = 2-Br | B21: X = 4-Ph | |

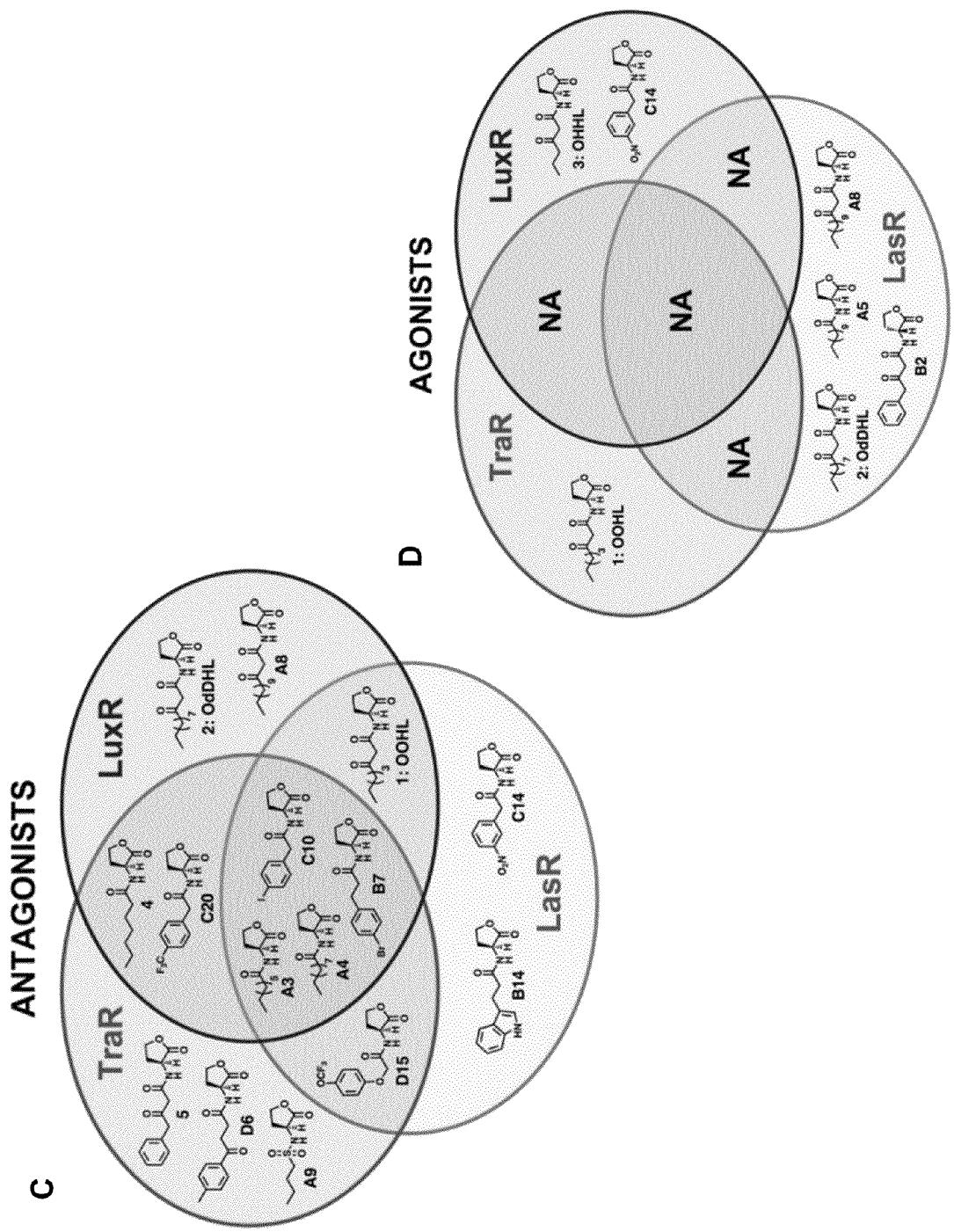
Figure 13, continued

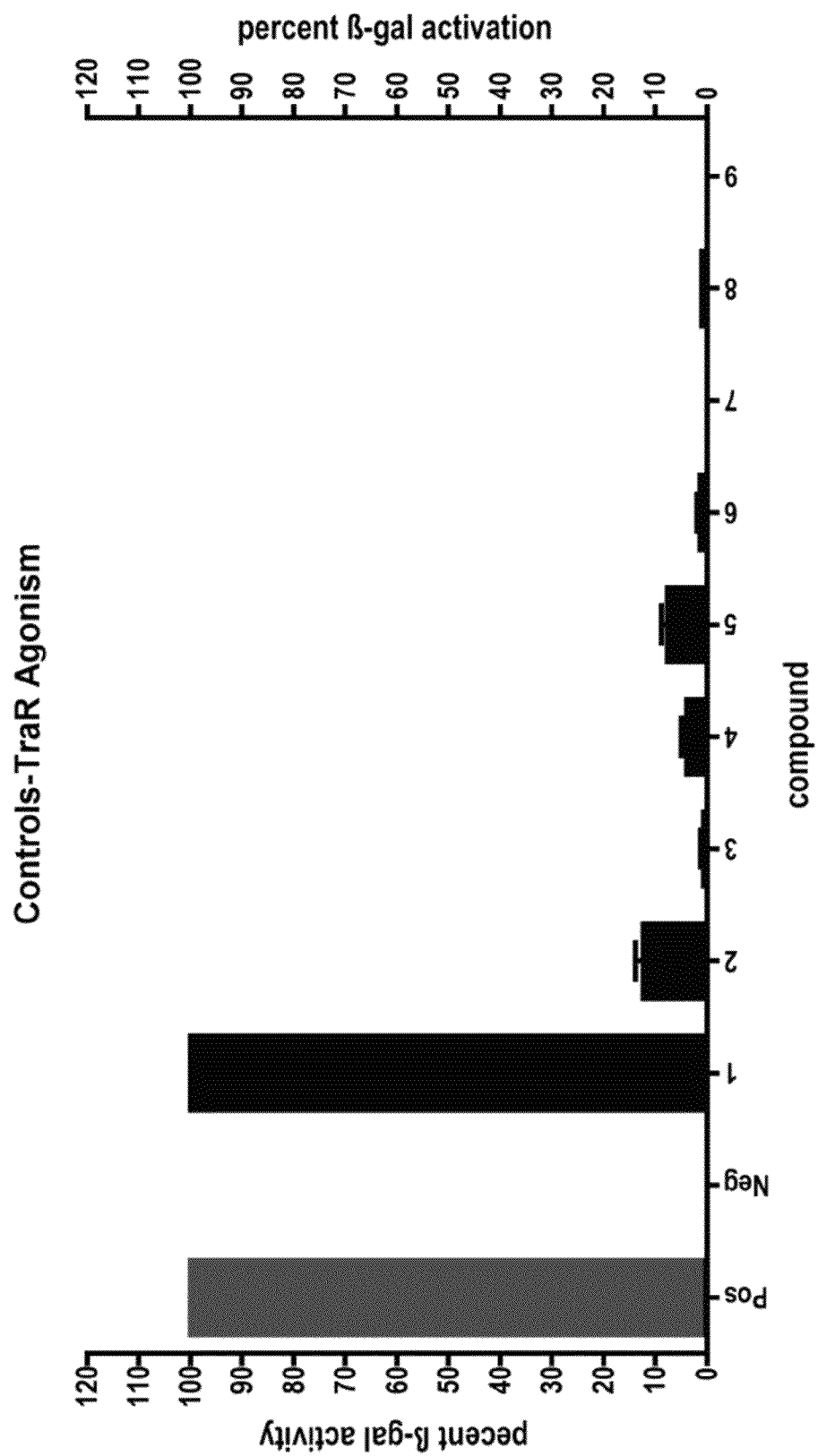
Figure 18, continued

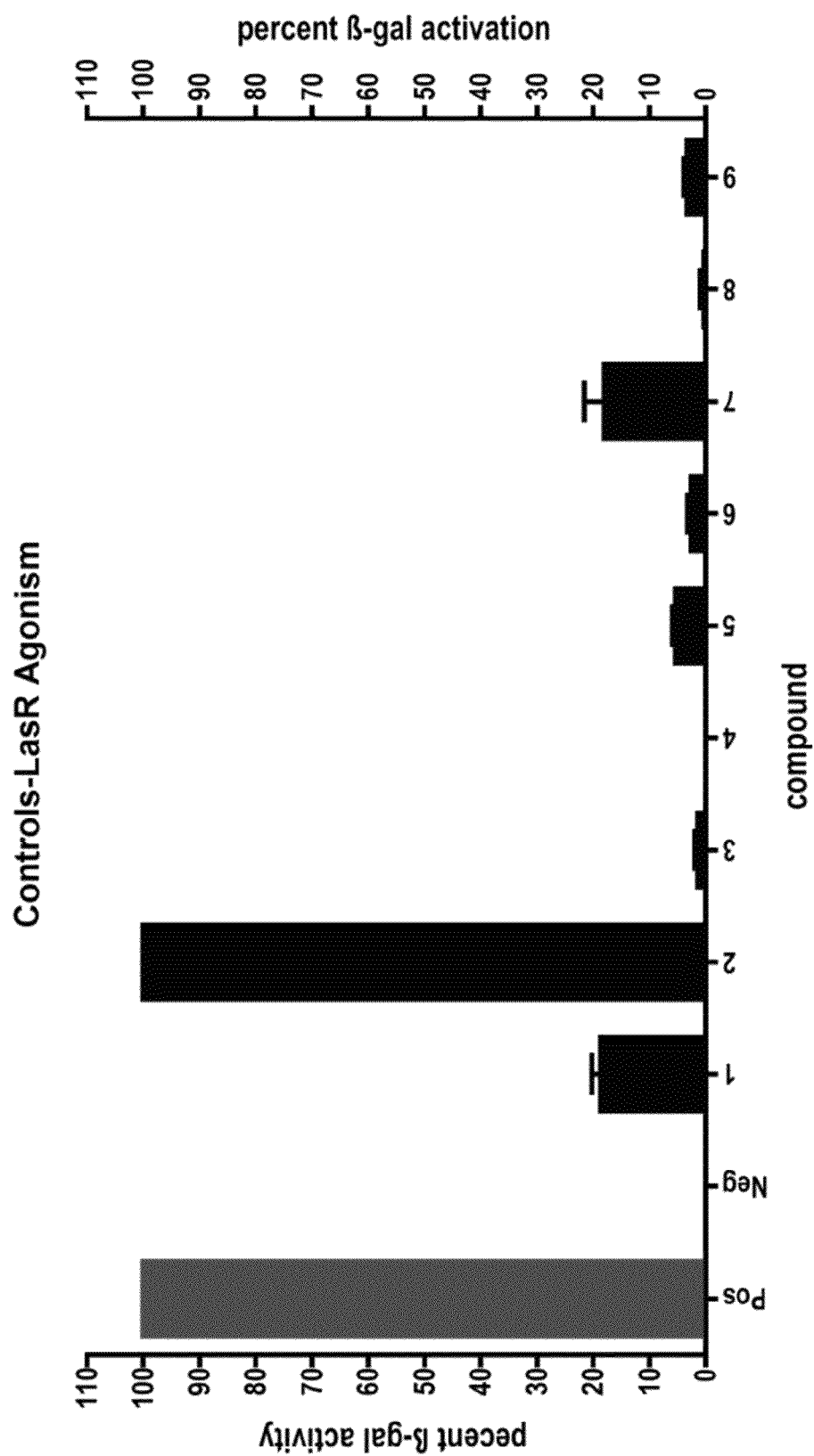
Figure 19, continued

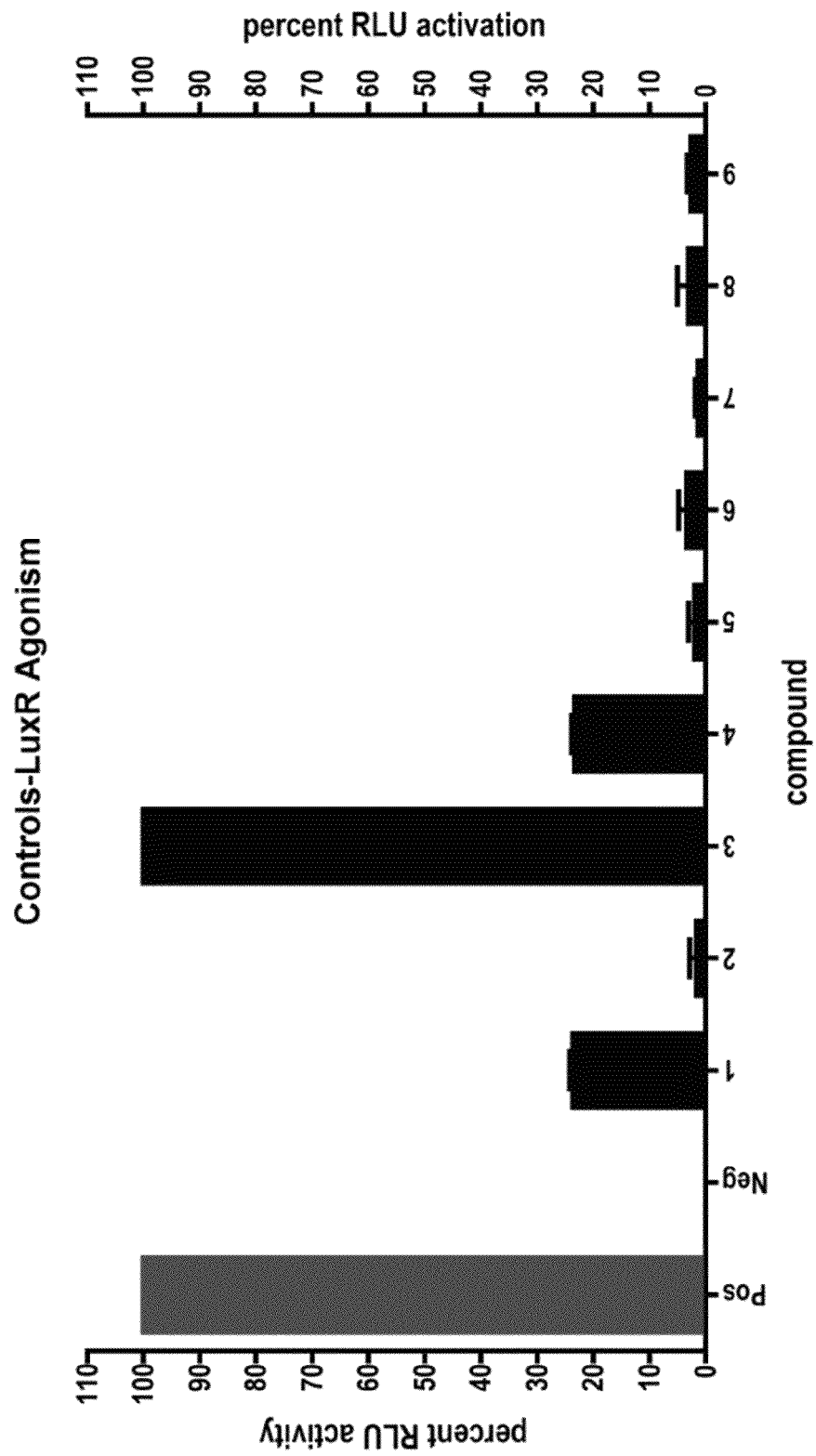
Figure 20, continued

*P. aeruginosa* LasR data - *E. coli.* pJN105L strain

E

*P. aeruginosa* LasR data - *E. coli.* pJN105L strain
Q
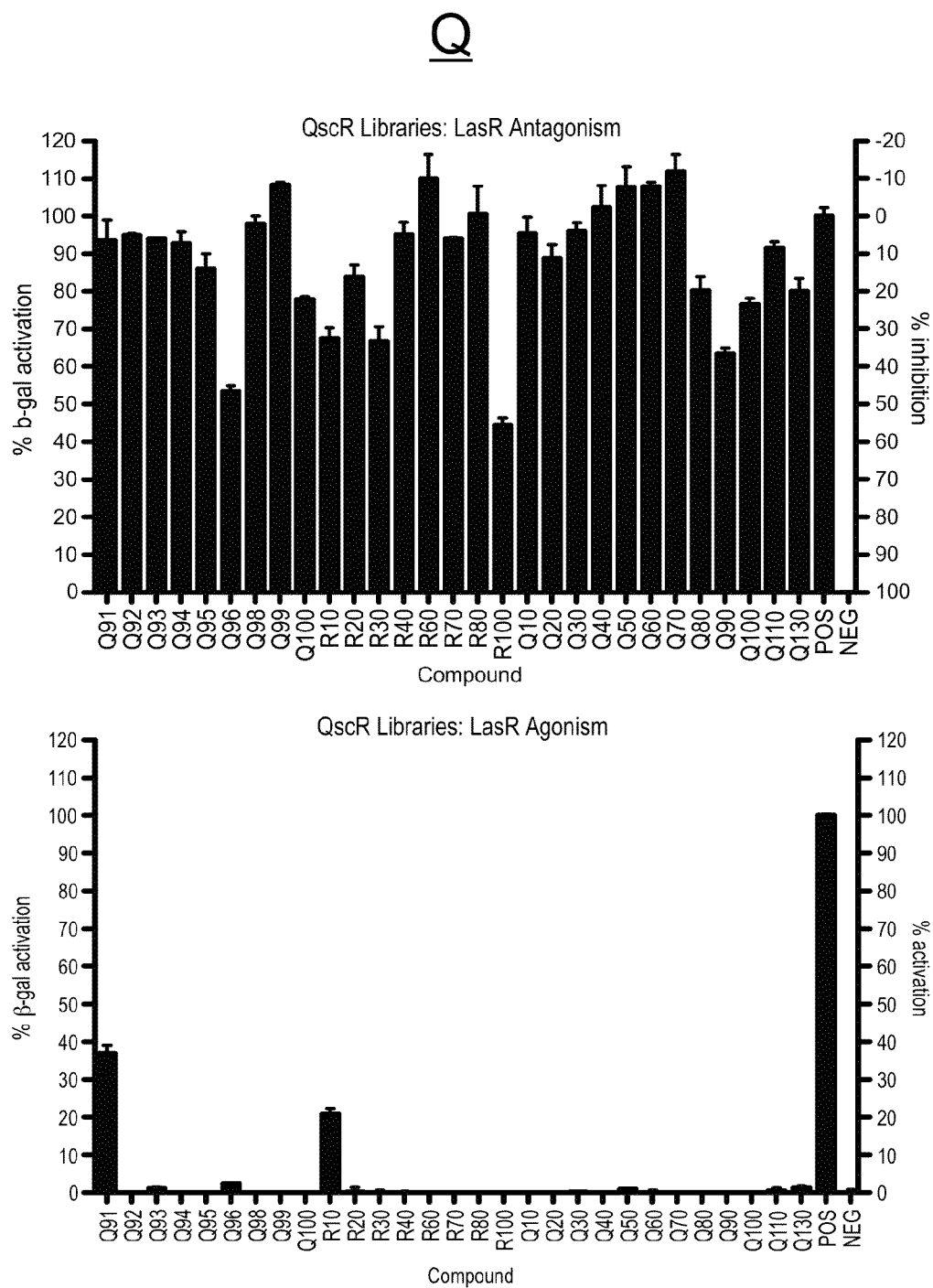
Figure 35, continued

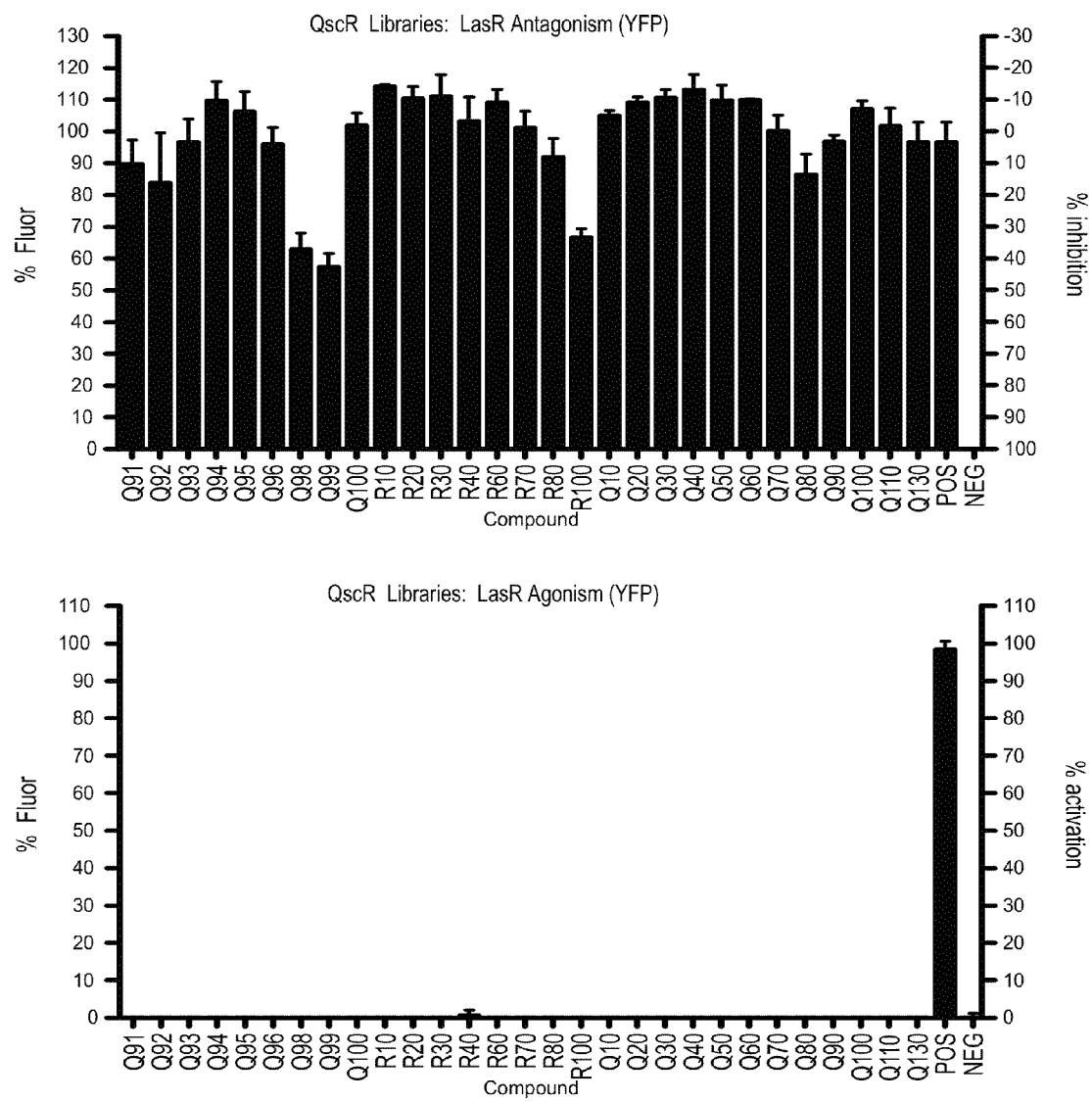
Figure 36, continued

P. aeruginosa QscR - E. coli pJN105Q strain
Q
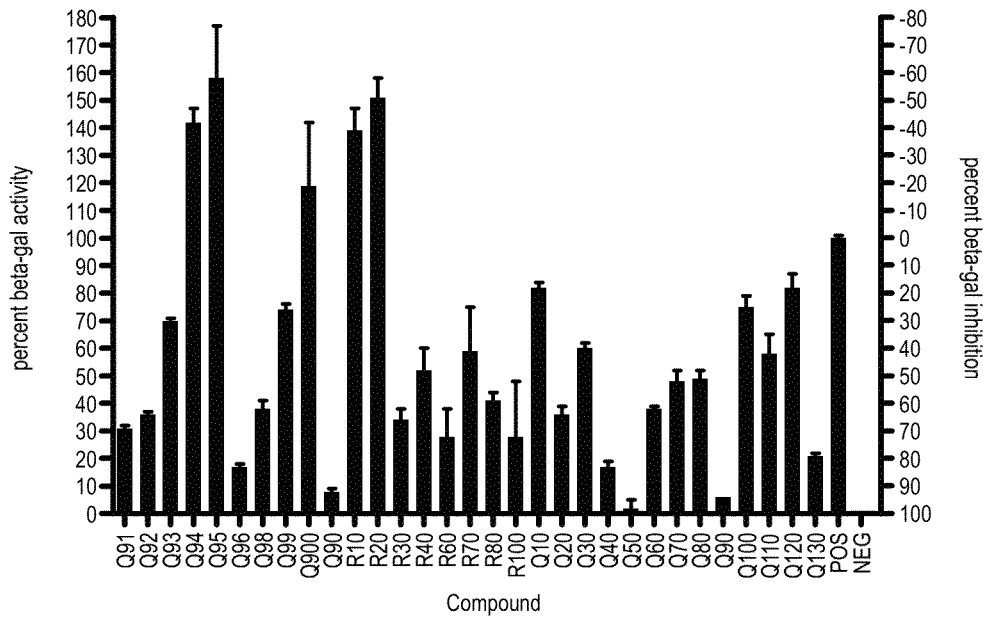
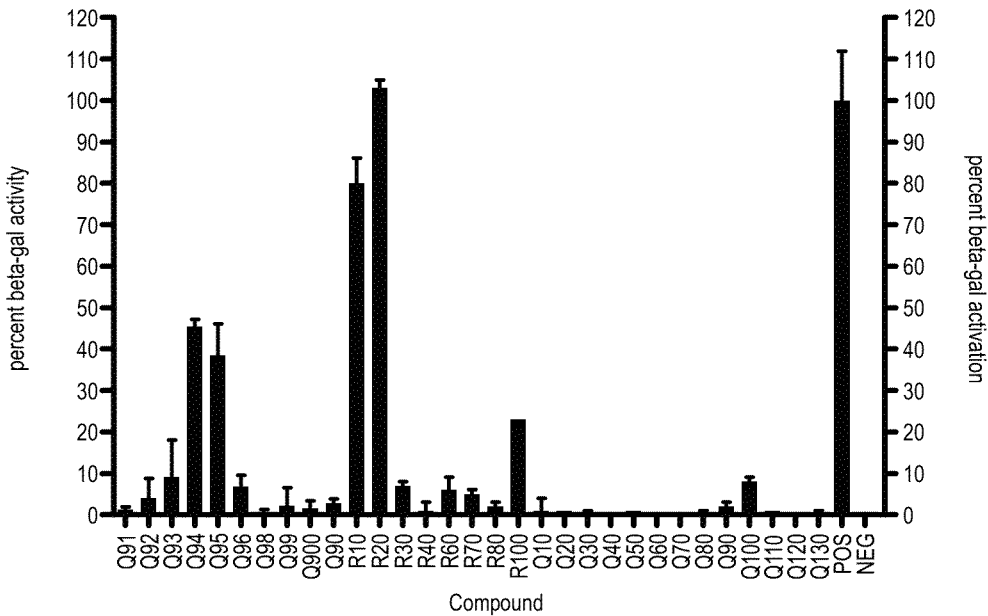
Figure 37, continued

*A. tumefaciens* TraR - *A. tumefaciens* WCF strain
Q
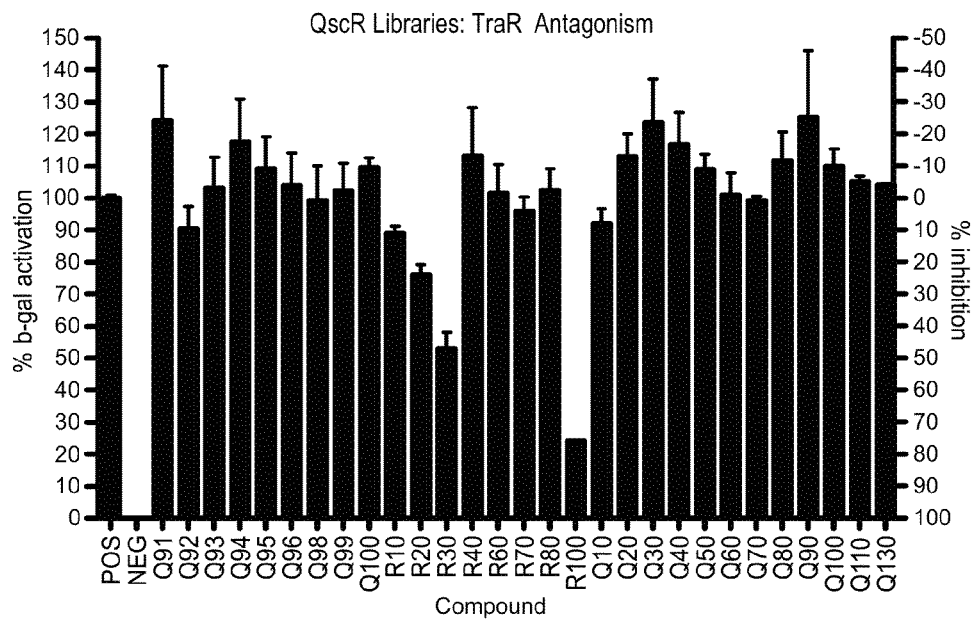
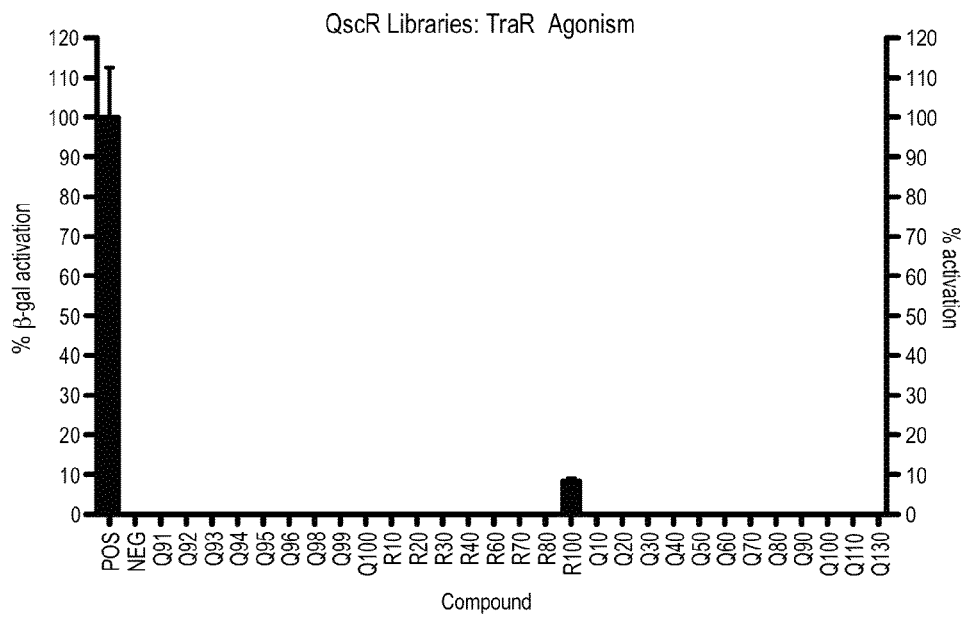
Figure 38, continued

*V. fischeri* LuxR - *V. fischeri* ES114 -*luxI* strain
Q
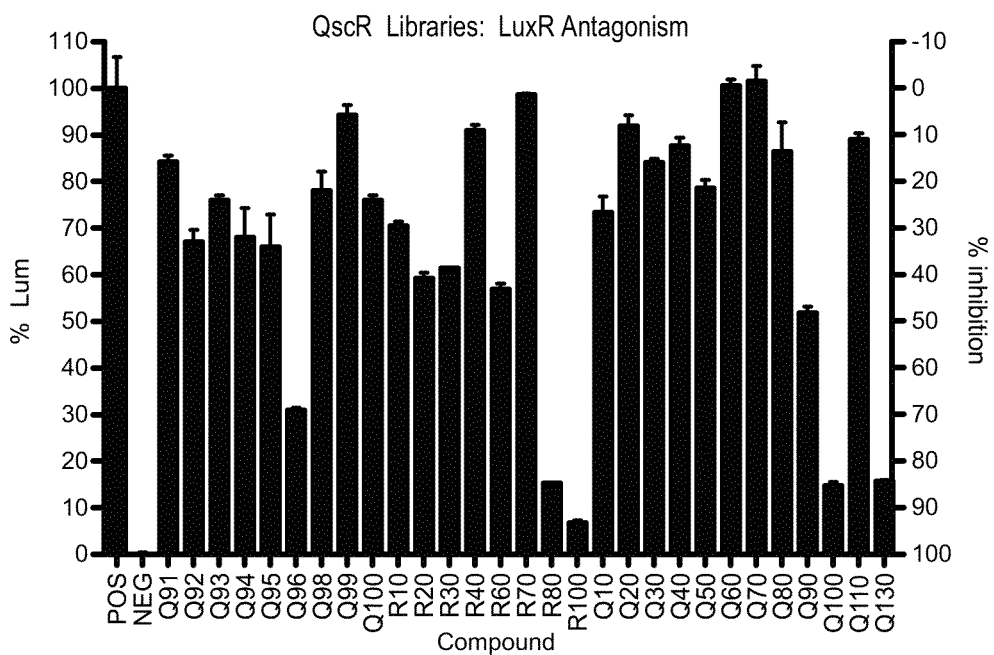
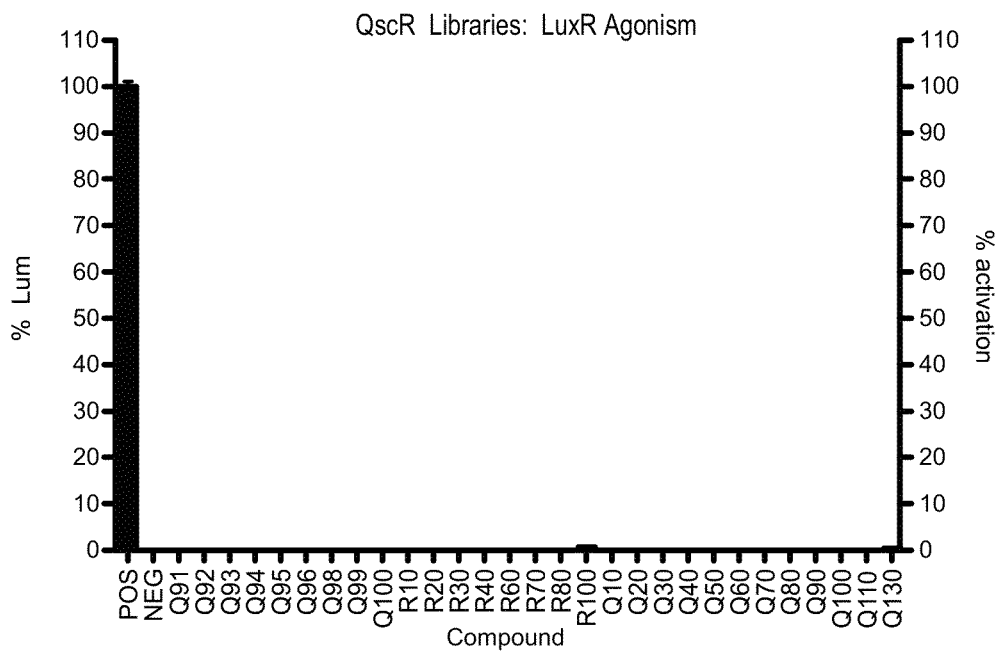
Figure 39, continued

E library hits

LasR Hits (pJN105L)
Agonists (>30% activation)

E11(7)

LasR Hits (pJN105L)
Antagonists (>70% Inhibition)

LuxR Hits (ES114 -luxI)
Agonists (>30% activation)

LuxR Hits (ES114 -luxI)
Antagonists (>85% Inhibition)

TraR Hits (WCF)
Antagonists (>70% Inhibition)

MODULATION OF BACTERIAL QUORUM SENSING WITH SYNTHETIC LIGANDS

CROSS REFERENCE TO RELATED APPLICATION

This application is a division of U.S. patent application Ser. No. 12/051,826, filed Mar. 19, 2008, which claims priority under 35 U.S. C. §119(e) to U.S. Provisional Patent Application Nos. 60/895,598, 60/912,345, and 60/974,026 filed on Mar. 19, 2007, Apr. 17, 2007, and Sep. 20, 2007, respectively, each of which is hereby incorporated by reference in its entirety.

STATEMENT REGARDING FEDERALLY SPONSORED RESEARCH OR DEVELOPMENT

This invention was made with U.S. government support under Award No. AI063326 awarded by the National Institutes of Health. The U.S. government has certain rights in the invention.

BACKGROUND OF THE INVENTION

Many microbial pathogens cause tremendous damage worldwide, in humans as well as in animals and crop plants. The continuing emergence of multiple-drug-resistant pathogen strains has necessitated finding new compounds that can be used in antimicrobial treatment. In general, two strategies exist for controlling pathogens, either kill the pathogen or attenuate its virulence such that it does not damage the host.

The strategy of attenuating bacterial virulence has the advantage of not creating selective pressure in favor of drug resistant strains. Antimicrobial compounds having virulence-attenuating but not cell-killing effects are expected to remain effective for longer periods of time than conventional antibiotics because of the lack of development of drug resistance. This approach has, however, suffered from a lack of specific targets for rational drug design.

Many bacteria use autoinducer ligands to monitor their population densities in a phenomenon called quorum sensing. At high cell densities, bacteria use this chemical signaling process to switch from a nomadic existence to that of multicellular community. This lifestyle switch is significant, as numerous pathogenic bacteria use quorum sensing to turn on virulence pathways and form drug-impervious communities called biofilms that are the basis of myriad chronic infections. Over 80% of bacterial infections in humans involve the formation of biofilms, as exemplified in lung infections by *Pseudomonas aeruginosa*, which is the primary cause of morbidity in cystic fibrosis patients. The treatment of infections by pathogens that form biofilms costs over $1 billion/year in the US alone.

The control of gene expression in response to cell density was first described in the marine luminous bacteria *Vibrio fischeri* and *Vibrio harueyi*. Quorum sensing bacteria synthesize, release, and respond to specific acyl-homoserine lactone ("AHL" or "HSL") signaling molecules called autoinducers ("AI") to control gene expression as a function of cell density. The classical quorum-sensing pathway comprises at least three components: a membrane associated receptor/transcription factor; a diffusible signal, the autoinducer; and a recognition site in the promoter region of the target gene. The autoinducer binds to the receptor causing the receptor/AI complex to be internalized. This, in turn, allows the receptor or receptor/AI complex to bind to the promoter region of the target gene or genes altering transcription and down-regulating or up-regulating gene expression. In most cases, this includes increased AI expression, thereby resulting in a cascade effect.

In recent years it has become apparent that many Gram-negative bacteria employ one or more quorum sensing systems. The quorum-sensing system is an attractive antibacterial target because it is not found in humans and is critical for high level bacterial virulence. Bacterial quorum sensing systems comprise AHL derivatives with different acyl side chains to regulate, in a cell-density dependent manner, a wide variety of physiological processes unique to the life-cycle of each microbe. These processes include: swarming, motility, biofilm formation, conjugation, bioluminescence and/or production of pigments, antibiotics and enzymes. For example, in *P. aerugniosa* quorum sensing pathways affect the expression of various exoenzymes, biofilm formation and cell-cell spacing. Other bacteria react to quorum sensing stimulation by expressing proteases and pectinases, expressing pili, entering stationary phase, emerging from lag phase and initiating cell division.

Biofilms are dense extracellular polymeric matrices in which the bacteria embed themselves. Biofilms allow bacteria to create a microenvironment that attaches the bacteria to the host surface and which contains excreted enzymes and other factors allowing the bacteria to evade host immune responses including antibodies and cellular immune responses. Such biofilms can also exclude antibiotics. Further, biofilms can be extremely resistant to removal and disinfection. For individuals suffering from cystic fibrosis, the formation of biofilms by *P. aerugniosa* is eventually fatal. Other bacteria also respond to quorum sensing signals by producing biofilms. Biofilms are inherent in dental plaques, and are found on surgical instruments, food processing and agriculture equipment and water treatment and power generating machinery and equipment.

Because of the virulence factors it triggers, the bacterial quorum-sensing system offers a novel target for use in modulating the virulence of pathogenic bacteria. All acyl-homoserine lactone quorum-sensing systems described to date, except that of *V. harueyi*, utilize AI synthases encoded by a gene homologous to luxI of *V. fischeri*. The response to the autoinducer is mediated by a transcriptional activator protein encoded by a gene homologous to luxR of *V. fischeri* (Bassler and Silverman, in Two Component Signal Transduction, Hoch et al., eds., Am. Soc. Microbiol. Washington D.C., pp. 431-435, 1995). Thus, the AHL quorum sensing system is present in a broad spectrum of pathogenic bacteria.

Gram-negative bacteria represent numerous relevant pathogens using quorum-sensing pathways. Besides *P. aeruginosa*, other quorum sensing bacteria include: *Aeromonas hydrophila, A. salmonicida, Agrobacterium tumefaciens, Burkholderia cepacia, Chromobacterium violaceum, Enterobacter agglomeran, Erwinia carotovora, E. chrysanthemi, Escherichia coli, Nitrosomas europaea, Obesumbacterium proteus, Pantoea stewartii, Pseudomonas aureofaciens, P. syringae, Ralstonia solanacearum, Rhisobium etli, R. leguminosarum, Rhodobacter sphaeroides, Serratia liguefaciens, S. marcescens, Vibrio anguillarum, V. fischeri, V. cholerae, Xenorhabdus nematophilus, Yersinia enterocolitica, Y. pestis, Y. pseudotuberculosis, Y. medievalis,* and *Y. ruckeri.* Studies on the above listed bacteria indicate that, while the AI is generally an AHL compound, the genes affected as well as the phenotypes resulting from induction of the promoter differ according to the particular life cycle of each bacterium. Further, quorum sensing stimulation typically results in altered expression of multiple genes.

In addition to affecting multiple genes, some bacteria have multiple stages of quorum sensing response. In these bacteria, the different stages of quorum sensing may be induced by different ligand/receptor pairs and result in the expression of different sets of genes with similarly distinct phenotypes. For example, *V. harveyi* has two independent density sensing systems (Signaling Systems 1 and 2), and each is composed of a sensor-autoinducer pair. Signaling System 1 is composed of Sensor 1 and autoinducer 1 (AI-1), which is an N-4,3-hydroxybutanoyl)-L-homoserine lactone (see Bassler et al., Mol. Microbiol. 9: 773-786, 1993). Signaling System 2 is composed of Sensor 2 and autoinducer 2 (AI-2) (Bassler et al., Mol. Microbiol. 13: 273-286, 1994). The structure of AI-2 heretofore has not been determined. Nor have the gene(s) involved in biosynthesis of AI-2 been identified. Signaling System 1 is a highly specific system proposed to be used for intra-species communication and Signaling System 2 appears to be less species-selective, and is hypothesized to be for inter-species communication (Bassler et al., J. Bacteriol. 179: 4043-4045, 1997). Other research indicates that *V. cholerae* also has two stages of quorum-sensing response. The first, limits biofilm production, so that the microbe can escape the biofilm once it has passed through harsh environments such as the host's stomach. The second stage initiates swarming once the bacterium have escaped the biofilm and multiplied in the gut; allowing the bacteria to leave the host and start the cycle again.

Because of the diversity of quorum sensing ligands and phenotypes, having a large number of quorum sensing compounds with which to probe diverse quorum sensing responses allows clinicians to identify ways to modulate or attenuate such responses. Further, if synthetic quorum sensing analogs are available, a greater diversity of responses maybe identified other than those resulting from the native ligand. In addition, developing a synthetic route to quorum sensing compounds provides a quick, more efficient way of producing analogs that does not rely on time-consuming techniques of molecular biology and is not based on the backbone of a native ligand. In addition, this strategy of attacking pathogenic bacteria via their quorum-sensing pathways provides methods of controlling bacterial virulence without resorting to antibiotics. This allows treatment of bacterial infections without inducing antibiotic resistance and the concomitant breeding of "superbugs".

Recent studies in vivo have shown that the virulence of *P. aeruginosa* lacking one or more genes responsible for quorum sensing is attenuated in its ability to colonize and spread within the host. Similarly, elimination of the AHL synthase in several plant pathogenic bacteria has led to complete loss of infectivity (Beck von Bodman, 1998, Proc. Natl. Acad. Sci. USA 95:7687-7692; Whitehead et al., 2001, Microbiol. Rev. 25:365-404). Transgenic plant systems engineered to express AHL synthases ectopically, to produce inducing levels of AHLs, have shifted the balance of host-microbe interactions in favor of disease resistance (Fray et al., 1999, Nat. Biotechnol. 171:1017-1020; Mae et al., 2001, Mol. Plant Microbe Interact. 14:1035-1042). It is thought that the production of endogenous AHL compounds by plants is the basis of varying degrees of disease resistance and susceptibility (Teplitski et al., 2000, Mol. Plant-Microbe Interact. 13:637-648). The halogenated furanones produced by some marine algae are known to have a pronounced effect suppressing marine biofouling. Some furanones have also been shown to affect *V. cholerae* by eliminating its ability to express genes associated with their virulence phase.

The current understanding is that, at some threshold AHL concentration (and related cell density), the AHL ligand (AI) will bind its cognate receptor, a LuxR-type protein, and activate the transcription of target genes involved in group behavior. (Fuqua, C.; Greenberg, E. P. *Nat. Rev. Mol. Cell Biol.* 2002, 3, 685-695.) Blocking the binding of the endogenous AHL to its receptor with a non-native AHL is an attractive strategy for quorum sensing control.

In addition to their pathogenic costs, quorum sensing bacteria also have significant economic impact in industries other than health care. For example, in agriculture, various species of the genera *Rhizobium, Bradyrhizobium* and *Sinorhizobium* are important plant symbionts helping legumes to fix nitrogen, while, species of the genera *Erwinia, Xanthomonas* and *Pseudomonas* are responsible for significant food-spoilage. Other industries, such as power generation, paper making and water treatment are subject to biofouling by many types of slime forming bacteria, such as *Deinococcus geothermalis*.

Nevertheless, the pace of AHL analog discovery has been slow as the majority of AHLs synthesized to date have been generated in poor yields and low purities and screened on an ad hoc basis (Eberhard, A.; Schineller, J. B. *Methods Enzymol.* 2000, 305, 301-315; Reverchon, S.; Chantegrel, B.; Deshayes, C.; Doutheau, A.; Cotte-Pattat, N. *Bioorg. Med. Chem. Lett.* 2002, 12, 1153-1157; Zhu, J.; Beaber, J. W.; More, M. I.; Fuqua, C.; Eberhard, A.; Winans, S. C. *J. Bacteriol.* 1998, 180, 5398-5405). Currently there are no antibacterial compounds that target the bacterial quorum sensing system to reduce bacterial virulence and increase susceptibility to bactericidal antibiotics. Therefore, new synthetic approaches are required for the generation of AHL analogs and the systematic evaluation of the effects of AHL ligand structure on quorum sensing. In addition, non-native AHL-analogs may provide significant benefits in their ability to stimulate quorum pathways without resulting increased virulence and pathogenicity.

SUMMARY OF THE INVENTION

The present invention provides compounds and methods for modulation of quorum sensing of bacteria. In an embodiment, the compounds of the present invention are able to act as replacements for naturally occurring bacterial quorum sensing ligands in a ligand-protein binding system; that is; they imitate the effect of natural ligands and produce an agonistic effect. In another embodiment, the compounds of the present invention are able to act in a manner which disturbs or inhibits the naturally occurring ligand-protein binding system in quorum sensing bacteria; that is, they produce an antagonistic effect.

Compounds of this invention include those having a wide range of acyl groups attached to cyclic head groups as discussed herein below. The acyl groups can comprise aliphatic hydrocarbon chains of various lengths, and/or aromatic or heteroaromatic species, all of which are optionally substituted with non-hydrogen functional groups including, but not limited to, ether, halide, sulfonyl, nitro, azido, amide, alkenyl, alkynyl, hydroxyl, additional acyl groups and combinations thereof as described in more detail below. Cyclic head groups of the compounds of this invention include those of formula:

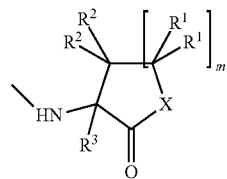

where m is 1-4, X is O, S, NH or $C(R^2)_2$ (including $CH_2$) each $R^1$, $R^2$ and $R^3$ is independently selected from the group consisting of a hydrogen, an branched or unbranched C1-C12 acyclic aliphatic group, an optionally substituted $C_1$-$C_{12}$ alkyl, alkenyl or alkynyl group, an aryl group having $C_1$-$C_{20}$ carbon atoms, a $C_1$-$C_{12}$ alkoxy group, a hydroxyl group, a nitro group, a nitrile group, an azido group, an acyl group (—CO—H, —CO—R, —CO—N(R')$_2$), an amino group (—N(R')$_2$), or a protecting group, where optional substitution is described below and includes among others, substitution with one or more halogens (particularly fluorines), one or more OH or alkoxy groups (particularly C1-C3 alkoxy groups), one or more amino groups (—N(R')$_2$ including —NH$_2$) where R' is hydrogen, optionally substituted $C_1$-$C_{12}$ alky (including $C_1$-$C_6$ and C1-C3 alkyl), and optionally substituted C1-C12 aryl (including phenyl).

The present invention also provides methods of increasing or reducing the virulence of quorum sensing bacteria. In one aspect, the method comprises contacting a bacterium with an effective amount of a compound of the present invention. In another aspect, the method comprises contacting a bacterium with a therapeutically effective amount of a pharmaceutically acceptable salt or ester of the compounds of the present invention. In yet another aspect, the method comprises contacting a bacterium with a precursor which can form an effective amount of a compound of the present invention.

In an embodiment, the methods of the present invention can be used for disrupting a biofilm formed by a quorum sensing bacterium. A method of the present invention for disrupting a biofilm comprises contacting the biofilm with an effective amount of a compound of the present invention. In an embodiment, the methods of the present invention can be used to diminish or inhibit biofilm production. Alternatively, the methods of the present invention can be used for causing a quorum sensing bacterium to initiate or enhance biofilm production.

In an embodiment, the methods of the present invention can be used for inhibiting or diminishing the symbiotic behavior of a quorum sensing bacteria. In another embodiment, the methods of the present invention can be used for stimulating, initiating, or enhancing the symbiotic behavior of a quorum sensing bacteria.

In another embodiment of the methods, the compounds of the present invention can be administered to a subject to initiate an immune response. In an embodiment, the administration of an effective amount of a compound of the present invention to a subject can initiate or enhance the symbiotic behavior of quorum sensing bacteria in the subject. In an embodiment, the administration of an effective amount of a compound of the present invention to a subject can disrupt a biofilm of quorum sensing bacteria in the subject. In an embodiment, the administration of an effective amount of a compound of the present invention to a subject can initiate or enhance the symbiotic behavior of a target species or a selected strain of a target species of quorum sensing bacteria in the subject. In an embodiment, the administration of an effective amount of a compound of the present invention to a subject can regulate the virulence of quorum sensing bacteria in the subject. In an embodiment, the administration of an effective amount of a compound of the present invention to a subject can regulate the virulence of a target species or a selected strain of a target species of quorum sensing bacteria in the subject.

The methods of the present invention also provide for regulation of the level of virulence of quorum sensing bacteria. In an embodiment, a mixture of the compounds of the present invention is brought into contact with a quorum sensing bacteria to selectively regulate the virulence of the bacteria. The amount of each compound in the mixture is that amount effective to achieve a desired effect on regulation of virulence. The methods of the present invention also provide for regulation of the production of a biofilm by quorum sensing bacteria. In an embodiment, a mixture of the compounds of the present invention is brought into contact with a quorum sensing bacteria or bacterial biofilm to selectively regulate the biofilm production by the bacteria. The amount of each compound in the mixture is that amount effective for desired regulation of biofilm formation.

The methods of the present invention also provide for regulation of the virulence, biofilm production, or symbiotic behavior of a quorum sensing bacteria by contacting the bacteria with a photoactive compound and illuminating the bacteria and photoactive compound. In an embodiment, illuminating a photoactive compound of the present invention can change the agonistic or antagonistic behavior of the compound.

In an embodiment, the present invention provides a surface coating or polymer having incorporated therein a compound of the present invention. The amount of compound or polymer in the surface coating is that sufficient to provide antimicrobial or antifouling effect. In an embodiment, the compounds of the present invention are useful as an antimicrobial and/or antifouling agent. Compounds of the present invention are further useful in a medical, scientific, and/or biological application.

In one aspect, the present invention provides a composition comprising one or more compounds of the present invention and a carrier or diluent. In a preferred embodiment, the carrier or diluent comprises a liquid. Such a liquid may comprises an aqueous solvent or a non-aqueous solvent. An exemplary solvent comprises one or more organic solvents. The carrier or diluent may also comprise an ionic liquid. In an embodiment of this aspect, the composition comprises an organic or inorganic polymeric substance. The polymeric substance may comprise one or more compounds of the present invention, admixed with a polymer, bound to a polymer, or adsorbed on to a polymer. In an exemplary embodiment of this aspect, the composition is in the form of a solution or suspension of said at least one compounds of the present invention, preferably in an aerosol or powder formulation.

In an embodiment of this aspect, the composition is formulated as a disinfectant or cleaning formulation. In another embodiment, the composition is in the form of a powder, a solution, a suspension, a dispersion, an emulsion, or a gel. In an exemplary embodiment, the composition is in the form of a pharmaceutical composition comprising a pharmaceutically acceptable carrier, diluent, and/or excipient and one or more compounds of the present invention. The composition may be in a form suitable for parenteral or non-parenteral administration. A preferred composition may be formulated for topical, intradermal, intramuscular, intraperitoneal, intravenous, subcutaneous, intranasal, epidural, ophthalmic, or oral administration. In an embodiment of this aspect the composition is formulated for administration by infusion or bolus injection, absorption through epithelial or mucocutanous linings and may be administered together with other biologically active agents. In an embodiment, the composition may further be formulated for use in an inhaler or nebulizer.

In another aspect, the present invention provides a method of treating an infection in a human or animal subject, the method comprising administration to the subject of an effective amount of one or more compounds of the present invention. In an embodiment, the treatment is therapeutic or prophylactic.

In a related embodiment, the present invention provides a method of treating an infection or condition in a subject that is characterized by biofilm formation, the method comprising administering one or more compounds of the present invention. In an embodiment, the condition is cystic fibrosis. In an embodiment, the condition is dental caries, periodontitis, otitis media, muscular skeletal infections, necrotizing fasciitis, biliary tract infection, osteomyelitis, bacterial prostatitis, native valve endocarditis, cystic fibrosis pneumonia, or meloidosis. In an embodiment, the condition is a nosocomial infection; preferably the infection is ICU pneumonia or an infection associated with sutures, exit sites, arteriovenous sites, scleral buckles, contact lenses, urinary catheter cystitis, peritoneal dialysis (CAPD) peritonitis, IUDs, endotracheal tubes, Hickman catheters, central venous catheters, mechanical heart valves, vascular grafts, biliary stent blockage, orthopedic devices, or penile prostheses. In an embodiment, the infection is a skin infection, a burn infection, or a wound infection. According to this aspect, the subject may preferably be an immunocompromised individual.

The present invention further provides a method for treating or preventing biofilm formation on a surface, the method comprising contacting said surface with one or more compounds in an amount effective for affecting biofilm formation of the present invention. In an embodiment, the surface is a non-biological surface. In an embodiment, the surface is a natural surface. In an embodiment, the surface is a surface of a plant, seed, wood, fiber or hair. In an embodiment, the surface is a biological surface; preferably the surface is a surface of a tissue, membrane, or skin. In an embodiment, the surface is a hard surface; preferably the surface comprises a metal, an organic polymer, an inorganic polymer, a natural elastomer, a synthetic elastomer, glass, wood, paper, concrete, rock, marble, gypsum, or ceramic. In an embodiment, the said surface is coated or wherein the surface is a coating; in a preferred embodiment, the coating comprises enamel, varnish, or paint.

In an embodiment of this aspect, the surface is a soft surface, an may be the surface of a fiber comprising a yarn, a textile, a vegetable fiber, or rock wool. In another embodiment, the surface is a porous surface. In an embodiment, the surface is a surface of process equipment or components of cooling equipment. In a preferred embodiment, the process equipment is or is a component of a cooling tower, a water treatment plant, a dairy processing plant, a food processing plant, a chemical process plant, or a pharmaceutical process plant. In a preferred embodiment the surface is that of a filter or a membrane filter.

In an embodiment of this aspect, the surface is a surface of a toilet bowl, a bathtub, a drain, a high-chair, a counter top, a vegetable, a meat processing room, a butcher shop, food preparation areas, an air duct, an air-conditioner, a carpet, paper or woven product treatment, a diaper, personal hygiene products and a washing machine. In another embodiment, the surface is an industrial surface or a medical surface; preferably the surface is a surface in a hospital, a veterinary hospital, a mortuary, or a funeral parlor.

In another aspect, the compounds of the present invention are useful as a component of a dentifrice, a mouthwash, or a composition for the treatment of dental caries; for treatment of acne; or for cleaning and/or disinfecting contact lenses. The compounds of the present invention are further useful for incorporation into the surface of a medical device or an implant device. Preferably the implant device is an artificial heart valve, hip joint, an indwelling catheter, pacemaker, or surgical pin. The compounds of the present invention are further useful as an antifouling coating. The present invention further provides an optical lens, wherein at least a part of a surface of the lens is associated with one or more compounds of the present invention. Preferably, the optical lens is a contact lens.

In another aspect, the present invention provides a biofilm removing or inhibiting composition comprising one or more compounds of the present invention in an amount effective for removing or inhibiting biofilm formation and a vehicle or carrier, wherein the amount of the mixture is effective to remove or disrupt a bacterial biofilm or inhibit normal biofilm formation. An embodiment of this aspect may further comprise a surfactant selected from the group consisting of an anionic surfactant, a nonionic surfactant, an amphoteric surfactant, a biological surfactant, and any combination of these; or a compound selected from the group consisting of a biocide, a fungicide, an antibiotic, and any combination of these.

In another aspect, the present invention provides a method of removing a biofilm from a surface, the method comprising the step of administering a cleaning-effective amount of one or more compounds of the present invention to a biofilm-containing surface. A preferred method of this aspect comprises the step of administering an effective amount of one or more compounds of the present invention to the surface, wherein the amount is effective to prevent biofilm formation. Such a surface may be a hard or rigid surface or a surface selected from the group consisting of glazed ceramic, porcelain, glass, metal, wood, chrome, plastic, vinyl, formica, and the surface of a drainpipe. In an embodiment, the surface is a soft or flexible surface, or the surface is selected from the group consisting of a shower curtain or liner, upholstery, laundry, clothing, and carpeting. The compounds of the present invention are useful for removing or disrupting a biofilm is produced by a bacterium of the class *Pseudomonas*, a bacterium is of the species *Pseudomonas Aeuroginosa*, or an organism selected from the group consisting of bacteria, algae, fungi and protozoa.

In another aspect, the invention provides a medicament for treating an infection or for disruption of a biofilm which comprises one or more of the compounds of this invention e.g., those of formula FX1, and a method for making a medicament which comprises one or more of the compounds of this invention. In particular; the method comprises the step of combining one or more compounds of this invention with a pharmaceutically acceptable carrier to form a pharmaceutical composition for treatment of infection and/or biofilm formation.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Figure 1A:
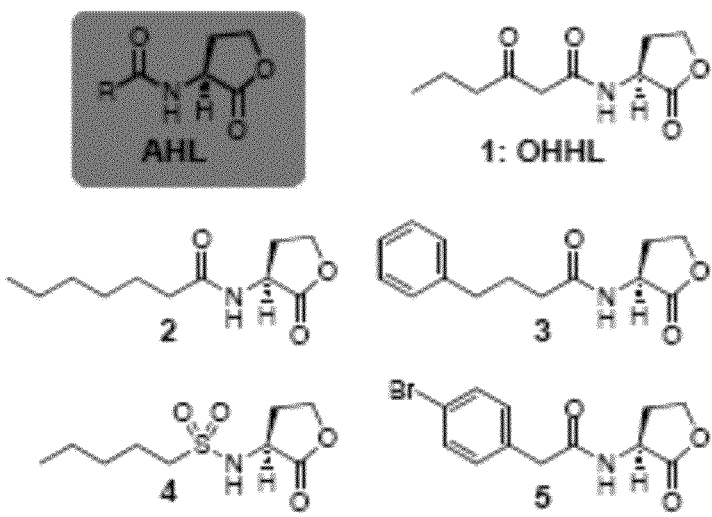
FIG. 1 provides a) Structures of a generic AHL, OHHL (1) (the natural autoinducer ligand of *V. fischeri*), and selected known synthetic inhibitors of LuxR or other R protein function (2-5). b) Solid-phase synthetic route to PHL library 11.

Unless defined otherwise, all technical and scientific terms used herein have the broadest meanings as commonly understood by one of ordinary skill in the art to which this invention pertains. In addition, hereinafter, the following definitions apply:

As defined herein, "contacting" means that a compound of the present invention is provided such that it is capable of making physical contact with another element, such as a microorganism, a microbial culture, a biofilm, or a substrate. In another embodiment, the term "contacting" means that a compound of the present invention is introduced into a subject receiving treatment, and the compound is allowed to come in contact in vivo.

Aliphatic groups include straight chain, branched, and cyclic groups having a carbon backbone having from 1 to 30 carbon atoms. Aliphatic groups include alkyl groups, alkenyl groups, alkynyl groups, and aryl groups. Aliphatic groups are optionally substituted with one or more non-hydrogen substituents. Substituted aliphatic groups include among others those which are substituted with aryl groups, which in turn can be optionally substituted. Substituted aliphatic groups include fully halogenated or semihalogenated aliphatic groups, such as aliphatic groups having one or more hydrogens replaced with one or more fluorine atoms, chlorine atoms, bromine atoms and/or iodine atoms. Substituted aliphatic groups include fully fluorinated or semifluorinated aliphatic groups, such as aliphatic groups having one or more hydrogens replaced with one or more fluorine atoms. Aliphatic groups are optionally substituted with one or more protecting groups.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, 7-, or 8-member ring. The carbon rings in cyclic alkyl groups can also carry aliphatic groups. Cyclic alkyl groups can include bicyclic and tricyclic alkyl groups. Alkyl groups are optionally substituted with one or more non-hydrogen substituents. Substituted alkyl groups include among others those which are substituted with aliphatic groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms.

An alkoxy group is an alkyl group, as broadly discussed above, linked to oxygen and can be represented by the formula R—O—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry aliphatic groups. Cyclic alkenyl groups can include bicyclic and tricyclic aliphatic groups. Alkenyl groups are optionally substituted with one or more non-hydrogen substituents. Substituted alkenyl groups include among others those which are substituted with aliphatic groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Alkynyl groups include straight-chain, branched and cyclic alkynyl groups. Alkynyl groups include those having 1, 2 or more triple bonds and those in which two or more of the triple bonds are conjugated triple bonds. Alkynyl groups include those having from 2 to 20 carbon atoms. Alkynyl groups include small alkynyl groups having 2 to 3 carbon atoms. Alkynyl groups include medium length alkynyl groups having from 4-10 carbon atoms. Alkynyl groups include long alkynyl groups having more than 10 carbon atoms, particularly those having 10-20 carbon atoms. Cyclic alkynyl groups include those having one or more rings. Cyclic alkynyl groups include those in which a triple bond is in the ring or in an alkynyl group attached to a ring. Cyclic alkynyl groups include those having a 3-, 4-, 5-, 6-, 7-, 8-, 9- or 10-member carbon ring and particularly those having a 3-, 4-, 5-, 6- or 7-member ring. The carbon rings in cyclic alkynyl groups can also carry aliphatic groups. Cyclic alkynyl groups can include bicyclic and tricyclic aliphatic groups. Alkynyl groups are optionally substituted with one or more non-hydrogen substituents. Substituted alkynyl groups include among others those which are substituted with alkyl or aryl groups, which groups in turn can be optionally substituted. Alkynyl groups include acetyl, methylacetyl, 1-pentynyl, and 2-pentynyl, all of which are optionally substituted. Substituted alkynyl groups include fully halogenated or semihalogenated alkynyl groups, such as alkynyl groups having one or more hydrogens replaced with one or more fluorine atoms, chlorine atoms, bromine atoms and/or iodine atoms. Substituted alkynyl groups include fully fluorinated or semifluorinated alkynyl groups, such as alkynyl groups having one or more hydrogens replaced with one or more fluorine atoms.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Protecting groups are groups substituted onto an aliphatic hydrocarbon for protection of one or more substituents, for example protection of alcohols, amines, carbonyls, and/or carboxylic acids. Protecting groups include, but are not limited to, acetyl groups, MEM groups, MOM groups, PMB groups, Piv groups, THP groups, TMS groups, TBDMS groups, TIPS groups, methyl ethers, Cbz groups, BOC groups, FMOC groups, benzyl groups, PMP groups, acetal groups, ketal groups, acylal groups, dithiane groups, methyl esters, benzyl esters, t-butyl esters, and silyl esters. These and other protecting groups known in the art of organic synthesis may be optionally used as a substituent of an aliphatic group.

Optional substitution of aliphatic groups includes substitution with one or more aliphatic groups, wherein the aliphatic groups are optionally substituted.

Optional substituents for aliphatic groups include among others: —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; wherein R is selected from the group consisting of, a hydrogen, a halogen, an amine group, a substituted or unsubstituted unbranched C$_1$-C$_{12}$ acyclic aliphatic group, a substituted or unsubstituted branched C$_1$-C$_{12}$ acyclic aliphatic group, a substituted or unsubstituted C$_3$-C$_8$ cycloalkyl group, a substituted or unsubstituted C$_3$-C$_8$ cycloalkenyl group, a fluorinated C$_1$-C$_{12}$ alkyl group, a substituted or unsubstituted aryl group, a substituted or unsubstituted heterocycle, a substituted or unsubstituted C$_1$-C$_{12}$ alkoxy group, a fluorinated C$_1$-C$_{12}$ alkoxy group, a hydroxyl group, a nitrile group, an azide group, a nitro group, an acyl group, a thiol group, a protecting group, —COOR, —COR, —CON(R)$_2$, —OCON(R)$_2$, —N(R)$_2$, —SR, —SO$_2$R, —SOR, —OCOOR, —SO$_2$N(R)$_2$, and —OR; additionally, R and R can form a ring.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The term "effective amount" is used generically herein to refer to the amount of a given compound or in case of a mixture the combined amount of mixture components that provides a measureable effect for a listed function. For example, in certain aspects of the invention, a compound of the invention is contacted with an element in order to disrupt a biofilm and in this case, the effective amount or combined effective amount of the compound or compounds is that amount that shows a measurable disruption of a biofilm. The effective amount will vary dependent upon the stated function, the environment or element being contacted, the organism forming the biofilm or which is to be contacted, the state of development of the biofilm, among other conditions of the use of the compound. It will be understood by one of ordinary skill in the art, that for a given application, the effective amount can be determined by application of routine experimentation and without undue experimentation by methods that are described herein or that are known in the art.

The term "therapeutically effective amount" is used generically herein to refer to the amount of a given compound or in case of a mixture the combined amount of mixture components when administered to the individual (including a human, or non-human animal) that provides a measureable therapeutic effect for a listed disease, disorder or condition to at least partially ameliorate a symptom of such disease, disorder or condition. The present invention provides methods of treating disorders, diseases conditions and symptoms in a human or non-human animal and particularly in a human, by administering to an individual in need of treatment or prophylaxis, a therapeutically effective amount of one or more compounds of this invention to the individual in need thereof. The result of treatment can be partially or completely alleviating, inhibiting, preventing, ameliorating and/or relieving the disorder, condition or one or more symptoms thereof. As is understood in the art, the therapeutically effective amount of a given compound will depend at least in part upon, the mode of administration, any carrier or vehicle (e.g., solution, emulsion, etc.) employed, the extent of damage and the specific individual (human or non-human) to whom the compound is to be administered (age, weight, condition, sex, etc.). The dosage requirements needed to achieve the "therapeutically effective amount" vary with the particular compositions employed, the route of administration, the severity of the symptoms presented and the particular subject being treated. Based on the results obtained in standard pharmacological test procedures, projected daily dosages of active compound can be determined as is understood in the art.

Administration is intended to encompass administration of a compound, pharmaceutically acceptable salt, solvate or ester thereof alone or in a pharmaceutically acceptable carrier thereof or administration of a prodrug derivative or analog of a compound of this invention which will form an equivalent amount of the active compound or substance within the body. An individual in need of treatment or prophylaxis includes those who have been diagnosed to have a given disorder or condition and to those who are suspected, for example, as a consequence of the display of certain symptoms, of having such disorders or conditions.

Compounds of this invention can be employed in unit dosage form, e.g. as tablets or capsules. In such form, the active compound or more typically a pharmaceutical composition containing the active compound is sub-divided in unit dose containing appropriate quantities of the active compound; the unit dosage forms can be packaged compositions, for example, packaged powders, vials, ampules, pre-filled syringes or sachets containing liquids. The unit dosage form can be, for example, a capsule or tablet itself, or it can be the appropriate number of any such compositions in package form.

The dosage can vary within wide limits and as is understood in the art will have to be adjusted to the individual requirements in each particular case. By way of general guidance, the daily oral dosage can vary from about 0.01 mg to 1000 mg, 0.1 mg to 100 mg, or 10 mg to 500 mg per day of a compound of formulas herein or of the corresponding amount of a pharmaceutically acceptable salt thereof. The daily dose may be administered as single dose or in divided doses and, in addition, the upper limit can also be exceeded when this is found to be indicated.

Any suitable form of administration can be employed in the method herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts.

Compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol. Administration includes any form of administration that is known in the art and is intended to encompass administration in any appropriate dosage form and further is intended to encompass administration of a compound, alone or in a pharmaceutically acceptable carrier. Pharmaceutical carriers are selected as is known in the art based on the chosen route of administration and standard pharmaceutical practice.

The compounds of this invention can also be administered to the eye, preferably as a topical opthalmic formulation. The compounds of this invention can also be combined with a preservative and an appropriate vehicle such as mineral oil or liquid lanolin to provide an opthalmic ointment. The compounds of this invention may be administered rectally or vaginally in the form of a conventional suppository. The compounds of this invention may also be administered transdermally through the use of a transdermal patch containing the active compound and a carrier that is inert to the active compound, is non toxic to the skin, and allows delivery of the agent for systemic absorption into the blood stream via the skin.

The compounds of the invention may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

Pharmaceutical compositions and medicaments of this invention comprise one or more compounds in combination with a pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety. The invention also encompasses method for making a medicament employing one or more compounds of this invention which exhibit a therapeutic effect.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Suitable examples of liquid carriers for oral and parenteral administration include water of appropriate purity, aqueous solutions (particularly containing additives, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form. The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethyl-lamine, tripropylamine, ethanolamine, lysine, arginine, N-ethylpiperidine, piperidine, polymine resins and the like. Compounds of formula I can also be present in the form of zwitterions.

Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, Methyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The invention expressly includes pharmaceutically usable solvates of compounds according to formulas herein. The compounds of formula I can be solvated, e.g. hydrated. The solvation can occur in the course of the manufacturing process or can take place, e.g. as a consequence of hygroscopic properties of an initially anhydrous compound of formulas herein (hydration).

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, *Experimental and computational approaches to estimate solubility and permeability in drug discovery and development settings*, Adv. Drug Del. Rev., 2001, 46, 3-26 and Arup K. Ghose, Vellarkad N. Viswanadhan, and John J. Wendoloski, *A Knowledge-Based Approach in Designing Combinatorial or Medicinal Chemistry Libraries for Drug Discovery*, J. Combin. Chem., 1999, 1, 55-68.) In general a preferred drug for oral administration exhibits no more than one violation of the following rules:
(1) Not more than 5 hydrogen bond donors (e.g., nitrogen or oxygen atoms with one or more hydrogens);
(2) Not more than 10 hydrogen bond acceptors (e.g., nitrogen or oxygen atoms);
(3) Molecular weight under 500 g/mol and more preferably between 160 and 480; and
(4) log P less than 5 and more preferably between −0.4 to +5.6 and yet more preferably −1<log P<2.

Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P<2.

The compounds of this invention may contain one or more chiral centers. Accordingly, this invention is intended to include racemic mixtures, diasteromers, enantiomers and mixture enriched in one or more stereoisomer. The scope of the invention as described and claimed encompasses the racemic forms of the compounds as well as the individual enantiomers and non-racemic mixtures thereof.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

As used herein, the term "treating" includes preventative as well as disorder remittent treatment. As used herein, the terms "reducing", "suppressing" and "inhibiting" have their commonly understood meaning of lessening or decreasing.

In certain embodiments, the present invention encompasses administering the compounds useful in the present invention to a patient or subject. A "patient" or "subject", used equivalently herein, refers to an animal. In particular, an animal refers to a mammal, preferably a human. The subject either: (1) has a condition remediable or treatable by administration of a compound of the invention; or (2) is susceptible to a condition that is preventable by administering a compound of this invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

In an embodiment, a compound of the present invention comprises a compound having the formula (FX1):

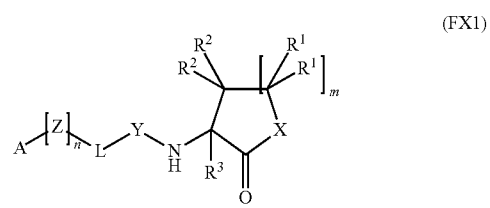

(FX1)

or a pharmaceutically acceptable salt or ester thereof,
wherein m is 1, 2, 3, or 4;
each $R^1$, $R^2$, and $R^3$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; wherein R is selected from the group consisting of, a hydrogen, a halogen, an amine group, a substituted or unsubstituted unbranched $C_1$-$C_{12}$ acyclic aliphatic group, a substituted or unsubstituted branched $C_1$-$C_{12}$ acyclic aliphatic group, a substituted or unsubstituted $C_3$-$C_8$ cycloalkyl group, a substituted or unsubstituted $C_3$-$C_8$ cycloalkenyl group, a fluorinated $C_1$-$C_{12}$ alkyl group, a substituted or unsubstituted aryl group, a substituted or unsubstituted heterocycle, a substituted or unsubstituted $C_1$-$C_{12}$ alkoxy group, a fluorinated $C_1$-$C_{12}$ alkoxy group, a hydroxyl group, a nitrile group, an azide group, a nitro group, an acyl group, a thiol group, and a protecting group; additionally, R and R can form a ring.

X is selected from the group consisting of S, O, NH, and CH$_2$.
Y is selected from the group consisting of:

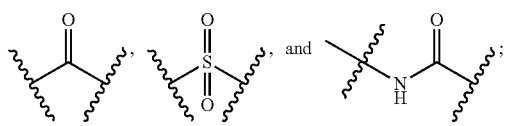

L is

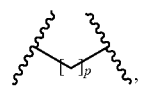

wherein one or more CH$_2$ groups may be replaced by NH, O, S, a carbonyl (C=O), or a sulfonyl (S=O or O=S=O); two adjacent CH$_2$ groups may be replaced by —CH=CH— or —C≡C—; and wherein p is selected from the range of 0 to 15;

Z is selected from the group consisting of:

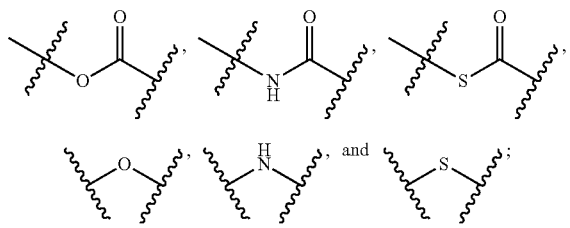

and n can be one or zero to moderate the presence or absence of the group;

A is an aryl group, a $C_5$-$C_8$ cycloalkyl group, a $C_5$-$C_8$ cycloalkenyl group, a heterocycle having a ring size of 5 to 8 atoms with 1, 2, or 3 hetereoatoms in the ring, an unbranched $C_1$-$C_{12}$ acyclic aliphatic group, or a branched $C_1$-$C_{12}$ acyclic aliphatic group, all of which may have one or more non-hydrogen substituents selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; wherein R is selected from the group consisting of, a halogen, an amine group, a substituted or unsubstituted unbranched $C_1$-$C_{12}$ acyclic aliphatic group, a substituted or unsubstituted branched $C_1$-$C_{12}$ acyclic aliphatic group, a substituted or unsubstituted $C_3$-$C_8$ cycloalkyl group, a substituted or unsubstituted $C_3$-$C_8$ cycloalkenyl group, a fluorinated $C_1$-$C_{12}$ alkyl group, a substituted or unsubstituted aryl group, a substituted or unsubstituted heterocycle, a substituted or unsubstituted $C_1$-$C_{12}$ alkoxy group, a fluorinated $C_1$-$C_{12}$ alkoxy group, a hydroxyl group, a nitrile group, an azide group, a nitro group, an acyl group, a thiol group, and a protecting group; additionally, R and R can form a ring.

In an embodiment, a compound of the present invention comprises a compound having the formula FX1, wherein A is selected from the group consisting of a substituted aryl group, an unsubstituted aryl group, a substituted $C_5$-$C_8$ cycloalkyl group, and an unsubstituted $C_5$-$C_8$ cycloalkyl group.

In an embodiment, a compound of the present invention comprises a compound having the formula FX1, wherein A is selected from the group consisting of:

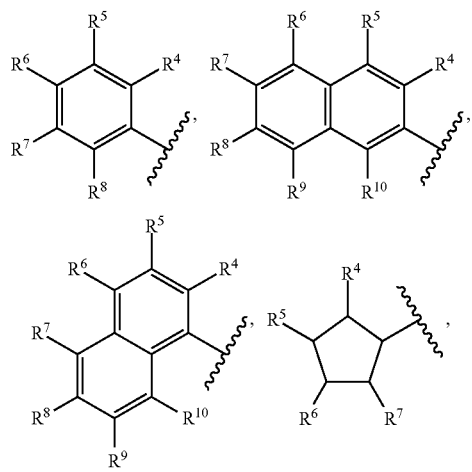

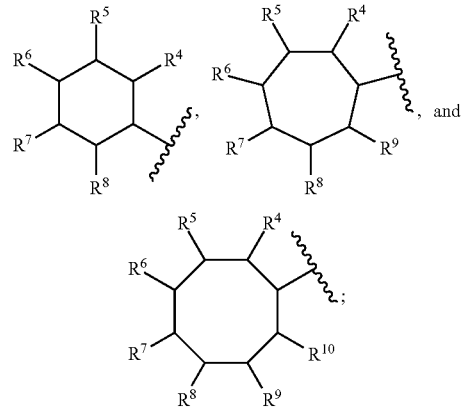

wherein $R^4$, $R^5$, $R^6$, $R^7$, $R^8$, $R^9$, and $R^{10}$ are each independently selected from the group consisting of a hydrogen, —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; wherein R is selected from the group consisting of, a halogen, an amine group, a substituted or unsubstituted unbranched $C_1$-$C_{12}$ acyclic aliphatic group, a substituted or unsubstituted branched $C_1$-$C_{12}$ acyclic aliphatic group, a substituted or unsubstituted $C_3$-$C_8$ cycloalkyl group, a substituted or unsubstituted $C_3$-$C_8$ cycloalkenyl group, a fluorinated $C_1$-$C_{12}$ alkyl group, a substituted or unsubstituted aryl group, a substituted or unsubstituted heterocycle, a substituted or unsubstituted $C_1$-$C_{12}$ alkoxy group, a fluorinated $C_1$-$C_{12}$ alkoxy group, a hydroxyl group, a nitrile group, an azide group, a nitro group, an acyl group, a thiol group, and a protecting group; additionally, R and R can form a ring.

In an embodiment, a compound of the present invention comprises a compound having the formula FX1, wherein A is an alkyl substituted aryl group.

In an embodiment, a compound of the present invention comprises a compound having the formula FX1, wherein A is selected from the group consisting of:

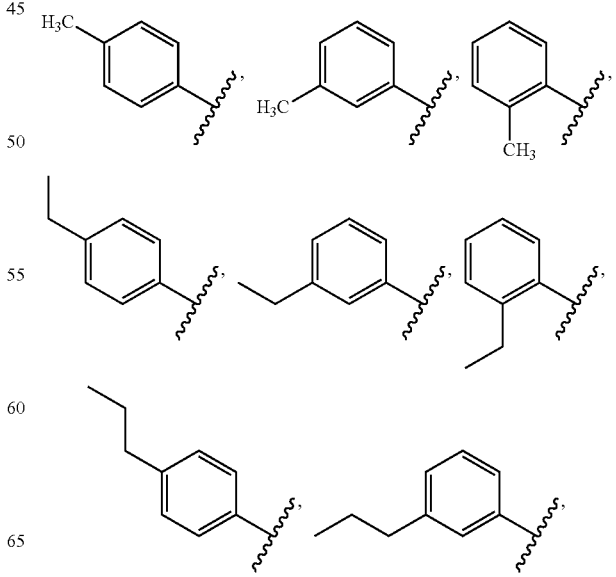

-continued

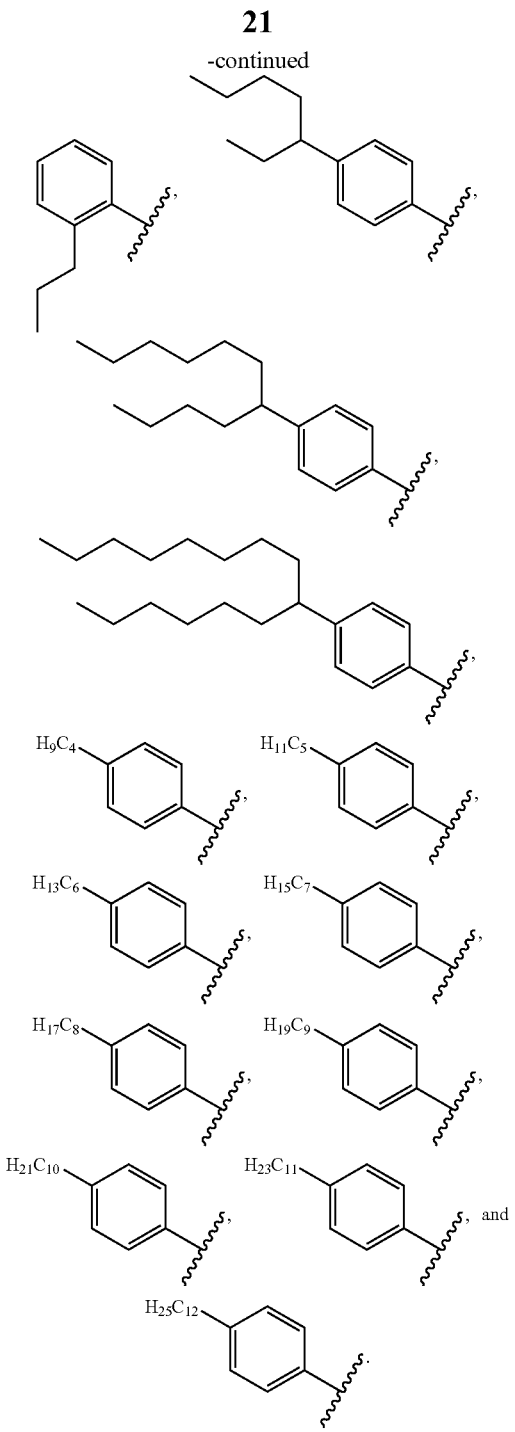

In an embodiment, a compound of the present invention comprises a compound having the formula FX1, wherein A is a halogen or nitrile substituted aryl group.

In an embodiment, a compound of the present invention comprises a compound having the formula FX1, wherein A is selected from the group consisting of:

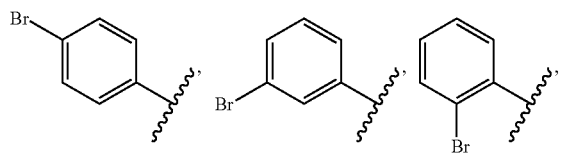

-continued

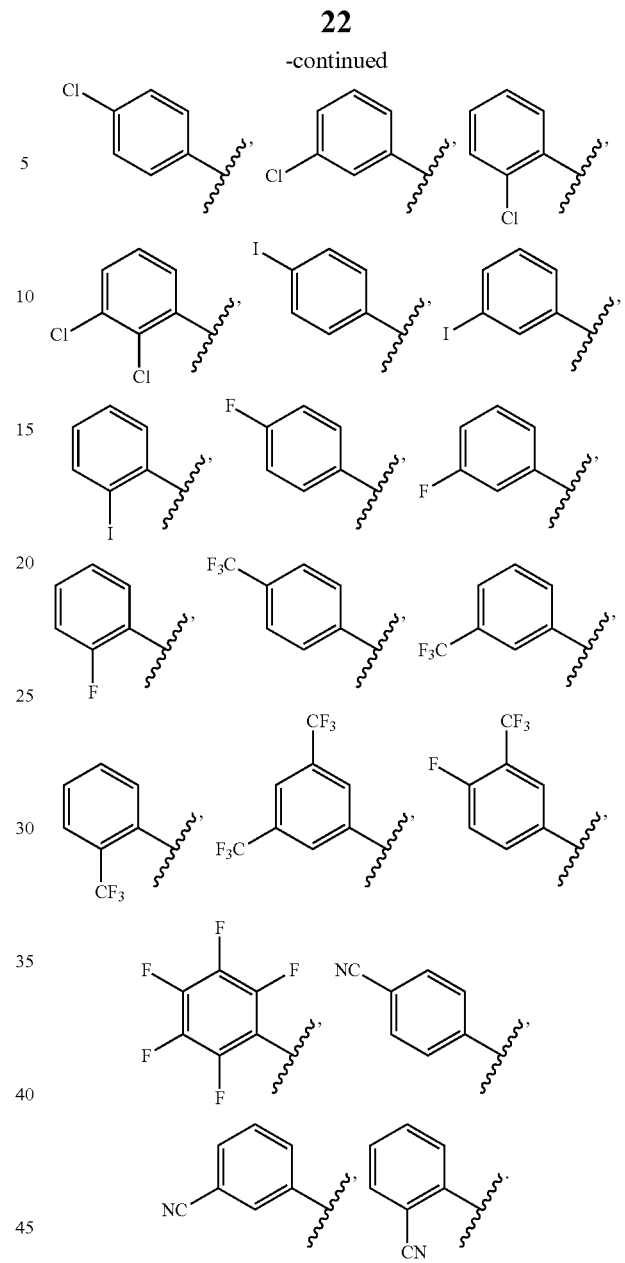

In an embodiment, a compound of the present invention comprises a compound having the formula FX1, wherein A is selected from the group consisting of:

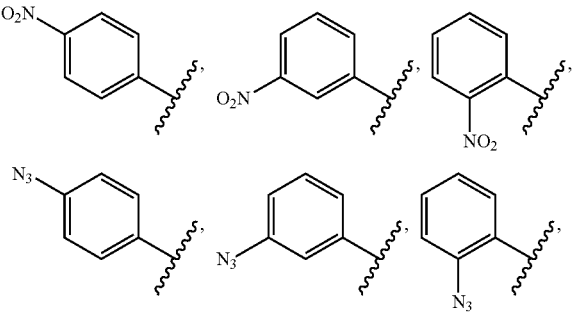

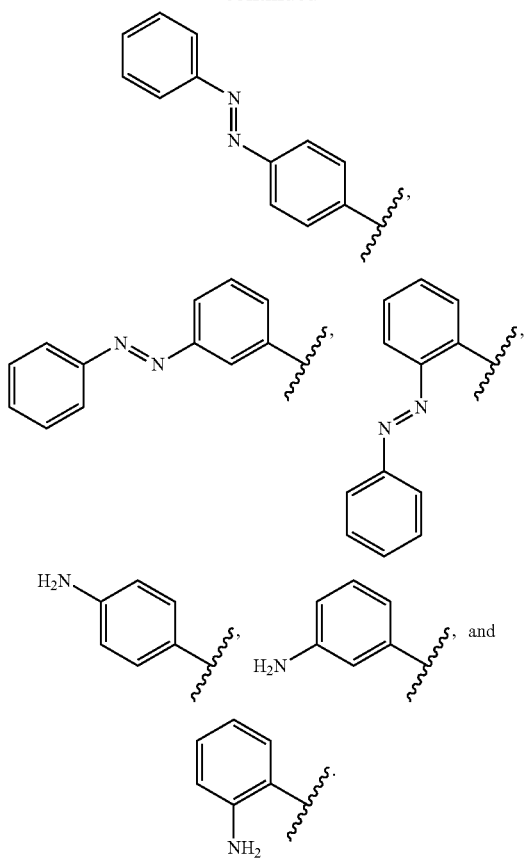

In an embodiment, a compound of the present invention comprises a compound having the formula FX1, wherein A is a hydroxyl, thiol, or alkoxy substituted aryl group.

In an embodiment, a compound of the present invention comprises a compound having the formula FX1, wherein A is selected from the group consisting of:

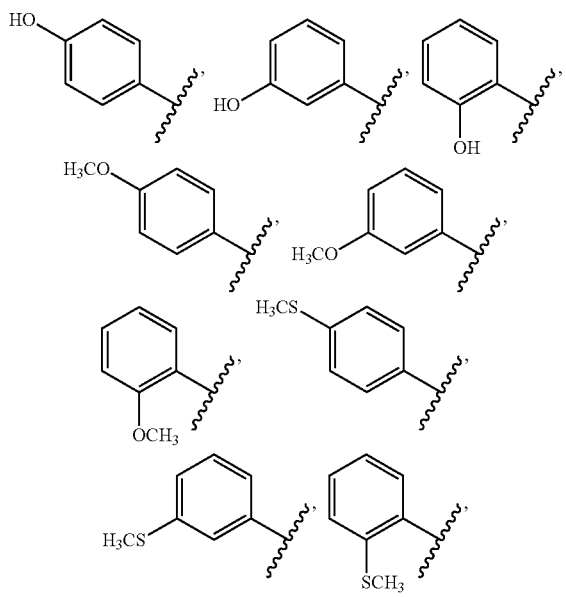

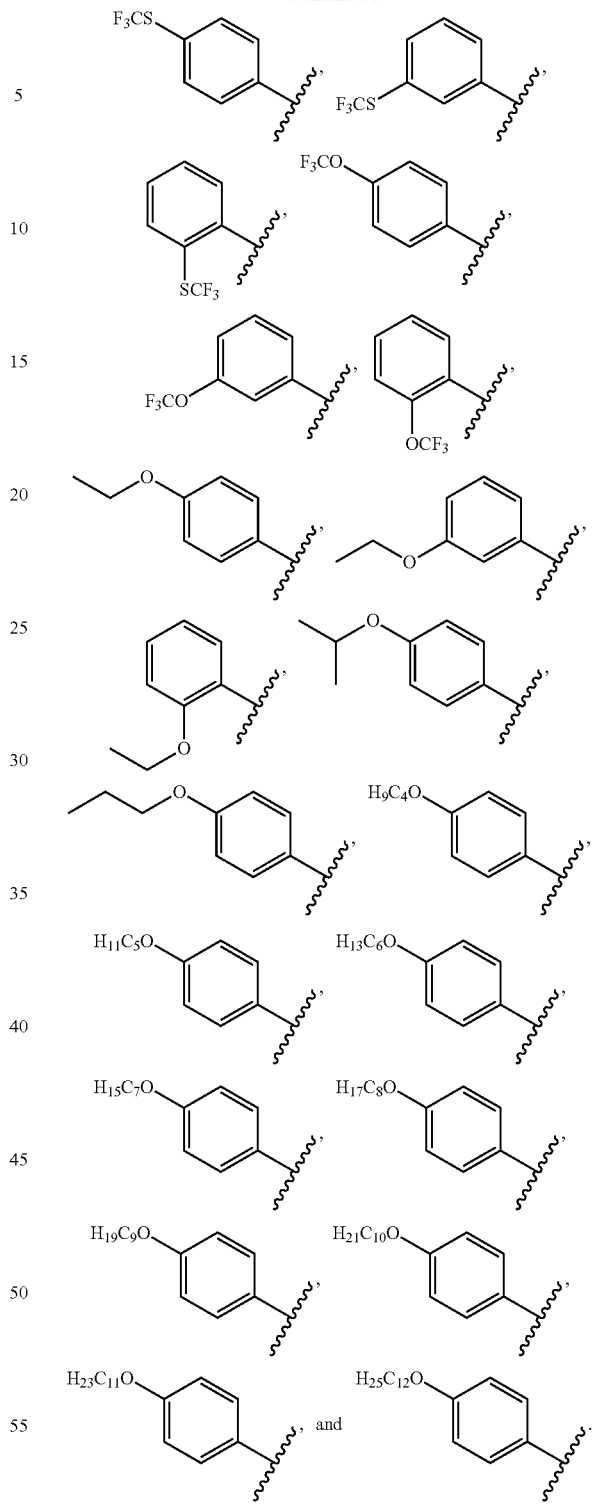

In an embodiment, a compound of the present invention comprises a compound having the formula FX1, wherein A is an aryl group having one or more protecting group substituents.

In an embodiment, a compound of the present invention comprises a compound having the formula FX1, wherein A is selected from the group consisting of:

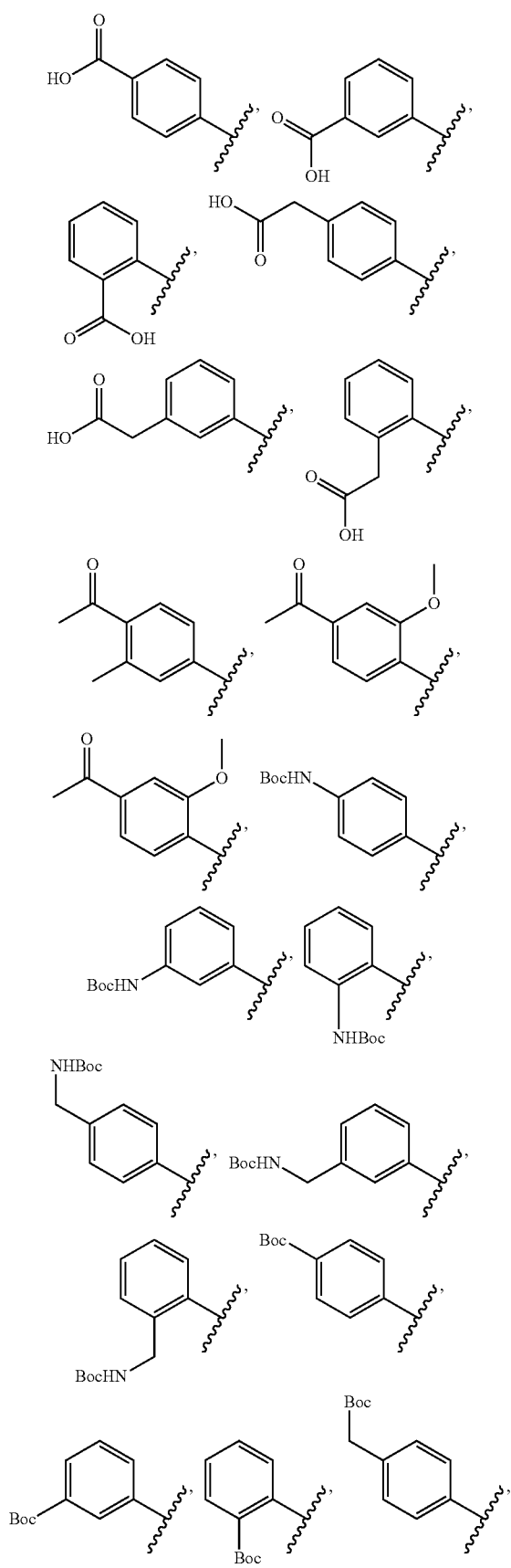
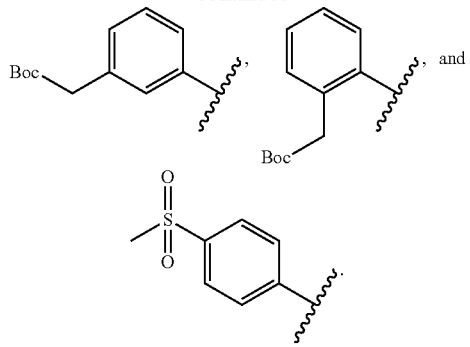
In an embodiment, a compound of the present invention comprises a compound having the formula FX1, wherein A is selected from the group consisting of:
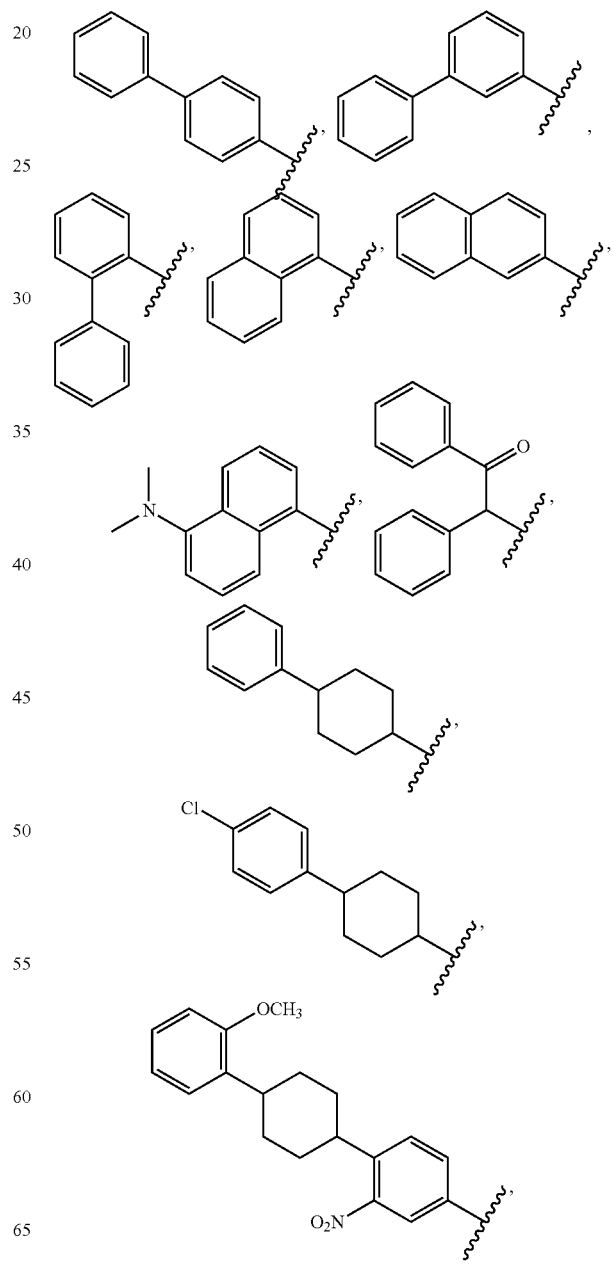

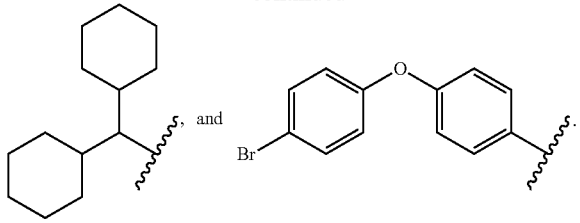

In an embodiment, a compound of the present invention comprises a compound having the formula FX1, wherein A is selected from the group consisting of:

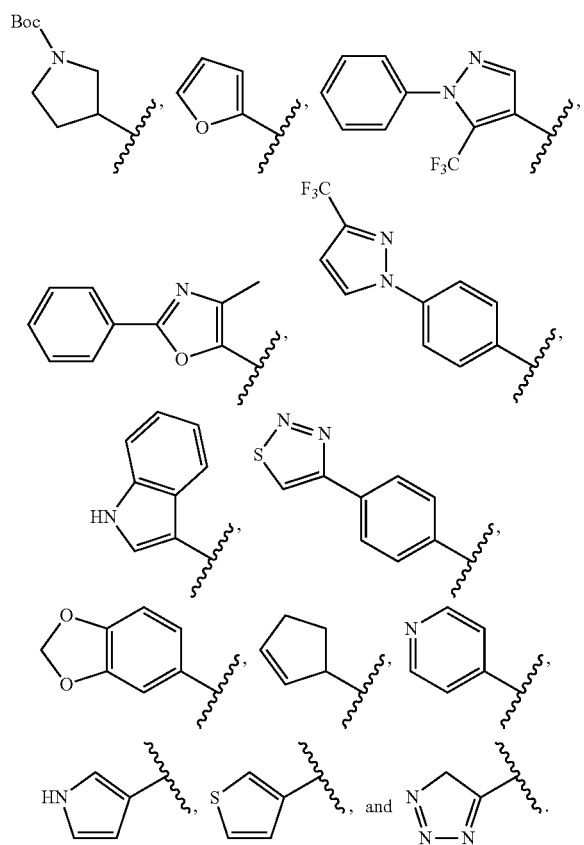

In an embodiment, a compound of the present invention comprises a compound having the formula FX1, wherein A is selected from the group consisting of a substituted or unsubstituted unbranched $C_1$-$C_{12}$ acyclic aliphatic group, and a substituted or unsubstituted branched $C_1$-$C_{12}$ acyclic aliphatic group.

In an embodiment, a compound of the present invention comprises a compound having the formula FX1, wherein A is selected from the group consisting of a fluorinated unbranched $C_1$-$C_{12}$ acyclic aliphatic group, and a fluorinated $C_1$-$C_{12}$ acyclic aliphatic group.

In an embodiment, a compound of the present invention comprises a compound having the formula FX1, wherein A is selected from the group consisting of a fluorinated unbranched $C_1$-$C_{12}$ acyclic alkyl group In an embodiment, a compound of the present invention comprises a compound having the formula FX1, wherein A is selected from the group consisting of:
—$CF_3$, —$C_2F_5$, —$C_3F_7$, —$C_4F_9$, —$C_6F_{13}$, and —$C_7F_{15}$.

In an embodiment, a compound of the present invention comprises a compound having the formula FX1, wherein A is a protecting group.

In an embodiment, a compound of the present invention comprises a compound having the formula FX1, wherein A is selected from the group consisting of —BOC, and —NH-BOC.

In a specific embodiment, the invention provides compounds of formula FX1, for uses as described herein, wherein A-$[Z]_n$-L-Y is a group other than a $C_1$-$C_{14}$— alkyl group, a $C_1$-$C_{14}$— alkyl-CO—$CH_2$— group or a $C_1$-$C_{14}$-alkyl-$CX_4X_5$—$CH_2$— group where $X_4$ and $X_5$ are independently selected from H, $NH_2$, or SH.

In a specific embodiment, the invention provides compounds of formula FX1, for uses as described herein, wherein when X is O are H, A-$[Z]_n$-L-Y is a group other than a $C_1$-$C_{14}$— alkyl group, a $C_1$-$C_{14}$-alkyl-CO—$CH_2$— group or a $C_1$-$C_{14}$-alkyl-$CX_4X_5$—$CH_2$— group where $X_4$ and $X_5$ are independently selected from H, $NH_2$, or SH.

In a specific embodiment, the invention provides compounds of formula FX1, for uses as described herein, wherein when X is O, and all of $R^1$, $R^2$ and $R^3$ are hydrogen, A-$[Z]_n$-L-Y is a group other than a $C_1$-$C_{14}$— alkyl group, a $C_1$-$C_{14}$-alkyl-CO—$CH_2$— group or a $C_1$-$C_{14}$-alkyl-$CX_4X_5$—$CH_2$— group where $X_4$ and $X_5$ are independently selected from H, $NH_2$, or SH.

In a specific embodiment, the invention provides compounds of formula FX1, for uses as described herein, wherein when X is O, m is 1, and all of $R^1$, $R^2$ and $R^3$ are hydrogen, A-$[Z]_n$-L-Y is a group other than a $C_1$-$C_{14}$— alkyl group, a $C_1$-$C_{14}$-alkyl-CO—$CH_2$— group or a $C_1$-$C_{14}$-alkyl-$CX_4X_5$—$CH_2$— group where $X_4$ and $X_5$ are independently selected from H, $NH_2$, or SH In a specific embodiment, the invention provides compounds of formula FX1, for uses as described herein, wherein when X is $CH_2$, A-$[Z]_n$-L-Y is a group other than a $C_1$-$C_{14}$— alkyl group, a $C_1$-$C_{14}$-alkyl-CO—$CH_2$— group or a $C_1$-$C_{14}$-alkyl-$CX_4X_5$—$CH_2$— group where $X_4$ and $X_5$ are independently selected from H, $NH_2$, or SH.

In a specific embodiment, the invention provides compounds of formula FX1, for uses as described herein, wherein when X is $C(R^2)_2$, A-$[Z]_n$-L-Y is a group other than a $C_1$-$C_{14}$— alkyl group, a $C_1$-$C_{14}$-alkyl-CO—$CH_2$— group or a $C_1$-$C_{14}$-alkyl-$CX_4X_5$—$CH_2$— group where $X_4$ and $X_5$ are independently selected from H, $NH_2$, or SH.

In a specific embodiment, the invention provides compounds of formula FX1, for uses as described herein, wherein when X is $CH_2$, and all of $R^1$, $R^2$ and $R^3$ are hydrogen, A-$[Z]_n$-L-Y is a group other than a $C_1$-$C_{14}$— alkyl group, a $C_1$-$C_{14}$-alkyl-CO—$CH_2$— group or a $C_1$-$C_{14}$-alkyl-$CX_4X_5$—$CH_2$— group where $X_4$ and $X_5$ are independently selected from H, $NH_2$, or SH.

In a specific embodiment, the invention provides compounds of formula FX1, for uses as described herein, wherein when X is $CH_2$, m is 1, and all of $R^1$, $R^2$ and $R^3$ are hydrogen, A-$[Z]_n$-L-Y is a group other than a $C_1$-$C_{14}$— alkyl group, a $C_1$-$C_{14}$-alkyl-CO—$CH_2$— group or a $C_1$-$C_{14}$— alkyl-$CX_4X_5$—$CH_2$— group where $X_4$ and $X_5$ are independently selected from H, $NH_2$, or SH.

In a specific embodiment, the invention provides compounds of formula FX1, for uses as described herein, wherein when X is $CH_2$, m is 2, and all of $R^1$, $R^2$ and $R^3$ are hydrogen, A-$[Z]_n$-L-Y is a group other than a $C_1$-$C_{14}$— alkyl group, a $C_1$-$C_{14}$-alkyl-CO—$CH_2$— group or a $C_1$-$C_{14}$— alkyl-$CX_4X_5$—$CH_2$— group where $X_4$ and $X_5$ are independently selected from H, $NH_2$, or SH.

In a specific embodiment, the invention provides compounds of formula FX1, for uses as described herein, wherein A is a group other than a $C_1$-$C_{14}$ alkyl group. In other specific embodiments, the invention provides compounds of formula FX1, for uses as described herein, wherein when X is O and all of $R^1$, $R^2$ and $R^3$ are hydrogen, A is a group other than a $C_1$-$C_{14}$ alkyl group. In additional embodiments, the invention provides compounds of formula FX1, for uses as described herein, wherein when X is $C(R^2)_2$, A is a group other than a $C_1$-$C_{14}$ alkyl group. In additional embodiments, the invention provides compounds of formula FX1, for uses as described herein, wherein when X is $C(R^2)_2$, and m is 1, A is a group other than a $C_1$-$C_{14}$ alkyl group. In additional embodiments, the invention provides compounds of formula FX1, for uses as described herein, wherein when X is $C(R^2)_2$, and m is 2, A is a group other than a $C_1$-$C_{14}$ alkyl group. In other embodiments, the invention provides compounds of formula FX1, for uses as described herein, wherein when X is $CH_2$, and all of $R^1$, $R^2$ and $R^3$ are hydrogen, A is a group other than a $C_1$-$C_{14}$ alkyl group. In other embodiments, the invention provides compounds of formula FX1, for uses as described herein, wherein when X is $CH_2$, m is 1 and all of $R^1$, $R^2$ and $R^3$ are hydrogen, A is a group other than a $C_1$-$C_{14}$ alkyl group. In other embodiments, the invention provides compounds of formula FX1, for uses as described herein, wherein when X is $CH_2$, m is 2, and all of $R^1$, $R^2$ and $R^3$ are hydrogen, A is a group other than a $C_1$-$C_{14}$ alkyl group.

In a specific embodiment, the invention provides compounds of formula FX1, for uses as described herein, wherein when X is O, m is 1 and Y is CO, A-$[Z]_n$-L- is a group other than a phenyl, a —$CH_2$-phenyl, a —$(CH_2)_2$-phenyl, —$(CH_2)$—O-phenyl, —$CH_2$—$CH(CH_3)$-phenyl, —$(CH_2)$—CO-phenyl, —$(CH_2)$—NH-phenyl, —$(CH_2)$—S-phenyl, —$(CH_2)$—SO-phenyl, or a —$(CH_2)$—$SO_2$-phenyl.

In a specific embodiment, the invention provides compounds of formula FX1, for uses as described herein, wherein when X is S, m is 1 and Y is CO, A-$[Z]_n$-L- is a group other than a phenyl, a —$CH_2$-phenyl, a —$(CH_2)_2$-phenyl, —$CH_2$—$CH(CH_3)$-phenyl, —$CH_2$—O-phenyl, —$(CH_2)$—CO-phenyl, —$(CH_2)$—NH-phenyl, —$(CH_2)$—S-phenyl, —$(CH_2)$—SO-phenyl, or a —$(CH_2)$—$SO_2$-phenyl.

In a specific embodiment, the invention provides compounds of formula FX1, for uses as described herein, wherein when Y is CO, A-$[Z]_n$-L- is a group other than a phenyl, a —$CH_2$-phenyl, a —$(CH_2)_2$-phenyl, —$(CH_2)$—O-phenyl, —$CH_2$—$CH(CH_3)$-phenyl, —$(CH_2)$—CO-phenyl, —$(CH_2)$—NH-phenyl, —$(CH_2)$—S-phenyl, —$(CH_2)$—SO-phenyl, or a —$(CH_2)$—$SO_2$-phenyl.

In a specific embodiment, the invention provides compounds of formula FX1, for uses as described herein, A-[Z]-L- is a group other than a phenyl, a —$CH_2$-phenyl, a —$(CH_2)_2$-phenyl, —$(CH_2)$—O-phenyl, —$CH_2$—$CH(CH_3)$-phenyl, —$(CH_2)$—CO-phenyl, —$(CH_2)$—NH-phenyl, —$(CH_2)$—S-phenyl, —$(CH_2)$—SO-phenyl, or a —$(CH_2)$—$SO_2$-phenyl.

In a specific embodiment, the invention provides compounds of formula FX1, for uses as described herein, wherein when X is O, m is 1 and Y is CO, A-$[Z]_n$-L- is a group other than a -cyclohexyl group, a —$CH_2$-cyclohexyl, or a —$(CH_2)_2$-cyclohexyl.

In a specific embodiment, the invention provides compounds of formula FX1, for uses as described herein, wherein when X is S, m is 1 and Y is CO, A-$[Z]_n$-L- is a group other than a -cyclohexyl group, a —$CH_2$-cyclohexyl, or a —$(CH_2)_2$-cyclohexyl.

In a specific embodiment, the invention provides compounds of formula FX1, for uses as described herein, wherein when Y is CO, A-$[Z]_n$-L- is a group other than a -cyclohexyl group, a —$CH_2$-cyclohexyl, or a —$(CH_2)_2$-cyclohexyl.

In a specific embodiment, the invention provides compounds of formula FX1, for uses as described herein, A-$[Z]_n$-L- is a group other than a -cyclohexyl group, a —$CH_2$-cyclohexyl, or a —$(CH_2)_2$-cyclohexyl.

In a specific embodiment, the invention provides compounds of formula FX1 for uses as described herein, wherein when X is O, m is 1 and Y is CO, A-$[Z]_n$-L- is a group other than a pyridine or a dithiane. In a specific embodiment, the invention provides compounds of formula FX1 for uses as described herein, wherein when X is S, m is 1 and Y is CO, A-$[Z]_n$-L- is a group other than a pyridine or a dithiane. In a specific embodiment, the invention provides compounds of formula FX1 for uses as described herein, wherein when Y is CO, A-[Z]-L- is a group other than a pyridine or a dithiane. In a specific embodiment, the invention provides compounds of formula FX1 for uses as described herein, A-$[Z]_n$-L- is a group other than a pyridine or a dithiane.

In specific embodiments, the invention provides compounds of formula FX1 other than those having formula I

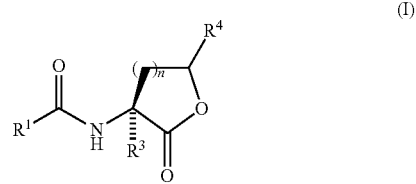

where n is 1, 2 or 3, wherein if n=1, the ring C bound to the substituted amino can be a chiral center, $R^1$ is selected from —H, —$(CH_2)_aCH_3$, —$(CH_2)_aCOR^2$, —$(CH_2)_aCHOHR^2$, —$(CH_2)_aR^6$, —O—$(CH_2)_aCH_3$, —$(CH_2)_aHC=CH$, —HC=CH$(CH_2)_aCH_3$, —$(CH_2)_aHC=CH(CH_2)_bCH_3$, —$R^6HC=CHR^7$, —$R^6C\equiv CR^7$, substituted and unsubstituted $C_3$-$C_8$ cycloalkyl, substituted and unsubstituted $C_3$-$C_8$ aryl, three to eight member substituted and unsubstituted heterocyclic rings, where the heteroatom is at least one of O, S or N, $R^2$ is selected from —H, —$(CH_2)_aCH_3$, substituted and unsubstituted $C_3$-$C_8$ cycloalkyl, substituted and unsubstituted $C_3$-$C_3$ aryl, three to eight member substituted and unsubstituted heterocyclic rings, where the heteroatom is at least one of O, S or N, $R^3$ is Selected from —H, —$CH_2CH_3$, —$CH_3$, $R^4$ is selected from —H, —$CH_2$—$R^5$, $R^5$ is —H, $R^6$ and $R^7$ are the same or different, selected from —H, substituted and unsubstituted $C_3$-$C_8$ cycloalkyl, substituted and unsubstituted $C_3$-$C_8$ aryl, three to eight member substituted and unsubstituted heterocyclic rings, where the heteroatom is at least one of O, S or N, and a and b are independently integers from 0 to 15.

In other specific embodiments, the invention provides compounds of formula FX1 other than those of formula II:

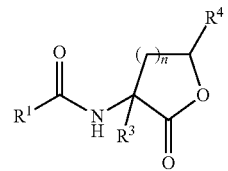

where $R^1$, $R^3$, $R^4$, and n are as defined in the preceding paragraph.

In additional embodiments, the invention provides compounds of formula FX1 other than those of formula I or II above where $R^1$ is —$CH_2$—$COR^2$, $C_6H_{13}$,

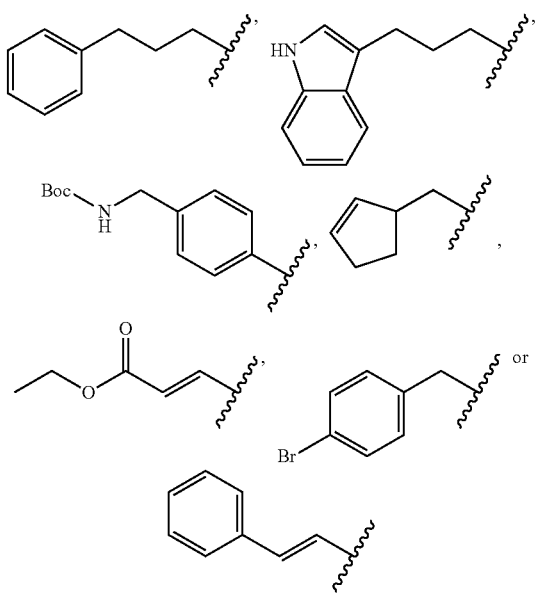

and
R² is

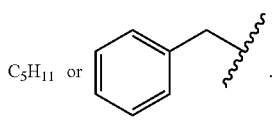 [SMILES: *Cc1ccccc1 ; "C5H11"]

The invention includes compounds of formula FX1 which exhibit activity as antagonist of quorum sensing in bacteria, particularly specific bacteria disclosed herein. The invention also includes compounds of formula FX1 which exhibit activity as agonist of quorum sensing in bacteria, particularly specific bacteria disclosed herein.

In an embodiment, compounds of formula FX1 have activity as an agonist or antagonist of native quorum sensing compounds. In an embodiment, compounds of formula FX1 can be used to selectively adjust the virulence, biofilm production, or symbiotic behavior of a quorum sensing bacteria. In an embodiment, compounds of formula FX1 can be administered to a subject to initiate an immune response towards a quorum sensing bacteria.

In an embodiment, certain compounds are preferred for selectively adjusting the virulence, biofilm production, or symbiotic behavior of a particular species or strain of a particular species of quorum sensing bacteria. In an embodiment, preselected mixtures of L- and D-isomers of compounds of the present invention can be used to selectively adjust the virulence, biofilm production, or symbiotic behavior of a particular species or strain of a particular species of quorum sensing bacteria.

In an embodiment, the compounds of the present invention are useful as a combinatorial library comprising a preselected mixture of two or more compounds of the present invention. In an embodiment, the two or more compounds can each be used to separately selectively adjust the virulence, biofilm production, or symbiotic behavior of a particular species or strain of a particular species of quorum sensing bacteria.

The invention may be further understood by the following non-limiting examples.

EXAMPLES

Example 1

From Antagonist to Super-Agonist: Structural Isomers of N-Phenylacetanoyl-L-Homoserine Lactones Elicit Strong and Opposite Quorum Sensing Responses in *Vibrio fischeri*

Abstract:

Bacteria monitor their population densities using low molecular weight ligands in a process known as quorum sensing. At sufficient cell densities, bacteria can change their mode of growth and behave as multicellular communities that play critical roles in both beneficial symbioses and in the pathogenesis of infectious disease. The development of non-native ligands that can block quorum-sensing signals has emerged as a promising new strategy to attenuate these divergent outcomes. Here, we report that N-phenylacetanoyl-L-homoserine lactones are capable of either inhibiting or, in some cases, strongly inducing quorum sensing in the bacterial symbiont *Vibrio fischeri*. Moreover, simple structural modifications to these ligands have remarkable effects on activity. For example, movement of a single substituent on the phenylacetanoyl group transforms potent quorum sensing antagonists into quorum sensing agonists. Studies of these structural isomers have revealed one of the first synthetic superagonists of quorum sensing, and to our knowledge the first super-agonist to be reported in *V. fischeri*, N-(3-nitro-phenylacetanoyl)-L-homoserine lactone. Together, these ligands represent a powerful new class of chemical probes with the potential to significantly expand the current understanding of quorum sensing and its role in host/bacteria interactions.

Bacteria can assess their local population densities using low molecular weight molecules (autoinducers), and alter gene expression at high cell number to behave as a group. This process, termed quorum sensing, is widely used by bacteria to initiate group behaviors that have direct and often devastating impacts on human health and the environment. For example, numerous bacterial pathogens use quorum sensing to initiate infection. In contrast, symbiotic bacteria use these pathways to commence mutually beneficial relationships with their hosts. As these important processes are controlled by chemical signals, there is intense and growing interest in the development of non-native ligands that can intercept these signals and attenuate or mimic quorum-sensing outcomes.

Quorum sensing is best characterized in gram-negative Proteobacteria, which use diffusible N-acylated-L-homoserine lactones (AHLs) and their cognate receptors (R proteins) for intercellular communication (FIG. 1a). Considerable research efforts have focused on the synthesis of ligands that can disrupt AHL-R protein binding and inhibit quorum sensing, yet potent and general R protein antagonists remain scarce. Likewise, compounds exhibiting heightened activities relative to native AHLs (i.e., super-agonists of quorum sensing) are also of significant interest, as they could potentially initiate bacterial behaviors at lower cell numbers than required in natural environments. For example, super-agonists could be used to determine whether beneficial symbioses could be initiated earlier during colonization by a symbiont, or whether a pathogen could be forced to initiate infection too early and be cleared by a host's immune response. Such experiments would help illuminate the relationships between bacterial group behavior and host responses. However, only two super-agonists of R protein activity have been reported to date, and these compounds have yet to be tested in vivo.

New synthesis and design strategies are needed to expand the current set of quorum sensing modulators active in gram-negative bacteria. Unfortunately, the structures of known antagonists and agonists vary widely and their mechanisms of action are unclear; thus, no obvious rationales have emerged for new ligand design. To address this problem, we have been engaged in the design of focused, combinatorial libraries of ligands for the modulation of quorum sensing. Here, we report the discovery of a family of non-native AHLs capable of either inhibiting or, in some cases, strongly inducing quorum sensing in the marine symbiont *Vibrio fischeri*. In addition, we report the first super-agonist of quorum sensing in *V. fischeri*. These ligands provide a new blueprint for the design of both quorum sensing agonists and antagonists and represent powerful new chemical probes to investigate the mechanisms of bacterial communication.

*V. fischeri* colonizes the light-producing organs of certain marine fish and squids and uses quorum sensing to initiate bioluminescence at high cell densities. Quorum sensing is mediated in part by an AHL signal, N-(3-oxo-hexanoyl)-L-homoserine lactone (OHHL, 1), and its cytoplasmic receptor, LuxR (FIG. 1a). OHHL is synthesized by the LuxI protein at low basal levels, and high cell densities are required to achieve a sufficient concentration of OHHL for LuxR binding (≥100 nM in vivo); thereafter, the OHHL-LuxR complex activates the transcription of luminescence genes and other genes involved in symbiosis, and illuminates the fish or squid light organ. Quorum sensing in *V. fischeri* represents the best-characterized quorum sensing signaling pathway to date; however, the role of quorum sensing in host-*V. fischeri* symbiosis is complex and remains poorly understood. As a first step toward studying the interplay between quorum sensing and bacterial symbioses, we sought to identify non-native signal molecules that could intercept quorum sensing in *V. fischeri*.

Certain AHLs with non-native acyl chains have been reported to inhibit LuxR protein function in reporter gene assays. These antagonists include N-heptanoyl-L-homoserine lactone (2) and N-(4-phenylbutanoyl)-L-homoserine lactone (3) and N-pentylsulfonyl-L-homoserine lactone (4) (FIG. 1a): N-(4-bromo-phenylacetanoyl)-L-homoserine lactone (4-bromo PHL 5) is a potent antagonist of LuxR homologs in several other gram-negative bacteria (FIG. 1a). For example, 4-bromo PHL 5 inhibits R protein function in *Agrobacterium tumefaciens* at a 1:1 ratio against native AHL ligand, as determined by reporter gene assays. As the putative ligand binding sites of the known R proteins have considerable sequence homology (70-80%), we hypothesized that PHLs might also modulate LuxR activity in *V. fischeri*, and if so, represented a promising ligand class with which to initiate this study.

Figure 1B:
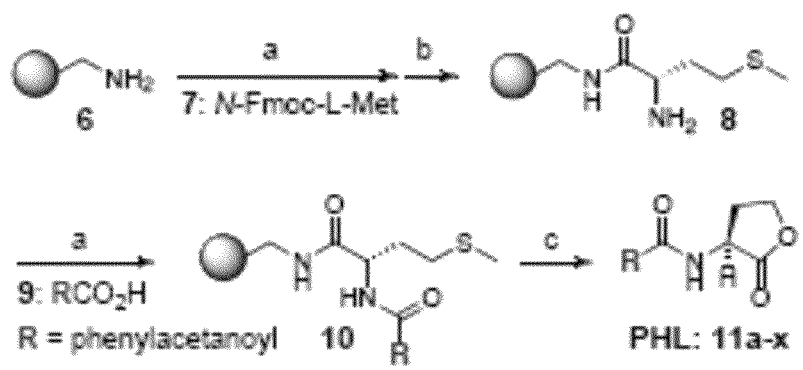

PHLs can be readily synthesized using a microwave-assisted, solid-phase route to AHLs previously reported by our laboratory (FIG. 1b). Using this method, we synthesized a small, focused library of 24 PHLs to systematically examine the effects of different phenylacetanoyl moieties on ligand activity. This route gave PHL products 11a-x (FIG. 2) in excellent purities (ca. 95%), good isolated yields (>65%), and sufficient quantities (i.e., 30 mg per compound) for multiple biological experiments.

Non-native ligands are commonly assessed for R protein agonism and antagonism using bacterial reporter strains. These strains lack AHL synthase genes, but retain their native R genes. Exogenous AHL ligand is therefore required for R protein activation, which can be measured by reporter gene read-outs based on luminescence or fluorescence. The majority of synthetic LuxR modulators have been evaluated using the luxR plasmid pSB401 in various *Escherichia coli* strains. We therefore began our biological evaluation of PHL library 11 using the *E. coli* strain JM109 (pSB401). Competitive inhibition assays were performed in the presence of both OHHL and PHLs 11 (at a 1:1 ratio), while agonism assays were performed with PHLs alone. The known LuxR protein inhibitors 2-4 and 4-bromo PHL 5 served as important controls for these studies (FIG. 1a). However, unacceptably large error values in the luminescence data (see Supporting Information) forced us to seek an alternate strain. We found that a Δ-luxI derivative of *V. fischeri* ES114, in which the native lux operon behaves as the bioluminescent reporter, gave highly reproducible luminescence data in these assays. This non-standard reporter strain was used for all subsequent primary assays in this study.

Figure 2:
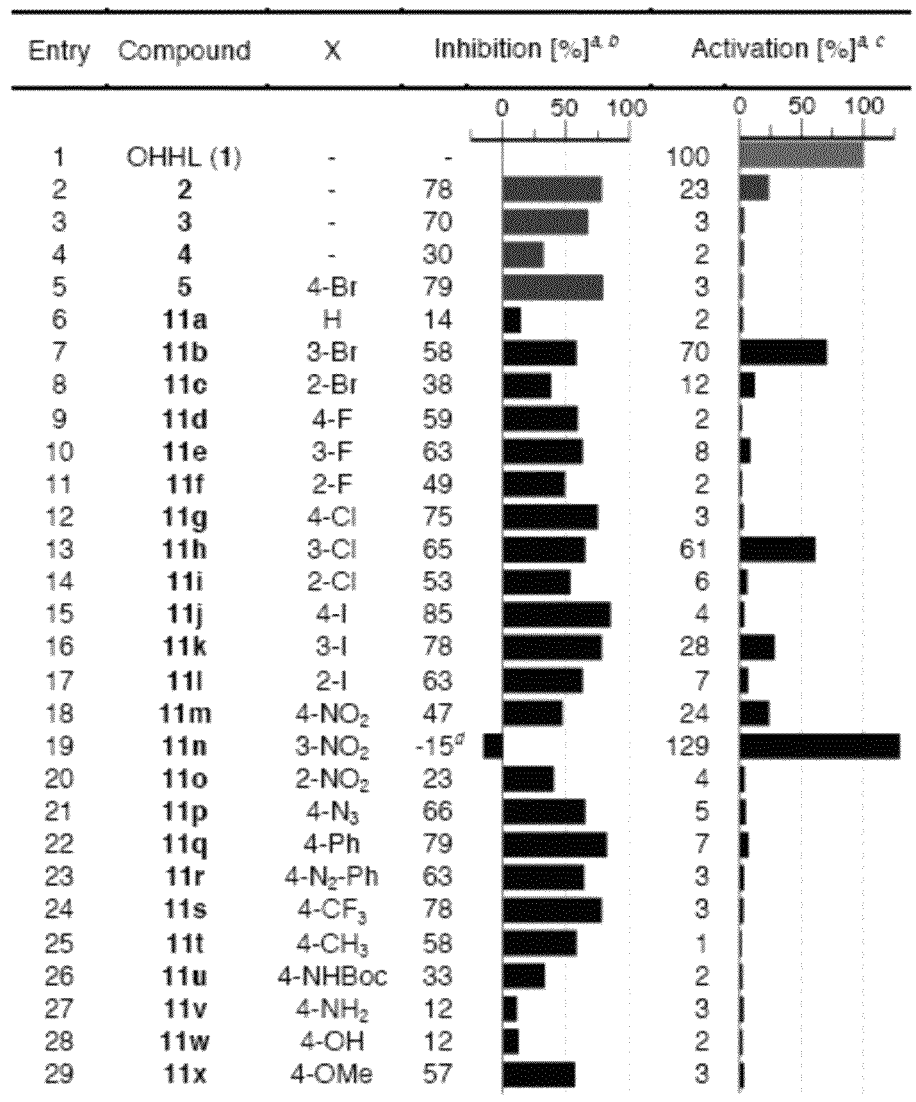
FIG. 2 provides structures and primary antagonism and agonism screening data for PHL library 11 in *V. fischeri* (Δ-luxI).

The antagonism assays in *V. fischeri* revealed several active PHL ligands and a number of striking structure-activity relationships (SARs) (FIG. 2). First, the control compound 4-bromo PHL 5 showed 79% inhibition at a 1:1 ratio with native ligand 1 (entry 5; both ligands at 5 µM). This result supported our hypothesis that PHLs could modulate LuxR function. Indeed, 50% of the PHL library 11 exhibited 50% inhibition in this assay. Inhibitory activity was extremely dependent on the substituents and their relative locations on the phenylacetanoyl group. For example, replacement of the 4-bromide with a hydrogen in PHL 11a abolished inhibitory activity (entry 6). PHLs with bromo (5, 11a-b), chloro (11g-i), and iodo substituents (11j-l) exhibited a ca. 10% increase in antagonism as the halogen was moved from the 2- to the 3- to the 4-position on the phenyl ring. Antagonistic activity also increased slightly with increasing halogen size, with 4-iodo PHL 11j exhibiting the highest activity (entry 15; 85%) for the halogen series.

In general, sterically large and lipophilic groups in the 4-position enhanced PHL (11) antagonism in *V. fischeri* (Δ-luxI). This is exemplified by the high activities of 4-phenyl PHL 11q and 4-trifluoromethyl PHL 11s (ca. 80% inhibition; FIG. 2). In contrast, hydrogen-bond donating substituents in the 4-position engendered the lowest inhibitory activities (i.e., 4-amino PHL 11v and 4-hydroxy PHL 11w). The nitro PHL series (11m-o), however, showed a more complicated activity trend, with 3-nitro PHL 11n showing no inhibitory activity relative to the 2- and 4-nitro PHLs (entries 18-20; see below). We determined IC50 values for the most potent PHL inhibitors identified in this assay, along with the most potent controls (2 and 5) for comparison. The 4-iodo PHL 11j and 4-trifluoromethyl PHL 11s exhibited the lowest IC50 values in this study, with PHL 11s at least two-fold more active than control compound 2 (0.6 µM vs. 1.4 µM, respectively).

Similar assays were performed on PHL library 11 to screen for agonistic activity in *V. fischeri* (Δ-luxI). Again, we observed striking trends in the activities for PHLs with halogen and nitro groups (at 200 µM compound; FIG. 2). In contrast to the antagonism data, the 3-substituted compound in each of these PHL families showed the strongest activity relative to the 2- and 4-substituted derivatives, with the 3-bromo 11b, 3-chloro 11h, and 3-nitro 11n PHLs exhibiting at least 60% luminescence induction relative to native OHHL at the same concentration. Remarkably, simply shifting substituents on the PHL phenyl ring by a single carbon converted these ligands from LuxR antagonists to LuxR agonists. Moreover, 3-nitro PHL 11n was able to induce 29% higher luminescence than OHHL in this primary assay (entry 19). This result was extraordinary, and explained the unusual inhibition trends for the nitro PHL series (11m-o; see above).

For a more quantitative comparison of ligand activity, we determined EC50 values for our most active PHL agonists (11b, 11h, and 11n) and OHHL in *V. fischeri* (Δ-luxI). These studies identified 3-nitro PHL 11n as the most active LuxR agonist, exhibiting a ten-fold lower EC50 than OHHL (0.3 µM vs. 3 µM, respectively). We performed analogous dose-response studies with 11n and OHHL in wild-type *V. fischeri* ES114, and observed similarly heightened activity for PHL 11n relative to OHHL. The super-agonistic activity of PHL 11n in *V. fischeri* relative to OHHL could be easily visualized by luminescence imaging with a CCD camera. We also examined the activity of 11n and OHHL in a L-luxR derivative of *V. fischeri* ES114. Neither 11n nor OHHL induced any detectable luminescence in this strain, which suggests that 11n, like the native ligand OHHL, exerts its activity through the LuxR protein (see below). The discovery of compound 11n is significant, as it is one of the first synthetic super-agonist of quorum sensing reported and to our knowledge the first super-agonist active in *V. fischeri*.

In view of the structural similarity of PHLs 11 to native AHLs and the assay data and subtle SAR described above, these ligands likely target the LuxR ligand-binding site and inhibition or activation is based on the specific binding mode and thus resulting affinity of the ligand. Further, we do not believe that these changes in activity simply reflect the different chemical properties of the PHLs. This view is supported by several observations. First, the percentage of PHL 11 lactone hydrolysis (which abolishes activity for native AHLs) is minimal and identical to that of OHHL over the time course of these luminescence assays. Second, higher lipophilicity within the PHL series, and therefore higher potential cell permeability, does not correlate with enhanced antagonistic or agonistic activity (FIG. 2). This is further exemplified by the D-enantiomers of control antagonists 3 and 5, which have identical lipophilicities as 3 and 5, yet exhibit markedly reduced activities (ca. 20% inhibition). Third, the functionalities on PHLs 11 are unreactive under the assay conditions tested. We have performed molecular modeling studies of several PHLs and OHHL docked into the putative ligand binding site of LuxR (built in silico from the one known structure of an R protein, TraR) to further test this hypothesis. The results of these studies suggest that the LuxR binding site can readily accommodate PHLs, yet is better able to accommodate 3-substituted PHLs (agonists) relative to 4-substituted PHLs (antagonists), and that activation or inhibition of LuxR may depend on the balance of favorable hydrogen-bonding and unfavorable steric interactions within the binding pocket. While additional biochemical and structural studies will be required to fully elucidate PHL function in *V. fischeri*, these initial calculations provide support that PHLs 11 target LuxR.

In summary, we have discovered that PHLs elicit remarkable and varied quorum sensing responses in the bacterial symbiont *V. fischeri*. This family of ligands includes some of the most active antagonists and agonists of gram-negative bacterial quorum sensing reported to date. One significant outcome of this work is the observation that subtle alteration to substituents and their placement on the phenylacetanoyl moiety dramatically influence ligand activity. These changes do not simply abolish activity, but rather convert potent antagonists into agonists. A second major outcome of this investigation is the discovery of the first synthetic super-agonist of quorum sensing in *V. fischeri*, PHL 11n. This ligand displays 10-fold higher activity relative to native autoinducer OHHL, and is one of the first known super-agonists of quorum sensing in gram-negative bacteria. Collectively, PHLs represent a new and valuable set of chemical tools for the study of quorum sensing in *V. fischeri* and provide broad insights into the roles of quorum sensing in bacterial symbioses. Preliminary experiments indicate super-agonist 11n is well tolerated by the main symbiotic partner of *V. fischeri*, the Euprymna scolopes squid, and is active in vivo.

Methods.

Ligand Synthesis.

PHL library 11, OHHL (1) and control compounds 2, 3 and 5 were prepared according to FIG. 1*b* using reported methods, except the final cleavagecyclization step was performed at RT for 24 h. Control 4 was synthesized in an analogous fashion except DMAP and 1-pentanesulfonyl chloride replaced reagents (a) and 9 in FIG. 1*b*. Compounds were submitted to biological assays following cleavage and an aqueous work-up without further purification.

Compound Handling and Reagents.

Stock solutions of synthetic compounds (10 mM) were prepared in DMSO. All biological reagents were purchased from Fisher Scientific. Luria Bertani (LB) and LB salt media (LBS) were prepared as instructed with pH=7.5 (LBS contained an additional 1.5% NaCl, 0.3% glycerol, and 50 nM Tris-HCl).

Bacterial Strains.

The *E. coli* strain used for these studies was JM109 (pSB401). The *V. fischeri* stains were ES114, ES114 (Δ-luxI), and ES114 (Δ-luxR).

Luminescence Assays.

For agonism assays, an appropriate amount of AHL stock solution was added into a 96-well plate. An overnight culture of *E. coli* or *V. fischeri* was diluted 1:10 with appropriate media (LB plus 10 µg/mL tetracycline for *E. coli*; LBS for *V. fischeri*). A 200-µL portion of the diluted culture was added to each well of the plate. Plates were grown for 4-8 h with shaking (200 rpm; 30° C. for *E. coli* and RT for *V. fischeri*). Luminescence was measured using a multilabel plate reader and normalized to cell density. Antagonism screens were performed in an analogous manner against OHHL at its approximate EC50 values (10 nM in *E. coli*; 5 µM in *V. fischeri*). Similar methods were used for dose response assays, except the concentrations of PHL (11) or control varied between $2 \times 10^{-2}$ and $2 \times 10^5$ nM. All assays were performed in triplicate. Graphpad Prism software was used to calculate $IC_{50}$ and $EC_{50}$ values.

General Experimental Information.

General. $^1$H NMR spectra were recorded on a Bruker AC-300 spectrometer in deuterated solvents at 300 MHz. Electrospray ionization (ESI) MS were obtained using a Shimadzu LCMS-2010a system (Columbia, Md.) equipped with two pumps (LC-10ADvp), controller (SCL-10Avp), UV diode array detector (SPD-M10Avp), and single quadrupole analyzer. GC-MS data were obtained using a Shimadzu GC-17A system (Columbia, Md.) equipped with a QP-5000 mass spectrometer. A Restek RTX-5 cross bond 95% polysiloxane GC column was used with following general gradient: injection temperature 300° C.; initial oven temperature 100° C.; hold 3 min; ramp at 20° C./min to 300° C.; hold 2-15 min for a total run time of 15-30 min.

All chemical reagents were purchased from commercial sources (Alfa-Aesar, Aldrich, Acros, and Sigma) and used without further purification. Solvents were purchased from commercial sources (Aldrich and J. T. Baker) and used as is, with the exception of dichloromethane ($CH_2Cl_2$), which was distilled over calcium hydride immediately prior to use. All solid-phase syntheses were performed using aminomethyl polystyrene resin (NovaBiochem, 100-200 mesh; loading 1.1-1.2 mmol/g)

Microwave Instrumentation.

Microwave-assisted solid-phase reactions were carried out using either a Milestone Microsynth Labstation or CEM Discover commercial microwave (MW) reactor. All MW-assisted reactions were performed using temperature control to monitor MW irradiation.

Solid-Phase Library Synthesis Techniques.

Solid-phase reactions were performed in either 100 mL round bottom flasks in the Milestone MW reactor or 10 mL glass CEM MW vessels (part #908035) in the CEM MW reactor. Liquid reagents were dispensed during synthesis using either disposable syringes or Brinkman Eppendorf pipettmen (calibrated for variable solvent delivery) equipped with disposable polypropylene pipette tips. Between synthesis steps, the solid-phase resin was washed with solvents stored in polypropylene Nalgene squirt bottles. Large quantities of resin were washed in a standard glass frit. Small quantities of resin were washed on a Vac-Man vacuum manifold (Promega, part #: A7231) in 8 mL polypropylene sample reservoirs (Alltech, part #: 210208) equipped with 20 μm frits (Alltech, part #: 211408).

Structures of 24-Member PHL Library 11.

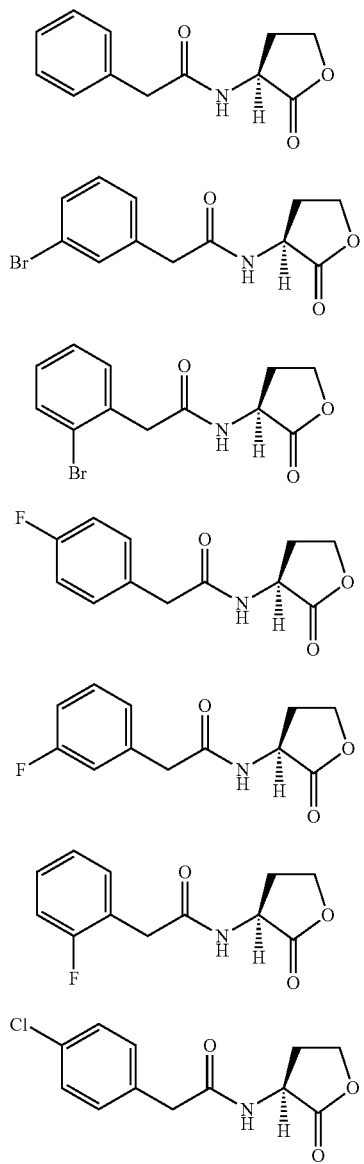
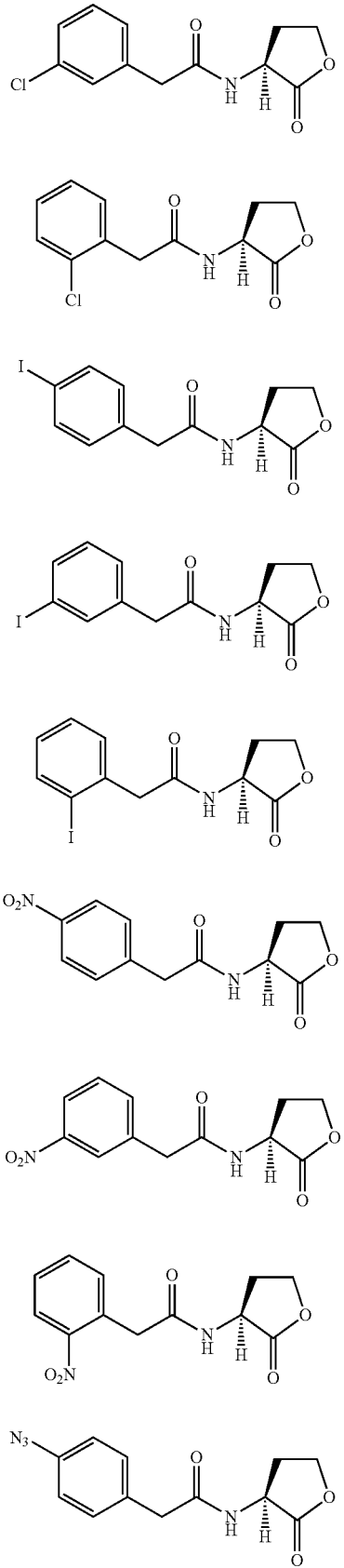

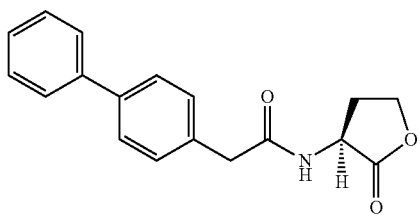
11q

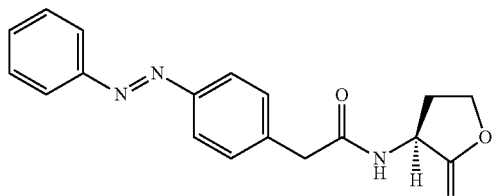
11r

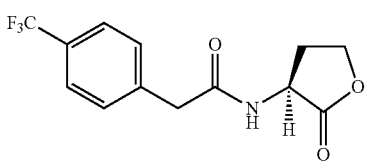
11s

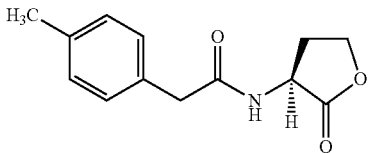
11t

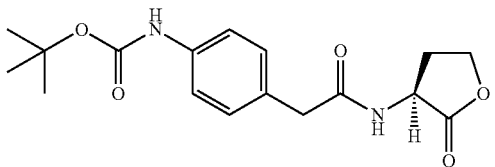
11u

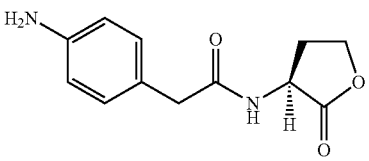
11v

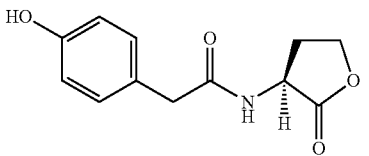
11w

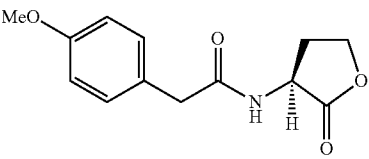
11x

Characterization Data for AHL Derivatives.

Characterization data for OHHL (1) and control compounds 2, 3, and 5 matched those published previously. $^1$H NMR, $^{13}$C NMR, IR, MS, and optical rotation data was as expected for control compound 4 and PHL library 11.

Biological Screening Protocols.

Compound handling and reagents. Stock solution of synthetic compounds (10 mM) were prepared in DMSO and stored at −20° C. in sealed vials. The solutions were allowed to come to room temperature prior to use in assays. Solvent resistant polypropylene (Corning Costar cat. no. 3790) or polystyrene (Corning Costar cat. no. 3997) 96-well multititer plates were used when appropriate. All biological reagents were purchased from Fisher and used according to enclosed instructions. LB medium was prepared according to packaging with a pH=7.5. LBS medium was prepared from 20 g dehydrated LB broth, 15 g NaCl, 30 mL glycerol, and 7.8 g Tris-HCl with a final pH=7.5.

Instrumentation.

Absorbance and luminescence measurements were obtained using a PerkinElmer Wallac 2100 EnVision™ multilabel plate reader using Wallac Manager v1.03 software. A 595 nm filter was used for measuring bacterial cell density ($OD_{600}$).

*E. coli* Assay Procedures.

Figure 3:
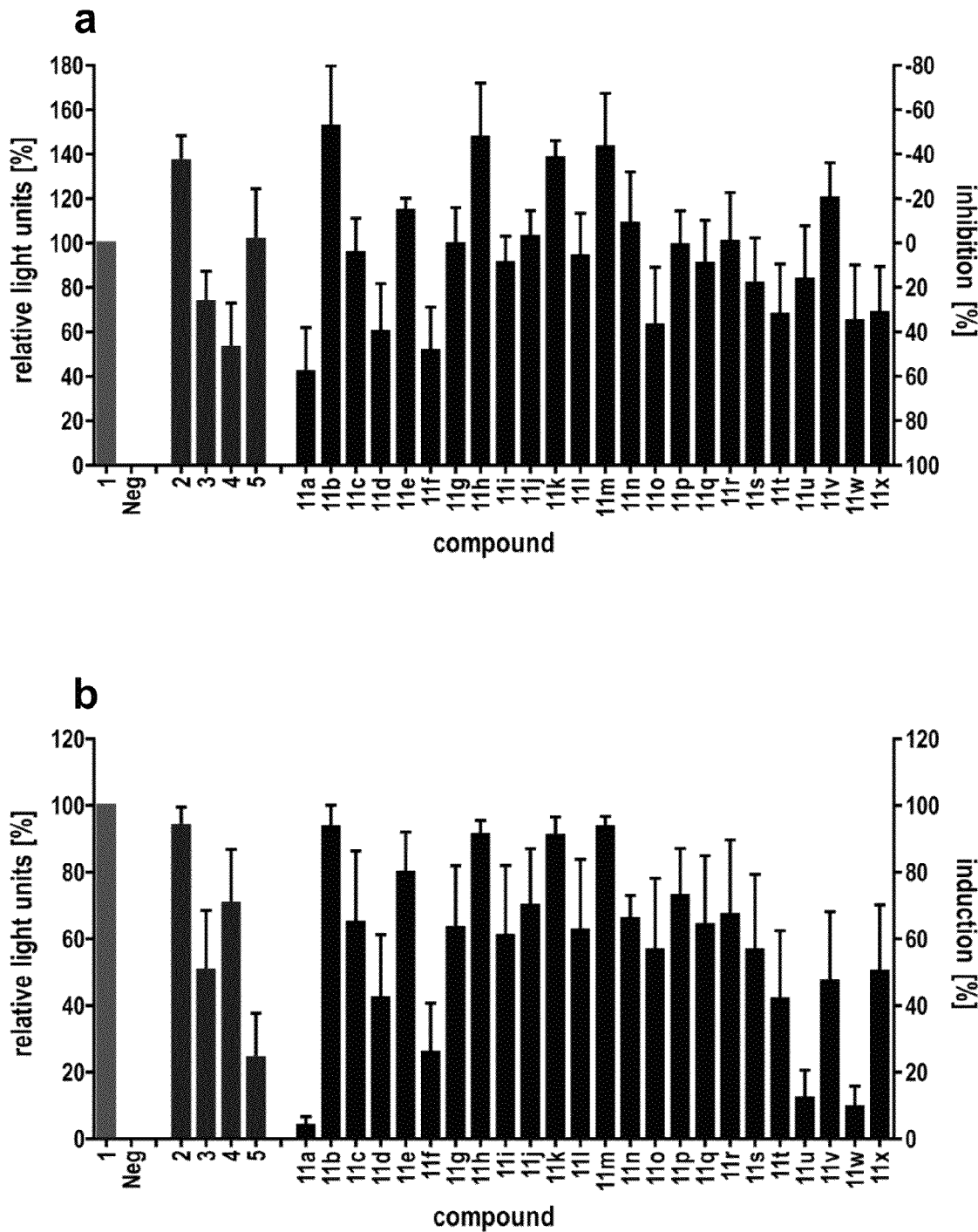
FIG. 3 provides primary antagonism and agonism screening data for library 11 in *E. coli* JM109 (pSB401).

For primary agonism assays, an appropriate amount of concentrated control or PHL (11) stock solution, to give a final concentration of 15 μM, was added to wells in a 96-well multititer plate. An overnight culture of *E. coli* JM109 (pSB401) was diluted 1:10 with LB medium (containing 10 μg/mL tetracycline). A 200-μL portion of the diluted culture was added to each well of the plate. Plates were grown at 30° C. with shaking (200 rpm) until the $OD_{600}$=0.35-0.4 (6-8 h). Luminescence then was measured and normalized to cell density per well. Primary antagonism assays were performed in a similar manner except the PHL 11 or control was screened at 15 μM against 20 nM OHHL 1 ($EC_{50}$ of autoinducer in this strain). All assays were performed in triplicate. The primary data is shown in FIG. 3.

*Vibrio fischeri* Assay Procedures.

Figure 4:
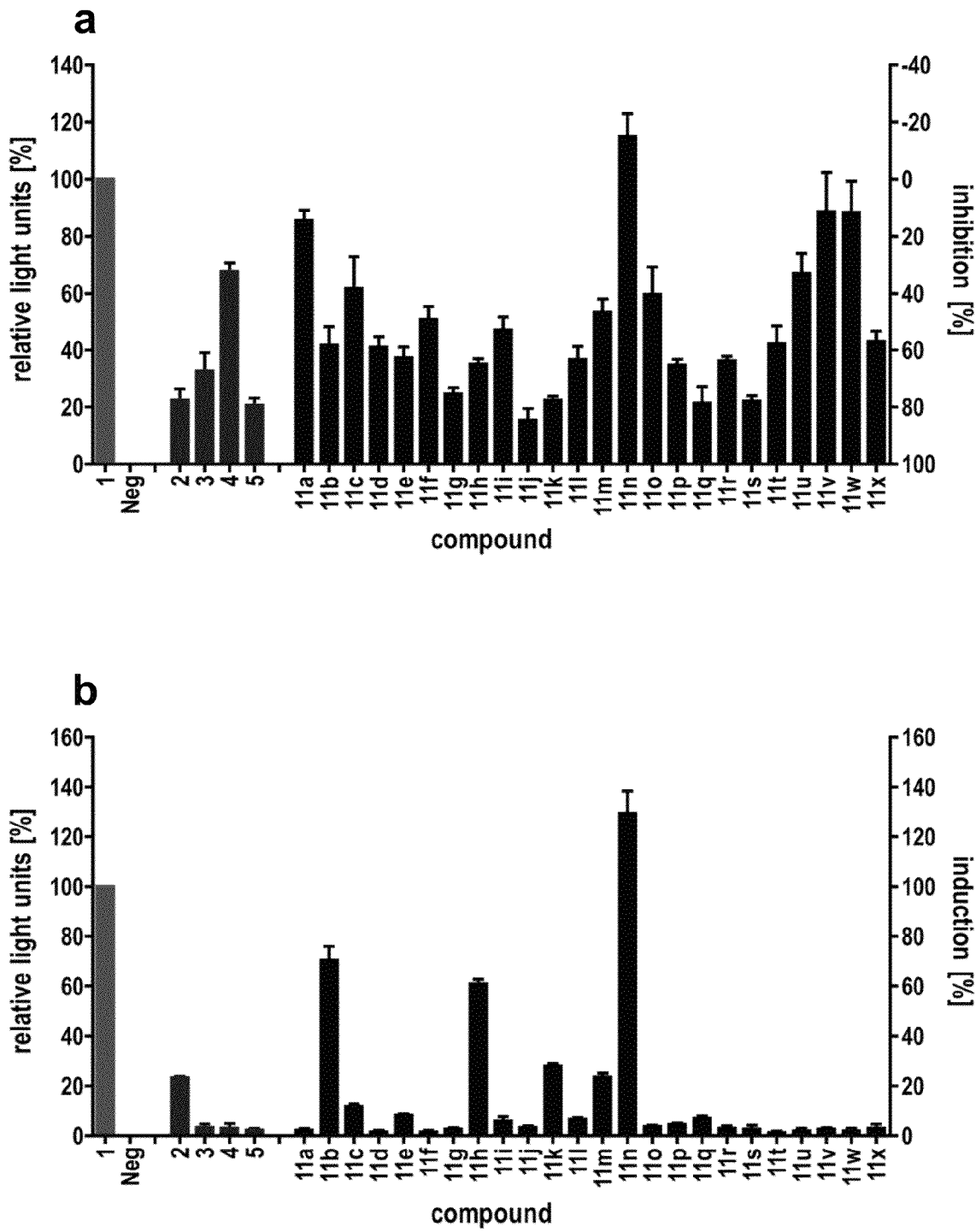
FIG. 4 provides primary antagonism and agonism screening data for library 11 in *V. fischeri* ES114 (Δ-luxI).

For primary agonism assays, an appropriate amount of concentrated control or PHL (11) stock solution, to give a final concentration of 200 μM, was added to wells in a 96-well multititer plate. An overnight culture of *V. fischeri* ES114 (WT, Δ-luxI or Δ-luxR) was diluted 1:10 with LBS medium. A-200 μL portion of the diluted culture was added to each well of the plate. Plates were grown at RT with shaking (200 rpm) until the $OD_{600}$=0.35-0.4 (4-6 h). Luminescence then was measured and normalized to cell density per well. Primary antagonism assays were performed in a similar manner except the PHLs 11 or control was screened at 5 μM against 5 μM OHHL 1 (ca. $EC_{50}$ of autoinducer in this strain). Similar methods were used for dose response assays, except the concentrations of controls and PHLs 11 used were between 0.02 and 2×10$^5$ nM. All assays were performed in triplicate. The primary data is shown in FIG. 4. $IC_{50}$ and $EC_{50}$ values were calculated using GraphPad Prism software using a sigmoidal curve fit.

The dose response antagonism curves for control AHL 2 and PHL 11m start to slope upwards at the higher concentrations tested. Ongoing studies in our laboratory are focused on developing an understanding of this phenomenon.

Primary Antagonism Screening Data for D-3 and D-5 in *V. fischeri*

PHLs D-3 and D-5 were synthesized according to FIG. 1b except N-Fmoc-D-methionine was used instead of N-Fmoc-L-methionine (7) and were isolated in similar yields and purities as PHLs 3 and 5, respectively.

Computational Modeling of the LuxR Ligand Binding Site and PHL Ligands.

Computational Methods.

All molecular modeling experiments were performed using the MOE software suite (v. 2006.08; Chemical Computing Group of Canada). A model of the AHL binding site in LuxR was generated from the X-ray crystal structure of TraR from *A. tumefaciens* (co-crystallized with its native AHL ligand (N-3-oxooctanoyl-L-homoserine lactone; OOHL) and DNA; pdb code: 1L3L). This is the only available structure of a LuxR homolog. As there is low overall structural homology between LuxR and TraR (ca. 20%), we only performed modeling studies on the binding site region of TraR (ca. 80% homology). We defined this site as a sphere with a radius of 12 Å centered on the lactone ring of OOHL. Each of the residues on the TraR ligand-binding site was replaced by the corresponding residues from LuxR according to the sequence alignment by Whitehead et al. This alignment has been used in previous homology modeling studies of LuxR.

A conformational database of OHHL (1) and selected PHLs (11) was created and minimized. The conformations were generated with the MMFF94x force field using Conformation Import in MOE. A limit of 4.5 kcal/mol strain energy was imposed with a 100-conformation limit for each molecule. Duplicate conformations were removed with a heavy atom RMSD tolerance of 0.5 Å (0.75 Å for conformations with strain greater than 3.5 kcal/mol). This database was superimposed over the minimized natural ligand OHHL (1) and then scored for best RMS fit. These poses then were docked and minimized into the mutated LuxR binding domain. The docking and minimizations were performed using the AMBER99 force field, with allowance of flexibility of the receptor and gradient change set to 0.01. Ten separate docking poses were determined for each ligand and models were generated from the poses with the lowest overall ligand to receptor strain energy.

Figure and Table Headings.

FIG. 1. a) Structures of a generic AHL, OHHL (1) (the natural autoinducer ligand of *V. fischeri*), and selected known synthetic inhibitors of LuxR or other R protein function (2-5). b) Solid-phase synthetic route to PHL library 11. Reagents and conditions: a=DIC, HOBT, CHCl$_3$/DMF, µW 50° C. (2×10 min); b=µW 150° C., 7 min; c=1.5 M CNBr in 5 mL CHCl$_3$, 2 mL H$_2$O, 40 µL TFA, RT, 24 h. DIC=N,N'-diisopropylcarbodiimide. HOBT=Nhydroxybenzotriazole. µW=temperature-controlled microwave irradiation.

FIG. 2. Structures and primary antagonism and agonism screening data for PHL library 11 in *V. fischeri* (Δ-luxI).

FIG. 3. Primary antagonism and agonism screening data for library 11 in *E. coli* JM109 (pSB401). a) Antagonism screen performed using 15 µM of synthetic ligand against 20 nM of native ligand 1 (red). Negative control (Neg) contains no compound. Control ligands (2-5) in blue. b) Agonism screen performed using 15 µM of ligand. Error bars, s.d. of the means of triplicate samples.

FIG. 4. Primary antagonism and agonism screening data for library 11 in *V. fischeri* ES114 (Δ-luxI). a) Antagonism screen performed using 5 µM of synthetic ligand against 5 µM of native ligand (OHHL, 1). Positive control (1) in red. Negative control (Neg) contains no compound. Control ligands (2-5) in blue. b) Agonism screen performed using 200 µM of ligand. Error bars, s.d. of the means of triplicate samples.

Example 2

Small Molecule Modulation of Quorum Sensing Revealed by the Systematic Evaluation of Synthetic Ligands Across Three Gram-Negative Bacterial Species Abstract:

Bacteria monitor their population densities using low molecular weight ligands in a phenomenon called quorum sensing. At high cell densities, bacteria use this chemical signaling process to change their mode of growth and behave as multicellular communities that play essential roles both in the pathogenesis of infectious disease and in beneficial symbioses. There is intense and growing interest in the development of synthetic ligands that can intercept quorum sensing signals and attenuate these divergent outcomes. Both broad spectrum and species specific modulators of quorum sensing hold significant value as small molecule tools for fundamental studies of this complex cell-cell signaling process and for future biocontrol applications. However, synthetic inhibitors or activators of quorum sensing in one species, let alone multiple, remain scarce. Here, we report the design and synthesis of four focused collections of non-native N-acylated-L-homoserine lactones and the systematic evaluation of these ca. 100 ligands across three relevant gram-negative bacterial species: the pathogens *Agrobacterium tumefaciens* and *Pseudomonas aeruginosa*, and the model symbiont *Vibrio fischeri*. These studies have revealed some of the most potent synthetic modulators of quorum sensing reported to date. Moreover, several of these ligands exhibit agonistic or antagonistic activity in all three species, while other ligands are only active in one strain. Selected ligands either inhibited or promoted the production of a key virulence factor in wild-type *P. aeruginosa*, elastase, depending on their concentration. We present a unifying rationale for quorum sensing modulation by these new ligands that is based on competitive weak agonism. Together, this work provides broad new insights into the molecular features required for species-specific, small molecule inhibition or activation of quorum sensing in gram-negative Proteobacteria. Additionally, it provides a powerful and expansive set of chemical tools for the further investigation of quorum sensing pathways.

Introduction.

Bacteria produce and monitor low molecular weight molecules (autoinducers) to assess their population densities in a behavior called quorum sensing. The concentration of these signaling molecules in a given environment is proportional to the number of bacteria present. With a sufficient number of bacteria present (a "quorum"), bacteria will alter gene expression so as to carry out a range of processes that require the cooperation of a large number of cells, including secretion of virulence factors, biofilm formation, antibiotic production, bioluminescence, sporulation, and conjugation. These diverse processes have widespread and often devastating effects on human health, agriculture, and the environment. In the case of pathogenic bacteria, quorum sensing allows the bacteria to amass in sufficiently large numbers before launching a coordinated attack on a host and overwhelming its defenses. Symbiotic bacteria, in contrast, have co-opted quorum sensing pathways to commence mutually beneficial relationships with their hosts at high cell densities. As interception of quorum sensing represents a new strategy to control both pathogenesis and symbiosis, there is significant interest in the development of non-native ligands that can block or mimic native autoinducer signals and attenuate quorum-sensing outcomes. Such molecules would represent valuable tools to further study the molecular mechanisms of quorum sensing, and could potentially serve as scaffolds for new anti-infectives and biocontrol agents.

Figure 5:
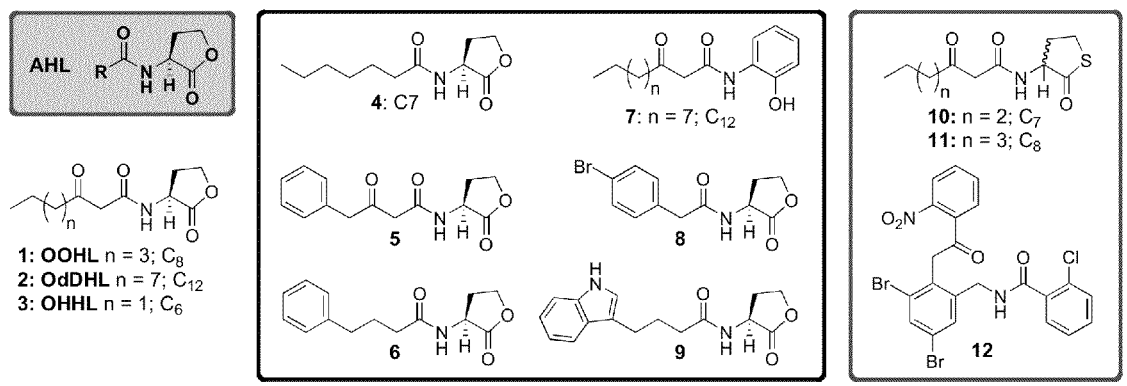
FIG. 5 illustrates generic structure for N-acylated-L-homoserine lactones (AHLs), and structures of selected native AHL ligands and known synthetic inhibitors of R protein function.
Figure 6:
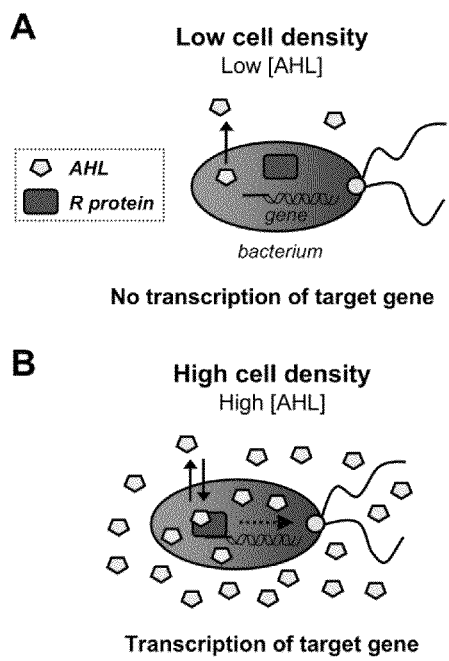
FIG. 6 illustrates a schematic of quorum sensing in gram-negative bacteria.

Quorum sensing is best characterized in the gram-negative Proteobacteria, which use diffusible N-acylated L-homoserine lactones (AHLs) and their cognate cytoplasmic receptors (R proteins) for intercellular signaling (FIG. 5). The AHL ligand is generated by an inducer synthase (I protein) at low basal levels, and high cell densities are required to achieve a sufficient intracellular concentration of ligand for R protein binding; thereafter, the AHL-R protein complex activates (or, in a few cases, represses) transcription of target genes involved in bacterial group behavior. A schematic of this process is shown in FIG. 6. Thus, through quorum sensing, bacterial populations can efficiently couple gene expression to fluctuations in cell-population density. To date, this signaling process has been most extensively studied in three gram-negative species: *Agrobacterium tumefaciens, Pseudomonas aeruginosa*, and *Vibrio fischeri*. As such, these three species represent the best model organisms for intervention with synthetic quorum sensing modulators.

*A. tumefaciens, P. aeruginosa*, and *V. fischeri* each utilize quorum sensing for remarkably different purposes. *A. tumefaciens* is a widespread plant pathogen and uses quorum sensing in its induction of crown gall tumors on plant hosts under the control of N-(3-oxo-octanoyl)-L-homoserine lactone (OOHL, 1; FIG. 5) and its receptor, TraR. TraR is the best characterized R protein to date, and is the only R protein for which a three-dimensional structure of the full length protein has been determined by X-ray crystallography. This structure was that of a ternary complex of TraR, OOHL, and DNA, and revealed that the TraR:OOHL complex binds DNA as a homodimer and that OOHL is completely engulfed in a hydrophobic pocket of TraR upon DNA binding. *P. aeruginosa* is both a plant and human pathogen and uses two AHL signaling molecules, N-(3-oxo-dodecanoyl)-L-homoserine lactone (OdDHL, 2; FIG. 5) and N-butanoyl-L-homoserine lactone (BHL), and two R proteins, LasR and RhlR, respectively, to control the expression of an arsenal of virulence factors that cause extensive tissue damage in infection, including elastase B and hemolysin. Recent work has shown that *P. aeruginosa* also uses quorum sensing to regulate biofilm formation. These is tremendous interest in AHL-medicated quorum sensing in *P. aeruginosa* due to the prevalence of this opportunistic bacterium in life threatening hospital-acquired infections and in chronic lung infections associated with cystic fibrosis. An X-ray structure of the N-terminal ligand binding domain of LasR complexed to OdDHL was recently reported, and exhibited a structure highly homologous to that of TraR. In contrast to these two bacterial pathogens, *V. fischeri* uses quorum sensing as part of beneficial symbiosis: this marine bacterium colonizes the light-producing organs of certain marine fish and squids and uses quorum sensing to initiate bioluminescence at high cell densities. Quorum sensing is mediated in part by N-(3-oxo-hexanoyl)-L-homoserine lactone (OHHL, 3; FIG. 5), and its cognate receptor, LuxR. As AHL-mediated quorum sensing was first reported in *V. fischeri*, the OHHL/LuxR system represents the canonical quorum sensing circuit in gram-negative bacteria.

Considerable research efforts over the past 20 years have focused on the design and synthesis of ligands that can disrupt AHL-R protein binding and inhibit quorum sensing outcomes in these three bacterial species, yet potent R protein antagonists remain scarce. The known antagonists are mainly structural mimics of native AHLs, and four of the most active R protein antagonists are shown in FIG. 5: N-heptanoyl-L-homoserine lactone (4), active against TraR; N-(3-oxo-phenylbutanoyl)- and N-(phenylbutanoyl)-L-homoserine lactones (5 and 6), active against LuxR, and the 2-aminophenol analog of OdDHL (7), active against LasR. Likewise, compounds exhibiting heightened activities relative to native AHLs (i.e., super-activators of quorum sensing) are also of significant interest, as they could potentially initiate bacterial behaviors at lower cell numbers than required in natural environments. However, only two such super-activators of quorum sensing have been reported to date, and their activity in vivo is yet to be established.

Clearly, new synthesis and design strategies are needed to expand the current set of quorum sensing modulators active in gram-negative bacteria. Unfortunately, the structures of known antagonists and agonists vary widely and their mechanisms of action are unclear; thus, no obvious rationales have emerged for new ligand design. Moreover, to our knowledge, the known antagonists and agonists of quorum sensing have only been examined in one bacterial species. Therefore, we currently do not know whether these compounds modulate a range of different R proteins or target one R protein specifically. As such, the molecular features that confer broad range activity or specificity to synthetic quorum sensing modulators in gram-negative bacteria remain unknown. The moderate sequence homology of the ca. 50 known R proteins in their putative ligand binding sites in 70-80%, and suggests that, if non-native AHLs target these sites, both broad spectrum and species specific ligands potentially could be developed. Ligands with either of these activity profiles would be of significant value as chemical probes to study quorum sensing, most notably in in vivo environments harboring multiple species.

To address these challenges, we have been engaged in the design of focused, combinatorial libraries of synthetic ligands for the modulation of quorum sensing in a range of bacterial species. This work has resulted in our recent discovery of two new and potent antagonists of R protein function in *A. tumefaciens* and *P. aeruginosa*, 4-bromo-phenylacetanoyl HL (8) and indole AHL (9) (FIG. 5). Here, we report the design and synthesis of four focused collections on non-native AHLs and the parallel evaluation of these compounds against the R proteins from *A. tumefaciens, P. aeruginosa*, and *V. fischeri*. Each of the libraries was designed to probe the role of key features of AHL structure on quorum sensing activity, including acyl chain length, lactone stereochemistry, and functionality on acyl group. These studies represent the first systematic investigation of non-native AHL function across multiple gram-negative bacterial species, and have revealed both an expansive new set of synthetic R protein agonists and antagonists and the most comprehensive set of structure-activity relationships for non-native AHL ligands reported to date. Furthermore, we have identified quorum sensing modulators that are either active in all strains or selective for only one, and we present a rationale for their differing modes of action. Several of these ligands are amongst the most potent activators or competitive inhibitors of R protein function known and represent powerful new chemical tools to probe bacterial communication. Together, the ligands described herein and the biological insights they provide have the potential to significantly broaden our current understanding of quorum sensing and its roles in host-bacteria interactions.

Experimental Section.

Chemistry.

All reagents were purchased from commercial sources (Acros, Alfa-Aesar, Maybridge, and Sigma-Aldrich) and used without further purification. Solvents were purchased from commercial sources (Aldrich and J. T. Baker) and used as is, with the exception of dichloromethane (CH$_2$Cl$_2$), which was distilled over calcium hydride immediately prior to use. All solid-phase syntheses were performed using aminomethyl polystyrene resin (NovaBiochem, 100-200 mesh; loading 1.1-1.2 mmol/g). Microwave-assisted solid-phase reactions were carried out using either Milestone or CEM commercial microwave (MW) reactors under temperature control. Full details of the instrumentation and analytical methods used in this work can be found in the Supporting Information.

Ligand Synthesis.

Figure 7:
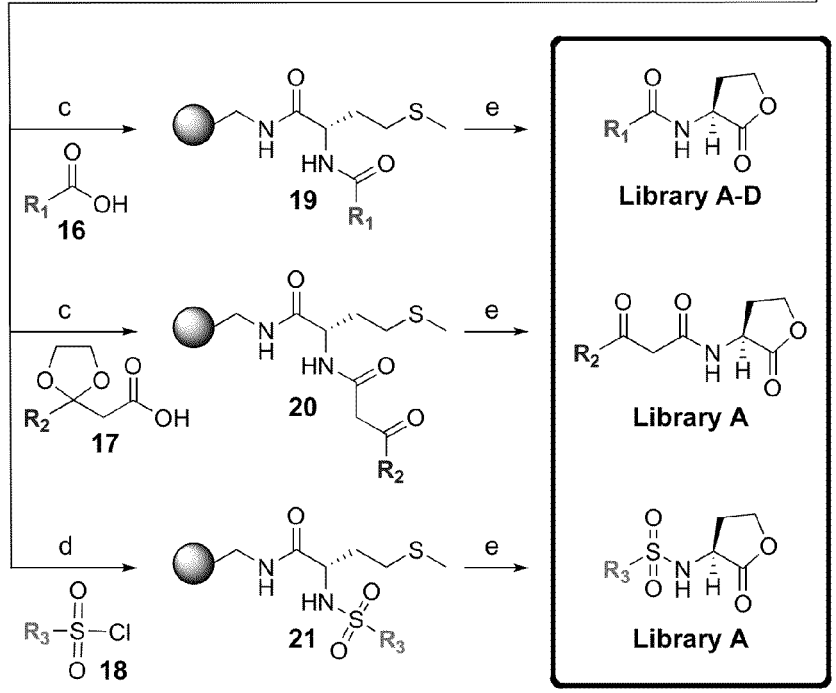
FIG. 7 shows a solid-phase synthetic route to AHL Libraries A-D.

AHL libraries A-D, native ligands OOHL (1), OdDHL (2), and OHHL (3), and control compounds 4-6, 8, and 9 were prepared according to FIG. 7 using reported methods on a 20 mg scale, except the final cyclization-cleavage step was performed at RT for 24 h. The 1,3-dioxolane protected β-keto acids building blocks (14) were prepared via a modified version of the methods reported by Barnick and Rathke. Sulfonyl chloride building blocks (15) were prepared according to the method reported by Castang et al. Control compound 7 was prepared in solution according to a reported method. Purities and isolated yields for AHL libraries A-D, native ligands, and control compounds were >93% and 55-85%, respectively. Compounds were submitted to biological assays following resin cleavage and an aqueous work-up without further purification.

Compound Handling.

Stock solutions of synthetic compounds (10 mM) were prepared in DMSO and stored at room temperature when not in use. Solvent resistant polypropylene or polystyrene 96-well multititer plates were used when appropriate for small molecule screening. The concentration of synthetic ligand and native ligands used in the primary antagonism and agonism assays and their relative ratio were chosen to provide the most obvious differences between inhibitors and activators.

Bacteriology.

All biological reagents were purchased from Fisher Scientific and used according to enclosed instructions. *Agrobacterium* minimal media (AB) was prepared as previously reported. Luria-Bertani (LB) and LB salt media (LBS) were prepared as instructed with pH=7.5 (LBS contained an additional 1.5% NaCl, 0.3% glycerol, and 50 nM Tris-HCl). Buffers and solutions (Z buffer, 0.1% aq. SDS, phosphate buffer, 1M Na$_2$CO$_3$) for Miller absorbance assays in *A. tumefaciens* and *E. coli* were prepared as described. The three bacterial reporter strains used in this study were: *A. tumefaciens* WCF47 (pCF372), *E. coli* DH5a (pJN105L pSC11), and *V. fischeri* ES114 (D-luxI). *P. aeruginosa* PAO1 was used in elastase B production assays. Absorbance and luminescence measurements were obtained using a PerkinElmer Wallac 2100 EnVision™ multilabel plate reader using Wallac Manager v1.03 software. A 595 nm filter was used for measuring bacterial cell density (OD$_{600}$). All assays were performed in triplicate.

*A. tumefaciens* Reporter Gene Assay Protocols.

For primary TraR agonism assays, an appropriate amount of concentrated control or AHL stock solution, to give a final concentration of 15 μM, was added to wells in a 96-well multititer plate. An overnight culture of *A. tumefaciens* WCF47 (pCF372) was diluted to an OD$_{600}$ of 0.1 in fresh AB minimal medium containing 400 μg/mL octopine and 50 μg/mL streptomycin. A 200 μL-portion of the diluted culture was added to each well of the multititer plate containing AHLs. Plates were grown at 28° C. for 18-20 h in a rotary shaking incubator (200 rpm). The cultures were then assayed for β-galactosidase activity following the Miller assay method. Briefly, 200 μL aliquots of bacteria from each of the wells were added to wells of a polystyrene 96-well plate and the OD$_{600}$ of each well was recorded. Next, 50 μL aliquots from each well were transferred to a solvent resistant 96-well plate containing 200 μL Z buffer, 8 μL CHCl$_3$ and 4 μL 0.1% aq. sodium dodecylsulfate (SDS). This suspension was mixed via repetitive pipetting, after which the CHCl$_3$ was allowed to settle. A 100-μL aliquot from each well was transferred to a fresh polystyrene 96-well plate, and 20 μL of substrate, o-nitrophenyl-β-D-galactopyranoside (ONPG, 4 μg/mL in phosphate buffer), was added at time zero. After the development of appropriate yellow color (ca. 15-35 min), the reaction was terminated by the addition of 50 μL of 1 M Na$_2$CO$_3$. Absorbance at 420 nm and 550 nm was measured for each well using a plate reader, and Miller units were calculated according to standard methods. Primary TraR antagonism assays were performed in a similar manner except the AHL or control was screened at 10 μM against 100 nM OOHL 1 (EC$_{50}$ of autoinducer in this strain).

*E. coli* LasR Reporter Gene Assay Protocols.

For primary LasR agonism assays, an appropriate amount of concentrated control or AHL stock solution, to give a final concentration of 15 μM, was added to wells in a 96-well multititer plate. An overnight culture of *E. coli* DH5a (pJN105L pSC11) grown at 37° C. was subculture by diluting ¹⁄₁₀ in fresh LB medium containing 100 μg/mL ampicillin and 15 μg/mL gentamicin and shaking at 37° C. until OD$_{600}$=0.3. Arabinose (4 mg/mL) was then added to induce the LasR promoter and a 200 μL-portion of this culture was added to each well of the multititer plate containing AHLs. Plates were grown at 37° C. for 2 hours in a rotary shaking incubator (200 rpm; OD$_{600}$=0.45). The cultures were then assayed for activity following the identical β-galactosidase assay protocols used in the *A. tumefaciens* reporter gene assays.

*V. fischeri* Reporter Gene Assay Protocols.

For primary LuxR agonism assays, an appropriate amount of concentrated control or AHL stock solution, to give a final concentration of 200 μM, was added to wells in a 96-well multititer plate. An overnight culture of *V. fischeri* ES114 (D-luxI) was diluted 1:10 with LBS medium: A 200-μL portion of the diluted culture was added to each well of the multititer plate. Plates were grown at RT with shaking (200 rpm) until the OD$_{600}$=0.35-0.4 (4-6 h). Luminescence then was measured and normalized to cell density per well. Primary LuxR antagonism assays were performed in a similar manner except the AHL or control was screened at 5 μM against 5 μM OHHL 3 (ca. EC$_{50}$ of autoinducer in this strain).

Dose Response Reporter Gene Assays.

The dose response reporter gene assays were performed according to the protocols outlined above, except the concentrations of control compounds and AHLs were between 0.02 and 2×10$^5$ nM. IC$_{50}$ and EC$_{50}$ values were calculated using GraphPad Prism software (v. 4.0) using a sigmoidal curve fit.

Elastase B Production Assay in *P. aeruginosa*.

Elastase B activity in *P. aeruginosa* was measured according to a previously reported method, with the following modifications. *P. aeruginosa* PAO1 was grown overnight in LB media at 37° C., after which it was diluted to an OD$_{600}$=0.1. Portions (2 mL) of this culture was added to test tubes containing synthetic compounds to give final concentrations of 20 μM or 200 μM and incubated for 12-14 h at 37° C. with 200 rpm shaking. The OD$_{600}$ was measured for each tube, after which the contents of the tubes were filtered through a 0.2 mm Whatman filter to remove all cellular matter. A 100 μL-aliquot of the supernatant was added to 900 μL of an Elastin Congo Red Solution (5 mg of Elastin Congo red substrate per 1 mL of 100 mM Tris-HCl, 1 mM CaCl$_2$ (pH 7.2)) and incubated for 12 h at 37° C. with 250 rpm shaking. The contents of these tubes were then filtered in order to remove unreacted Elastin Congo red substrate. Elastase B activity was then calculated (normalized) by dividing the absorbance of the cleaved Congo red ($OD_{492}$) by the cell density ($OD_{600}$ of the cells before first filtration).

Results and Discussion.

Ligand Design and Synthesis.

AHLs bearing non-native acyl chains represent the most extensively studied structure class of non-native quorum sensing modulators in *A. tumefaciens*, *P. aeruginosa*, and *V. fischeri*. Modifications to the lactone ring of AHLs, including inversion of stereochemistry and replacement of the lactone with different carbocyclic or heterocyclic functionalities, have been examined to a lesser extent. Clear structure-activity relationships (SAR) for quorum sensing modulation are yet to be established due to the relatively limited set of ligands examined to date. The use of different bacterial reporter gene strains and assay procedures to assess agonistic or antagonistic activity has further hindered comparison between past studies. Our analysis of this prior work revealed the following basic activity trends for synthetic R protein modulators in *A. tumefaciens*, *P. aeruginosa*, and *V. fischeri*: (1) changing the number of carbons in the acyl chain relative to the native AHL could either weaken a ligand's agonistic activity and/or convert the ligand into a weak antagonist, (2) introduction of terminal phenyl groups to the acyl tail could result in compounds with antagonistic activity, and (3) inversion of lactone stereochemistry (L to D) nearly abolished agonistic and antagonistic activity for certain AHLs with native and non-native acyl chains.

These trends did not provide us with an obvious strategy for the rationale design of new and selective modulators of quorum sensing in these three species. However, they did offer a foundation from which to design and construct focused libraries of non-native AHL ligands to systematically examine the structural features required for agonistic or antagonist activity across the three species. In this study, we sought to investigate three broad structural features of AHLs: (1) acyl chain length, (2) lactone stereochemistry, and (3) functional group diversity in the acyl chain. We designed four small, focused libraries of AHLs (A-D) that allowed us to probe each of these features individually and in tandem. These libraries were synthesized rapidly using a microwave-assisted, solid-phase route to AHLs previously reported by our laboratory (FIG. 7). This route allows for the straightforward construction of either L- or D-lactones through the use of either L- or D-methionine (Met, 11) in the initial acylation step, and the introduction of a wide variety of acyl groups, including simple alkyl, 3-keto-alkyl, and sulfonyl moieties (13-15). The ca. 100 AHLs were isolated with excellent purities (ca. 95%), good yields (>65%), and in sufficient quantities (i.e., 30 mg per compound) for multiple biological experiments (see Experimental Section). This route was also utilized for the synthesis of native AHLs (1-3) and known antagonists (4-6, 8, and 9) for use as essential control compounds in our biological assays. Discussions of the design of each library and its analysis in primary R protein antagonism and agonism assays in *A. tumefaciens*, *P. aeruginosa*, and *V. fischeri* are outlined in turn below.

Quorum Sensing Agonism and Antagonism Assays.

Non-native ligands are commonly assessed for R protein agonism and antagonism using bacterial reporter strains. These strains lack their AHL synthase (I) genes, but retain their native R genes. In the presence of exogenously added AHL ligand, the R protein-AHL complex will activate transcription of a promoter (most commonly an i gene) that controls reporter gene expression. Therefore, R protein activity, and consequently ligand activity, can be measured using standard reporter gene read-outs based on absorbance, luminescence, or fluorescence. This method provides a straightforward and high-throughput assay for small molecule agonism and antagonism of R protein function.

We selected three bacterial reporter strains for the R protein agonism and antagonism assays in this study: *A. tumefaciens* WCF47 (pCF372), *E. coli* DH5a (pJN105L pSC11), and *V. fischeri* ES114 (Δ-luxI). This *A. tumefaciens* strain produces the enzyme β-galactosidase upon TraR activation and ligand activity can be measured using standard Miller absorbance assays in the presence of a colored enzyme substrate (i.e., o-nitrophenyl-β-D-galactopyranoside (ONPG)). The *E. coli* strain harbors LasR from *P. aeruginosa* and also reports LasR activity by b-galactosidase production; we therefore measured LasR activity in this strain using Miller absorbance assays analogous to those for TraR in *A. tumefaciens*. We initially examined a Δ-lasI Δ-rhlI derivative of *P. aeruginosa* with a green fluorescent protein (GFP) reporter gene in these primary assays, as we sought to assay our synthetic ligands in the native backgrounds for each of the three R proteins; however, unacceptably large error values in the assay data forced us to seek this alternate strain (data not shown). We found that this heterologous *E. coli* system provided reproducible data, albeit the differences between R protein activators and inhibitors were somewhat muted relative to the other two strains (see below). Lastly, the *V. fischeri* strain retains its native lux operon, which allows LuxR activation or inhibition to be measured by luminescence. We recently found that this strain, while not typically used to assess the activity of non-native AHL ligands against LuxR, is straightforward to manipulate and provides highly reliable small molecule screening data.

Libraries A-D were screened in competitive R protein antagonism and agonism assays in these three reporter strains (see Experimental Section for details). Competitive antagonism assays were performed in the presence of native AHL ligand and synthetic ligand, at ratios ranging from 1:1 to 100:1, respectively, against the native ligand at its $EC_{50}$ value. Agonism assays were performed with synthetic ligand alone. The native ligands OOHL, OdDHL, and OHHL and the known R protein inhibitors 4-9 served as critical controls for these experiments (FIG. 5). None of the library members or controls displayed insolubility or affected bacterial growth over the time course of these assays. Further, no ligand was found to degrade (by lactonolysis, proteolysis, or reaction with biological reagents) over the time course of these assays (as determined by LC-MS or GC-MS).

AHL Library A: Design and Primary Assay Data.

Figure 8:
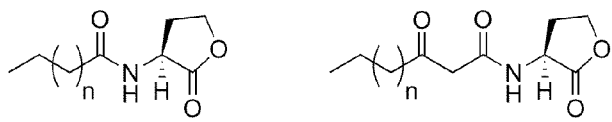
FIG. 8 illustrates structures of AHL Library A.
Figure 8:
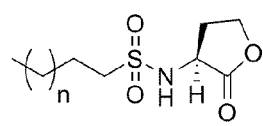

Library A was designed to test the effects of different aliphatic acyl, 3-keto acyl, and sulfonyl groups on AHL ligand activity in the three bacterial species. The structures of this 16-member focused library are shown in FIG. 8, and represent the most structurally simple AHL derivatives examined in this study. AHLs A1-A6, A9, and A7 are naturally occurring AHL utilized by other gram-negative bacteria for quorum sensing and have been evaluated in a range of R protein agonism or antagonism assays previously. Several of the sulfonyl compounds in Library A, C10-C15, were reported by Castang et al. to inhibit LuxR activity in a heterologous *E. coli* reporter strain at a low to moderate level, with activity maximal at a 5-carbon chain length (i.e., C11) and decreasing at successively longer carbon chains. Collectively, however, these ligands have not been examined in the three reporter strains utilized in this study. Therefore, Library A was designed to provide important benchmark data for comparison of ligand antagonistic and agonistic activity between the strains.

The antagonism and agonism assay data for Library A is listed in Table 1, and reveal several prominent trends in ligand activity within and between species. Turning first to the antagonism data, each of the R proteins was inhibited by control native ligands that were close in carbon length to their native AHL (entries 1-3), corroborating previously reported experiments. In addition, all of the control antagonists showed modest to strong inhibitory activity in the three strains (entries 4-6, 8 and 9), with the exception of 2-aminophenol A15 that was surprisingly inactive (entry 7). This latter result contrasted with previous reports that A15 is a strong inhibitor of LasR activity in similar assays; however, these studies involved a different reporter strain. The simple aliphatic AHLs A1-A6 displayed increasing and decreasing inhibitory activity trends against the three R proteins that correlated with increasing carbon number, with inhibition being maximal at $C_8$ (A3) for LasR and $C_{10}$ for TraR and LuxR (A4). The long chain, 3-keto AHLs A9 and A7 exhibited minimal antagonistic activity against TraR and LasR, yet were moderate to good inhibitors of LuxR, respectively (entries 16-17). Interestingly, 3-keto-AHLs with longer acyl chains ($C_{12}$: A8 and $C_{14}$: A7) displayed stronger inhibitory activity in LuxR relative to those with chains closer in length to its native ligand (C6: OHHL).

Antagonism by sulfonyl HLs (C10-C17) against the three R proteins also correlated with carbon number, and the most striking trends in inhibitory activity were observed against TraR and LuxR (entries 18-25). Inhibition was maximal at $C_6$ (C12) in TraR, with activity largely increasing up until this carbon length and then decreasing thereafter. Sulfonyl HL C12, with a seven atom long acyl tail including the sulfur, displayed analogous inhibitory activity as control heptanoyl HL A12 (entry 4; 93%), suggesting that seven atoms in AHL acyl tails enhances antagonistic activity in TraR. In LuxR, inhibitory activity generally increased with increasing carbon length, with $C_9$ (C15) exhibiting the highest level of inhibition (entry 23; 81%). Here, inhibitory activity increase gradually from $C_4$ to $C_9$ and decreased only minimally at the longer chain lengths tested (C16-C17). These results directly contrast with those of Castang et al. for sulfonyl HLs (see above) and highlight the differences in ligand activity observable using native and heterologous reporter strains in these primary screening assays. Again, the sulfonyl HL with 10 atoms in its acyl tail (C15) and the decanoyl AHL (A4) were the most active inhibitors of their structure class, indicating that acyl chain atom number also plays a role in antagonistic activity against LuxR. Finally, the sulfonyl HLs displayed only weak to moderate inhibition against LasR, with the longest chain compound studied (C17: C11) displaying the highest inhibitory activity (entry 25; 21%). In contrast to TraR and LuxR, the dodecanoyl AHL (A12) did not inhibit LasR at a similar level as this sulfonyl HL with 12 atoms in its acyl tail, but rather activated LasR (see below). Overall, these studies confirmed that the length of acyl tail on both synthetic and native AHLs plays an exquisite role in antagonistic activity in these three strains. Further, potent antagonists were identified that exhibit selectivity either for a specific R protein (most notably, C12 against TraR) or for all three R proteins (A3 and A4).

Far fewer synthetic agonists were identified in Library A relative to antagonists (Table 1). None of the ligands agonized TraR to an appreciable level. This result corroborates TraR agonism data reported by Zhu et al. for related AHL derivatives. As OOHL appears to be completely engulfed in the TraR ligand binding site in the X-ray crystal structure of the TraR:OOHL complex, and is required for the proper folding TraR, it is reasonable to speculate that specific interactions in this site must be met for the proper folding and activation of TraR. Similarly, only a few ligands activated LuxR, with C and C aliphatic AHLs (A2 and A12) and 3-keto-C AHL (OOHL) displaying ca. 25% activation at 200 mM. Thus, within Library A, only compounds with structures closely related to the native ligand for LuxR (OHHL) were LuxR agonists.

The results from the LasR agonism screen of Library A were more striking. Here, we identified two ligands that substantially activated LasR (ca. 85% activation at 5 mM): $C_{12}$ AHL A5 and 3-keto-$C_{14}$ A7 (entries 14 and 17). Moreover, these two ligands selectively activated LasR relative to TraR and LuxR. The $C_{10}$ AHL (A4) and OOHL also displayed agonistic activity, albeit reduced (544%; entries 1 and 13), indicating that in analogy to LuxR, AHLs in Library A with structures most similar to the native ligand for LasR (OdDHL) were effective LasR agonists. These data trends correlated with those reported by Passador et al. for the same compounds (yet in an alternate E. coli LasR reporter strain). However, these researchers also report 3-keto-$C_{10}$ AHL (A9) to exhibit analogous agonistic activity as 3-keto-$C_{14}$ (A7); the former ligand failed to activate LasR in our assays (entry 16). This result is puzzling, in view of the structural similarity of this ligand to the other moderate to strong LasR activators that we identified (A5, A7, and A4). Likewise, we also observed that the 2-aminophenol control antagonist, A15, which failed to inhibit LasR in our E. coli reporter strain (see above), exhibited weak agonism instead in this assay (entry 7; 18%). These differences in activity for ligands A9 and A15 further exemplifies the disparities that can arise between small molecule screening data acquired in different reporter strains, and underscores the need for caution in comparing these separate studies.

Overall, the agonism screening data was in stark contrast to the antagonism data for Library A. Very few ligands in Library A were capable of activating either TraR, LasR, or LuxR, yet the majority of the library displayed some level of antagonism in these primary assays, ranging from weak to almost complete inhibition. Making the assumption that these ligands could target R proteins (see below), we interpreted these initial results using the following model: these three R proteins can bind a range of different AHL ligands, and these ligands can displace the native AHL ligand at the concentrations tested. However, only a few ligands are capable of binding and activating the R protein at these concentrations. In Library A, these ligands were very close in structure to the native ligand for the R protein. Zhu et al. forwarded a similar hypothesis in their study of synthetic modulators of TraR. We built on this rationale as we examined Libraries B through D in subsequent studies.

AHL Library B: Design and Primary Assay Data.

We designed Library B to investigate the roles of the following AHL structural features on R protein antagonism and agonism: (1) lactone stereochemistry, (2) acyl group aromaticity and (3) alkyl "spacer" length between aromatic groups and the HL ring. We examined these three features by perturbing the structures of known active compounds: an agonist, OOHL, the control antagonists, A13 and A14, and our previously reported antagonists, 4-bromo-phenylacetanoyl HL (4-bromo PHL, A17) and indole AHL A18 (FIG. 5). The effect of lactone stereochemistry on R protein activation has only been examined for a limited set of native AHLs, and to our knowledge, was yet to be examined in synthetic AHL R protein antagonists. Further, the role of acyl group aromaticity and spacer length on ligand activity, specifically in our antagonists A17 and A18, was unknown. The structures of Library B are shown in FIG. 9, and their antagonism and agonism data in the three reporter strains, along with data for pertinent control compounds, are listed in Table 2.

Examination of Library B in the reporter gene assays revealed several intriguing SARs that dictated AHL ligand activity against R proteins. First, the D-enantiomer of OOHL (A24) displayed no antagonistic activity across all three strains (entry 8, Table 2). Likewise, inversion of stereochemistry in control antagonists A13 and A14 (to give D-AHLs A25 and A26) reduced their inhibitory activity by ca. 40-60% in TraR (entries 9 and 10). A similar ca. 40% reduction in inhibitory activity was also observed for A26 in LuxR; however, A25 exhibited analogous activity as its L-stereoisomer A13 (ca. 45%). The activity trends for A25 and A26 were yet more complex in LasR; here, A25 displayed strong agonistic as opposed to antagonistic activity (see below), while A26 inhibited LasR at a comparable level to its L-stereoisomer A14 (ca. 20%). In contrast, the D-stereoisomers isomers of our control 4-bromo and indole antagonists, A28 and A29, showed uniformly reduced inhibitory activity across all three strains, ranging from ca. 90% reduction for A28 in TraR to ca. 50% for both A28 and A29 in LasR and LuxR (entries 11 and 12). These results suggest that AHL stereochemistry, in concert with acyl chain structure, plays a multifaceted role in AHL-medicated R protein activation and inhibition. One effect is clear, however; inversion of lactone stereochemistry does not completely abolish antagonistic activity for the ligands examined in this study.

Figure 9:
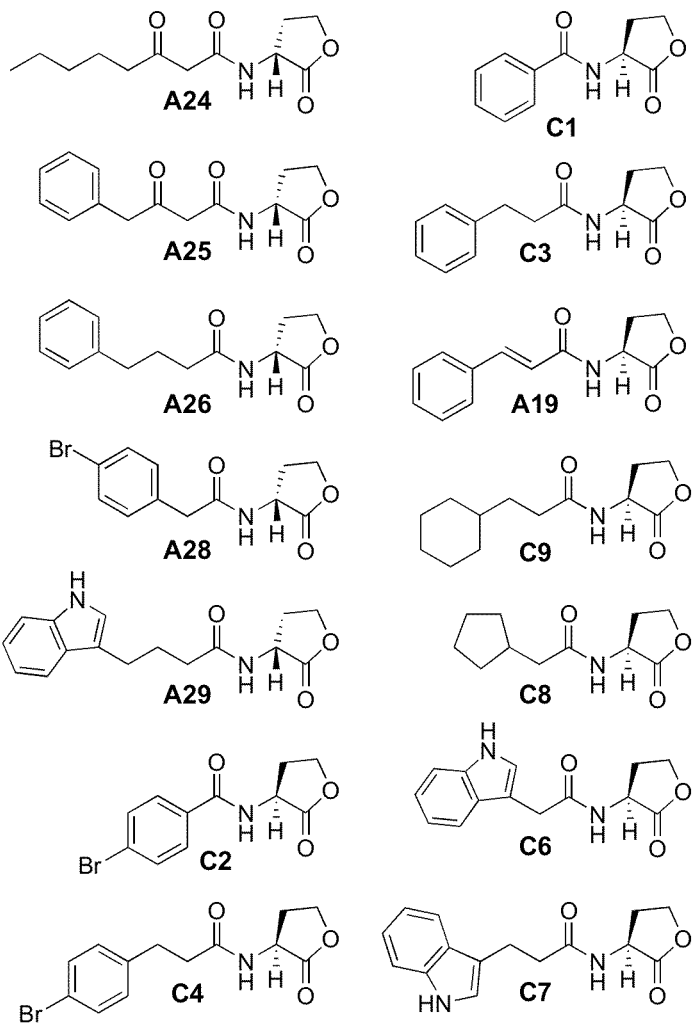
FIG. 9 illustrates structures of AHL Library B.

The remaining members of Library B were designed to probe the role of acyl chain structure on antagonistic activity for controls A17 and A18 (FIG. 9). Shortening the alkyl spacer in 4-bromo PHL A17 by one carbon (to give C2) dramatically reduced its inhibitory activity in all three R proteins, ranging from 90% in TraR to ca. 50% in LasR and LuxR (entry 13, Table 2). However, lengthening the alkyl spacer by one carbon delivered a ligand (C4) with equivalent inhibitory activity to A17 in TraR and LuxR, and two-fold higher inhibitory activity in LasR (entry 14). Notably, C4 was also almost two-fold more active than the potent control antagonist A18 (52% vs. 36%, respectively), and amongst the most potent inhibitors of LasR identified in these primary assays. Removing the 4-bromide substituent from benzoyl AHL C2 (to give C1) had little effect on an already low antagonistic activity, while removing the 4-bromide from the potent antagonist C4 (to give C3) had a more significant impact, reducing inhibition by at least 50% across all three strains (entry 16). In turn, the cyclohexyl analog of C3, AHL C9, displayed slightly enhanced antagonistic activity in TraR and LasR relative to C3, and activity against LuxR comparable to the most potent inhibitors, C4 and A17 (ca. 80%; entry 18). The related cyclopentyl analog, C8, exhibited similar trends, albeit muted, in antagonistic activity as C9 across all three strains. Introduction of unsaturation into the alkyl spacer (i.e., in AHL A19), as opposed to in the cyclic moiety, had little impact on inhibitory activity relative to the saturated analog, C3. Finally, shortening the alkyl spacer of indole AHL A18 by one or two carbons (i.e., in C6 and C7) had only a minor effect on inhibitory activity in TraR, while these shorter indole analogs were ca. 40% less active than A18 in LuxR (entries 20 and 21).

These results for Library B reveal several trends in antagonistic activity for synthetic AHLs: (1) a flexible carbon spacer of at least one carbon and a 4-bromo substituent is necessary for appreciable activity in ligands structurally related to 4-bromo PHL A17, with AHL C4 the most active inhibitor across the three R proteins, (2) aromatic functionally was not essential for LuxR inhibition in ligands related to A17 (e.g., AHL C9), and (3) a three-carbon spacer was optimal for inhibition in ligands structurally related to indole A18 and most apparent for LuxR.

In analogy to Library A, very few agonists were identified in screening Library B. Indeed, only one ligand with considerable agonistic activity against one R protein, LasR, was identified: the D-enantiomer of control antagonist 13, D-AHL A25 (entry 9, Table 2). This ligand was capable of activating LasR at 84% relative to the native ligand OdDHL under the assay conditions. Indeed, AHL A25 is unique, as this D-AHL displays strong agonistic activity and its L-stereoisomer, AHL 13, is virtually inactive in LasR (but is a good to strong antagonist in TraR and LuxR, respectively; entry 4). This trend is opposite to what has been observed for native AHL ligands, where the L-stereoisomer is an active agonist and the D-stereoisomer is almost inactive; we observed this latter trend in the current study for OOHL. The reasons behind this trend reversal for A25 remain unclear, and in view of the complicated antagonistic activity displayed by the limited set of D-enantiomers in Library B (see above), suggests that lactone stereochemistry will bean important feature to probe in the future design of synthetic R protein modulators. However, despite our current lack of a mechanistic understanding for its activity, D-AHL A25 represents a new and selective tool to probe LasR activity, and therefore quorum sensing, in *P. aeruginosa*.

AHL Library C: Design and Primary Assay Data.

Figure 10:
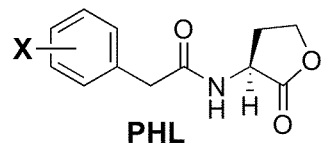
FIG. 10 illustrates structures of AHL Library C.

Control compound 4-bromo PHL A17, previously reported by our laboratory to be a potent antagonist of TraR and LasR, is one of the most active R protein antagonists known. Our examination of Library B above revealed that subtle structural changes to the acyl chain of PHL All had dramatic effects on inhibitory activity against TraR, LasR, and LuxR. Specifically, the presence or absence of a 4-bromo substituent on the aromatic ring in AHLs C2, C4, C1, and C3 had a significant impact on activity relative to A17. In Library C, we sought to systematically examine the role of substituents on the phenylacetanoyl group on PHL-mediated R protein antagonism and agonism. The structures of Library C are shown in FIG. 10; each of the 25 library members was designed to test the effects of electronically or sterically different functionalities and their position on the acyl group phenyl ring. We recently examined a subset of Library C is LuxR antagonism and agonism assays, and identified several potent PHL inhibitors and activators of LuxR in the same *V. fischeri* strain utilized in this study. These preliminary studies provide a foundation for this systematic examination of a Library C across the three strains.

The antagonism and agonism primary screening data for Library C and pertinent control compounds are listed in Table 3. These assays identified the largest percentage of potent antagonists and agonists in this study (37% of the library have activities of ≥50% in at least one strain), which serves to validate the PHL structure as a scaffold for the design of potent modulators of R protein function. Furthermore, these assays revealed that both antagonistic and agonistic activity was exquisitely affected by the nature and position of the substituents on the PHL phenyl ring, as predicted. As observed in Libraries A and B, the majority of the active ligands in Library C were antagonists. Replacement of the 4-bromide of PHL A17 with a hydrogen in B3 largely abolished inhibitory activity across the three strains (entry 5, Table 3), in analogy to what was observed for the one carbon longer analogs C4 and C3 in Library B, respectfully. The mono-halogen (B4-B11, and B13-B15) and nitro series (B16-

B18) exhibited remarkable trends in inhibitory activity against all three R proteins (entries 6-19). These trends were most pronounced in TraR. Namely, inhibition dramatically increased (from ca. 1% to 90%) as the halogen or nitro substituents were moved from the 2- to the 3- to the 4-positions on the PHL phenyl ring. Inhibition also increased with substituent size, with 4-iodo PHL (B13) and 4-nitro PHL (B16) inhibiting at the highest level in this series (ca. 90%). The mono-halogenated PHLs displayed the same trends in antagonistic activity, albeit slightly muted within each series, in LuxR; however, the nitro series (B16-B18) displayed a more complicated activity pattern, with 4-nitro PHL (B16) only moderately inhibiting LuxR (47%) and, more notably, 3-nitro PHL (B17) dramatically activating LuxR (entries 17 and 18; see below). Uniform, yet still different, antagonistic activity trends were observed for the mono-halogen and nitro PHL series in LasR. Here, the 3-substituted PHL displayed the high inhibitory activity, followed by the 4- and 2-substituted derivatives. Antagonism still increased with increasing substituent size, in analogy to TraR, with the 3-iodo (B14) and 3-nitro (B17) exhibiting the highest antagonistic activity in LasR for the series (ca. 55%). Moreover, these two ligands were the most potent LasR inhibitors identified in these primary assays. A final halogenated PHL, pentafluoroaromatic PHL (B19), was designed to examine whether a reversed aromatic quadrupole could enhance PHL-mediated R protein modulation; this ligand displayed minimal inhibitory activity in TraR and LasR that was analogous to its non-fluorinated analog B3, and only low inhibitory activity (40%) against LuxR (entry 20), suggesting that such interactions, if operative, do not play a significant role in ligand activity.

The remaining PHLs in Library C were designed to further probe the effects of electronics and sterics in the 4-position of the acyl chain phenyl ring on R protein modulation. Both the 4-azido PHL (B20) and 4-phenyl PHL (B21) were moderate to strong inhibitors of TraR and LuxR (ca. 70%, entries 21 and 22, Table 3). The activity of azido PHL (B20) is particularly notable, as this inhibitor could have value as a potential photoaffinity labeling tool for R proteins and provide insights into the ligand binding site for PHLs. Likewise, 4-phenyl PHL (B21) instructed us that sterically larger groups could be tolerated on the phenyl ring of PHL-derived R protein inhibitors. This finding shaped our design of the final AHL library in this study, Library D (see below). Interestingly, neither B20 nor B21 displayed significant inhibitory activity in LasR.

The 4-methyl and 4-perfluoromethyl PHLs (B24 and B23) exhibited striking and opposite activities in the antagonism assays. The 4-methyl PHL B24 was a weak to moderate inhibitor of all three R proteins, antagonizing at up to a 4-fold lower level relative to the 4-bromo PHL control (A17). As a methyl group is roughly equivalent in steric size to a bromide, this activity trend indicated that substituent size alone does not dictate inhibitory activity. In contrast, the 4-perfluoromethyl PHL B23 displayed equivalent antagonistic activity as A17 in all three strains. This result suggests, along with the other antagonism data outlined above for Library C, that electron-withdrawing and lipophilic groups in the 4-position enhance PHL inhibitory activity against R proteins. This hypothesis is further corroborated by the low to moderate antagonistic activity displayed by PHLs B26, B25, B27-B29, all which contain electron-donating in the 4-position of the PHL phenyl ring. Further, the two PHLs in this set with hydrogen bond donors in the 4-position (i.e., 4-amino (B26) and 4-hydroxy (B27) PHLs) are the amongst the weakest inhibitors in Library C, suggesting a structural feature (and potential intermolecular interaction) that can lower PHL inhibitory activity.

The agonism assays for Library C revealed six PHLs that were capable of R protein activation (Table 3). The most potent agonists were highly selective for LuxR, with only 4-N-tertbutoxycarbonyl-PHL (B25) slightly activating LasR (27%, entry 26), and no PHLs activating TraR. We focus on the LuxR activators here. Again, we observed striking trends in the activities for PHLs with halogen and nitro groups. In contrast to the antagonism data for these PHLs in LuxR, the 3-substituted compound in each series showed the strongest activity relative to the 2- and 4-substituted derivatives, with the 3-bromo B10, 3-chloro B8, and 3-nitro B17 PHLs exhibiting at least 60% luminescence induction relative to native OHHL at the same concentration (200 mM). Remarkably, simply shifting substituents on the PHL phenyl ring by a single carbon converted these ligands from LuxR antagonists to LuxR agonists. Moreover, 3-nitro PHL B17 was able to induce 29% higher luminescence than the native ligand for LuxR, OHHL, in this primary assay (entry 18). This result was extraordinary, and explained the unusual inhibition trend for the nitro PHL series in LuxR (B16-B18; see above). Few super-activators of R protein activity have been reported; therefore, our discovery of 3-nitro PHL B17 as a super-activator of LuxR is significant. Finally, the 3-iodo PHL (B14) and 4-nitro PHL (B16) displayed antagonism in these assays, albeit at considerably lower levels relative to B10, B8, and B17 (ca. 25%).

Overall, the screening data for Library C indicate that the PHL structure is a highly versatile scaffold for the design of both R protein antagonists and agonists, and that seemingly simple structural modifications to the PHL phenyl ring can have a major effect on ligand activity. Most notably, these structural modifications can convert potent antagonists into agonists. These studies have revealed some of the most potent and species specific R protein modulators in this study, including 4-iodo PHL (B13) that inhibits all three R proteins, 3-nitro PHL (B17) that strongly inhibits LasR but also super-activates LuxR, and 4-phenyl PHL (B21) and 4-trifluormethyl PHL (B23) that strongly inhibit TraR and LuxR but are considerably less active against LasR in these primary assays. Again, we interpreted these differences in activity to reflect different binding modes of these ligands for their target R protein (see below). The PHL antagonists can bind and displace the native ligand over the concentration tests in these assays; however, and only the PHL agonists are capable binding in a mode that will activate the target.

AHL Library D: Design and Primary Assay Data.

Library D (FIG. 11) contained the most structurally diverse set of AHLs in this study, and was designed to broadly examine the effects of a range of different acyl chains on AHL-mediated R protein antagonism and agonism. These acyl chains differed significantly in terms of overall size and the type and placement functional groups. However, in view of the numerous active PHL ligands identified in Library C, we deliberately installed aromatic functionality (or at least one p-system) in the acyl chains of the majority of Library D. For ease of synthesis, we also selected acyl side chains that could be installed using commercially available carboxylic acids. The competitive antagonism and agonism assay data for Library D and selected control compounds is listed in Table 4.

Library D contained several new and potent synthetic inhibitors of TraR, LasR, and LuxR. The most active compounds and those displaying interesting SAR trends are described here. AHLs A23, D1-D3, and A20 displayed negligible inhibitory activity against TraR, and only low to modest inhibitory activity against LasR and LuxR, suggesting that their compact, unsaturated and/or heterocyclic acyl groups significantly reduced activity against these three R proteins (entries 10-14, Table 4). AHL D13, in contrast, was a strong inhibitor of TraR (90%), a decent inhibitor of LuxR (68%), and a moderately weak inhibitor of LasR (28%; entry 15). A clear rationale for the heightened antagonistic activity of D13 relative to A23, D1-D3, and A20 was not obvious. Interestingly, enlarging the substituent in the 4-position of the aromatic ring from a methyl group in D13 to an n-propyl group in D12 halved the inhibitory activity in TraR and LasR, yet had no effect on inhibitory activity against LuxR (entry 16). The AHLs in Library D with heterocyclic (D4), aromatic (D5, D6, A21, and D11), or carbocyclic functionality (D9) directly adjacent to the carbonyl of the acyl group exhibited minimal inhibitory activity against TraR. Only two AHLs in this group (D6 and D11) were reasonably strong inhibitors of LuxR (ca. 60%); notably, these two AHLs both contained benzoyl groups and had the longest acyl chains of this ligand set (entries 20 and 22). AHL D11 was also a modest inhibitor of LasR, yet D6 displayed only minimal activity against LasR. The cyclohexyl AHL derivative D9 was only a strong inhibitor of LasR, with activity analogous to that of the indole AHL control A18 (36%; entry 23).

The three AHLs in Library D with phenyl ether functionality in their acyl chains (D10, D14, and D15) displayed clear trends in antagonistic activity across the three strains. Notably, these three compounds had a two atom spacer between the carbonyl group and the aromatic ring in their acyl chains, analogous to the potent inhibitor C4 identified in Library B (see above). First, all three phenyl ether AHLs were only modest inhibitors of LuxR (ca. 45%; entries 24-26, Table 4). However, 4-trifluoromethyl phenyl ether AHL D10 was a potent inhibitor of TraR and the strongest inhibitor of LasR identified in Library D (90% and 49% inhibition, respectively; entry 24). The two structurally-similar 4-keto phenyl ethers (D14 and D15) exhibited disparate activates in both TraR and LasR; D14 was virtually inactive against TraR, while D15 was similar in activity to D10 and one of the most potent inhibitors of TraR uncovered in this study (entries 25 and 26). Likewise, D15 was 50% more active against LasR relative to D14, albeit with lower antagonistic activity overall relative to that observed in TraR. Interestingly, compounds D14 and D15 only differ in the placement of a substituent on the aromatic ring of the acyl group, with D14 displaying a 2-substituent and D15 a 3-substituent, respectively. This result suggests that, similar to the PHL series in Library C, inhibitory activity can increase in this phenyl ether series when substituents on the aromatic ring are placed closer to the 4-position. Again, subtle changes to aromatic acyl chains had significant effects on ligand activity in these antagonism assays.

The remaining four members of Library D (D7, D8, C5, and B22) contained the most sterically bulky acyl chains examined in this study. These four AHLs exhibited minimal inhibitory activity against TraR, analogous to the low antagonistic activity observed for the relatively bulky AHLs D4-D6, A21, D11, and D9 in TraR. This result suggested that TraR cannot accommodate bulky AHL ligands in its ligand binding site, and is in accord with the X-ray crystal structures of TraR that show a rigid and enclosed binding site. In contrast, the most sterically bulky ligand of this set (D7) was a strong inhibitor of LasR and the most active of the four (entry 27, Table 4), indicating that LasR can more easily accommodate AHL ligands with bulky acyl chains relative to TraR. Finally, AHLs D7 and D8 were only weak inhibitors of LuxR. However, the azobenzene AHL derivatives C5 and B22 displayed medium to moderately strong antagonistic activity against LuxR (46% and 63%, respectively; entries 29 and 30). These compounds are of interest due to the photoisomerization ability of the azobenzene moiety; for example, their antagonistic activity could be altered upon cis/trans isomerization, as this conformational shift may cause the ligand to dislodge from (or bind differently in) the ligand binding site. These azobenzene AHL ligands (C5 and B22), along with the 4-azido PHL antagonist (B20) identified in Library C, could represent novel photoactive tools for the study of R protein function; such experiments are the focus of on-going studies in our laboratory.

Similar to Library A-C, the agonism screen of Library D revealed few synthetic agonists. Indeed, no library members were agonists of TraR and LuxR. Three ligands (D9, D10, and D7), however, were weak activators of LasR (ca. 33%, entries 23, 24, and 27; Table 4). The structures of these AHLs were not highly similar, but each had a relativity bulky acyl chain containing aromatic functionality. Intriguingly, these three ligands were also the most potent antagonists of LasR identified in Library D (see above). Moreover, their percent antagonistic activities were approximately equivalent to their percent agonistic activities. The concentration of synthetic ligand tested in the LasR antagonism and agonism assays was identical (5 mM), while the antagonism assays also contained the native ligand OdDHL (A8, at 7.5 nM). This result suggested that, at such a high level of synthetic ligand relative to OdDHL in the antagonism assays (ca. 1000-fold), the synthetic ligand was simply out competing the native ligand for LasR, and the percent antagonism measured in this assay was actually percent agonism. Therefore, the synthetic ligands can bind and activate LasR at 5 mM, but not to the same level as OdDHL at 7.5 nM alone. This interpretation implies that D9, D10, and D7 are not antagonists of LasR at 5 mM, but rather are competitive weak or partial agonists, and had a significant impact on the development of our future hypotheses for the mechanism of R protein modulation by the active ligands identified in this study (see below).

Examination of Synthetic LasR Antagonists in a Virulence Factor Production Assay.

As the primary assays for LasR antagonists and agonists were preformed in a heterologous *E. coli* reporter strain, we sought to determine if the active ligands identified in these screens also showed activity in the native strain for LasR, *P. aeruginosa*. Such experiments would test the validity of using this *E. coli* reporter strain for the identification of modulators of LasR in *P. aeruginosa*. We performed elastase B production inhibition assays in *P. aeruginosa*, as this assay provides a straightforward method for the examination of LasR activity in wild-type *P. aeruginosa*. The metalloprotease elastase B is a virulence factor that is produced by *P. aeruginosa* and under the control of LasR. Synthetic ligands that inhibit LasR should therefore also inhibit the production of elastase B, and this can be measured by a standard enzymatic assay in the presence of a substrate for elastase B (elastin). We examined the most potent LasR inhibitors identified in Libraries A-D (B14, B17, C4, and D10), plus selected controls (A17, A18, and B21), using a previously reported colometric assay for elastase B in *P. aeruginosa* (PAO1) that employs an elastin-congo red substrate. The assay data is shown in FIG. 12, and revealed several potent synthetic inhibitors of elastase B, and thus LasR, in wild-type *P. aeruginosa*.

Figure 12:
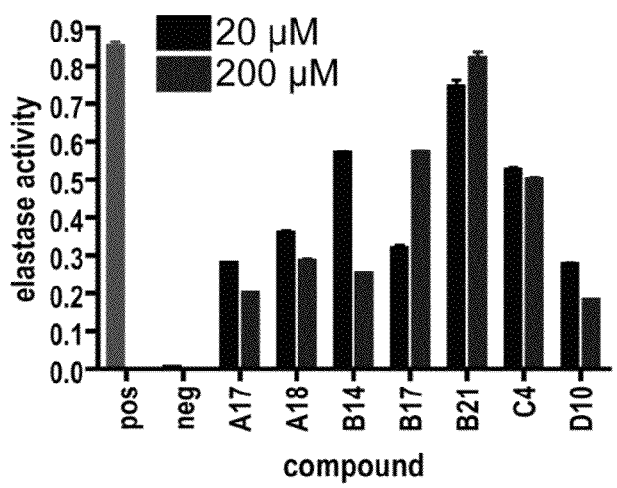
FIG. 12 shows elastase B production inhibition assay in *P. aeruginosa* PAO1.

The 4-bromo PHL A17 and indole AHL A18 controls were strong inhibitors of elastase B production in this assay, inhibiting enzyme activity by ca. 76% and 67% respectively (FIG. 12). PHL B21 was chosen as a control for this assay, as this ligand only exhibited weak LasR inhibition in the *E. coli* reporter strain, and we sought to determine if it would also show weak activity in the elastase production assay. Accordingly, B21 poorly antagonized elastase B production. The new LasR antagonists identified in this work (B14, B17, C4, and D10) all strongly inhibited elastase B production (up to ca. 79% for phenyl ether AHL D10). Notably, all four of these ligands inhibited LasR activity to the same level in the *E. coli* reporter gene assay (ca. 53%), yet exhibited dissimilar levels of elastase B inhibition in this assay (ranging from 79% to 35%). Further, 3-nitro PHL B17 was also observed to activate elastase B production at 10-fold higher concentration (200 mM vs. 20 mM; FIG. 12), while the inhibitory activity of other three ligands (B14, C4, and D10) was either comparable or slighted stronger at 200 mM relative to 20 mM. The reasons behind this concentration-dependent change in activity for B17, but not B14, C4, and D10, are unclear. Nevertheless, this virulence factor production assay demonstrated that the active inhibitors we uncovered in the *E. coli* LasR reporter strain assays are indeed inhibitors of LasR in *P. aeruginosa*. This result serves to validate the use of this reporter strain for the primary screening of synthetic modulators of LasR.

Dose Response Analyses of Active Compounds.

To obtain more quantitative data about the activity of the synthetic R protein antagonists and agonists identified in the primary assays of Libraries A-D, we performed does response assays in the three reporter strains and determined either $IC_{50}$ or $EC_{50}$ values for the ligands. To narrow the study, we only examined the most active antagonists in each library and antagonist controls in inhibition dose response assays. This corresponded to 31 ligands displaying inhibitory activities of >80% against TraR, >35% against LasR, and/or >75% against LuxR. In turn, the 14 ligands displaying appreciable agonism (ca. >20% in LasR and >60% in LuxR) were examined in dose response activation assays. Again, no ligands were uncovered in the four libraries that were appreciable agonists of TraR. The calculated $IC_{50}$ and $EC_{50}$ values for these active antagonists and agonists are listed in Tables 5 and 6, respectively.

$IC_{50}$ Values for Synthetic AHL Antagonists.

The $IC_{50}$ values for all of antagonists ranged from high nanomolar to low micromolar, and over 50% of these ligands (20 compounds) had lower $IC_{50}$ values than those for the control antagonists reported in this study. This was a significant result simply in view of numbers, as few potent synthetic antagonist of R proteins have been reported. Further, several new antagonists were identified that either selectively inhibited one or two R proteins, or were inhibitors of all three R proteins. The structures of the most active ligands are shown in FIG. 13A, and their selectivities for R protein targets are illustrated using a Venn diagram for clarity. Butane sulfonyl AHL C10, phenyl ether AHL D10, and bulky AHL D13 were the most active inhibitors of TraR, with each inhibiting TraR by 50% at ca. 5.5:1 against native ligand OOHL (A10) (entries 23, 29, and 30; Table 5). Notably, C10 was highly selective for TraR over LasR and LuxR, while D10 and D13 exhibited moderate cross-inhibitory activity against LasR and LuxR, respectively. Interestingly, the most active inhibitor of LasR identified was OOHL (A10), the native AHL ligand from *A. tumefaciens*, which inhibiting LasR by 50% at ca. 10:1 against OdDHL (A8) (entry 1). In contrast, previous studies by Passador et al. in an alternate *E. coli* LasR reporter stain did not reveal OOHL (A10) as an active inhibitor. The second most active antagonist of LasR in this study was 3-nitro PHL B17, inhibiting by 50% at ca. 60:1 against OdDHL (entry 17). Indole AHL C7, the one carbon shorter homolog of control antagonist AHL A18, was the next most active inhibitor of LasR identified (entry 21). In terms of selectivity for R protein, OOHL (A10) inhibited LasR and to a lesser degree LuxR, while B17 and A18 were most discriminatory for LasR.

The most potent inhibitors uncovered in this study were active against LuxR, displaying 50% inhibition at ca. 10-fold lower concentrations relative to the native ligand OHHL (A11). Here, a naturally-occurring AHL ligand was identified again as the most active inhibitor, OdDHL (A8) from *P. aeruginosa* (FIG. 13A). Remarkably, OdDHL (A8) was capable of inhibiting LuxR activity by 50% at ca. 1:12.5 against the native ligand OHHL (A11) (entry 2, Table 5). This result was in accord with previous work of Schaefer et al. that indicated OdDHL (A8) can strongly inhibit LuxR, albeit in an alternate reporter strain. The non-native 4-trifluoromethyl PHL B23 displayed a similarly high level of antagonistic activity at ca. 1:8 against OHHL (A11) (entry 19). AHL A7, the C14 analog of OdDHL (A8), was the next most potent inhibitor of LuxR (entry 10). Both OdDHL (A8) and A7 were selective inhibitors of LuxR, while PHL (B23) was a potent inhibitor of both LuxR and TraR. Finally, several ligands were identified that were strong inhibitors of all three R proteins: C8 AHL A3, 4-iodo PHL 613, and 4-bromo phenylpropionoyl HL C4 represent the most active inhibitors overall (FIG. 13A).

$EC_{50}$ Values for Synthetic AHL Agonists.

It is obvious from FIGS. 16A and 16B that far fewer agonists were identified in our primary screens relative to antagonists, and that the active ligands show exquisite selectivity for individual R proteins. The dose response activation studies revealed several ligands with $EC_{50}$ values against LasR comparable to the native ligand OdDHL (A8) (Table 6). The $C_{12}$ AHL A5 and 3-oxo C14 AHL A7 displayed the lowest $EC_{50}$ values (40 and 10 nM, respectively), and these values supported activity data previously reported by Passador et al. for these two compounds. Not surprisingly, these two LasR activators were similar in structure to that of the OdDHL (A8) (see FIG. 13B). D-AHL A25 was far less structurally analogous, and exhibited a 50-fold lower $IC_{50}$ value relative to OdDHL (A8) (entry 7); this synthetic LasR activator remains notable, however, as it represents to our knowledge the most active D-AHL reported to date. Nevertheless, the most remarkable outcome of our dose response activation studies was that 3-nitro PHL B17 displayed an $EC_{50}$ value against LuxR that was ca. 10-fold lower than that for OHHL (A11) (0.35 vs. 3.00). Additional studies of B17 indicated that this PHL also exerts it super-agonistic activity in wild-type *V. fischeri*. This result was remarkable, as there are only two other reported synthetic super-agonists of R proteins, and no known super-agonists of the model symbiont *V. fischeri*. PHL B17 is structurally dissimilar to these other two ligands, and represents a powerful new tool to probe the roles of quorum sensing in beneficial bacterial symbioses.

SAR Analysis of Active Ligands.

The dose response analyses identified the most active R protein modulators in Libraries A-D (FIGS. 16A and 16B), and we carefully inspected these structures in an attempt to determine SAR that conveyed R protein specificity or activity across all three R proteins. We constructed computational pharmacophores from the most active ligands for each R protein to aid in these analyses (see Supporting Information). Such study however did not reveal an obvious set of structural features that tuned ligand activity; the effects were far more subtle. To start, all of the AHL ligands in this study are structurally similar as they share the homoserine lactone functionality. Selectivity therefore must be determined by the acyl group. Our SAR analyses of the most active ligands in this study provided the following broad trends:

1. Acyl groups of moderate size and containing either aromatic functionality with electron withdrawing groups or straight chain aliphatic functionality are active in TraR, LasR, and LuxR.

2. The PHL appears to be a privileged scaffold for R protein modulation and displays a diverse range of activities across all three proteins. This suggests that the phenylacetanoyl group can uniquely position aromatic functionality so as to elicit different outcomes on R protein activity.

3. TraR is the most sensitive to the length of the acyl group, as activity drops of dramatically for ligands with acyl tails longer than eight atoms. This is in accord with its native ligand, OOHL (A10), which contains an octanoyl group.

4. LasR is the most tolerant of a diversity of different functionality and steric size on the AHL acycl chain, suggesting that it has a more open ligand binding site than TraR. This result is in accord with the recent X-ray crystal structure of LasR.

5. LuxR is most strongly inhibited or activated by ligands with medium to long (6-14 carbon), 3-oxo-aliphatic acyl groups or PHL ligands with substituents in the 3-position.

Biological Targets of Synthetic AHL Antagonists and Agonists.

As introduced above, in view of the structural similarity of the synthetic AHLs in Libraries A-D to native AHLs and the assay data and subtle SAR described above, we hypothesize that these ligands target R protein ligand-binding sites and inhibition or activation is based on the specific binding mode and thus resulting affinity of the ligand. Further, we do not believe that these changes in activity simply reflect the different chemical properties of the synthetic AHLs. This view is supported by several observations. First, the percentage of lactone hydrolysis (which abolishes activity for native AHLs) for the synthetic ligands was minimal and identical to that of the native ligands over the time course of the reporter gene assays. Second, the functionalities on Libraries A-D were unreactive under the assay conditions tested (see above). Third, higher ligand lipophilicity, and therefore higher potential cell permeability, did not correlate with, enhanced antagonistic or agonistic activity (Tables 1-6). This was further exemplified by the D-AHLs A25, A26, A28, and A29 in Library B (FIG. 9), which have identical lipophilicities as control antagonists A13, A14, A11 and A18, respectively, yet exhibit markedly different activities (Table 2). We have performed molecular modeling studies of several of the most active synthetic AHLs docked into the ligand binding site of TraR and LasR (using the X-ray crystal structures), and docked into the putative ligand binding site for LuxR (built in silico from TraR); see Supporting Information) to further test this hypothesis. The results of these preliminary studies suggest that all three ligand binding sites can readily accommodate the synthetic AHLs, and that activation or inhibition of LuxR may depend on the balance of favorable hydrogen-bonding and unfavorable steric interactions within the binding pocket.

Mechanism of R Protein Modulation by Synthetic Ligands.

Further insight into how our synthetic ligands were modulating R protein function was acquired through additional analysis of the primary screening data and dose response studies outlined above. Several ligands displayed complicated activity trends in the primary antagonism and agonism assays. For example, in our primary screens of Library D, AHLs D9, D10, and D7 inhibited and activated LasR to the same degree (ca. 35%). In addition, we observed that several of our synthetic antagonists exhibited dose response inhibition curves that started to slope back up at higher concentrations (D10 included). It appeared that these ligands were capable of inhibiting R proteins responses at lower concentration relative to the native ligand, but were also capable of activating at higher concentrations. Dose response activation assays of these compounds revealed that they were in fact agonists of R proteins, albeit weakly active. The dose response activation curve started to curve up at precisely the concentration where their respective dose response antagonism curve started to upturn. The elastase production assay data for PHL B17 corroborated this behavior: this PHL was capable of both inhibiting and activating elastase B production in P. aeruginosa at low and high concentrations, respectively (FIG. 12).

Overall, we rationalized these data in the following manner: (1) at low concentration relative to the native AHL ligand, the compounds are unable to suppress R protein function and the activity of the native ligand is dominant, and (2) at high concentration relative to the native AHL ligand, the compounds successfully out compete the native ligand and can agonize the R protein, albeit not the same level as the native ligand over the concentrations tested. The behavior of these compounds at middle range concentrations, where the ligands act to suppress activation of the native ligand, is more complex. Our current interpretation of this phenomena is as follows:

We obtained further data to support this hypothesis through the examination of the super-agonist, B17, in dose antagonism response assays against OHHL (A11). While additional biochemical and structural studies will be required to fully elucidate how these ligands function in A. tumefaciens, P. aeruginosa, and V. fischeri, these dose response experiments and the computational experiments described above provide support that the synthetic AHLs identified in this study target R proteins.

Summary and Conclusions.

We have designed and synthesized four focused collections of synthetic AHL ligands, and systematically examined these ca. 100 compounds in three bacterial reporter strains to determine their ability to modulate R protein function and related quorum sensing outcomes. These studies have revealed some of the most potent synthetic antagonists and agonists reported to date of the well-characterized R proteins TraR, LasR, and LuxR. Several of the LasR antagonists were capable of strongly inhibiting virulence factor production in P. aeruginosa that is essential for pathogenesis. In addition, we have determined critical SARs that confer antagonistic and agonistic activity for these synthetic AHL ligands against the three R proteins. In general, the AHLs modulating TraR and LuxR contained were sterically more compact and less lipophilic than those for LasR. Molecular modeling experiments of the ligand binding sites One significant outcome of this work is the observation that subtle alteration to substituents and their placement on the acyl moiety dramatically influence ligand activity. This effect was most remarkable in the PHL library (Library C), where these structural changes did not simply abolish activity, but rather convert potent antagonists into agonists. Tangentially, we also found that certain synthetic D-AHLs are capable of strongly activating R proteins, i.e. the LasR activator A25. This ligand represents to our knowledge the first reported D-AHL capable of modulating an R protein. A second major outcome of this investigation is the discovery of the first synthetic super-agonist of quorum sensing in V. fischeri, PHL B17. This ligand displays 10-fold higher activity relative to native autoinducer OHHL, and is one of the first known super-agonists of quorum sensing in gram-negative bacteria.[42,43] The third important outcome of this work, and most noteworthy, was our discovery that several of the most potent "antagonists" identified in the reporter gene assays exert their activity via a competitive agonism mechanism. Biochemical and structural experiments are ongoing in our laboratory to fully elucidate their mechanisms of action. Collectively, the synthetic AHLs identified herein represent a new and valuable set of chemical tools for the study of quorum sensing in gram-negative bacteria and could, with further development, provide broad insights into the roles of quorum sensing in bacterial pathogenesis and in beneficial symbioses. Preliminary experiments in invertebrate model systems indicate that several of these ligands are tolerated and can modulate quorum sensing responses in vivo.

Figure and Table Headings

FIG. 5. Generic structure for N-acylated-L-homoserine lactones (AHLs), and structures of selected native AHL ligands (1-3) and known synthetic inhibitors of R protein function (4-9). The number of carbons (C) in selected aliphatic acyl groups are indicated for clarity.

FIG. 6. Schematic of quorum sensing in gram-negative bacteria. (A) Bacteria constitutively produce small amounts of cell permeable AHL. (B) At a high cell density, the concentration of AHL reaches a threshold level within the cell, and the AHL binds its cognate receptor (an R protein). This ligand/receptor complex then binds and activates transcription of a target gene.

FIG. 7. Solid-phase synthetic route to AHL Libraries A-D. Reagents and conditions: a=DIC, HOBT, $CHCl_3$/DMF, mW 50° C. (2×10 min); b=mW 150° C., 7 min; c=DMAP, $CHCl_3$, d=CNBr, TFA, $CHCl_3$/$H_2O$, RT, 24 h. Notes and abbreviations: **N-Fmoc-D-Met used in the construction of compounds A24-A26, A28, and A29 in Library B. DIC=N,N'-diisopropylcarbodiimide. HOBT=N-hydroxybenzotriazole. DMF=dimethylformamide; DMAP=4-dimethylaminopyridine; mW=temperature-controlled microwave irradiation.

FIG. 8. Structures of AHL Library A. General structural features tested: (1) aliphatic acyl group length and (2) replacement of acyl carbonyl with a sulfonyl group. The number of carbons (C) in aliphatic acyl groups are indicated for clarity.

Table 1. Antagonism and agonism assay data for Library A in three bacterial reporter strains. [a] All assays performed in triplicate; Error did not exceed about ±10%. β-galactosidase production or luminescence in the absence of added ligand was less than about 5%. Negative inhibition values indicate the compound activates at the tested concentration. Shaded compounds are controls. Data of high significant is bolded for clarity. [b] Strain: *A. tumefaciens* WCF47 (pCF372). Absorbance data measured in Miller units and normalized to OOHL (A10). c Screen performed using 10 μM synthetic ligand against 100 nM OOHL (A10). d Screen performed using 10 μM ligand. [e] Strain: *E. coli* DH5α (pJN105L pSC11). Absorbance data measured in Miller units and normalized to OdDHL (A8).[f] Screen performed using 5 μM synthetic ligand against 7.5 nM OdDHL (A8). [g] Screen performed using 5 μM ligand. [h] Strain: *V. fischeri* ES114 (Δ-luxI). Luminescence data measured in relative light units and normalized to OHHL (A11). [i] Screen performed using 5 μM synthetic ligand against 5 μM OHHL (A11).[j] Screen performed using 200 μM ligand.

FIG. 9. Structures of AHL Library B. General structural features tested: (1) lactone stereochemistry in OHHL and control compounds A25 and A26 and (2) alkyl spacer length and aromaticity in control compounds A17 and A18.

Table 2. Antagonism and agonism assay data for Library B in three bacterial reporter strains. See footnotes for Table 1.

FIG. 10. Structures of AHL Library C. PHL=N-phenylacetanoyl-L-homoserine lactone. General structural features tested: (1) different substituents and (2) their placement on the acyl group phenyl ring.

Table 3. Antagonism and agonism assay data for Library C in three bacterial reporter strains. See footnotes for Table 1.

Figure 11:
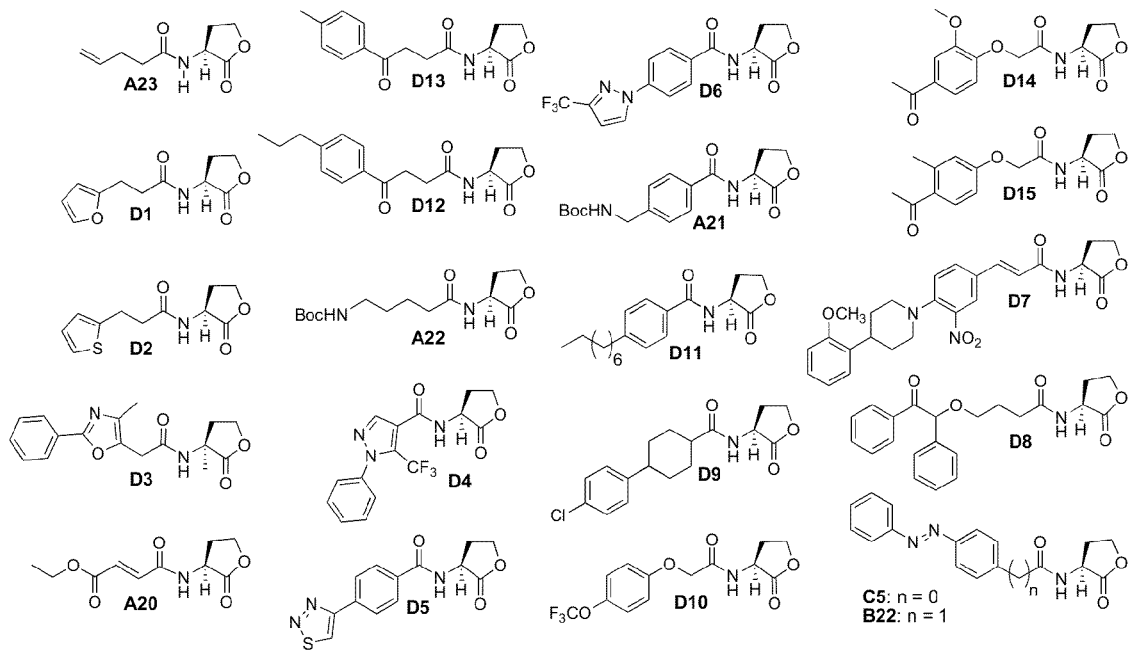
FIG. 11 illustrates structures of AHL Library D.

FIG. 11. Structures of AHL Library D. General structural features tested: (1) varying functionalities on the acyl group and (2) varying acyl group sizes.

Table 4. Antagonism and agonism assay data for Library D in three bacterial reporter strains. See footnotes for Table 1.

FIG. 12. Elastase B production inhibition assay in *P. aeruginosa* PAO1. Selected synthetic ligands in Libraries A-D examined for inhibitory activity at two concentrations. Positive control (pos)=*P. aeruginosa* in the absence compound. Negative control (neg)=growth media. Error bars, s.d. of the means of triplicate samples.

Table 5. $IC_{50}$ values for most active antagonists across the three strains. See Table 1 footnotes for details of strains. IC50 values determined by testing compounds over a range of concentrations (about 0.02 to about $2\times10^5$ nM) against native AHL ligand in each reporter strain. [b] Determined against 100 nM OOHL (A10). [c] Determined against 7.5 nM OdDHL (A8). [d] Determined against 5 μM OHHL (A11). [e]—Not determined. [f] Dose response curve did not reach 100% inhibition over the concentrations tested; IC50 value calculated from the partial dose response inhibition curve reported. Value in parentheses equals the concentration at which the compound elicits its maximal inhibition.

Table 6. $EC_{50}$ values for most active agonists across the three strains. See Table 1 footnotes for details of strains. EC50 values determined by testing compounds over a range of concentrations (about 2 to about $2\times10^5$ nM) in each reporter strain. [b]—Not determined. Dose response curve did not plateau over the concentrations tested. [d] Dose response curve reached a plateau over the concentrations tested, yet the level of maximal induction was lower than that for the natural ligand; EC50 value calculated from this dose response activation curve. Value in parentheses equals the maximum induction value achievable (at 200 μM ligand) relative to OHHL A10.

Figure 13:
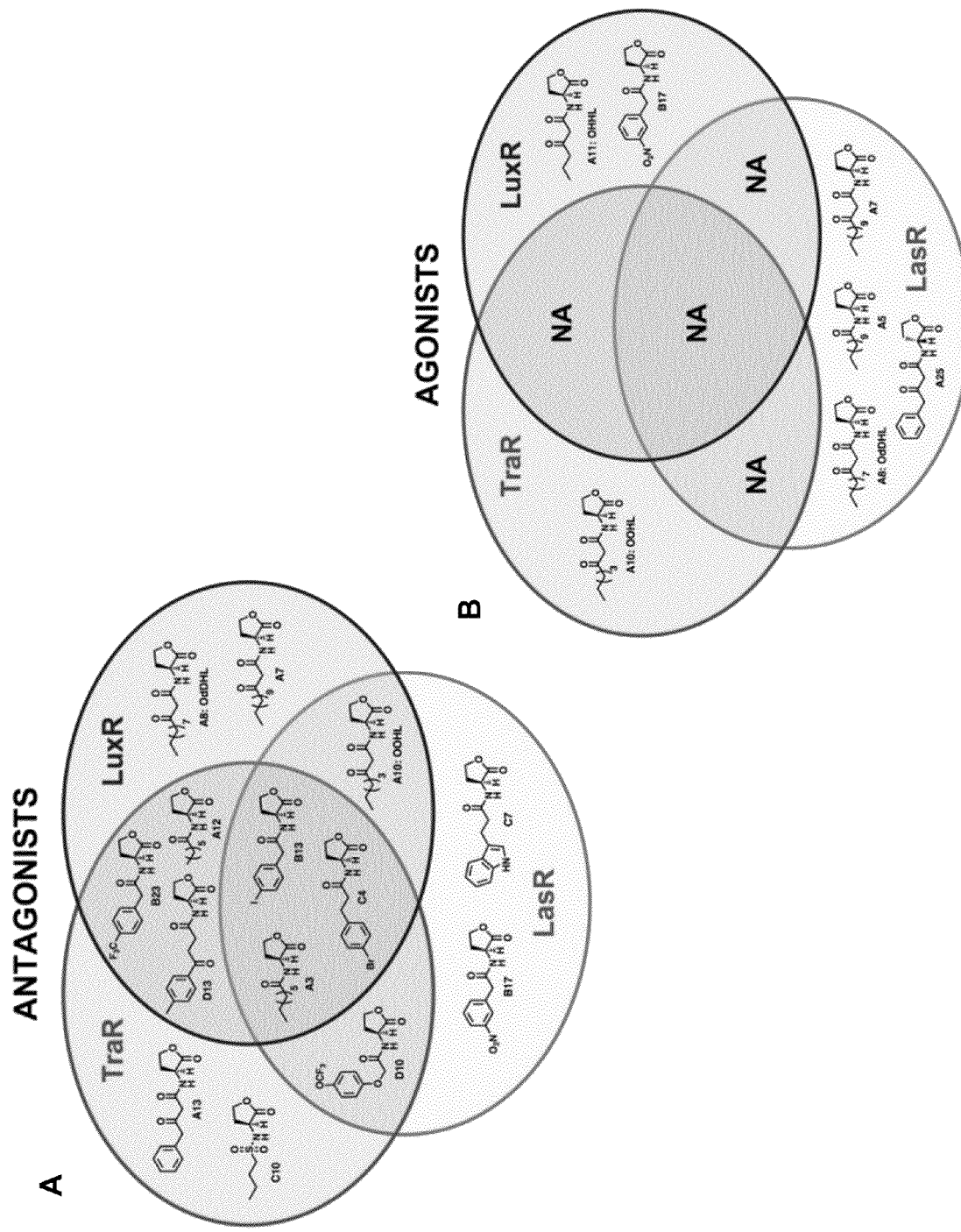
FIG. 13 illustrates Venn diagrams showing the structures of most potent R proteins antagonists and agonists identified and their selectively for different R proteins over the concentrations tested.
Figure 14:
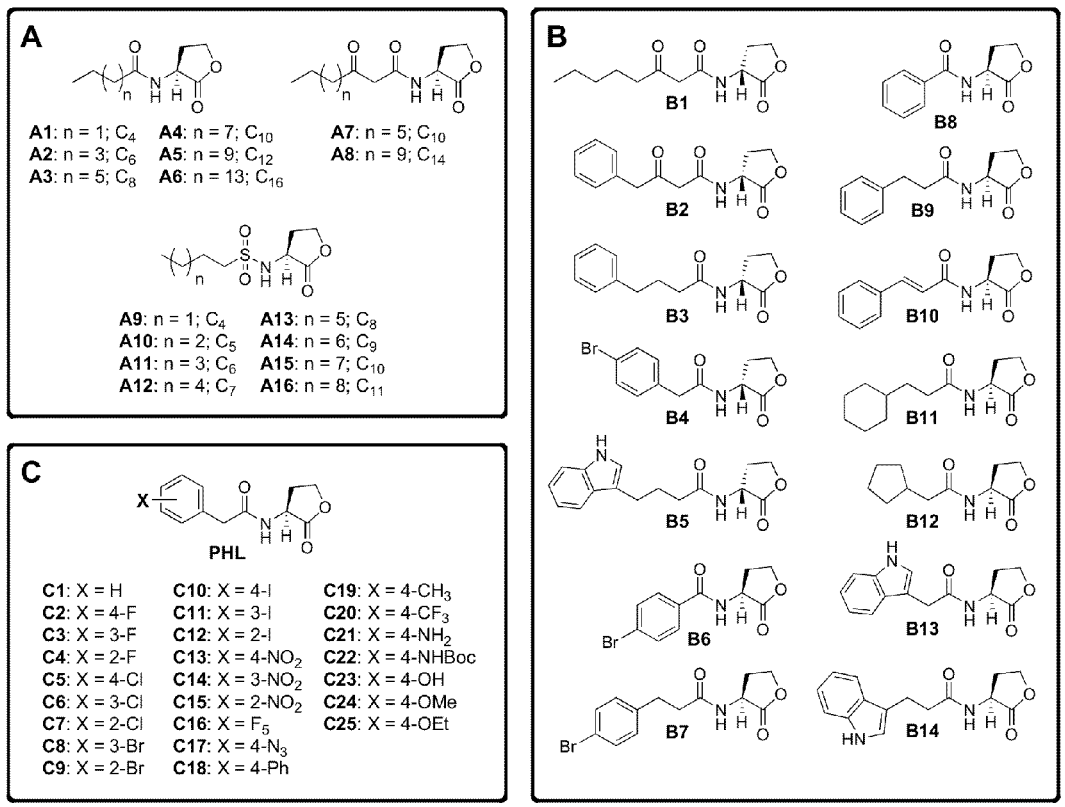
FIG. 14 illustrates structures of AHL Libraries A-C.
Figure 15:
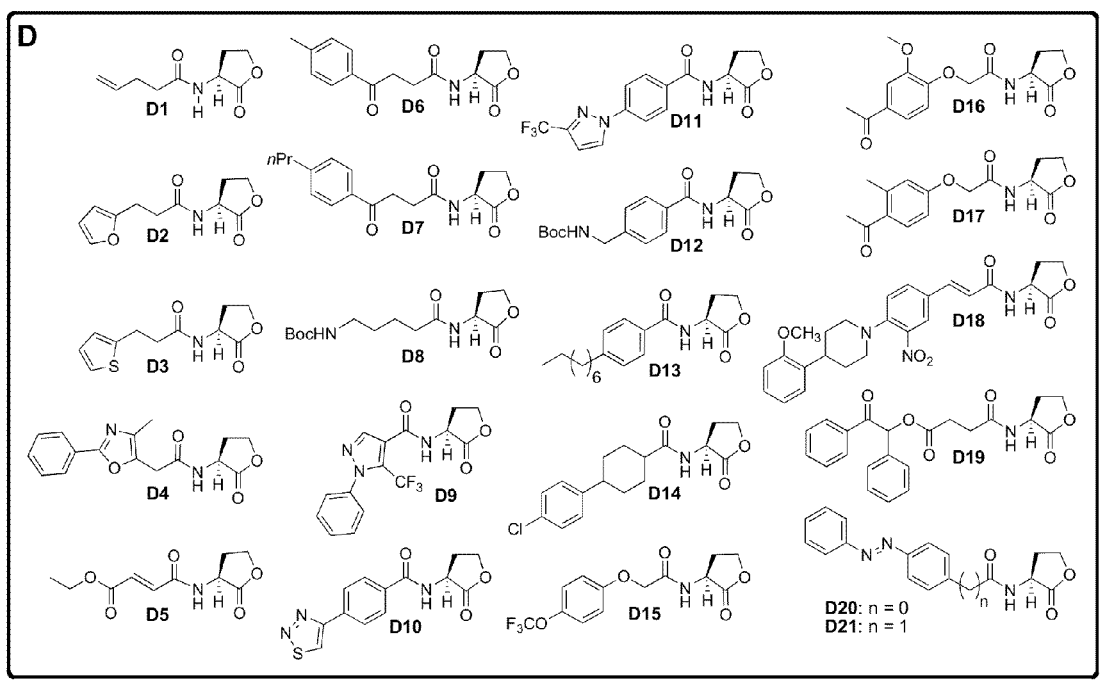
FIG. 15 illustrates structures of AHL Library D.

FIG. 13. Venn diagrams showing the structures of most potent R proteins antagonists and agonists identified and their selectively for different R proteins over the concentrations tested in this study. Ligands in the intersections of the circles have significant selectivity for two or more R proteins. (A) Diagram of the 12 most active antagonists from Libraries A-D and the two most active control antagonists (A12 and A13). (B) Diagram of the four most active agonists from Libraries A-D and the three native AHL ligands (OOHL (A10), OdDHL (A8), and OHHL (A11)). NA=no applicable ligands identified.

REFERENCES AND NOTES

Example 2

Bassler, B. L.; Losick, R. *Cell* 2006, 125, 237-246.
Waters, C. M.; Bassler, B. L. *Ann. Rev. Cell Dev. Biol.* 2005, 21, 319-346.
Fuqua, C.; Parsek, M. R.; Greenberg, E. P. *Annu. Rev. Genet.* 2001, 35, 439
de Kievit, T. R.; Iglewski, B. H. *Infect. Immun.* 2000, 68, 4839-4849.
Hall-Stoodley, L.; Costerton, J. W.; Stoodley, P. *Nat. Rev. Microbiol.* 2004, 2, 95-108.
Winans, S. C. *Trends Microbiol.* 1998, 6, 382-383.

Greenberg, E. P., Quorum Sensing in Gram-Negative Bacteria: An Important Signaling Mechanism in Symbiosis and Disease. In *Microbial Ecology and Infectious Disease*, Rosenberg, E., Ed. American Society for Microbiology: Washington, D.C., 1999; pp 112-122.
Ruby, E. G. *Annu. Rev. Microbiol.* 1996, 50, 591-624.
Lyon, G. J.; Muir, T. W. *Chem. Biol.* 2003, 10, 1007-1021.
Gonzalez, J. E.; Keshavan, N. D. *Microbiol. Mol. Biol. Rev.* 2006, 70, 859-875.
Fuqua, C.; Greenberg, E. P. *Nat. Rev. Mol. Cell Biol.* 2002, 3, 685-695.
Whitehead, N. A.; Barnard, A. M.; Slater, H.; Simpson, N. J.; Salmond, G. P. *FEMS Microbiol. Rev.* 2001, 25, 365-404.
Welch, M.; Mikkelsen, H.; Swatton, J. E.; Smith, D.; Thomas, G. L.; Glansdorp, F. G.; Spring, D. R. *Molecular Biosystems* 2005, 1, 196-202.
Zhu, J.; Oger, P. M.; Schrammeijer, B.; Hooykaas, P. J.; Farrand, S. K.; Winans, S. C. *J. Bacteriol.* 2000, 182, 3885-95.
Zhang, R. G.; Pappas, T.; Brace, J. L.; Miller, P. C.; Oulmassov, T.; Molyneaux, J. M.; Anderson, J. C.; Bashkin, J. K.; Winans, S. C.; Joachimiak, A. *Nature* 2002, 417, 971-974.
Vannini, A.; Volpari, C.; Gargioli, C.; Muraglia, E.; Cortese, R.; De Francesco, R.; Neddermann, P.; Marco, S. D. *EMBO J.* 2002, 21, 4393-401.
Van Delden, C.; Iglewski, B. H. *Emerg. Infect. Dis.* 1998, 4, 551-60.
Smith, R. S.; Iglewski, B. H. *Curr. Opin. Microbiol.* 2003, 6, 56-60.
Davies, D. G.; Parsek, M. R.; Pearson, J. P.; Iglewski, B. H.; Costerton, J. W.; Greenberg, E. P. *Science* 1998, 280, 295-8.
Lyczak, J. B.; Cannon, C. L.; Pier, G. B. *Clin. Microbiol. Rev.* 2002, 15, 194.222.
Bottomley, M. J.; Muraglia, E.; Bazzo, R.; Carfi, A. *J. Biol. Chem.* 2007, in press.
Visick, K. L.; Ruby, E. G. *Curr. Opin. Microbiol.* 2006, 9, 632-638.
Lupp, C.; Urbanowski, M.; Greenberg, E. P.; Ruby, E. G. *Mol. Microbial.* 2003, 50, 319-331.
Eberhard, A.; Widrig, C. A.; McBath, P.; Schineller, J. B. *Arch. Microbial.* 1986, 146, 35-40.
Schaefer, A. L.; Hanzelka, B. L.; Eberhard, A.; Greenberg, E. P. *J. Bacterial.* 1996, 178, 2897-2901.
Passador, L.; Tucker, K. D.; Guertin, K. R.; Journet, M. P.; Kende, A. S.; Iglewski, B. H. *J. Bacterial.* 1996, 178, 5995-6000.
Kline, T.; Bowman, J.; Iglewski, B. H.; de Kievit, T.; Kakai, Y.; Passador, L. *Bioorg. Med. Chem. Lett.* 1999, 9, 3447-52.
Zhu, J.; Beaber, J. W.; More, M. I.; Fuqua, C.; Eberhard, A.; Winans, S. C. *J. Bacterial.* 1998, 180, 5398-405.
Ikeda, T.; Kajiyama, K.; Kita, T.; Takiguchi, N.; Kuroda, A.; Kato, J.; Ohtake, H. *Chem. Lett.* 2001, 314-315.
Reverchon, S.; Chantegrel, B.; Deshayes, C.; Doutheau, A.; Cotte-Pattat, N. *Bioorg. Med. Chem. Lett.* 2002, 12, 1153-1157.
Castang, S.; Chantegrel, B.; Deshayes, C.; Dolmazon, R.; Gouet, P.; Haser, R.; Reverchon, S.; Nasser, W.; Hugouvieux-Cotte-Pattat, N.; Doutheau, A. *Bioorg. Med. Chem. Lett.* 2004, 14, 5145-5149.
Frezza, M.; Castang, S.; Estephane, J.; Soulere, L.; Deshayes, C.; Chantegrel, B.; Nasser, W.; Queneau, Y.; Reverchon, S.; Doutheau, A. *Bioorg. Med. Chem.* 2006, 14, 4781-4791.
Hentzer, M., et al. *EMBO J.* 2003, 22, 3803-3815.
Persson, T.; Hansen, T. H.; Rasmussen, T. B.; Skinderso, M. E.; Givskov, M.; Nielsen, *J. Org. Biomol. Chem.* 2005, 3, 253-262.
Rasmussen, T. B.; Givskov, M. *Microbiology* 2006, 152, 895-904.
Smith, K. M.; Bu, Y. G.; Suga, H. *Chem. Biol.* 2003, 10, 81-89.
Smith, K. M.; Bu, Y.; Suga, H. *Chem. Biol.* 2003, 10, 563-571.
Jog, G. J.; Igarashi, J.; Suga, H. *Chem. Biol.* 2006, 13, 123-128.
Glansdorp, F. G.; Thomas, G. L.; Lee, J. J. K.; Dutton, J. M.; Salmond, G. P. C.; Welch, M.; Spring, D. R. *Org. Biomol. Chem.* 2004, 2, 3329-3336.
Muh, U.; Schuster, M.; Heim, R.; Singh, A.; Olson, E. R.; Greenberg, E. P. *Antimicrob. Agents Chemother.* 2006, 50, 3674-3679.
Taha, M. O.; Al-Bakri, A. G.; Zalloum, W. A. *Bioorg. Med. Chem. Lett.* 2006, 16, 5902-5906.
Muh, U.; Hare, B. J.; Duerkop, B. A.; Schuster, M.; Hanzelka, B. L.; Heim, R.; Olson, E. R.; Greenberg, E. P. *Proc. Natl. Acad. Sci. U.S.A.* 2006, 103, 16948-16952.
Janssens, J. C.; Metzger, K.; Daniels, R.; Ptacek, D.; Verhoeven, T.; Habel, L. W.; Vanderleyden, J.; De Vos, D. E.; De Keersmaecker, S. C. *Appl. Environ. Microbiol.* 2007, 73, 535-544.
Geske, G. D.; Wezeman, R. J.; Siegel, A. P.; Blackwell, H. E. *J. Am. Chem. Soc.* 2005, 127, 12762-12763.
Lin, Q.; Blackwell, H. E. *Chem. Commun.* 2006, 2884-2886.
Gorske, B. C.; Blackwell, H. E. *Org. Biomol. Chem.* 2006, 4, 1441-1445.
Geske, G. D.; O'Neill, J. C.; Blackwell, H. E. *ACS Chem. Biol.* 2007, in press.
Barnick, J. W. F. K.; van der Baan, J. L.; Bickelhaupt, F. *Synthesis* 1979, 79, 787-788.
Rathke, M. W.; Nowak, M. A. *Synth. Commun.* 1985, 15, 1039-1049.
Miller, J. H., *Experiments in Molecular Genetics*. Cold Spring: 1972; p 352-355.
Lee, J. H.; Lequette, Y.; Greenberg, E. P. *Mol. Microbiol.* 2006, 59, 602-609.
Stover, C. K., et al. *Nature* 2000, 406, 959-64.
Zhu, J.; Winans, S. C. *Proc. Natl. Acad. Sci. U.S.A.* 2001, 98, 1507-12.
Fleming, S. A. *Tetrahedron* 1995, 51, 12479-12520.
Schultz, T.; Quenneville, J.; Levine, B.; Toniolo, A.; Martinez, T. J.; Lochbrunner, S.; Schmitt, M.; Shaffer, J. P.; Zgierski, M. Z.; Stolow, A. *J. Am. Chem. Soc.* 2003, 125, 8098-8099.
Nakayama, K.; Endo, M.; Majima, T. *Chem. Commun.* 2004, 2386-7.
Behrendt, R.; Renner, C.; Schenk, M.; Wang, F.; Wachtveitl, J.; Oesterhelt, D.; Moroder, L. *Angew. Chem., Int. Ed. Engl.* 1999, 38, 2771-2774.

Example 3

Systematic Evaluation of N-Acylated Homoserine Lactones in Multiple Species and New Insights into their Mechanisms of Action Bacteria use a language of low molecular weight ligands to assess their population densities in a process called quorum sensing. This chemical signaling process plays a pivotal role both in the pathogenesis of infectious disease and in beneficial symbioses. There is intense interest in the development of synthetic ligands that can intercept quorum-sensing signals and attenuate these divergent outcomes. Both broad-spectrum and species-selective modulators of quorum sensing hold significant value as small molecule tools for fundamental studies of this complex cell-cell signaling process and for future biomedical and environmental applications. Here, we report the design and synthesis of focused collections of non-native N-acylated homoserine lactones and the systematic evaluation of these ~90 ligands across three Gram-negative bacterial species: the pathogens *Agrobacterium tumefaciens* and *Pseudomonas aeruginosa*, and the model symbiont *Vibrio fischeri*. This study is the first to report and compare the activities of a set of ligands across multiple species, and has revealed some of the most potent synthetic modulators of quorum sensing to date. Moreover, several of these ligands exhibit agonistic or antagonistic activity in all three species, while other ligands are only active in one or two species. Analysis of the screening data revealed that at least a subset of these ligands modulate quorum sensing via a partial agonism mechanism. We also demonstrate that selected ligands can either inhibit or promote the production of elastase B, a key virulence factor in wild-type *P. aeruginosa*, depending on their concentrations. Overall, this work provides broad insights into the molecular features required for small molecule inhibition or activation of quorum sensing in Gram-negative bacteria. In addition, this study has supplied an expansive set of chemical tools for the further investigation of quorum sensing pathways and responses.

Introduction.

Bacteria produce and monitor low molecular weight molecules (autoinducers) to assess their population densities in a behavior called quorum sensing. The concentration of these signaling molecules in a given environment is proportional to the bacterial cell density. When bacteria reach a sufficiently high population density, they will alter gene expression so as to carry out a range of processes that require the cooperation of a large number of cells, including secretion of virulence factors, biofilm formation, antibiotic production, bioluminescence, sporulation, and conjugation. These diverse processes have widespread and often devastating effects on human health, agriculture, and the environment. In the case of pathogenic bacteria, quorum sensing allows the bacteria to amass in sufficiently high densities before launching a coordinated attack on a host and overwhelming its defenses. Symbiotic bacteria, in contrast, have co-opted quorum sensing pathways to commence mutually beneficial relationships with their hosts at high cell densities. As interception of quorum sensing represents a strategy to possibly control both pathogenesis and symbiosis, there is significant interest in the development of non-native ligands that can block or mimic native autoinducer signals and attenuate quorum-sensing outcomes. Such molecules would represent tools to study the molecular mechanisms of quorum sensing and probe its validity as an anti-infective target.

Quorum sensing is best characterized in the Gram-negative Proteobacteria, which use N-acylated L-homoserine lactones (AHLs, FIG. 5) and their cognate cytoplasmic receptors (R proteins) for intercellular signaling. The AHL ligand is generated by inducer synthases (I proteins) at low basal levels, and high cell densities are required to achieve a sufficient intracellular concentration of ligand for R protein binding. Thereafter, the AHL:R protein complex most often homodimerizes and activates transcription of target genes required for bacterial group behavior. A schematic of this process is shown in FIG. 6. Thus, through quorum sensing, bacterial populations can efficiently couple gene expression to fluctuations in cell density. To date, this signaling process has been extensively studied in three Gram-negative bacteria: *Agrobacterium tumefaciens, Pseudomonas aeruginosa*, and *Vibrio fischeri*. As such, these three species represent excellent model organisms for intervention with synthetic quorum sensing modulators, and are the focus of the present study.

*A. tumefaciens, P. aeruginosa*, and *V. fischeri* each utilize quorum sensing for remarkably different purposes. *A. tumefaciens* is a widespread plant pathogen and uses quorum sensing in its induction of crown gall tumors on plant hosts under the control of N-(3-oxo-octanoyl)-L-homoserine lactone (OOHL, 1; FIG. 5) and its receptor, TraR. TraR is the only R protein for which a three-dimensional structure of the receptor bound to ligand and DNA has been determined by X-ray crystallography. This X-ray structure revealed that the OOHL (1):TraR complex binds DNA as a homodimer and that OOHL (1) is completely engulfed in a hydrophobic site on TraR upon DNA binding.

*P. aeruginosa* is both a plant and animal pathogen and uses two AHL signaling molecules, N-(3-oxo-dodecanoyl)-L-homoserine lactone (OdDHL, 2; FIG. 5) and N-butanoyl-L-homoserine lactone, and two R proteins, LasR and RhlR, respectively, to control the expression of an arsenal of virulence factors that cause extensive tissue damage during infection. There is tremendous interest in AHL-mediated quorum sensing in *P. aeruginosa* due to the prevalence of this opportunistic bacterium in life threatening hospital-acquired infections 18 and in chronic lung infections associated with cystic fibrosis. An X-ray structure of the N-terminal ligand-binding domain of LasR complexed to OdDHL (2) was recently reported, and exhibited a structure highly homologous to that of TraR, albeit with a slightly expanded ligand-binding pocket to accommodate its larger cognate ligand. 20 Similar to OOHL (1) in TraR, OdDHL (2) was shown to be completely engulfed in the LasR ligand-binding site. Biochemical experiments with both TraR and LasR suggest that native ligand is required for the folding of these proteins into their mature tertiary structures in vitro, and ligand is bound almost irreversibly.

In contrast to these two bacterial pathogens, *V. fischeri* uses quorum sensing to mediate a beneficial symbiosis. This marine bacterium colonizes the light-producing organs of certain marine fish and squids and uses quorum sensing to initiate bioluminescence and other mutually beneficial processes at high cell densities. Quorum sensing is mediated in part by N-(3-oxo-hexanoyl)-L-homoserine lactone (OHHL, 3; FIG. 5) and its cognate receptor, LuxR. The LuxR protein has been shown to bind OHHL (3) reversibly in vitro, suggesting that its ligand-binding site is more accessible than both TraR and LasR; structural data have not been reported, however, to support this hypothesis. As AHL-mediated quorum sensing was first characterized in *V. fischeri*, the LuxR system represents the canonical quorum sensing circuit in Gram-negative bacteria.

Considerable research efforts over the past 20 years have focused on the design and synthesis of ligands that can disrupt AHL-R protein binding and inhibit quorum sensing outcomes in these three bacterial species. However, synthetic antagonists of quorum sensing remain scarce. The known antagonists are mainly structural mimics of native AHLs, and four of the most active R protein antagonists are shown in FIG. 5: N-heptanoyl-L-homoserine lactone (4) reported by Zhu et al. and active against TraR, N-(3-oxo-phenylbutanoyl)- and N-(phenylbutanoyl)-L-homoserine lactones (5 and 6) reported by Reverchon I and active against LuxR, and the 2-aminophenol analog of OdDHL (7) reported by Smith et al. and active against LasR. Likewise, compounds exhibiting heightened activities relative to native AHLs (i.e., "super-activators" of quorum sensing) are also of significant interest, as they could potentially initiate bacterial group behaviors at lower cell densities than required in natural environments. However, only three such super-activators of quorum sensing have been reported to date. These three ligands are shown in FIG. 5: N-(3-oxoheptanoyl)- and N-(3-oxooctanoyl)-DL-homoserine thiolactones (10 and 11) capable of super-activating the LuxR homolog SdiA in *Salmonella enterica*, and the triphenyl signal mimic (12) capable of super-activating LasR.

Clearly, new synthesis and design strategies are needed to expand the current set of quorum sensing modulators active in Gram-negative bacteria. Unfortunately, the structures of the few known antagonists and agonists vary considerably and their mechanisms of action are unclear; thus, no obvious rationales have emerged for new ligand design. Moreover, to our knowledge, the known antagonists and agonists of quorum sensing have been examined primarily in one bacterial species. Therefore, we currently do not know whether these compounds target one R protein selectively or if they can modulate the functions of a range of different R proteins. As such, the molecular features that confer selectivity or broad-range activity to synthetic quorum-sensing modulators in Gram-negative bacteria remain unknown. The moderate sequence homology in the putative ligand-binding sites of the ~50 known R proteins (70-80%) suggests that if non-native ligands target these sites, both R protein-selective and broad spectrum ligands potentially could be developed. Ligands with either of these activity profiles would be of significant value as chemical probes to study quorum sensing, most notably in natural environments harboring multiple species.

To address these challenges, we have been engaged in the design of focused, combinatorial libraries of synthetic ligands for the modulation of quorum sensing in a range of different Gram-negative bacteria. Our preliminary work has resulted in the identification of five potent modulators of R protein function in either *A. tumefaciens, P. aeruginosa*, or *V. fischeri*, including the antagonists N-(4-bromo-phenylacetanoyl)-L-homoserine lactone (4-bromo PHL 8) and indole AHL (9) (FIG. 5). These initial studies surveyed a limited set of non-native AHLs, and were primarily focused on the discovery of R protein antagonists in one bacterial species. Here, we report the design and synthesis of four focused libraries of non-native AHLs, the parallel evaluation of these ~90 compounds for R protein antagonism and agonism in all three species (*A. tumefaciens, P. aeruginosa*, and *V. fischeri*), and a detailed analysis of these comparative screening data. Each of the libraries was designed to probe the role of key features of AHL structure on quorum sensing activity, including acyl chain length, lactone stereochemistry, and functionality on the acyl group. These studies represent the first comparative investigation of non-native AHL function across multiple Gram-negative bacteria. They have revealed an expansive new set of synthetic R protein modulators and the most comprehensive set of structure-activity relationships (SARs) for non-native AHL ligands reported to date. Furthermore, we have identified quorum-sensing modulators that are either selective for one or two species, or are active in all three species. Several of these ligands are among the most potent modulators of R protein function known, with the ability to inhibit or even super-activate R protein function at 10-fold lower concentrations than the native AHL ligand. We present our current rationales for the mechanisms of R protein modulation by these non-native AHLs, most notably by a partial agonism pathway. Together, the ligands described herein have the potential to significantly broaden the current understanding of quorum sensing and its roles in host-bacteria interactions.

Experimental.

Chemistry.

All reagents and solvents were purchased from commercial sources and used without further purification, with the exception of dichloromethane ($CH_2Cl_2$), which was distilled over calcium hydride. All solid-phase syntheses were performed using aminomethyl polystyrene resin (NovaBiochem, 100-200 mesh; loading 1.1-1.2 mmol/g). Microwave-assisted solid-phase reactions were carried out using either Milestone or CEM commercial microwave ($\mu$W) reactors under temperature control. Full details of the instrumentation and analytical methods used in this work can be found below.

Ligand Synthesis.

AHL Libraries A-D, OOHL (1), OdDHL (2), and OHHL (3), and the control compounds 4-6, 8, and 9 were prepared according to FIG. 7 using reported methods on a 20 mg scale, except the final cyclization-cleavage step was performed at RT for 24 h. The 1,3-dioxolane protected β-keto acids building blocks (17) were prepared via a modified version of the methods reported by Barnick and Rathke. Sulfonyl chloride building blocks (18) were prepared according to the method reported by Castang et al. Control compound 7 was prepared in solution according to our previously reported method. Purities and isolated yields for Libraries A-D, the native ligands, and the control compounds were 90-99% and 55-75%, respectively. Compounds were submitted to biological assays following resin cleavage and an aqueous work-up without further purification.

Compound Handling.

Stock solutions of synthetic compounds (10 mM) were prepared in DMSO and stored at room temperature in sealed vials. The amount of DMSO used in small molecule screens did not exceed 2% (by volume). Solvent resistant polypropylene or polystyrene 96-well multititer plates were used when appropriate for small molecule screening. The concentrations of synthetic AHL ligand used in the primary antagonism and agonism assays, and the relative ratios of synthetic ligand to native ligand (1:1 to ~100:1) in the antagonism assays, were chosen to provide the most obvious differences between inhibitors and activators for each bacterial reporter strain. The concentration of native ligand used in the antagonism assays was approximately equal to its $EC_{50}$ value in each bacterial reporter strain.

Bacteriology:

All biological reagents were purchased from Fisher Scientific and used according to enclosed instructions. *Agrobacterium* (AB) minimal medium was prepared as previously reported. Luria-Bertani (LB) and LB salt media (LBS) were prepared as instructed with pH=7.5 (LBS contained an additional 1.5% NaCl, 0.3% glycerol, and 50 nM Tris-HCl). Buffers and solutions (Z buffer, 0.1% aq. SDS, and phosphate buffer) for Miller absorbance assays in *A. tumefaciens* and *E. coli* were prepared as described. The three bacterial reporter strains used in this study were: *A. tumefaciens* WCF47 (Δ-traI) harboring a plasmid-born PtraI-lacZ fusion (pCF372), *E. coli* DH5α harboring the LasR expression vector pJN105L and a plasmid-born PlasI-lacZ fusion (pSC11), and *V. fischeri* ES114 (Δ-luxI). *P. aeruginosa* PAO1 was used in elastase B production assays. All bacteria were grown in a standard laboratory incubator with shaking (200 rpm) unless noted otherwise. Absorbance and luminescence measurements were obtained using a PerkinElmer Wallac 2100 EnVision™ multilabel plate reader using Wallac Manager v1.03 software. All bacteriological assays were performed in triplicate.

*A. tumefaciens* Reporter Gene Assay Protocols.

For primary TraR agonism assays, an appropriate amount of concentrated control or AHL stock solution (to give a final concentration of 10 μM) was added to wells in a 96-well multititer plate. An overnight culture of *A. tumefaciens* WCF47 (pCF372) was diluted 1:10 with fresh AB minimal medium containing 400 μg/mL octopine and 50 μg/mL streptomycin. A 200 μL portion of the diluted culture was added to each well of the multititer plate containing AHLs. Plates were incubated at 28° C. for 18-24 h. The cultures were then assayed for β-galactosidase activity following the Miller assay method. Briefly, 200 μL aliquots of bacteria from each of the wells were added to wells of a 96-well multititer plate, and the $OD_{600}$ of each well was recorded. Next, 50 μL aliquots from each well were transferred to a solvent resistant 96-well multititer plate containing 200 μL Z buffer, 8 μL $CHCl_3$ and 4 μL 0.1% aq. SDS. This suspension was mixed via repetitive pipetting, after which the $CHCl_3$ was allowed to settle. A 100 μL aliquot from each well was transferred to a fresh 96-well multititer plate, and 20 μL of substrate, o-nitrophenyl-β-D-galactopyranoside (ONPG, 4 μg/mL in phosphate buffer), was added at time zero. After the development of appropriate yellow color (ca. 20-30 min), the reaction was terminated by the addition of 50 μL of 1 M $Na_2CO_3$. Absorbances at 420 nm and 550 nm were measured for each well using a plate reader, and Miller units were calculated according to standard methods. Primary TraR antagonism assays were performed in a similar manner except the AHL or control was screened at 10 μM against 100 nM OOHL (1).

E. coli LasR Reporter Gene Assay Protocols.

For primary LasR agonism assays, an appropriate amount of concentrated control or AHL stock solution (to give a final concentration of 5 μM) was added to wells in a 96-well multititer plate. An overnight culture of E. coli DH5α (pJN105L pSC11) was diluted 1:10 with fresh LB medium containing 100 μg/mL ampicillin and 15 μg/mL gentamicin. This sub-culture was incubated at 37° C. until $OD_{600}$=0.3 (4-6 h). Arabinose (4 mg/mL) was then added to induce the LasR promoter, and a 200 μL portion of this culture was added to each well of the multititer plate containing AHLs. Plates were incubated at 37° C. until $OD_{600}$=0.45 (4-6 h). The cultures were then assayed for LasR activity following the identical β-galactosidase assay protocols used in the A. tumefaciens reporter gene assays (see above). Primary LasR antagonism assays were performed in a similar manner except the AHL or control was screened at 5 μM against 7.5 nM OdDHL (2).

V. fischeri Reporter Gene Assay Protocols.

For primary LuxR agonism assays, an appropriate amount of concentrated control or AHL stock solution (to give a final concentration of 200 vM) was added to wells in a 96-well multititer plate. An overnight culture of V. fischeri ES114 (Δ-luxI) was diluted 1:10 with LBS medium. A 200 μL portion of the diluted culture was added to each well of the multititer plate. Plates were incubated at RT until the $OD_{600}$=0.35-0.4 (4-6 h). Luminescence then was measured and normalized to cell density per well. Primary LuxR antagonism assays were performed in a similar manner except the AHL or control was screened at 5 μM against 5 μM OHHL (3).

Dose Response Reporter Gene Assays.

The dose response reporter gene assays were performed according to the protocols outlined above, except the concentrations of control compounds and AHLs were varied between 0.02 and $2 \times 10^6$ nM. $IC_{50}$ and $EC_{50}$ values were calculated using GraphPad Prism software (v. 4.0) using a sigmoidal curve fit.

Elastase B Production Assay in P. aeruginosa.

Elastase B activity in P. aeruginosa was measured according to a previously reported method, with the following modifications. P. aeruginosa PAO1 was grown overnight at 37° C. and then diluted 1:10 with fresh LB medium. Portions (2 mL) of this culture were added to test tubes containing synthetic compounds to give final compound concentrations of 20 μM or 200 μM. The tubes were incubated for 12-14 h at 37° C. The $OD_{600}$ was measured for each tube, after which the contents of the tubes were filtered through a 0.2 μm Whatman filter to remove all cellular matter. A 100 μL aliquot of the supernatant was added to 900 μL of an elastin-Congo red solution (5 mg of elastin-Congo red substrate per 1 mL of buffer (100 mM Tris-HCl, 1 mM $CaCl_2$, pH 7.2)) and incubated for 12 h at 37° C. with 250 rpm shaking. The contents of these tubes were then filtered in order to remove unreacted elastin-Congo red substrate, and the supernatant containing cleaved Congo red was isolated. A 200 μL aliquot of the supernatant was added to a 96-well multititer plate, and the $OD_{492}$ was measured. Elastase B activity was calculated by dividing the absorbance of the cleaved Congo red solution ($OD_{492}$) by the cell density ($OD_{600}$ of the cells before first filtration).

Background—AHL Library Design and Biological Assay Formats.

General Considerations for Ligand Design.

AHLs bearing non-native acyl chains represent the most extensively studied structure class of synthetic quorum sensing modulators in A. tumefaciens, P. aeruginosa, and V. fischeri. Modifications to the lactone ring of AHLs, including inversion of stereochemistry and replacement of the lactone with different carbocyclic or heterocyclic functionalities, have been examined to a lesser extent. Clear SARs for quorum sensing modulators are yet to be established due to the relatively limited set of ligands examined to date. The use of different bacterial reporter strains and assay procedures to assess agonistic or antagonistic activities against the same R protein has further hindered comparison between past studies. Our analysis of this prior work, however, revealed the following broad trends for synthetic R protein modulators in A. tumefaciens, P. aeruginosa, and V. fischeri: (1) changing the number of carbons in the acyl chain relative to the native AHL by 1-3 carbons can weaken a ligand's agonistic activity and/or convert the ligand into a weak antagonist, (2) inversion of lactone stereochemistry (L to D) nearly abolishes agonistic and antagonistic activities for AHLs with native and non-native acyl chains, and (3) introduction of terminal phenyl moieties on the acyl group can result in compounds with antagonistic activities.

These broad trends did not provide us with an obvious strategy for the rational design of new AHLs that modulate quorum sensing in these three bacteria. However, they did offer a foundation on which to design focused, combinatorial libraries of non-native AHL ligands to systematically examine the structural features required for agonistic or antagonistic activity across the three species. In this study, we sought to investigate three key structural features of AHLs: (1) acyl chain length, (2) lactone stereochemistry, and (3) functional group diversity in the acyl chain. We designed four focused libraries of AHLs (A-D) that allowed us to probe each of these features individually and in tandem. The X-ray crystal structure of TraR (i.e., the ligand-binding site) was also used to guide our initial ligand design.

Design of AHL Libraries A-D. Library A was designed to test the effects of different aliphatic acyl, 3-oxo acyl, and sulfonyl groups on AHL ligand activity in the three bacterial species. This library contained the most structurally simple AHL derivatives examined in this study, and several of these ligands have been shown to modulate R protein function previously (albeit largely in different bacterial strains than those utilized in this study). Therefore, Library A was also designed to provide critical benchmark R protein activation and inhibition data. Library B was designed to investigate the roles of the following AHL structural features: (1) lactone stereochemistry, (2) acyl group aromaticity, and (3) alkyl "spacer" length between aromatic groups and the HL ring. We examined these three features by perturbing the structures of known active compounds: the native agonist OOHL (1), the control antagonists of Reverchon et al. (5 and 6), and our previously reported antagonists, 4-bromo PHL 8 and indole AHL 9 (FIG. 5).

Library C consisted entirely of PHLs and was designed to systematically examine the role of phenylacetanoyl group substituents on R protein antagonism and agonism. This library was inspired in part by the strong antagonistic activity of 4-bromo PHL 8 toward TraR and LasR reported previously by our laboratory. Further, we recently examined a subset of the PHLs in Library C in LuxR antagonism and agonism assays, and identified several potent inhibitors and activators of LuxR; we sought to build on these initial findings in the current study. Lastly, Library D contained the most structurally diverse set of non-native AHLs synthesized to date (shown in FIG. 3), and was designed to broadly examine the influence of a range of different acyl groups on AHL-mediated R protein antagonism and agonism. These acyl substituents differed significantly in terms of overall size and the type and placement of functional groups. However, as many of the known active, non-native AHLs contain aromatic groups (see FIG. 5), we deliberately installed aromatic functionality (or at least one π-system) in the acyl chains of the majority of Library D.

Quorum Sensing Reporter Gene Assays.

The low stability of most R proteins in vitro has precluded the development of routine protein-ligand binding assays. As such, non-native ligands have been most commonly assessed for R protein antagonism and agonism in cell-based assays using bacterial reporter strains. These reporter strains lack their AHL synthase (I) genes, but retain their native R genes. In the presence of exogenously added AHL ligand, the AHL:R protein complex will activate transcription of a promoter that controls reporter gene expression. Therefore, R protein activity, and consequently ligand activity, can be measured using standard reporter gene read-outs, such as absorbance, luminescence, or fluorescence. This method provides a straightforward and high-throughput assay for small molecules that either agonize or antagonize (when examined in competition with native AHL ligand) R protein function.

We selected three bacterial reporter strains for the R protein antagonism and agonism assays in this study: *A. tumefaciens* WCF47 (pCF372), *E. coli* DH5α (pJN105L pSC11), 54 and *V. fischeri* ES114 (Δ-luxI) (see Experimental Section). This *A. tumefaciens* strain produces the enzyme β-galactosidase upon TraR activation and ligand activity can be measured using standard Miller absorbance assays in the presence of a colored enzyme substrate. The *E. coli* strain harbors LasR from *P. aeruginosa* and also reports LasR activity by β-galactosidase production. We initially examined a Δ-lasI Δ-rhlI derivative of *P. aeruginosa* with a green fluorescent protein reporter gene in these primary assays, as we sought to evaluate our synthetic ligands in the native backgrounds for each of the three R proteins. However, unacceptably large error values in the assay data (due in part to inconsistent cell growth) forced us to seek this alternate strain (data not shown). We found that the heterologous *E. coli* DH5α system provided reproducible data, although the differences between active and inactive LasR antagonists were somewhat muted relative to the other two strains. Finally, the *V. fischeri* reporter strain retains its native lux operon (yet lacks a functional luxI), which allows LuxR activation or inhibition to be measured by luminescence. We recently found that this strain, while not typically used to assess the activity of non-native AHL ligands against LuxR, is straightforward to manipulate and provides highly reliable small molecule screening data.

Results and Discussion.
Library Synthesis.

AHL Libraries A-D were synthesized rapidly using a microwave-assisted, solid-phase route to AHLs previously reported by our laboratory (FIG. 7). This route allowed for the straightforward construction of either L- or D-lactones through the use of either N-Fmoc-L- or D-methionine (Met, 14) in the initial acylation step, and the introduction of a wide variety of acyl groups, including simple alkyl, 3-oxo alkyl, and sulfonyl moieties (16-18). The ~90 AHLs were isolated in moderate to good yields (55-75%), with excellent purities (90-99%), and in sufficient quantities (~20 mg per compound) for full compound characterization and multiple biological experiments. This route was also utilized for the synthesis of the native AHLs (1-3) and known antagonists (4-6, 8, and 9) for use as control compounds in our biological assays.

Reporter Gene Assays Results.

Libraries A-D were screened in competitive R protein antagonism and agonism assays in the three bacterial reporter strains introduced above. Competitive antagonism assays were performed with synthetic ligand in the presence of native AHL ligand (at its approximate $EC_{50}$ value) at ratios ranging from 1:1 to 100:1 (synthetic vs. native AHL). Agonism assays were performed with synthetic ligand alone. The native ligands OOHL (1), OdDHL (2), and OHHL (3) and the known R protein antagonists 4-9 served as controls for these experiments (FIG. 5). Agonistic activity for each of the native ligands (1-3) was set to 100% in its corresponding strain for comparison. As expected, all of the control antagonists showed inhibitory activity in the three strains, albeit at varied levels (18-93%), with the exception of 2-aminophenol 7, which was surprisingly inactive (see Table 9). This latter result contrasted with previous reports that 7 is a strong inhibitor of LasR activity in similar assays; however, these studies involved a different LasR reporter strain. Heptanoyl HL (4), phenylbutanoyl HL (6), and 4-bromo PHL (8) were the most active control antagonists across all three strains; these three ligands exhibited similar levels of activity against each strain (~90% in TraR, 25% in LasR, and 76% in LuxR). Notably, neither the control compounds nor the library members were observed to be insoluble or affect bacterial growth over the time course of these assays (4-24 h). Further, no ligand was found to degrade (by lactonolysis, proteolysis, or reaction with biological reagents) over the time course of these assays (as determined by LC-MS or GC-MS; data not shown).

The reporter gene assays of Libraries A-D revealed a set of highly potent quorum sensing antagonists and agonists, along with several prominent trends in ligand activity within and between strains that could be correlated to structure. A detailed analysis of the SAR trends in the primary assay data for Libraries A-D will be reported elsewhere. Here, we focus on the most active R protein antagonists and agonists identified in Libraries A-D, which corresponded to 37 compounds. Thirty-one ligands were identified that displayed inhibitory activities of >80% against TraR, >35% against LasR, and/or >75% against LuxR. In turn, 14 ligands were identified as either LasR or LuxR agonists, with activities of >20% in LasR and/or >60% in LuxR. (No TraR agonists were identified in the four libraries.) Interestingly, several of the ligands were observed to be antagonists in one strain, yet were agonists in another. To obtain more quantitative data about the activity of these synthetic R protein antagonists and agonists, we performed dose response assays in the three reporter strains and determined either $IC_{50}$ or $EC_{50}$ values for the 37 ligands. The calculated $IC_{50}$ and $EC_{50}$ values for these compounds are listed in Tables 7 and 8, respectively.

$IC_{50}$ Values for Synthetic AHL Antagonists.

The $IC_{50}$ values for the antagonists ranged from high nanomolar to low micromolar concentrations, and over 60% of these ligands (20 compounds) had lower $IC_{50}$ values than those for the control antagonists reported in this study (Table 7). This high percentage of hits is significant (25% of the total library), as few potent synthetic antagonists of R proteins have been reported. Moreover, several new antagonists were identified that either selectively inhibited one or two R proteins, or inhibited all three R proteins. The structures of the most active antagonists are shown in FIG. 13C, and their observed selectivities for R protein targets are illustrated using a Venn diagram for clarity. Butane sulfonyl HL A9, bulky AHL D6, and phenyl ether AHL D15, were the most active inhibitors of TraR, with each inhibiting TraR by 50% at ~5.5:1 against native ligand OOHL (1) (entries 11, 29, and 30, respectively; Table 7). Notably, A9 and D6 were highly selective for TraR over LuxR and LasR, while D15 exhibited moderate cross-inhibitory activity against LasR.

Five ligands were identified with $IC_{50}$ values against LasR that were an order of magnitude lower than control antagonists 8 and 9 (Table 7). Interestingly, the most active inhibitor of LasR identified in this study was OOHL (1), the native AHL ligand from *A. tumefaciens*, which inhibited LasR by 50% at ~15:1 against OdDHL (2) (entry 1). The second most active antagonist of LasR in this study was the $C_{10}$ AHL A4, inhibiting by 50% at ~30:1 against OdDHL (2) (entry 9). In contrast, previous studies by Passador et al., using an alternate *E. coli* reporter stain, revealed neither OOHL (1) nor AHL A4 as active inhibitors of LasR. AHL B7 (the one-carbon longer homolog of control antagonist 4-bromo PHL 8) AHL B14 (the one-carbon shorter homolog of control antagonist indole AHL 9), and 3-nitro PHL C14 were the next most active inhibitors of LasR identified (entries 17, 19, and 26). In terms of selectivity for R protein, AHL B14 and 3-nitro PHL C14 were most selective for LasR, while OOHL (1) inhibited LasR, and, to a lesser degree, LuxR (see Table 9). Conversely, AHLs A4 and B7 were moderate to strong antagonists of all three R proteins (entries 9 and 17).

The most potent antagonists identified overall were active against LuxR. Remarkably, these ligands were capable of inhibiting LuxR by 50% at ~10-fold lower concentrations relative to its native ligand OHHL (3). Here, two aliphatic AHLs and one PHL were identified as the most potent antagonists: the native ligand for *P. aeruginosa*, OdDHL (2), $C_{10}$ AHL A4, and 4-trifluoromethyl PHL C20 (FIG. 13C). Both OdDHL (2) and A4 were capable of inhibiting LuxR activity by 50% at a ~1:12.5 ratio against OHHL (3) (entries 2 and 9, Table 7). This result corroborated previous work by Schaefer et al. that indicated OdDHL (2) and A4 can inhibit LuxR, albeit to a significantly lesser degree (again, this work was performed in an alternate LuxR reporter strain). The non-native, 4-trifluoromethyl PHL C20 displayed a similarly high level of antagonistic activity against LuxR at a ~1:8 ratio against OHHL (3) (entry 28). AHL A8, the $C_{14}$ analog of OdDHL (2), was the next most potent inhibitor of LuxR (entry 10). These four ligands varied significantly in terms of their selectivities; both OdDHL (2) and A8 were highly selective for LuxR, while PHL $C_{20}$ was a potent inhibitor of LuxR and TraR, and A4 again inhibited all three R proteins (see above).

$EC_{50}$ Values for Synthetic AHL Agonists.

It is obvious from FIG. 13D that far fewer R protein agonists were identified in our primary screens relative to antagonists (14 compounds), and that these agonists show exquisite selectivity for individual R proteins. The agonism dose response studies revealed several ligands with $EC_{50}$ values against LasR comparable to the native ligand OdDHL (2) (entry 2, Table 8). The $C_{12}$ AHL A5 and 3-oxo $C_{14}$ AHL A8 displayed the lowest $EC_{50}$ values (40 and 10 nM, respectively), and these values supported activity data previously reported by Passador et al. for these two compounds. Not surprisingly, these two LasR activators were similar in structure to OdDHL (2) (FIG. 13D). D-AHL B2 was far less structurally analogous, and exhibited a 50-fold higher $EC_{50}$ value relative to OdDHL (2) (entry 7, Table 8). This synthetic LasR activator is noteworthy, however, as it represents, to our knowledge, the most active D-AHL reported to date. Interestingly, the L-stereoisomer of B2, AHL 5, is virtually inactive against LasR (see Table 9). This trend is opposite to what has been observed for native AHL ligands, where the L-stereoisomer is an active R protein agonist and the D-stereoisomer is almost inactive.

The most remarkable outcome of our agonism dose response studies was in *V. fischeri*. Here, PHLs with substituents in the 3-position on the phenyl ring were the only non-native ligands displaying appreciable agonistic activity (C6, C8, and C14; Table 8). Most notably, we determined an $EC_{50}$ value for 3-nitro PHL C14 against LuxR that was ~10-fold lower than that for its native ligand OHHL (3) (0.35 vs. 3.0 µM). Additional studies of C14 in our laboratory have demonstrated that this PHL also exerts it super-agonistic activity in wild-type *V. fischeri*. This result was extraordinary, as there are only three other reported synthetic super-activators of R proteins (see above), and no known super-activators of the model symbiont *V. fischeri*. PHL C14 is structurally dissimilar to these other three ligands (10-12; FIG. 5), and represents a powerful new tool to probe the roles of quorum sensing in beneficial bacterial symbioses. Intriguingly, PHL C14 was also identified as a potent antagonist of LasR (see above; FIG. 13C), indicating a complex activity profile for PHLs as R protein modulators.

Examination of Synthetic LasR Antagonists in a Virulence Factor Production Assay.

As the primary assays for synthetic LasR modulators were performed in a heterologous *E. coli* reporter strain, we sought to determine if the active ligands identified in these screens were also active against LasR in *P. aeruginosa*. The metalloprotease elastase B is a virulence factor that is produced and excreted by *P. aeruginosa* under the control of LasR. Synthetic ligands that inhibit LasR should therefore also inhibit the production of elastase B, and this can be measured by a standard enzymatic assay in the presence of an elastase B substrate (elastin). We examined a set of LasR antagonists identified in the primary assays of Libraries A-D (B7, C11, C14, and D15), along with selected controls (8, 9, and C18), using a previously reported colometric assay for elastase B in *P. aeruginosa* (PAO1) that utilizes an elastin-Congo red substrate. Notably, controls 8 and 9 had been previously shown to inhibit LasR in a *P. aeruginosa* strain. PHL C18 was chosen as an additional control for this assay, as this ligand only exhibited weak LasR inhibition in the *E. coli* reporter strain (see Table 9), and we sought to determine if it would also show weak activity in the elastase B production assay.

Figure 16:
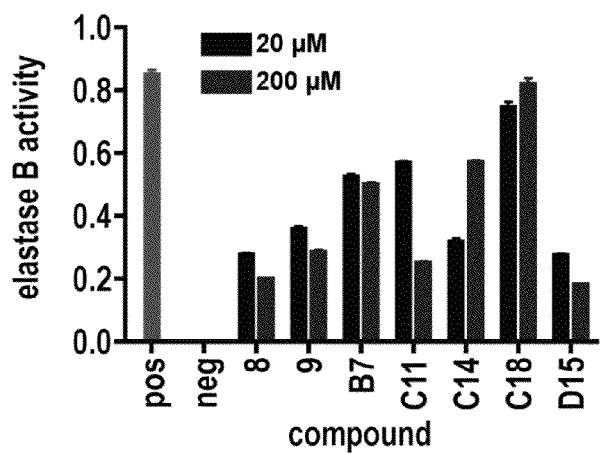
FIG. 16 provides data showing elastase B production inhibition assay in wild-type *P. aeruginosa*.

The assay revealed several potent synthetic inhibitors of elastase B production, and thus LasR, in wild-type *P. aeruginosa* (FIG. 16). As expected, the 4-bromo PHL 8 and indole AHL 9 controls were strong inhibitors of elastase B production in this assay, inhibiting enzyme activity by 77% and 66% at 200 µM, respectively, while PHL C18 poorly inhibited elastase B production (4% at 200 µM). We were pleased to observe that all of the new LasR antagonists (B7, C11, C14, and D15) were moderate to strong inhibitors of elastase B production at 200 µM (up to 79% for phenyl ether AHL D15). Interestingly, 3-nitro PHL C14 displayed increased inhibitory activity at 10-fold lower concentration (33% inhibition at 200 µM vs. 63% at 20 µM; FIG. 16), while the inhibitory activities of the other three ligands (B7, C11, and D15) were either comparable or slightly stronger at 200 μM relative to 20 μM. The reasons behind this concentration-dependent change in activity for PHL C14 were unclear, and we return to this observation below. Nevertheless, this virulence factor production assay demonstrated that the active inhibitors we uncovered in the *E. coli* LasR reporter strain assays are indeed inhibitors of LasR in *P. aeruginosa*, and served to validate the use of this reporter strain for the primary screening of synthetic modulators of LasR.

SAR Analysis of Active Ligands.

The dose response analyses above identified the most active R protein modulators in Libraries A-D (FIGS. 16C and 16D), and we carefully inspected these structures in an attempt to determine SARs that conveyed R protein selectivity or activity across the three species. Such study revealed that subtle structural differences tuned ligand selectivity and activity. A list of the eight most prominent SAR trends and R protein characteristics influencing antagonistic and agonistic activities for Libraries A-D is provided below:

1. In general, AHLs with acyl groups of moderate size (up to eight atoms long) and containing either aromatic functionality with electron-withdrawing groups or straight chain aliphatic functionality can antagonize TraR, LasR, and LuxR. AHL B7 exemplifies such a broad-spectrum antagonist.

2. The PHL appears to be a "privileged" scaffold for R protein modulation, as these ligands display a wide range of antagonistic and agonistic activities across all three R proteins in this study. Ligand activity is highly dependent on the structure and position of substituents on the phenyl group. Specifically, PHLs with electron-withdrawing and lipophilic substituents in the 4-position on the phenyl group display the strongest antagonistic activities against TraR and LuxR. The same trend holds true in LasR for PHLs with substituents in the 3-position.

3. Of the AHLs structurally related to control 4-bromo PHL 8, a flexible carbon spacer of at least one carbon between the lactone ring and an aromatic acyl group, and a 4-bromo substituent on the phenyl group engender the strongest antagonistic activity, with AHL B7 being the most active inhibitor in this structure class across the three R proteins.

4. A three-carbon spacer between the lactone ring and an aromatic acyl group is optimal for inhibition in ligands structurally related to control indole AHL 9. This trend is most apparent for LasR (i.e., AHL B14).

5. Sulfonyl groups can replace carbonyl groups on aliphatic AHL TraR and LuxR antagonists without significant loss in activity. The sulfonyl HLs in this study were most active against TraR (e.g., A9), yet virtually inactive against LasR.

6. TraR is the most sensitive to the length of the acyl group on AHLs, as inhibitory activity drops off dramatically for AHLs with acyl tails longer than eight atoms. This observation is in accord with both its native ligand, OOHL (1), which contains an octanoyl group, and the sterically constricted ligand-binding site of TraR as revealed by X-ray crystallography (assuming the synthetic ligands target the same site, see below).

7. LasR is the most tolerant of varying functionality on the AHL acyl chain, acyl chain size, and the stereochemistry of the homoserine lactone ring, suggesting that it has a larger ligand-binding site than TraR. This result is in accord with the X-ray crystal structure of LasR, assuming that synthetic AHLs target the same binding site on LasR (as with TraR, see below).

8. LuxR is most strongly inhibited by AHLs with medium to long (6-14 carbon), 3-oxo-aliphatic acyl groups and most strongly activated by PHL ligands with electron-withdrawing substituents in the 3-position.

Targets of Synthetic AHL Antagonists and Agonists.

In view of the structural similarities of the synthetic AHLs in Libraries A-D to native AHLs and the subtle SARs described above, we hypothesize that these ligands target R protein ligand-binding sites, and that inhibition or activation is based on the specific binding mode, and therefore affinity, of the ligand. Further, we do not believe that these changes in antagonistic or agonistic activity simply reflect the different chemical properties of the synthetic AHLs. This assertion is supported by several observations. First, the percentage of lactone hydrolysis (which abolishes activity for native AHLs) for the synthetic ligands was minimal and identical to that of the native ligands over the time course of the reporter gene assays (see above). Second, higher ligand lipophilicity, and therefore higher potential cell permeability, did not correlate with enhanced antagonistic or agonistic activity (Tables 7 and 8). This was further exemplified by the D-AHLs B1-B5, which have identical lipophilicities as OOHL (1) and control antagonists 5, 6, 8 and 9, respectively, yet exhibit markedly different activities (see Table 9). Third, as we previously reported, selected PHLs (e.g., PHL C14) failed to exhibit any activity in a Δ-luxR derivative of *V. fischeri* ES114, suggesting that these ligands exert their activity through the LuxR protein.

To further test our hypothesis that these ligands target R protein ligand-binding sites, we performed molecular modeling studies of several of the most active synthetic AHLs docked into the ligand-binding sites of TraR and LasR (using the X-ray crystal structures) and the putative ligand-binding site of LuxR (built in silico from TraR by homology modeling). The results of these studies suggest that all three ligand-binding sites can readily accommodate the synthetic AHLs, and that activation or inhibition of the R protein may depend on the subtle balance of favorable hydrogen-bonding and unfavorable steric interactions within the binding pocket. The LasR ligand-binding site appears to be the most accommodating in terms of ligand size, while the TraR ligand-binding site appears the most restrictive, and the LuxR ligand-binding site falls between these two extremes; these observations match the general SAR trends delineated above. While additional biochemical and structural experiments are needed to further test our hypothesis, these computational experiments further support the supposition that the synthetic AHLs identified in this study target R proteins.

Mechanistic Insights into R Protein Modulation by Synthetic Ligands.

Further insights into how our synthetic ligands modulate R protein function were acquired through additional scrutiny of the primary screening data and dose response studies outlined above. Several ligands displayed unexpected activity trends in these assays. For example, AHLs D14, D15, and D18 inhibited LasR in the presence of native ligand OHHL (3) in antagonism assays, yet activated LasR to the same level in agonism assays (~35%; see Table 9). More strikingly, we observed that over 60% of the AHL antagonists identified in this study exhibited antagonism dose response curves that started to slope back up at higher concentrations (see Table 7), indicating that these ligands were also capable of activating R proteins at higher concentrations. This trend could not be correlated with specific structural features, yet loosely correlated with ligand activity (i.e., those with the lowest $IC_{50}$ values) in TraR and LasR. Agonism dose response studies of these compounds revealed that they were in fact capable of activating R proteins at higher concentration, in some cases quite strongly (i.e., C14 in LasR). Indeed, the agonism dose response curves began to curve up at precisely the concentration where their respective antagonism dose response curves began to upturn. The 3-nitro PHL C14 exhibited this dual behavior in two other instances in this study. First, similar antagonism and agonism dose response curves could be generated for PHL C14 in *V. fischeri*, where this compound can behave as a super-activator. Second, PHL C14, initially identified as a LasR antagonist, was also capable of activating elastase B production in *P. aeruginosa* at high concentrations (see FIG. 16). These observations suggested that defining these AHLs exclusively as R protein antagonists or agonists, as we had up until this point, was incorrect.

This duality of ligand activity suggests that these "antagonists" (such as PHLs C13 in LuxR, D14, D15, D18, and C14 in LasR, and C20 in TraR) are actually best described as partial agonists. Partial agonists have properties of agonists and antagonists and are broadly characterized by three phenomena: (1) at middle-range concentrations, partial agonists act as antagonists, (2) the maximum response (efficacy) of a partial agonist is lower than that of the natural ligand for a target receptor, and (3) in dose response analyses against variable concentrations of the native ligand, the baseline activity increases with the concentration of partial agonist such that at high concentrations, activity is equal to the partial agonist's efficacy. Our primary antagonism assay data for the AHLs that displayed this dual activity were in accord with the first characteristic of partial agonism (e.g., see Table 7).

To examine if these AHLs also exhibit the two other defining characteristics of partial agonism, we carried out additional experiments with selected AHLs (C8 and C13 in LuxR, and D14, D15, and D18 in LasR). We performed agonism dose response studies of the five AHLs over a broader range of concentrations in the LasR and LuxR reporter strains, and determined that these ligands show lower agonism levels, or efficacies, than the native ligands OdDHL (2) and OHHL (3). Indeed, the maximal responses of these compounds were up to four-fold lower than the maximal response of the corresponding native ligand. Next, we performed dose response studies on PHL C13 in *V. fischeri* against varying concentrations of OHHL (3) to test the third distinguishing characteristic of partial agonism. We found that AHL C13 exhibited an increase in baseline activity that is expected for a partial agonist. Again, since the efficacy of a partial agonist is lower than that of the native ligand, the baseline dose did not reach a maximal response but instead reached a plateau at the efficacy level for C13. Similar two-dimensional dose response data also were obtained for C8, D14, D15, and D18 (data not shown). Together, these experiments provide strong support for a partial agonism mechanism for R protein modulation by these non-native AHLs.

The origins of this partial agonism by synthetic AHLs could be multifold, including lowered affinity of the ligand for the R protein, impeded folding (or destabilization) of the R protein upon ligand binding, lowered affinity of the R protein:ligand complex for homodimerization, formation of heterodimers with the R protein:native ligand complex, and/or lowered affinity of these homodimers or heterodimers for DNA. All such pathways would be in accord with the currently accepted mechanisms of action for native AHL ligands (see above). In turn, this partial agonism model also helps to explain the mechanism of super-agonism for PHL C14 in LuxR; here, this ligand may be capable of stabilizing LuxR to a greater extent relative to OHHL (2). Additional biochemical experiments are required to test these hypotheses and are on-going in our laboratory.

To our knowledge, these data represent the first definitive report of synthetic AHL ligands behaving as partial R protein agonists, and lead to many new and important questions. For example, do all of the ligands identified as agonists and antagonists in this study behave through a similar mechanism? If so, is this phenomenon dependent on the ligands having a HL head group? How do the SARs delineated above dictate partial agonist activity? What are the mechanisms of action of other reported AHL and non-AHL modulators of R protein function? We are actively seeking answers to these broad questions in order to fully understand the biochemical mechanisms of action of these synthetic ligands. In lieu of these answers, however, the activity trends for the synthetic AHLs identified in this study indicate that the mechanisms of small molecule modulation of R protein function are more complex than perhaps we originally anticipated.

Summary and Conclusions.

We have designed and synthesized four focused collections of synthetic AHL ligands and systematically examined these ~90 compounds in three bacterial reporter strains to determine their abilities to modulate R protein function. These studies have revealed some of the most potent synthetic antagonists and agonists of the well-characterized R proteins TraR, LasR, and LuxR reported to date. These ligands include AHL A4,4-bromo phenylpropionyl HL B7,4-iodo PHL C10, and 3-nitro PHL C14. Several of the LasR antagonists (most notably AHL D15) were capable of strongly inhibiting virulence factor production in *P. aeruginosa* that is essential for pathogenesis. In addition, we have identified critical structural features that confer antagonistic and agonistic activities to these synthetic AHL ligands against the three R proteins. In general, the AHLs modulating TraR and LuxR were sterically more compact and less lipophilic than those for LasR, with TraR being the most discriminatory in terms of ligand size. These data are in accord with the ligand-binding sites for TraR and LasR as indicated by recent X-ray crystal structures. Subtle alterations to substituents and their placement on the AHL acyl group dramatically influenced ligand activity. This effect was most remarkable in the PHL library (Library C), where these structural changes (e.g., shifting substituents from the 4- to the 3-position on the phenyl ring) did not simply abolish activity, but rather converted potent antagonists (or partial agonists) into agonists, or even a superagonist (i.e., C14). In addition, we also discovered that the synthetic D-AHL B2 is capable of strongly activating LasR. This ligand represents, to our knowledge, the first reported D-AHL capable of significantly modulating R protein activity.

Overall, the most significant outcome of this work is the identification of sets of ligands that selectively modulate one, two, or all three of the R proteins in this study (FIGS. 16C and 16D). This result fulfilled the overarching goal of the present study—to identify both selective and multi-species modulators of R proteins, and therefore quorum sensing responses, in Gram-negative bacteria. A second major outcome of this work was our discovery that many of the most potent R protein "antagonists" identified in the reporter gene assays exert their activities through a partial agonism mechanism. This represents a new paradigm for ligand activity against R proteins. Further, such partial agonists could hold significant promise for the exploration of the medicinal outcomes of quorum sensing modulation. Lastly, a third key outcome is the identification of such a large set of potent ligands through the synthesis and screening of a relatively limited set of AHLs (~90 compounds). This result suggests that we have only scratched the surface of the pool of non-native modulators of R protein function, and further underscores the utility of focused combinatorial libraries for the identification of such compounds. The design and examination of expanded compound libraries, containing AHL and non-AHL structures classes, is clearly warranted to further probe the features of chemical space essential for small molecule-mediated R protein activation and inactivation. The new SARs and mechanistic insights delineated in this study will shape the design of a such next-generation quorum sensing modulators.

In closing, the synthetic AHLs identified herein represent a new and expansive set of chemical tools for the study of quorum sensing in Gram-negative bacteria, and could, with further development, provide broad insights into bacterial pathogenesis and beneficial symbioses. We are actively engaged in such experiments to examine the scope and limitations of these compounds in vitro and in vivo. Preliminary work in invertebrate model systems indicates that several of these ligands are well tolerated and can modulate quorum-sensing responses in vivo.

Instrumentation and Analytical Methods.

General. $^1$H NMR spectra were recorded on a Bruker AC-300 spectrometer in deuterated solvents at 300 MHz. Chemical shifts are reported in parts per million (ppm, δ) using tetramethyl silane (TMS) as an internal reference (0.0 ppm). Couplings are reported in hertz. Electrospray ionization (ESI) MS were obtained using a Shimadzu LCMS-2010 system (Columbia, Md.) equipped with two pumps (LC-10ADvp), controller (SCL-10Avp), autoinjector (SIL-10ADvp), UV diode array detector (SPD-M10Avp), and single quadrupole analyzer. GC-MS data were obtained using a Shimadzu GC-17A system (Columbia, Md.) equipped with a QP-5000 mass spectrometer. A Restek RTX-5 cross bond 95% polysiloxane column was used for all GC-MS analyses. The standard GC method was as follows: injection temperature 300° C.; initial oven temperature 200° C.; hold 3 min; ramp at 20° C./min to 300° C.; hold 2-15 min for a total run time of 10-15 min. FT-IR spectra were recorded with a Bruker Tensor 27 IR spectrometer, outfitted with a single reflection MIRacle Horizontal attenuated total reflectance (ATR) unit from Pike Technologies. A ZnSe crystal with spectral range 20,000 to 650 cm$^{-1}$ was used for ATR-IR measurements. Optical rotations ($[\alpha]_{24D}$) were measured on a Perkin-Elmer 241 digital polarimeter at 25° C.

Microwave Instrumentation.

Microwave (μW)-assisted solid-phase reactions were performed in either a Milestone or CEM commercial μW reactor. The Milestone MicroSYNTH Labstation is a multimodal μW synthesis reactor equipped with a continuous power source (1000 W max). This instrument is interfaced with an Ethos MicroSYNTH Lab Terminal PC running EasyWave reaction monitoring software. The Milestone μW reactor is equipped with a fiber-optic temperature sensor that allows direct monitoring of the internal temperature of reaction vessels, and an infrared sensor (installed in the side wall of the reactor cavity) that monitors the surface temperature of any reaction vessel inside the cavity. The system also has a rotating plate in the cavity and the capability for stirring (using magnetic stir-bars) during reactions.

The CEM Discover is a monomodal μW synthesis reactor equipped with a 300 W (max) power source. The system has an attached Explorer automated synthesis workstation module, with four autosampler racks that each hold six samples. The instrument is interfaced with a Dell Inspiron PC running ChemDriver Discovery reaction-monitoring software. The CEM μW reactor is equipped with an infrared temperature sensor positioned below the reaction vessel to control temperature. The system also has the capability for stirring (using magnetic stir-bars) during reactions.

All μW-assisted reactions reported in this study were performed using temperature control to monitor and control μW irradiation.

Solid-Phase Synthesis Methods.

Solid-phase reactions were performed in either sealed 100 mL glass round-bottom flasks in the Milestone μW reactor or sealed 10 mL glass CEM μW vessels (part #908035) in the CEM μW reactor. Between synthesis steps, the solid-phase resin was washed with solvents stored in standard polypropylene Nalgene squirt bottles on a Vac-Man vacuum manifold (Promega, part #: A7231) using 8 mL polypropylene sample reservoirs (Alltech, part #: 210208) equipped with 20 μm frits (Alltech, part #: 211408). Liquid reagents were dispensed during synthesis using Brinkman Eppendorf pipettmen (calibrated for variable solvent delivery) equipped with disposable polypropylene pipette tips.

Selected Primary Reporter Gene Assay Data

Primary antagonism and agonism reporter gene assay data for the control compounds 1-9 and AHLs B1-B5, C18, D14, D15, and D18 in the *A. tumefaciens*, *E. coli* (LasR), and *V. fischeri* reporter strains are listed in Table 9. For brevity, the primary data for Libraries A-D in their entirety will be reported elsewhere. The three bacterial reporter strains used in this study were: *A. tumefaciens* WCF47 (Δ-traI) harboring a plasmid-born PtraI-lacZ fusion (pCF372), *E. coli* DH5α harboring the LasR expression vector pJN105L and a plasmid-born PlasI-lacZ fusion (pSC11), and *V. fischeri* ES114 (Δ-luxI).

Table 9. [a] All assays performed in triplicate; Error did not exceed ±10%. Shaded compounds are controls. β-galactosidase production or luminescence in the absence of added compound was less than 0.1%; Negative controls containing no compound were subtracted from each sample to account for background. Negative inhibition values indicate that the compound activates at the tested concentration. [b] Strain: *A. tumefaciens* WCF47 (pCF372). Assay data normalized to OOHL (1). [c] Screen performed using 10 μM synthetic ligand against 100 nM OOHL (1). d Screen performed using 10 μM ligand. [e] Strain: *E. coli* DH5α (pJN105L pSC11). Assay data normalized to OdDHL (2). [f] Screen performed using 5 μM synthetic ligand against 7.5 nM OdDHL (2). [g] Screen performed using 5 μM ligand. [h] Strain: *V. fischeri* ES114 (Δ-luxI). Assay data normalized to OHHL (3). [i] Screen performed using 5 μM synthetic ligand against 5 μM OHHL (3). [j] Screen performed using 200 μM ligand.

Example 4

Comparative Analysis of N-Acyl Homoserine Lactones Reveals Unique Structural Features that Dictate their Ability to Activate or Inhibit Quorum Sensing Bacterial quorum sensing is mediated by low molecular weight signals and plays a critical role in both the pathogenesis of infectious disease and beneficial symbioses. There is significant interest in the development of synthetic ligands that can intercept bacterial quorum sensing signals and modulate these important outcomes. Here, we report the design and comparative analysis of the effects of ~90 synthetic N-acylated homoserine lactones (AHLs) on quorum sensing in three Gram-negative bacterial species and a critical examination of the structural features of these ligands that dictate agonistic activity, antagonistic activity, and selectivity for different R proteins. These studies have revealed the most comprehensive set of structure-activity relationships to date that underlie AHL-mediated quorum sensing and provide a foundation on which to design next-generation ligands for use as chemical probes to study this complex signaling process.

Introduction.

Bacteria use small molecules and peptides to assess their local population densities in a process termed quorum sensing (QS). When they have amassed in sufficient number (or reached a "quorum"), bacteria will alter gene expression to behave as a group and initiate processes that play central roles in both pathogenesis and beneficial symbioses. These group behaviors are remarkable in their diversity, ranging from virulence factor and antibiotic production to biofilm formation and bioluminescence, and have direct and often devastating impacts on the bacterial host. As QS depends on a relatively simple language of low molecular weight compounds, there is significant interest in the design and synthesis of non-native molecules that can intercept QS signals and modulate these important outcomes. Such ligands would represent valuable molecular probes for studying the fundamental mechanisms of QS and elucidating the roles of this chemical signaling process in host/bacteria interactions. These studies are also essential for the continued evaluation of QS as a new therapeutic target.

QS is best characterized in the Gram-negative Proteobacteria, and thus the majority of research on synthetic modulators of QS has focused on this signaling pathway. The Proteobacteria use diffusible N-acylated L-homoserine lactones (AHLs) as their primary signaling molecules (FIG. 5); these ligands are produced by AHL synthases (or I proteins) and sensed by cytoplasmic receptors (or R proteins) that behave as transcription factors. At low cell densities, bacteria constitutively produce the AHL synthase, and thus the AHL ligand, at low levels. As the bacterial colony grows, however, the local concentration of AHL will likewise increase and eventually reach a threshold level at which the AHL will bind to its cognate R protein. Thereafter, the AHL-R protein complex will most often dimerize and bind to QS promoters to activate the transcription of genes required for bacterial group behaviors. This signaling pathway was first described in the bioluminescent marine symbiont *Vibrio fischeri*, and has been characterized in over 50 different Proteobacteria to date. Many of these bacteria are clinically and industrially important, most notably the opportunistic pathogen *Pseudomonas aeruginosa*, which uses QS to control virulence factor production and growth into drug impervious biofilms.

As AHL-R protein binding is an essential event in QS, there has been considerable research on the development of non-native AHLs that can inhibit this ligand-protein interaction. The majority of this work has focused on the three best characterized AHL-R protein systems (FIG. 5): N-(3-oxo-octanoyl)-L-homoserine lactone (OOHL, 1) and TraR in the plant pathogen *Agrobacterium tumefaciens*, N-(3-oxo-dodecanoyl)-L-homoserine lactone (OdDHL, 2) and LasR in the animal and plant pathogen *P. aeruginosa*, and N-(3-oxo-hexanoyl)-L-homoserine lactone (OHHL, 3) and LuxR in the marine symbiont *Vibrio fischeri*. However, potent antagonists remain scarce. Four of the most effective AHL-derived antagonists of these AHL-R protein systems reported to date are shown in FIG. 5: heptanoyl HL (4) active against TraR, 3-oxo-phenylbutanoyl- and phenylbutanoyl HLs (5 and 6) active against LuxR, and the 2-aminophenol analog of OdDHL (7) active against LasR. Further, as most non-native AHLs have only been tested against one bacterial species, the selectivities of these ligands for different R proteins are largely unknown. Insufficient structure-activity relationship (SAR) data for non-native AHLs within and between different Gram-negative bacteria has precluded the design of new ligands with improved activities against and selectivities for R proteins. Likewise, this dearth of SAR data has also protracted the design of non-native AHL activators of QS. The use of different assay procedures to assess agonistic or antagonistic activity against the same R protein has further complicated comparisons between past studies.

To address these challenges, our laboratory has embarked on the design and synthesis of focused, combinatorial libraries of non-native AHLs to identify SAR that engender both antagonistic and agonistic activities toward a range of different R proteins. Our preliminary comparative studies revealed several potent antagonists of both TraR and LasR, most notably 4-bromo phenylacetanoyl HL (PHL 8) and indole AHL (9) (FIG. 5). Recently, we reported the synthesis of a ~90-member AHL library and the systematic evaluation of these ligands to modulate R protein activity in *A. tumefaciens, P. aeruginosa*, and *V. fischeri*. These studies uncovered some of the most potent synthetic inhibitors and activators of R protein-mediated QS reported to date and provided broad new insights into their mechanism of action. Here, we report full details of the design of these libraries and a critical analysis of the primary R protein antagonism and agonism data for these ~90 ligands. These studies have afforded an extensive set of SAR data that dictate antagonistic and agonistic activity, and R protein selectivity for AHL ligands in *A. tumefaciens, P. aeruginosa*, and *V. fischeri*. Together, these data provide a valuable new roadmap for the design of next-generation ligands for use as chemical probes to study the mechanisms of QS and its complex roles in host/bacteria interactions.

Results and Discussion.

AHLs bearing non-native acyl chains represent the most extensively studied class of synthetic quorum sensing modulators in *A. tumefaciens, P. aeruginosa*, and *V. fischeri*. Structural modifications to the lactone ring, including inversion of stereochemistry, and replacement of the lactone with different carbo- or heterocycles have been examined to a lesser degree. Our analysis of this past work revealed that a systematic study of non-native AHLs across these three bacterial species was required to establish a set of explicit SARs for AHL modulators of QS.

We first sought to synthesize a focused, combinatorial library of AHLs that would allow us to probe key features of AHL structure, including (1) acyl chain length, (2) lactone stereochemistry, and (3) functional group diversity in the acyl chain. We designed and synthesized four AHL sub-libraries (A-D) that allowed us to investigate these three structural features individually and in tandem. An X-ray crystal structure of TraR from *A. tumefaciens* the ligand-binding site) was also consulted in silico to guide our initial ligand design; as the ligand-binding sites of TraR, LasR, and LuxR have ~70% sequence homology, we reasoned that such analysis was valuable. Next, we systemically examined these AHL libraries for both R protein antagonistic and agonistic activities in *A. tumefaciens, P. aeruginosa*, and *V. fischeri* using established reporter gene assays. Below we provide our detailed rationales behind the design of Libraries A-D, a brief description of our library synthesis and assay methods, and an in depth discussion of the primary antagonism and agonism data and the SAR trends revealed by these data.

Figure 17:
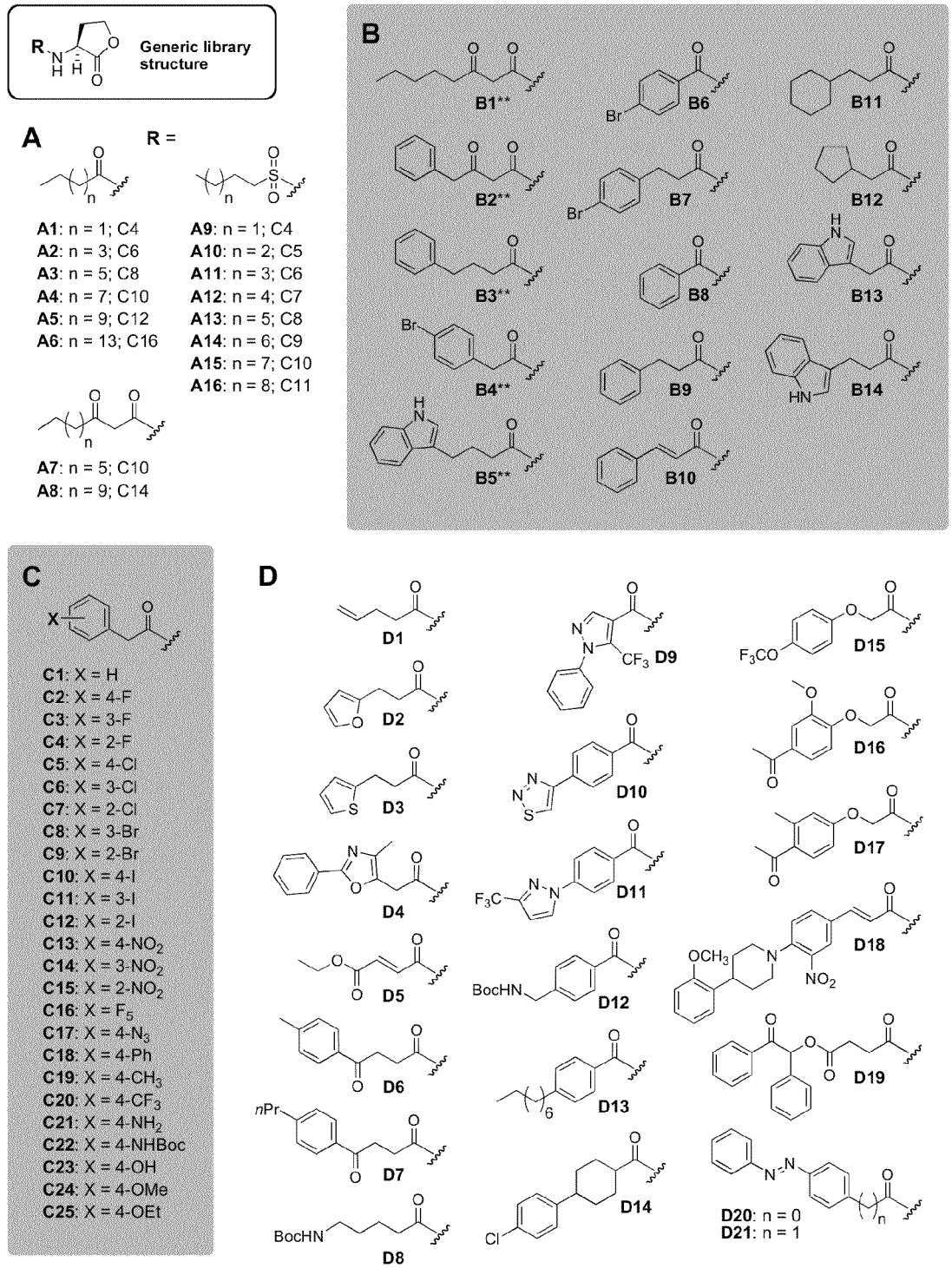
FIG. 17 illustrates structures of AHL Libraries A-D.

FIG. 17. Structures of AHL Libraries A-D. The number of carbons (C) in certain aliphatic acyl groups is indicated for clarity. **=Indicates the HL has D-stereochemistry; All others have L-stereochemistry.

Design of AHL Library A.

Library A was designed to test the effects of different aliphatic acyl, 3-keto acyl, and sulfonyl groups on AHL ligand activity in the three bacterial species. The structures of this 16-member focused library are shown in FIG. 17A, and represent the most structurally simple AHL derivatives examined in this study. AHLs A1-A8 are naturally occurring AHLs utilized by other Gram-negative bacteria for QS, and several have been evaluated in TraR, LasR, and/or LuxR agonism or antagonism assays previously. The $C_4$ AHL A1 is also utilized by *P. aeruginosa* as secondary signaling molecule for QS (via RhlR). Several of the sulfonyl compounds in Library A (A9-A14) were reported by Castang et al. to inhibit LuxR activity at a low to moderate level (in a heterologous *E. coli* LuxR reporter strain), with activity maximal at a five-carbon (six-atom) acyl chain length (i.e., A10). Collectively, however, these ligands have not been examined in the three bacterial strains utilized in this study. Consequently, Library A was designed to provide important benchmark data for the comparison of ligand antagonistic and agonistic activities between the strains.

Design of AHL Library B.

The structures of the second AHL library in this study, Library B, are shown in FIG. 17B. We designed Library B to investigate the roles of the following AHL structural features on R protein antagonism and agonism: (1) lactone stereochemistry, (2) acyl group aromaticity, and (3) alkyl "spacer" length between aromatic groups and the HL ring. We examined these three features by perturbing the structures of known active compounds: the native agonist OOHL (1), the two phenylbutanoyl HL control antagonists (5 and 6), and our two previously reported antagonists, 4-bromo PHL 8 and indole AHL 9 (FIG. 5). The effect of lactone stereochemistry on R protein activation had only been examined for a limited set of native AHLs, and to our knowledge, had yet to be examined in synthetic AHL antagonists. (We note that many synthetic AHLs have been tested in racemic form, or their stereochemistry was not explicit, which adds additional complexity to this analysis.) Lastly, the roles of acyl group aromaticity and spacer length on ligand activity, specifically in our antagonists 8 and 9, were unknown.

Design of AHL Library C.

The structures of Library C are shown in FIG. 17C; each of the 25 library members was designed to systemically test the effects of different functional groups and their position on the PHL phenyl ring. These functional groups differed significantly in terms of electronics and steric size, ranging from halogens to aromatic groups. Library C was inspired in part by the high antagonistic activity of control PHL 8 toward TraR and LasR reported previously by our laboratory. In addition, we recently examined a subset of the PHLs in Library C in LuxR antagonism and agonism assays, and identified several potent modulators of LuxR in *V. fischeri*. These preliminary studies underscore the value of the PHL scaffold for the design of new R protein modulators, and provide a foundation for the systematic examination of PHLs C1-C25 across the three strains in the current work.

Design of AHL Library D.

Library D contained the most structurally diverse set of synthetic AHLs reported to date (shown in FIG. 17D), and was designed to examine the effects of a range of different acyl groups on AHL-mediated R protein antagonism and agonism. These acyl groups differed extensively in terms of overall size and the type and placement of functional groups. However, as several active non-native AHLs contain aromatic groups (FIG. 5), we deliberately installed aromatic functionality (or at least one π-system) in all but one of the acyl groups of Library D. For ease of synthesis, we selected acyl groups that could be installed using commercially available carboxylic acids. Despite the higher molecular weight (~500 g/mol) and hydrophobic character of many of the ligands in Library D relative to the other ligands in this study (e.g., AHLs D18-D21), we did not encounter problems with compound insolubility in any of the biological assays reported herein (see Experimental Procedures).

Library Syntheses.

AHL Libraries A-D were synthesized rapidly using a microwave-assisted, solid-phase route to AHLs previously reported by our laboratory. The ~90 AHLs were isolated in moderate to good yields (55-75%) and with excellent purities (90-99%) (see Experimental Procedures).

Antagonism and Agonism Assay Methods.

We examined the abilities of Libraries A-D to modulate R protein activity using bacterial reporter strains. This method is most frequently used to assess the activities of non-native AHLs. These bacterial reporter strains lack their AHL synthase (I) genes, but retain their native R genes. In the presence of exogenously added AHL ligand, the AHL-R protein complex will bind to a promoter that controls reporter gene expression and activate transcription. Therefore, R protein activity, and consequently ligand activity, can be measured using standard reporter gene read-outs. Competitive antagonism assays are performed with synthetic ligand in the presence of native AHL ligand, while agonism assays are performed with synthetic ligand alone. We selected three bacterial reporter strains for the R protein agonism and antagonism assays in this study: *A. tumefaciens* WCF47 (pCF372), *E. coli* DH5α (pJN105L pSC11), and *V. fischeri* ES114 (Δ-luxI) (see Experimental Procedures). The *A. tumefaciens* strain produces β-galactosidase upon TraR activation and ligand activity can be measured using standard Miller absorbance assays in the presence of a colored enzyme substrate (o-nitrophenyl-M-alactoside). The *E. coli* strain harbors LasR from *P. aeruginosa* and also reports LasR activity by β-galactosidase production. We found that this heterologous *E. coli* strain provided more reproducible data than related *P. aeruginosa* reporters, although the differences between R protein antagonists and agonists were somewhat muted relative to the other two strains in this study. Lastly, the *V. fischeri* strain retains its native lux operon (yet lacks a functional luxI), which allows LuxR activation to be measured by luminescence.

Libraries A-D were screened in R protein antagonism and agonism assays in the three bacterial reporter strains introduced above (see Experimental Section). The native ligands OOHL (1), OdDHL (2), and OHHL (3) and the known R protein antagonists 4-9 served as critical controls for these experiments (FIG. 5). Thirty-one AHLs were identified that displayed inhibitory activities of >80% against TraR, >35% against LasR, and/or >75% against LuxR. In turn, 14 ligands were identified as either LasR or LuxR agonists, with activities of >20% in LasR and/or >60% in LuxR. (No TraR agonists were identified in the four libraries.) These ligands represent some of the most potent modulators of R proteins reported to date. Interestingly, several of the ligands were observed to be antagonists in one strain, yet were agonists in another. $IC_{50}$ or $EC_{50}$ values for these 37 ligands, an analysis of their structures and selectivities, and a discussion of their mechanism of action have been reported elsewhere. Here, we provide a detailed analysis of all of the primary antagonism and agonism assay data for AHL Libraries A-D and delineate broad SAR trends revealed by these data for each library.

Primary Assay Data for Control Compounds.

The primary assay data for control compounds 1-9 largely corroborated those of previously reported experiments (Table 10). Each of the R proteins was inhibited to some degree (15-89%) by control native ligands (1-3) that were close in carbon length to their native AHL (2 or 4 carbons different).

In addition, all of the control antagonists (4-9) showed inhibitory activity in the three strains, albeit varied (18-93%), with the exception of 2-aminophenol 7, which was surprisingly inactive (entry 7). Intriguingly, 2-aminophenol 7 weakly agonized LasR instead (18%). This latter result contrasted with previous reports that 7 is a strong inhibitor of LasR activity in similar assays; however, these studies involved a different LasR reporter strain. Heptanoyl HL (4), phenylbutanoyl HL (6), and 4-bromo PHL (8) were the most active control antagonists across all three strains (~90% in TraR, ~25% in LasR, and ~76% in LuxR). Heptanoyl HL (4) was also a weak LuxR agonist under the primary agonism assay conditions (entry 4; see below).

Primary Assay Data and SAR for Library A.

Table 10. Antagonism and agonism assay data for Library A and controls 1-9 in three bacterial reporter strains. All assays performed in triplicate; Error did not exceed ±10%. Shaded compounds are controls. Data of significance highlighted in bold. Negative controls containing no compound were subtracted from each sample to account for background. Negative inhibition values indicate that the compound activates at the tested concentration. See FIGS. 47-61 for primary assay data in bar graph format. $^b$ Strain: *A. tumefaciens* WCF47 (pCF372). Assay data normalized to OOHL (1). $^c$ Screen performed using 10 μM synthetic ligand against 100 nM OOHL (1). $^d$ Screen performed using 10 μM ligand. $^e$ Strain: *E. coli* DH5α (pJN105L pSC11). Assay data normalized to OdDHL (2). $^f$ Screen performed using 5 μM synthetic ligand against 7.5 nM OdDHL (2). $^g$ Screen performed using 5 μM ligand. $^h$ Strain: *V. fischeri* ES114 (Δ-luxI). Assay data normalized to OHHL (3). $^i$ Screen performed using 5 μM synthetic ligand against 5 μM OHHL (3). $^j$ Screen performed using 200 μM ligand.

The simple aliphatic AHLs (A1-A6) in Library A displayed inhibitory activity trends against the three R proteins that correlated with increasing carbon number, with inhibition being maximal at $C_8$ (A3) for LasR and $C_{10}$ (A4) for TraR and LuxR and then decreasing thereafter (Table 10, entries 12 and 13). The long chain, 3-oxo AHLs (A7 and A8) exhibited minimal activity against TraR and LasR, yet were moderate (47%) to good (77%) inhibitors of LuxR (entries 16 and 17, respectively). Of the three R proteins, LuxR appeared to be the most sensitive to inhibition by 3-oxo AHLs (i.e., by OOHL (1), OdDHL (2), control 6, A7, and A8). Interestingly, the 3-oxo AHL A8 displayed agonistic, as opposed to antagonistic, activity against LasR in this assay (entry 17; see below).

Antagonism by sulfonyl HLs (A9-A16) against the three R proteins also correlated with carbon number, and the most striking trends in inhibitory activity were observed against TraR and LuxR (Table 10, entries 18-25). Inhibition was maximal at $C_6$ (A11) in TraR, with activity largely increasing up until this carbon length and then decreasing thereafter. Notably, the sulfonyl HL A11, with a seven-atom acyl tail (including the sulfur), displayed analogous inhibitory activity as control heptanoyl HL 4 (entry 4; 93%), suggesting that seven atoms in AHL acyl tails enhances antagonistic activity in TraR. In LuxR, inhibitory activity for the sulfonyl HLs increased gradually from $C_4$ to $C_9$ and decreased only minimally at the longer acyl chain lengths tested (i.e., in A15 and A16), with $C_9$ (A14) exhibiting the highest inhibitory activity (entry 23; 81%). These results directly contrasted with those of Castang et al. for sulfonyl HLs (see above) and highlight the differences in ligand activity often observable when using different reporter strains. Again, the sulfonyl HL with 10 atoms in its acyl tail (A14) and the decanoyl AHL (A4) were the most active LuxR inhibitors of their structure classes, indicating that acyl chain atom number also plays a role in AHL antagonistic activity against LuxR.

Far fewer synthetic agonists were identified in Library A relative to antagonists (Table 10). None of these ligands activated TraR to an appreciable level. This result corroborates screening data reported by Zhu et al. for several related AHL derivatives, where no TraR agonists were identified. Similarly, only a few ligands activated LuxR, with the $C_6$ AHL A2, the $C_7$ control AHL 4, and OOHL (1) displaying ~25% activation. Thus, within Library A, only compounds with structures very closely related to the native LuxR ligand (OHHL, 3) were LuxR agonists.

The results from the LasR agonism screen of Library A were more striking. Here, we identified two ligands that substantially activated LasR (~85%): $C_{12}$ AHL A5 and 3-oxo $C_{14}$ A8 (Table 10; entries 14 and 17). Moreover, these two ligands selectively activated LasR relative to TraR and LuxR. The $C_{10}$ AHL A4 and OOHL (1) also displayed agonistic activity, albeit reduced (44%; entries 1 and 13), indicating that in analogy to LuxR, AHLs in Library A with structures most similar to the native LasR ligand (OdDHL, 2) were effective LasR agonists. These data trends correlated with those reported by Passador et al. for the same compounds (yet in an alternate *E. coli* LasR reporter strain). However, these researchers also reported that 3-oxo $C_{10}$ AHL (A7) exhibited analogous agonistic activity as 3-oxo $C_{14}$ (A8); the former ligand failed to activate LasR in our assays (entry 16). This result is puzzling, in view of the structural similarity of this ligand to the other moderate to strong LasR activators that we identified (i.e., A4, A5, and A8). This result again exemplifies the disparities that can arise when different reporter strains are utilized for small molecule screening, and underscores the need for caution in comparing separate studies.

Primary Assay Data and SAR for Library B.

Table 11. Antagonism and agonism assay data for Library B and selected controls in three bacterial reporter strains. See footnotes for Table 10.

Examination of Library B in the reporter gene assays revealed several intriguing SARs that dictated AHL ligand activity against R proteins (Table 11). First, the D-enantiomer of OOHL (B1) displayed no antagonistic activity in any of the three strains (entry 8). Likewise, inversion of stereochemistry in control antagonists 5 and 6 (to give D-AHLs B2 and B3) reduced their inhibitory activity by ~40-60% in TraR (entries 9 and 10). A similar ~40% reduction in inhibitory activity was also observed for D-AHL B3 in LuxR; however, D-AHL B2 exhibited analogous inhibitory activity as its L-stereoisomer 5 (~45%). The activity trends for D-AHLs B2 and B3 were yet more complex in LasR; here, B2 displayed strong agonistic as opposed to antagonistic activity (see below), while B3 inhibited LasR at a comparable level to its L-stereoisomer 6 (~20%). In contrast to B2 and B3, the D-stereoisomers of our control 4-bromo PHL and indole AHL antagonists, B4 and B5, showed uniformly reduced inhibitory activity across all three strains, ranging from ~90% reduction for B4 in TraR to at least 50% for both B4 and B5 in LasR and LuxR (entries 11 and 12). These results suggest that AHL stereochemistry, in concert with acyl chain structure, plays a multifaceted role in AHL-mediated R protein inhibition and activation. One effect is clear, however; inversion of lactone stereochemistry does not completely abolish antagonistic activity for the ligands examined in this study.

The remaining members of Library B were designed to probe the role of acyl chain structure on antagonistic activity for control antagonists 8 and 9. Shortening the alkyl spacer in 4-bromo PHL 8 by one carbon (to give benzoyl AHL B6) dramatically reduced its inhibitory activity in all three R proteins, ranging in reduction from 90% in TraR to ~50% in LasR and LuxR (Table 11, entry 13). However, lengthening the alkyl spacer by one carbon produced a ligand (B7) with equivalent inhibitory activity to control 4-bromo PHL 8 in TraR and LuxR, and two-fold higher inhibitory activity in LasR (entry 14). Notably, B7 was also almost two-fold as active as the potent, control antagonist 9 (52% vs. 36%, respectively), and amongst the most potent inhibitors of LasR identified in these primary assays. Removing the 4-bromide substituent from benzoyl AHL B6 (to give B8) had little effect on an already low antagonistic activity, while removing the 4-bromide from the potent antagonist B7 (to give B9) had a more significant impact, reducing inhibition by at least 50% across all three strains (entry 16). In turn, the cyclohexyl analog of B9, AHL B11 (entry 18), displayed slightly enhanced antagonistic activity in TraR and LasR relative to B9, and activity against LuxR analogous to the most potent non-native AHL inhibitor in Library B, B7 (~80%). Finally, shortening the alkyl spacer of control indole AHL 9 by one or two carbons (B14 and 613, respectively) had only a minor effect on inhibitory activity in TraR, while these shorter indole analogs were ~40% less active than control 9 in LuxR (entries 20 and 21). In contrast, the one-carbon shorter indole analog B14 exhibited heightened activity in LasR relative to control 9, and was one of the most potent LasR inhibitors identified in this study.

These results for Library B reveal several trends in antagonistic activity for synthetic AHLs: (1) a flexible carbon spacer of at least one carbon and a 4-bromo substituent are necessary for appreciable activity in ligands structurally related to 4-bromo PHL 8, with AHL B7 being the most active inhibitor across the three R proteins, (2) aromatic functionally is not essential for LuxR inhibition in ligands related to control PHL 8 (e.g., AHL B11), and (3) a three-carbon spacer is optimal for TraR and LuxR inhibition in ligands structurally related to control indole AHL 9, while a two carbon spacer is optimal for inhibition of LasR AHL B14).

In analogy to Library A, very few agonists were identified in screening Library B (Table 11). Indeed, only one ligand with considerable agonistic activity against one R protein, LasR, was identified: the D-enantiomer of control antagonist 5, D-AHL B2 (entry 9). This ligand was capable of activating LasR at 84% relative to the native ligand OdDHL (2) at equal concentrations. AHL B2 is unique, as this D-AHL displays strong agonistic activity and its L-stereoisomer, control AHL 5, is virtually inactive in LasR (but is a moderate to strong antagonist in LuxR and TraR, respectively; entry 4). This trend is opposite to what has been observed for native AHL ligands, where the L-stereoisomer is an active agonist and the D-stereoisomer is almost inactive; we observed this latter trend in the current study for OOHL (1). The reasons behind this trend reversal for B2 remain unclear, and in view of the complex antagonistic activity trends displayed by the limited set of D-enantiomers in Library B (see above), suggest that lactone stereochemistry will be an important feature to probe in the future design of AHL-derived QS modulators.

Primary Assay Data and SAR for Library C.

Table 12. Antagonism and agonism assay data for Library C and selected controls in three bacterial reporter strains. See footnotes for Table 10.

The antagonism and agonism primary screening data for Library C are listed in Table 12, and reveal the largest percentage of potent antagonists and agonists in this study (37% of the library have activities of ≥50% in at least one strain). This result serves to validate the PHL structure as a scaffold for the design of potent modulators of R protein function. As observed in Libraries A and B, the majority of the active ligands in Library C were antagonists. Replacement of the 4-bromide of control PHL 8 with a hydrogen in C1 largely abolished inhibitory activity across the three strains (Table 12, entry 5), in analogy to what was observed for the one-carbon-longer analogs B7 and B9 in Library B (see above). The mono-halogen (C2-C12) and nitro series (C13-C15) exhibited remarkable trends in inhibitory activity against all three R proteins (entries 6-19). These trends were most pronounced in TraR. Namely, inhibition dramatically increased (from ~1% to 90%) as the halogen or nitro substituents were moved from the 2- to the 3- to the 4-positions on the PHL phenyl ring. Inhibition also increased with substituent size, with 4-iodo PHL (C10) and 4-nitro PHL (C13) inhibiting at the highest level in this series (~90%). The mono-halogenated PHLs displayed the same trends in antagonistic activity in LuxR, albeit slightly muted within each series. However, the nitro series (C13-C15) displayed a more complicated activity pattern, with 4-nitro PHL (C13) only moderately inhibiting LuxR (47%) and, more notably, 3-nitro PHL (C14) dramatically activating LuxR (entries 17 and 18; see below). These assay data indicate that both antagonistic and agonistic activities are exquisitely affected by the nature and position of the substituents on the PHL phenyl ring.

Uniform antagonistic activity trends were also observed for the mono-halogen and nitro PHL series in LasR (Table 12). Here, in contrast to TraR and LuxR, the 3-substituted PHLs displayed the highest inhibitory activities, followed by the 4- and 2-substituted derivatives. Antagonism still increased with increasing substituent size, in analogy to TraR, with the 3-iodo (C11) and 3-nitro (C14) PHLs exhibiting the highest antagonistic activities in LasR for the series (~55%; entries 15 and 18). Moreover, these two ligands were the most potent LasR inhibitors identified in these primary assays. A final halogenated PHL, pentafluoroaromatic PHL (C16), was designed to examine whether its reversed aromatic quadrupole could enhance PHL-mediated R protein modulation (potentially through favorable π-stacking interactions). This ligand displayed minimal inhibitory activity in TraR and LasR that was analogous to its non-fluorinated analog C1, and only low inhibitory activity (40%) against LuxR (entry 20), suggesting that such interactions, if operative, do not play a significant role in ligand activity.

The remaining PHLs in Library C were designed to probe the effects of different substituents in the 4-position of the phenyl ring on R protein modulation. Both the 4-azido PHL (C17) and 4-phenyl PHL (C18) were moderate to strong inhibitors of TraR and LuxR (~70%; Table 12, entries 21 and 22). The activity of 4-azido PHL (C17) is particularly notable as the azido moiety renders this inhibitor photoactive, and thus C17 could have value as a potential photoaffinity labeling tool for R proteins and provide insights into the ligand-binding site for PHLs. Likewise, the activity of 4-phenyl PHL (C18) was significant, as it instructed us that sterically demanding groups could be tolerated on the phenyl ring of PHL-derived R protein antagonists.

The 4-methyl and 4-trifluoromethyl PHLs (C19 and C20) exhibited markedly different activities in the antagonism assays. The 4-methyl PHL C19 was only a weak to moderate inhibitor of all three R proteins (Table 12, entry 23), inhibiting at a two- to four-fold lower level relative to the 4-bromo PHL control (8). As a methyl group is roughly equivalent in steric size to a bromide, this activity trend indicated that substituent size alone does not dictate inhibitory activity for 4-substituted PHLs. In contrast, the 4-trifluoromethyl PHL C20 displayed equivalent antagonistic activity as control 4-bromo PHL 8 in all three strains (entry 24). This result suggests, along with the other antagonism data outlined above for Library C, that electron-withdrawing and lipophilic groups in the 4-position enhance PHL inhibitory activity against R proteins. This hypothesis is further corroborated by the low to moderate antagonistic activity displayed by PHLs C21-C25, all of which contain electron-donating groups in the 4-position of the phenyl ring. Further, the two PHLs in this set with hydrogen bond donors in the 4-position (i.e., 4-amino (C21) and 4-hydroxy (C23) PHLs) are amongst the weakest inhibitors in Library C (~7%), signifying a structural feature (and potential intermolecular interaction with R proteins) that can lower PHL inhibitory activity.

Turning next to agonism assays, six PHLs were identified in Library C that were capable of activating R proteins (Table 12). The most potent agonists were highly selective for LuxR, and we focus on these compounds here. Again, we observed striking trends in the activities for PHLs with halogen and nitro groups. In contrast to the antagonism data for these PHLs in LuxR, the 3-substituted compound in each series showed the strongest activity relative to the 2- and 4-substituted derivatives, with the 3-chloro C6, 3-bromo C8, and 3-nitro C14 PHLs exhibiting at least 60% luminescence induction relative to native OHHL (3) at equal concentrations. Amazingly, shifting substituents on the PHL phenyl ring by a single carbon converted these ligands from LuxR antagonists to LuxR agonists. Moreover, 3-nitro PHL C14 was able to induce 29% higher luminescence than the native ligand for LuxR in this primary assay (entry 18). This result was remarkable, and explained the unusual inhibition trends for the nitro PHL series in LuxR (C13-C15; see above). Few super-activators of R proteins have been reported; therefore, our discovery of 3-nitro PHL C14 as a super-activator of LuxR is significant. Additional studies in our laboratory have shown that PHL C14 can also super-activate LuxR in wild-type *V. fischeri* and is tolerated in invertebrate model systems, suggesting that this compound could have considerable value as a probe to study *V. fischeri*-host symbioses.

Overall, the screening data for Library C indicate that the PHL structure is a highly versatile scaffold for the design of both R protein antagonists and agonists, and that seemingly simple structural modifications to the PHL phenyl ring can have a major effect on ligand activity. Most notably, these structural modifications can convert potent antagonists into agonists (over the concentration range tested). These primary assays revealed some of the most potent and selective R protein modulators in this study, including 4-iodo PHL (C10) that inhibits all three R proteins, 3-nitro PHL (C14) that strongly inhibits LasR but remarkably also super-activates LuxR, and 4-phenyl PHL (C18) and 4-trifluoromethyl PHL (C20) that strongly inhibit TraR and LuxR but are considerably less active against LasR.

Primary Assay Data and SAR for Library D.

Table 13. Antagonism and agonism assay data for Library D and controls 1-9 in three bacterial reporter strains. See footnotes for Table 10.

Library D also contained several new and potent synthetic modulators of TraR, LasR, and LuxR (Table 13). The most active compounds or those displaying interesting SAR trends are described here. AHLs D1-D5 displayed negligible inhibitory activity against TraR, and only low to modest inhibitory activity against LasR and LuxR, suggesting that their compact, unsaturated, and/or heterocyclic acyl groups significantly reduced activity against these three R proteins (entries 10-14). AHL D6, in contrast, was a strong inhibitor of TraR (90%), a moderate inhibitor of LuxR (68%), and a relatively weak inhibitor of LasR (28%; entry 15). A clear rationale for the heightened antagonistic activity of D6 relative to D1-D5 was not obvious, except potentially its higher structural similarity to the potent control antagonists 5, 6, and 8. Interestingly, enlarging the substituent in the 4-position of the aromatic ring from a methyl group in D6 to an n-propyl group in D7 halved the inhibitory activity in TraR and LasR, yet had no effect against LuxR (entry 16).

The AHLs in Library D with aromatic (D9-D13) or carbocyclic functionality (D14) directly adjacent to the carbonyl in the acyl group exhibited minimal inhibitory activity against TraR (Table 13). Only two AHLs in this group (D11 and D13) were reasonably strong inhibitors of LuxR (~60%); notably, these two AHLs both contained benzoyl functionalities and had the most extended acyl chains of this ligand set (entries 20 and 22). AHL D13 was also a modest inhibitor of LasR (27%), while D11 was weakly active. The cyclohexyl AHL derivative D14, however, was a relatively strong inhibitor of LasR, with activity analogous to that of the indole AHL control 9 (36%; entry 23).

The three AHLs in Library D with phenyl ether functionality in their acyl chains (D15-D17) displayed clear inhibition trends across the three strains. Notably, these three compounds had a two-atom spacer between the carbonyl group and the aromatic ring in their acyl chains, analogous to the potent inhibitors B7 and B14 identified in Library B (see above). All three of these phenyl ether AHLs were only modest inhibitors of LuxR (~45%; Table 13, entries 24-26). However, 4-trifluoromethyl phenyl ether AHL D15 was a potent inhibitor of TraR and the strongest inhibitor of LasR identified in Library D (90% and 49% inhibition, respectively; entry 24). The two structurally-similar 4-keto phenyl ethers (D16 and D17) exhibited disparate activates in both TraR and LasR: D16 was virtually inactive against TraR, while D17 was similar in activity to D15 and one of the most potent inhibitors of TraR (92%) uncovered in these primary assays (entries 25 and 26). Likewise, D17 was 50% more active against LasR relative to D16. Interestingly, compounds D16 and D17 only differ in the placement of a substituent on the aromatic ring of the acyl group (2-methoxy vs. 3-methyl, respectively; FIG. 17D). This result suggests that, similar to the PHL series in Library C, inhibitory activity can increase in this phenyl ether series when substituents on the aromatic ring are placed closer to the 4-position.

The remaining four AHLs in Library D (D18-D21) contained the most sterically bulky acyl chains examined to date. These four AHLs exhibited minimal inhibitory activity against TraR, analogous to the low inhibitory activity observed for the relatively bulky AHLs D9-D14 (Table 13). In contrast, the most sterically bulky of this ligand set (D18) was a relatively strong inhibitor of LasR and the most active of the four (entry 27). Finally, the azobenzene AHL derivatives D20 and D21 displayed medium to moderately strong inhibitory activity against LuxR (46% and 63%, respectively; entries 29 and 30). These compounds are of interest due to the photoisomerization ability of the azobenzene moiety. For example, their inhibitory activity could be altered upon cis/trans isomerization, as this conformational shift may cause the ligand to dislodge from (or bind differently in) the ligand-binding site. Therefore, these azobenzene AHL ligands (D20 and D21), along with the 4-azido PHL antagonist (C17) identified in Library C, could represent novel photoactive tools for the study of R protein function.

Similar to Libraries A-C, the agonism screen of Library D revealed few synthetic agonists (Table 13). Indeed, no library members were agonists of TraR and LuxR. Three ligands (D14, D15, and D18), however, were weak activators of LasR (~33%, entries 23, 24, and 27). The structures of these AHLs were not highly similar, but each had a relativity bulky acyl chain containing aromatic functionality, most notably D18.

Intriguingly, these three ligands were also the most potent antagonists of LasR identified in Library D (see above). Moreover, their percent antagonistic activities were approximately equivalent to their percent agonistic activities. Additional studies of AHLs D14, D15, and D18 suggest that these ligands are not antagonists of LasR, but rather behave as partial agonists (see below) such a mechanism of action would explain these disparate primary assay data. On-going work in our laboratory is directed at fully understanding the mechanism of action for these and related AHL ligands.

General SAR-Trends for Libraries A-D.

Overall, we found that subtle changes to the AHL acyl group, some as simple as the addition or removal of one carbon or halogen, had dramatic effects on ligand activity in each of the three bacterial strains in this study. In general, AHLs with acyl groups of moderate size (up to eight atoms long) and containing either aromatic functionality with electron-withdrawing groups or straight chain aliphatic functionality can antagonize TraR, LasR, and LuxR. AHL B7 epitomizes such a broad-spectrum antagonist, and is one of the most active antagonists identified in this study. Within this class, sulfonyl groups can replace carbonyl groups on aliphatic AHL TraR and LuxR antagonists without significant loss in activity. Of the AHLs analyzed herein, the PHL appears to be a unique scaffold for R protein modulation, as members of this structure class display a wide range of antagonistic and agonistic activities across all three R proteins in this study. The 4- and 3-substituted PHLs display the most remarkable trends in activity, ranging from a potent antagonist of all three R proteins (C10) to a super-agonist of only LuxR (C14). Finally, inversion of lactone stereochemistry (from L to D) was not found to fully abolish activity for the AHLs examined herein; indeed, one D-AHL (B2) was shown to strongly activate LasR.

To obtain a better understanding of how different structural features of AHLs engender antagonistic and agonistic activities, we generated computational pharmacophore models for AHL modulators of each of the three R proteins. Preliminary studies from our laboratory suggest that many of the most potent "antagonists" identified in Libraries A-D may elicit their activity via a partial agonism mechanism (e.g., PHLs C20 in TraR, C14 in LasR, and C13 in LuxR, and bulky AHLs D14, D15, and D18 in LasR). Therefore, these ligands do not appear to inhibit R protein activity; rather, they simply are unable to activate the R protein to the same level as the native ligand. In view of these new mechanistic data, all of the primary antagonism and agonism assay data in this study were utilized to calculate AHL pharmacophore models for TraR, LasR, and LuxR. In general, the TraR pharmacophore exhibits an almost equal balance of hydrophobic functionality and H-bond acceptors and is relatively compact. The LuxR pharmacophore is similarly compact, yet has fewer H-bond acceptors relative to TraR. In contrast, the LasR pharmacophore is noticeably larger and exhibits an extensive hydrophobic surface. These differences in size for TraR and LasR are congruent with the compact and expanded AHL binding sites indicated by the TraR and LasR X-ray structures, respectively, assuming that these non-native AHLs target the same site. While a structure for LuxR is yet to be reported, using this same reasoning, the LuxR pharmacophore reflects a ligand-binding site for LuxR that is more similar to TraR than LasR. However, it is challenging to fully rationalize the selectivity profiles for the AHLs in this study using these calculated pharmacophores; structural studies of the R proteins with various ligands (e.g., by X-ray crystallography) will better illuminate the differences in activities, and are ongoing in our laboratory. These pharmacophore models are significant nonetheless as, to our knowledge, they are the first reported for AHL-derived QS modulators. We anticipate that these models, along with the extensive SAR data outlined above, will guide the design of new AHL and non-AHL QS modulators with improved activities and selectivities, and provide new avenues to study the chemistry and biology of bacterial communication.

Significance.

Bacteria use quorum sensing (QS) to control both pathogenesis and beneficial symbioses, and this chemical signaling process has attracted substantial interest as a therapeutic target. Non-native molecules that block or intercept QS pathways would have significant value as probes to study QS and its divergent outcomes at the molecular level, and could, with further development, provide scaffolds for therapeutic agents. The majority of the known QS modulators in Gram-negative bacteria are N-acylated homoserine lactones (AHLs). In this study, we have delineated key structural features of synthetic AHLs that render these ligands antagonists and agonists of QS. These structure-activity relationships were determined by the systematic synthesis and screening of focused libraries of AHLs in three bacterial species. This work is significant, as it represents the first comparative study of AHL-derived QS modulators. Moreover, this work serves as a foundation on which to design next-generation AHLs, and synthetic ligands in general, with improved activities and selectivities for QS. Lastly, we have discovered several of the most potent synthetic antagonists and agonists of QS known, as well as a set of photoactive AHL probes, which serve to further underscore the utility of focused combinatorial libraries for the identification of QS modulators.

Experimental Procedures.

Ligand Synthesis. AHL Libraries A-D and the control compounds 1-9 were prepared and characterized according to previously reported methods.

Compound Handling.

Stock solutions of synthetic compounds (10 mM) were prepared in DMSO. Competitive antagonism assays were performed with synthetic ligand in the presence of native AHL ligand (at its $EC_{50}$ value in each bacterial reporter strain). Agonism assays were performed with synthetic ligand alone. The concentrations of synthetic AHL ligand used in the antagonism and agonism assays, and the relative ratios of synthetic ligand to native ligand (1:1 to ~100:1) in the antagonism assays, were chosen to provide the most obvious differences between inhibitors and activators for each bacterial reporter strain (see Table 10). Positive controls for agonism assays (native ligand at selected concentrations) for antagonism assays (native ligand at its $EC_{50}$ value) were set to 100%.

Bacteriology.

The three bacterial reporter strains used in this study were: A. tumefaciens WCF47 (Δ-traI) harboring a plasmid-born PtraI-lacZ fusion (pCF372), E. coli DH5α harboring the LasR expression vector pJN105L and a plasmid-born PlasI-lacZ fusion (pSC11), and V. fischeri ES114 (L-luxI).

Reporter Gene Assay Protocols.

The TraR, LasR, and LuxR antagonism and agonism assays were performed as previously reported. None of the control compounds or library members were observed to be insoluble or affected bacterial growth over the time course of these assays (4-24 h). In addition, no ligand was found to degrade (by lactonolysis, proteolysis, or reaction with biological reagents) over the time course of these assays (as determined by LC-MS or GC-MS; data not shown).

Controls

Figure 18:
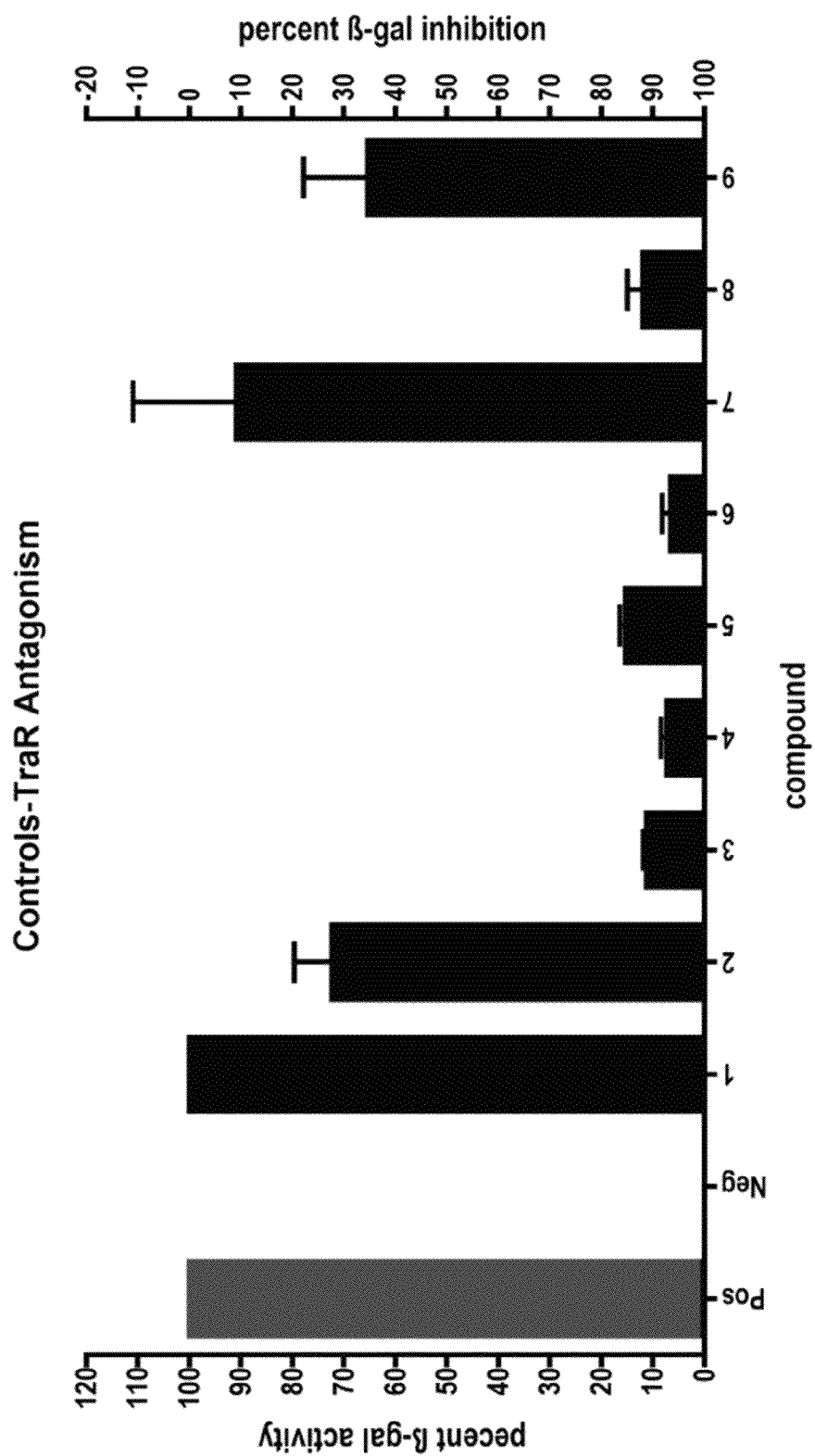
FIG. 18 provides primary antagonism and agonism data for control compounds 1-9 screened in *A. tumefaciens*.

FIG. 18. Primary antagonism and agonism data for control compounds 1-9 screened in *A. tumefaciens*. Top: Antagonism screen performed using 10 μM of synthetic ligand against 100 nM of OOHL (1). Positive control (pos)=100 nM of OOHL (1). Negative control (neg)=no compound. Bottom: Agonism screen performed using 10 μM of synthetic ligand. Positive control (pos)=10 μM of OOHL (1). Error bars, s.d. of the means of triplicate samples.

Figure 19:
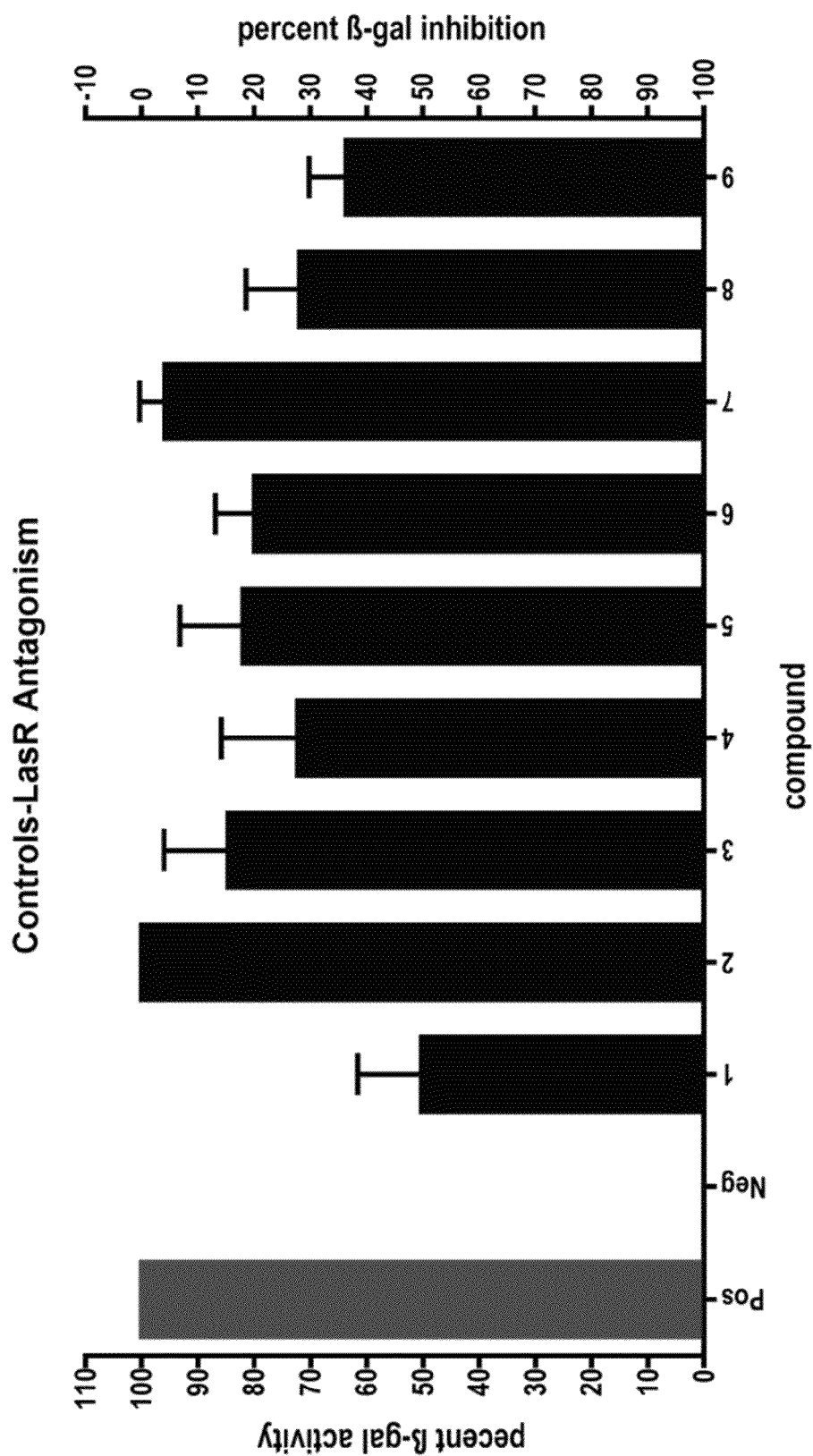
FIG. 19 provides primary antagonism and agonism data for control compounds 1-9 screened in *E. coli* (LasR reporter).

FIG. 19. Primary antagonism and agonism data for control compounds 1-9 screened in *E. coli* (LasR reporter). Top: Antagonism screen performed using 5 μM of synthetic ligand against 7.5 nM of OdDHL (2). Positive control (pos)=7.5 nM of OdDHL (2). Negative control (neg)=no compound. Bottom: Agonism screen performed using 5 μM of synthetic ligand. Positive control (pos)=5 μM of OdDHL (2). Error bars, s.d. of the means of triplicate samples.

Figure 20:
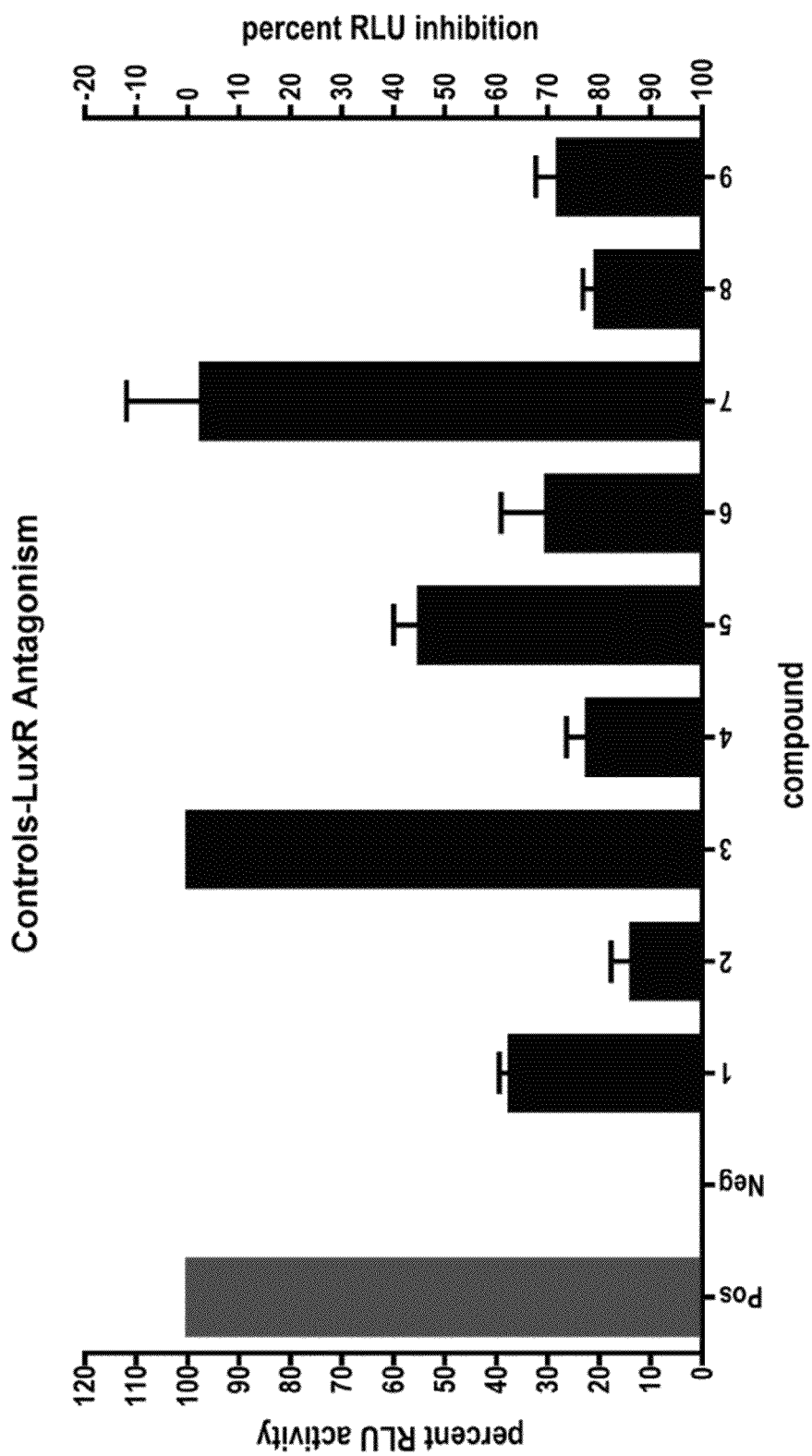
FIG. 20 provides primary antagonism and agonism data for control compounds 1-9 screened in *V. fischeri*.

FIG. 20. Primary antagonism and agonism data for control compounds 1-9 screened in *V. fischeri*. Top: Antagonism screen performed using 5 μM of synthetic ligand against 5 μM of OHHL (3). Positive (pos) control=5 μM of OHHL (3). Negative control (neg)=no compound. Bottom: Agonism screen performed using 200 μM of synthetic ligand. Positive control (pos)=200 μM of OHHL (3). Error bars, s.d. of the means of triplicate samples.

Figure 21:
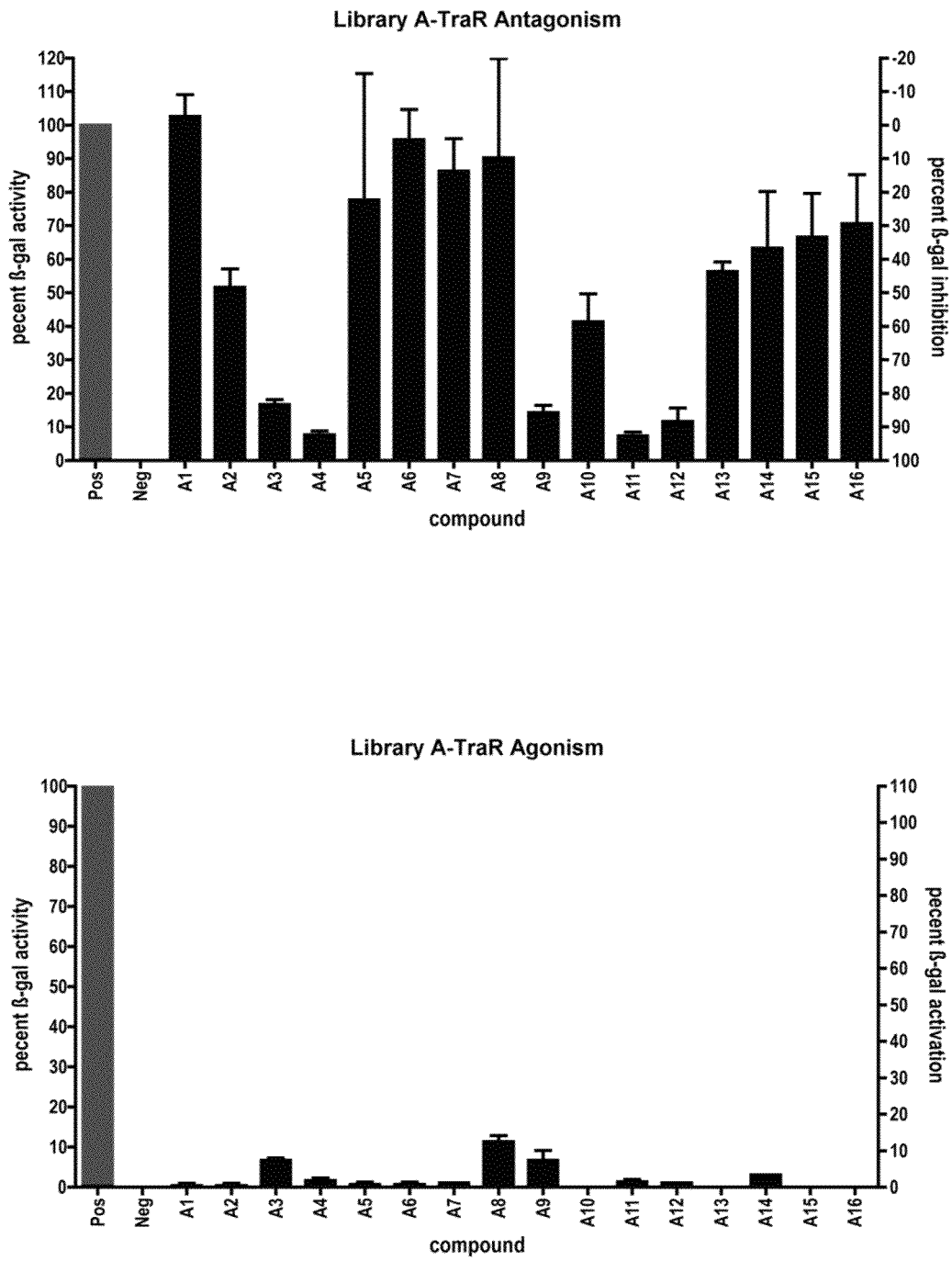
FIG. 21 provides primary antagonism and agonism data for Library A screened in *A. tumefaciens*.

*A. TUMEFACIENS* (TraR) PRIMARY DATA. FIG. 21. Primary antagonism and agonism data for Library A screened in *A. tumefaciens*. Top: Antagonism screen performed using 10 μM of synthetic ligand against 100 nM of OOHL (1). Positive control (pos)=100 nM of OOHL (1). Negative control (neg)=no compound. Bottom: Agonism screen performed using 10 μM of synthetic ligand. Positive control (pos)=10 μM of OOHL (1). Error bars, s.d. of the means of triplicate samples.

Figure 22:
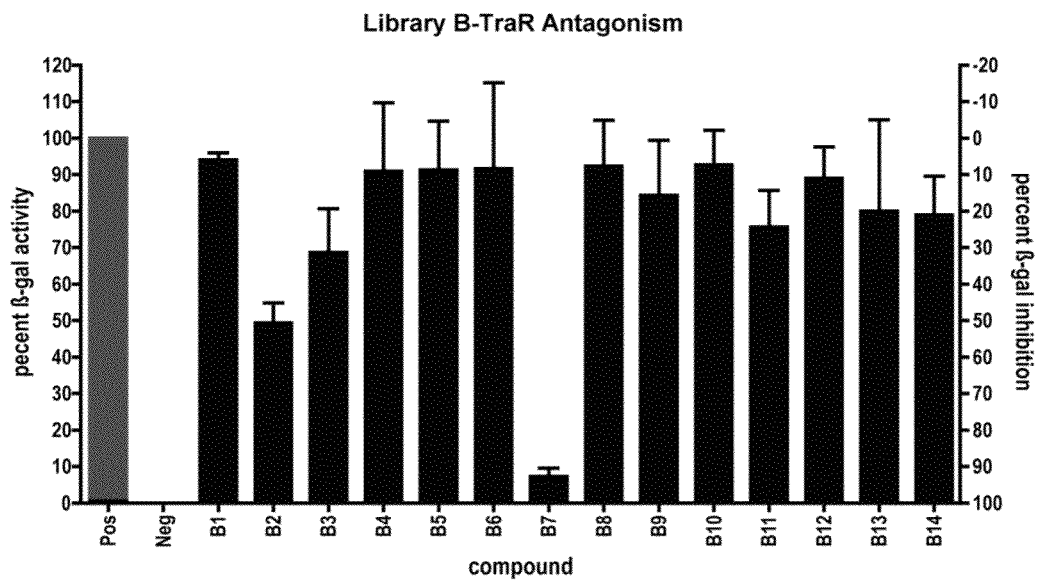
FIG. 22 provides primary antagonism and agonism data for Library B screened in *A. tumefaciens*.
Figure 22:
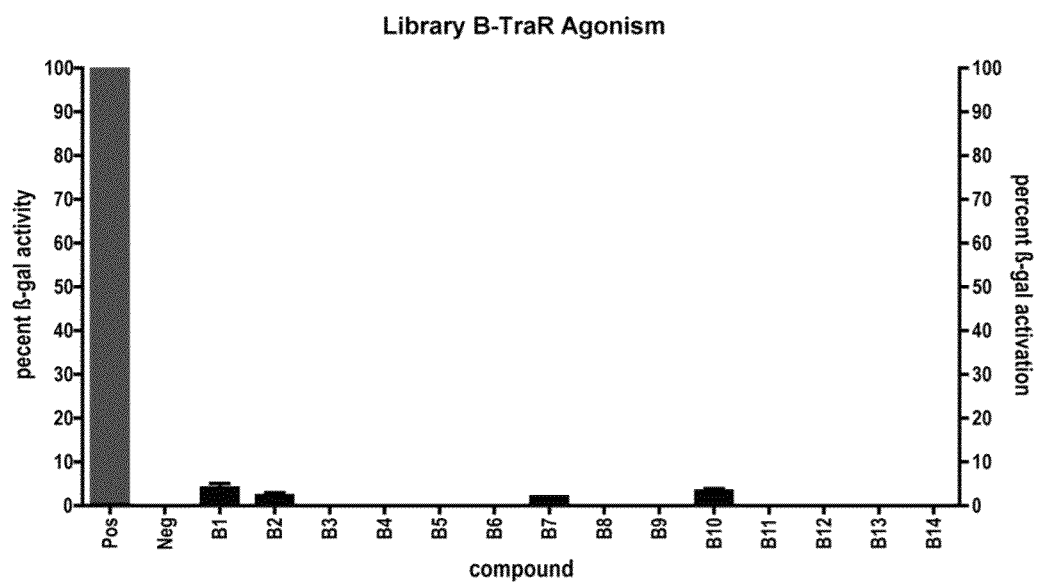

FIG. 22. Primary antagonism and agonism data for Library B screened in *A. tumefaciens*. Top: Antagonism screen performed using 10 μM of synthetic ligand against 100 nM of OOHL (1). Positive control (pos)=100 nM of OOHL (1). Negative control (neg)=no compound. Bottom: Agonism screen performed using 10 μM of synthetic ligand. Positive control (pos)=10 μM of OOHL (1). Error bars, s.d. of the means of triplicate samples.

Figure 23:
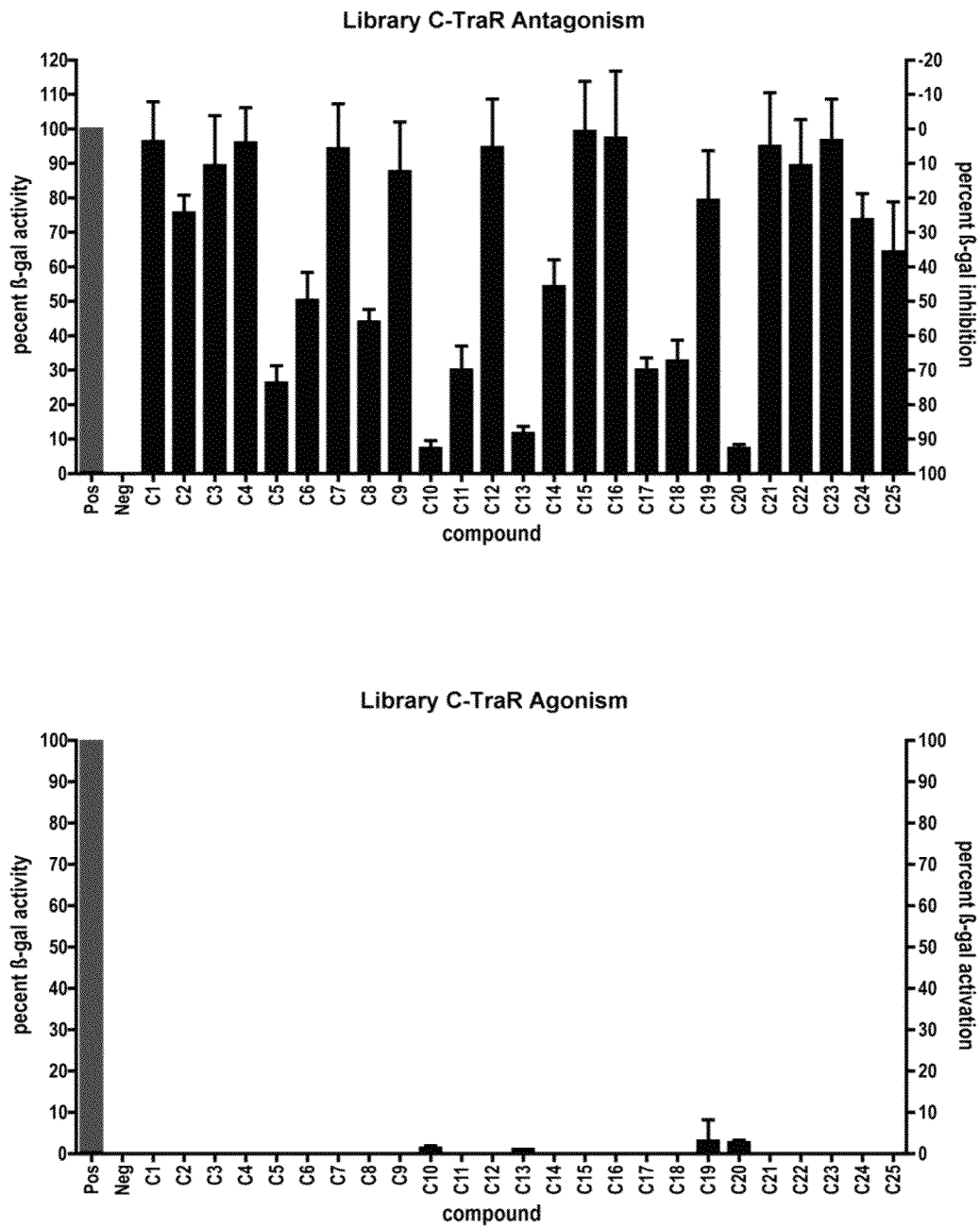
FIG. 23 provides primary antagonism and agonism data for Library C screened in *A. tumefaciens*.

FIG. 23. Primary antagonism and agonism data for Library C screened in *A. tumefaciens*. Top: Antagonism screen performed using 10 μM of synthetic ligand against 100 nM of OOHL (1). Positive control (pos)=100 nM of OOHL (1). Negative control (neg)=no compound. Bottom: Agonism screen performed using 10 μM of synthetic ligand. Positive control (pos)=10 μM of OOHL (1). Error bars, s.d. of the means of triplicate samples.

Figure 24:
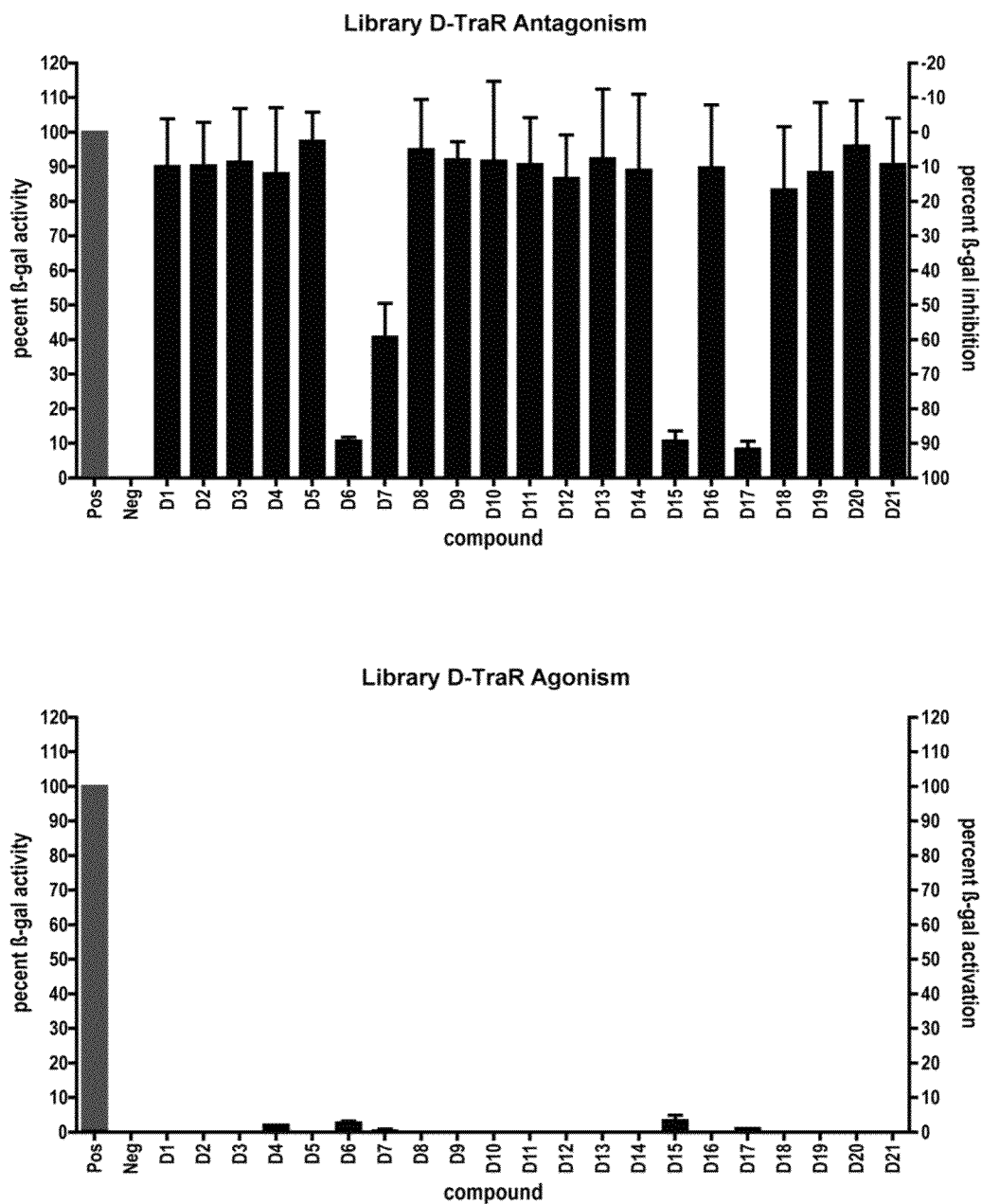
FIG. 24 provides primary antagonism and agonism data for Library D screened in *A. tumefaciens*.

FIG. 24. Primary antagonism and agonism data for Library D screened in *A. tumefaciens*. Top: Antagonism screen performed using 10 μM of synthetic ligand against 100 nM of OOHL (1). Positive control (pos)=100 nM of OOHL (1). Negative control (neg)=no compound. Bottom: Agonism screen performed using 10 μM of synthetic ligand. Positive control (pos)=10 μM of OOHL (1). Error bars, s.d. of the means of triplicate samples.

Figure 25:
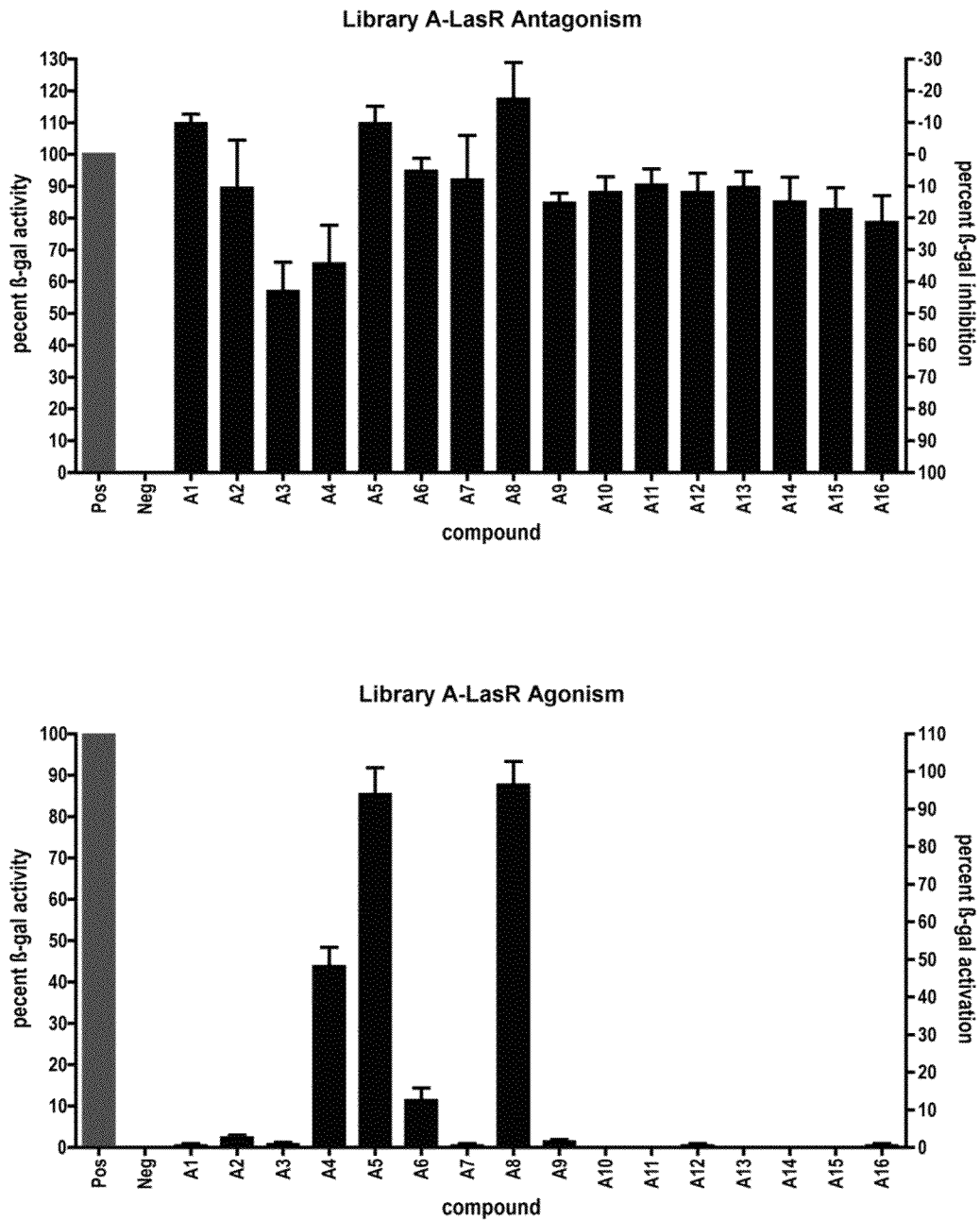
FIG. 25 provides primary antagonism and agonism data for Library A screened in *E. coli* (LasR reporter).

*E. COLI* (LasR) PRIMARY DATA. FIG. 25. Primary antagonism and agonism data for Library A screened in *E. coli* (LasR reporter). Top: Antagonism screen performed using 5 μM of synthetic ligand against 7.5 nM of OdDHL (2). Positive control (pos)=7.5 nM of OdDHL (2). Negative control (neg)=no compound. Bottom: Agonism screen performed using 5 μM of synthetic ligand. Positive control (pos)=5 μM of OdDHL (2). Error bars, s.d. of the means of triplicate samples.

Figure 26:
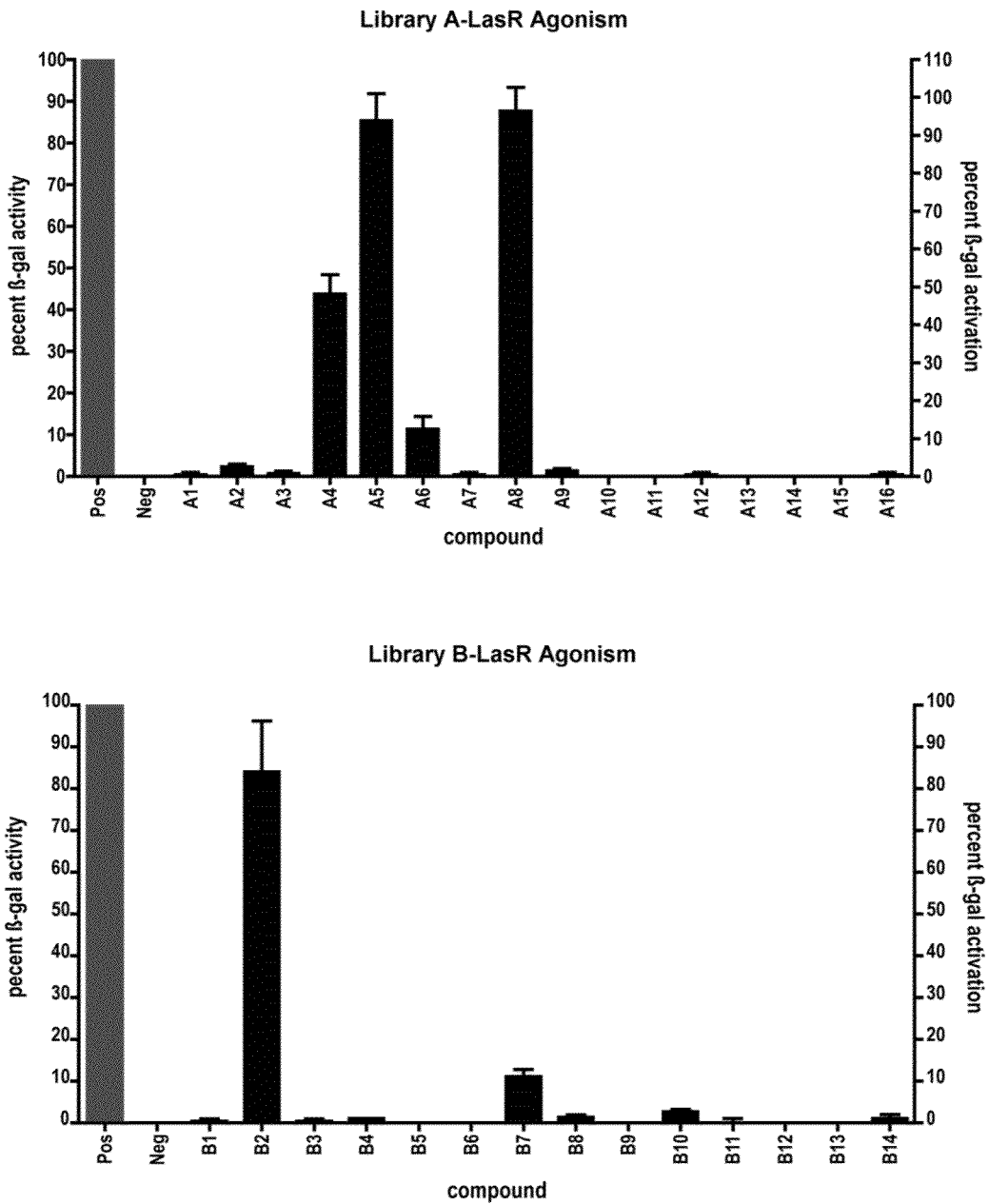
FIG. 26 provides primary antagonism and agonism data for Library B screened in *E. coli* (LasR reporter).

FIG. 26. Primary antagonism and agonism data for Library B screened in *E. coli* (LasR reporter). Top: Antagonism screen performed using 5 μM of synthetic ligand against 7.5 nM of OdDHL (2). Positive control (pos)=7.5 nM of OdDHL (2). Negative control (neg)=no compound. Bottom: Agonism screen performed using 5 μM of synthetic ligand. Positive control (pos)=5 μM of OdDHL (2). Error bars, s.d. of the means of triplicate samples.

Figure 27:
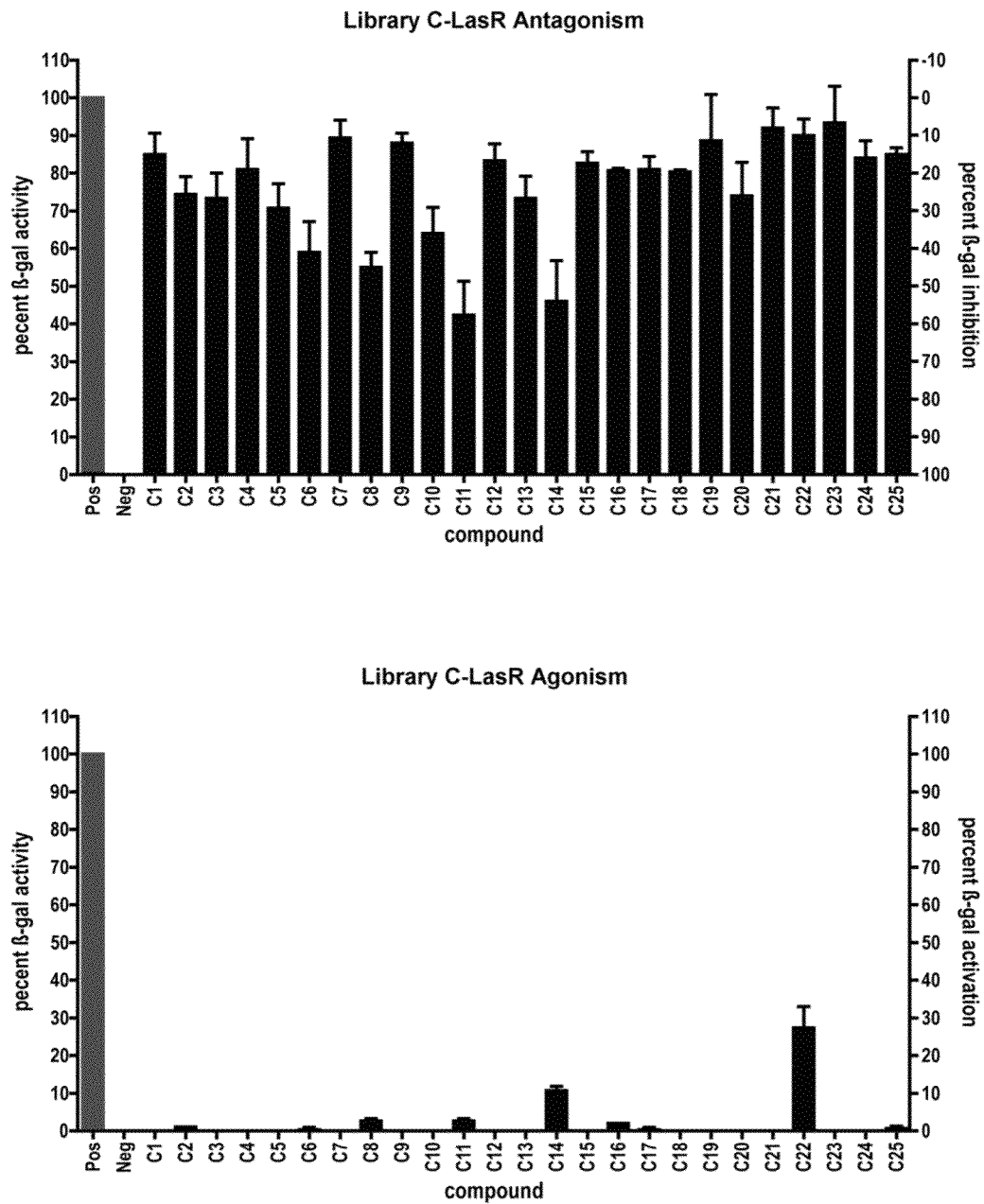
FIG. 27 provides primary antagonism and agonism data for Library C screened in *E. coli* (LasR reporter).

FIG. 27. Primary antagonism and agonism data for Library C screened in *E. coli* (LasR reporter). Top: Antagonism screen performed using 5 μM of synthetic ligand against 7.5 nM of OdDHL (2). Positive control (pos)=7.5 nM of OdDHL (2). Negative control (neg)=no compound. Bottom: Agonism screen performed using 5 μM of synthetic ligand. Positive control (pos)=5 μM of OdDHL (2). Error bars, s.d. of the means of triplicate samples.

Figure 28:
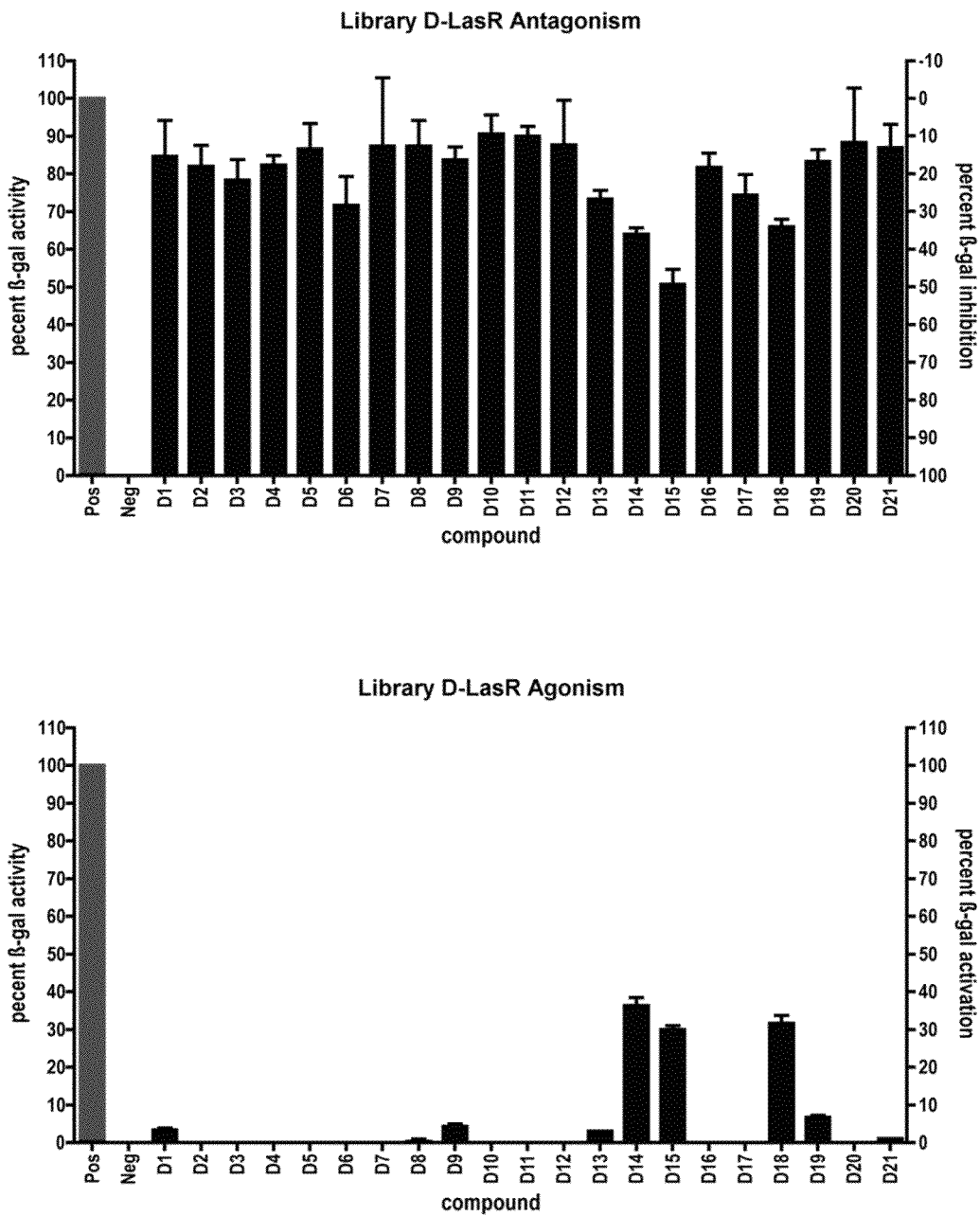
FIG. 28 provides primary antagonism and agonism data for Library D screened in *E. coli* (LasR reporter).

FIG. 28. Primary antagonism and agonism data for Library D screened in *E. coli* (LasR reporter). Top: Antagonism screen performed using 5 μM of synthetic ligand against 7.5 nM of OdDHL (2). Positive control (pos)=7.5 nM of OdDHL (2). Negative control (neg)=no compound. Bottom: Agonism screen performed using 5 μM of synthetic ligand. Positive control (pos)=5 μM of OdDHL (2). Error bars, s.d. of the means of triplicate samples.

Figure 29:
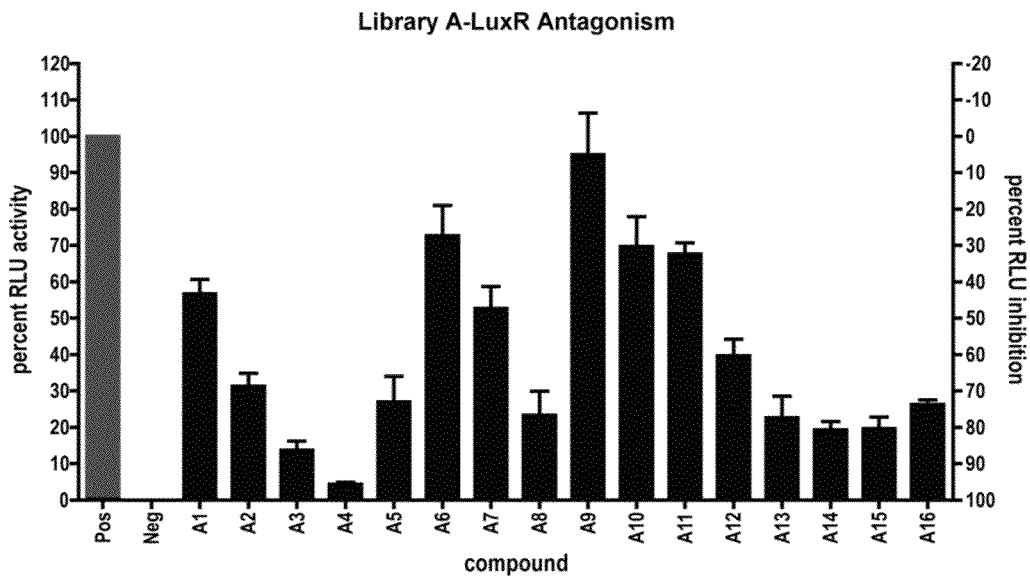
FIG. 29 provides primary antagonism and agonism data for Library A screened in *V. fischeri*.
Figure 29:
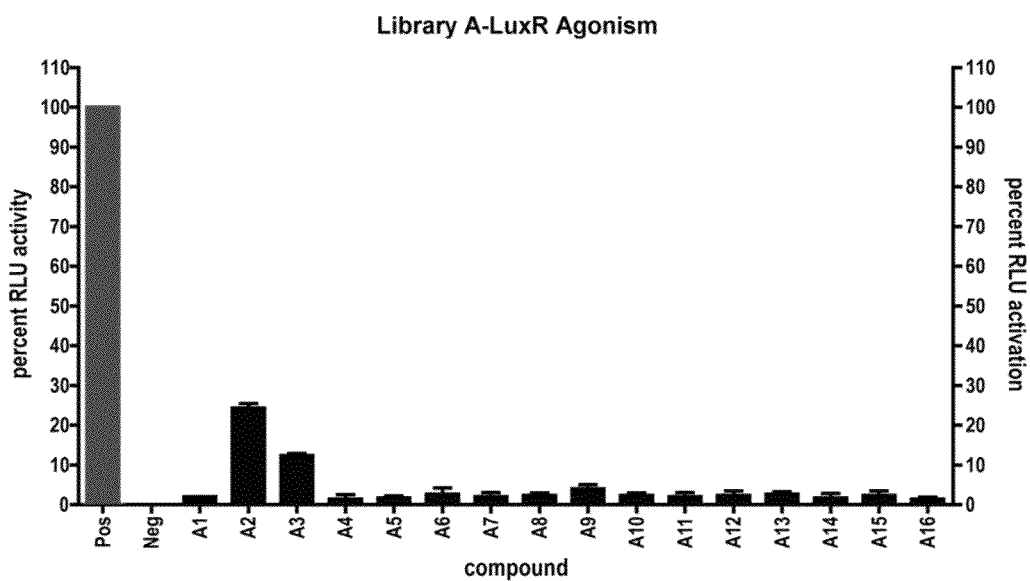

*V. FISCHERI* (LuxR) PRIMARY DATA. FIG. 29. Primary antagonism and agonism data for Library A screened in *V. fischeri*. Top: Antagonism screen performed using 5 μM of synthetic ligand against 5 μM of OHHL (3). Positive (pos) control=5 μM of OHHL (3). Negative control (neg)=no compound. Bottom: Agonism screen performed using 200 μM of synthetic ligand. Positive control (pos)=200 μM of OHHL (3). Error bars, s.d. of the means of triplicate samples.

Figure 30:
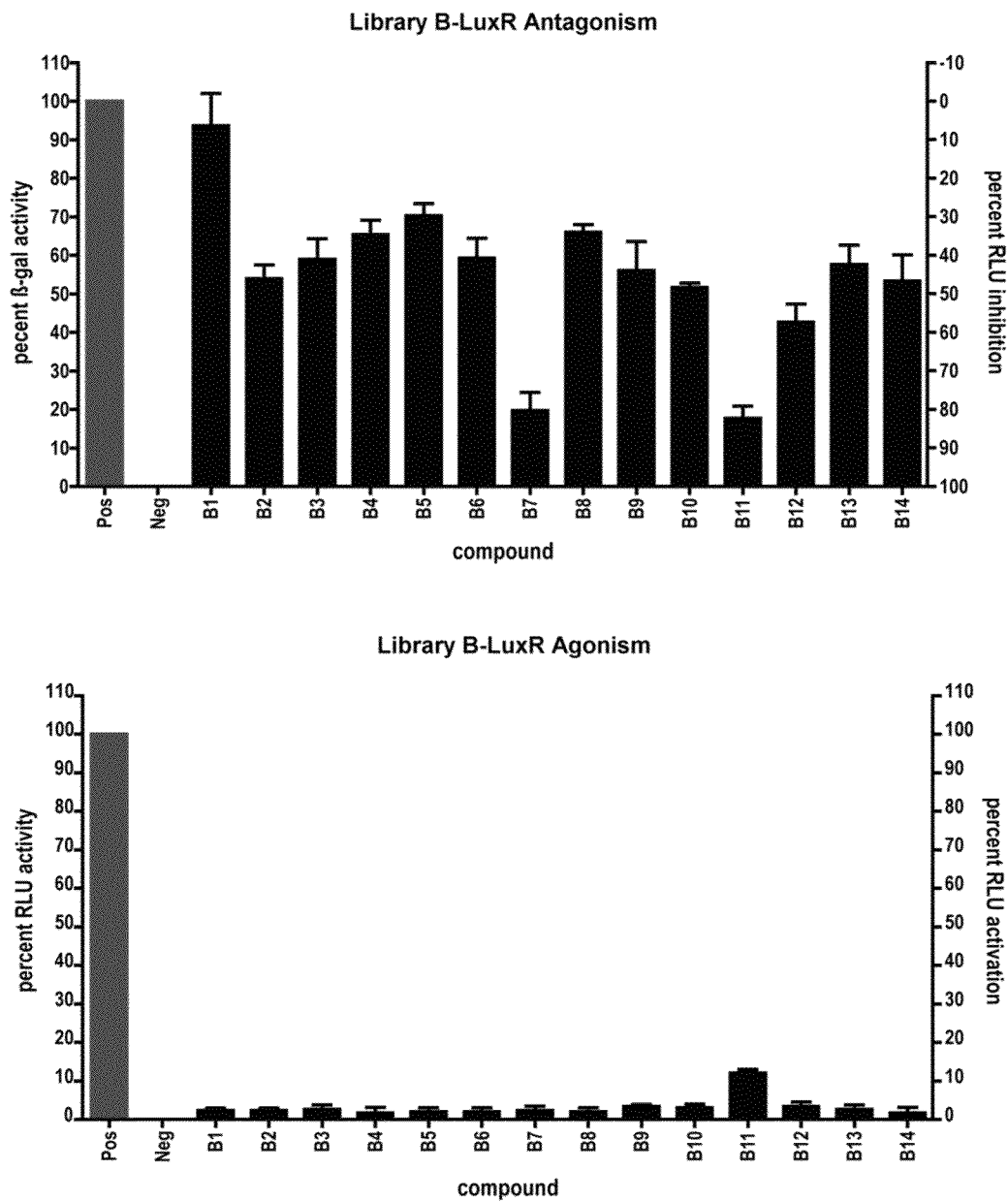
FIG. 30 provides primary antagonism and agonism data for Library B screened in *V. fischeri*.

FIG. 30. Primary antagonism and agonism data for Library B screened in *V. fischeri*. Top: Antagonism screen performed using 5 μM of synthetic ligand against 5 μM of OHHL (3). Positive (pos) control=5 μM of OHHL (3). Negative control (neg)=no compound. Bottom: Agonism screen performed using 200 μM of synthetic ligand. Positive control (pos)=200 μM of OHHL (3). Error bars, s.d. of the means of triplicate samples.

Figure 31:
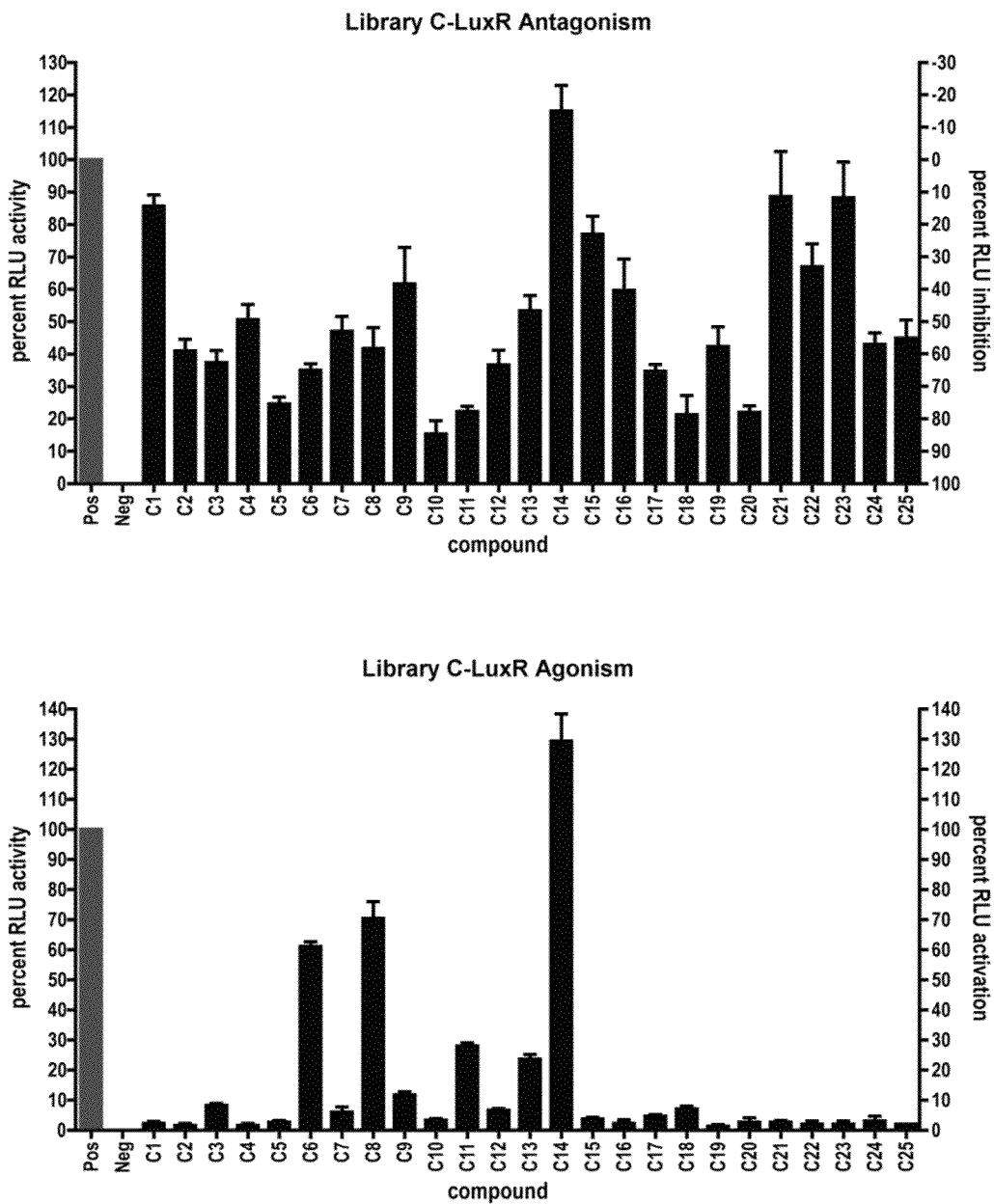
FIG. 31 provides primary antagonism and agonism data for Library C screened in *V. fischeri*.

FIG. 31. Primary antagonism and agonism data for Library C screened in *V. fischeri*. Top: Antagonism screen performed using 5 μM of synthetic ligand against 5 μM of OHHL (3). Positive (pos) control=5 μM of OHHL (3). Negative control (neg)=no compound. Bottom: Agonism screen performed using 200 μM of synthetic ligand. Positive control (pos)=200 μM of OHHL (3). Error bars, s.d. of the means of triplicate samples.

Figure 32:
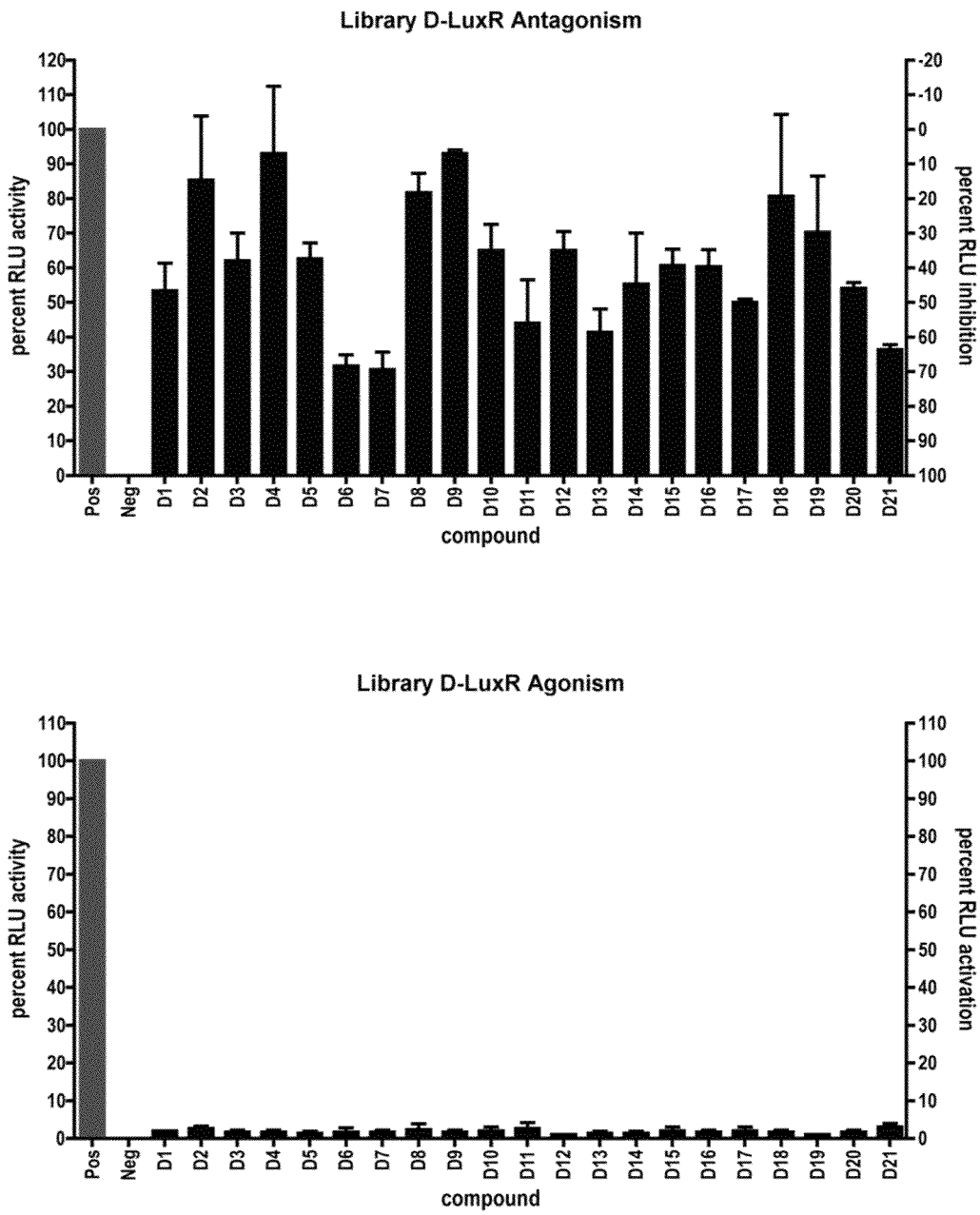
FIG. 32 provides primary antagonism and agonism data for Library D screened in *V. fischeri*.
Figure 33:
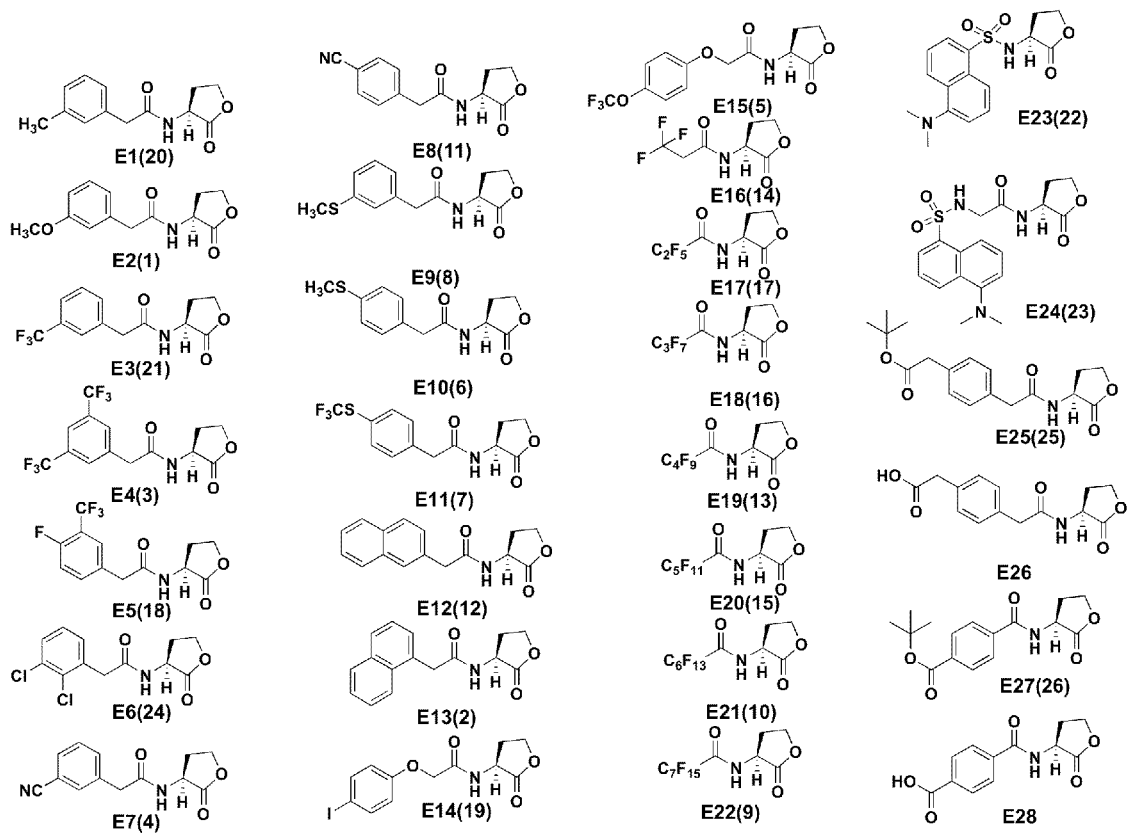
FIG. 33 illustrates structures of Library E.
Figure 34:
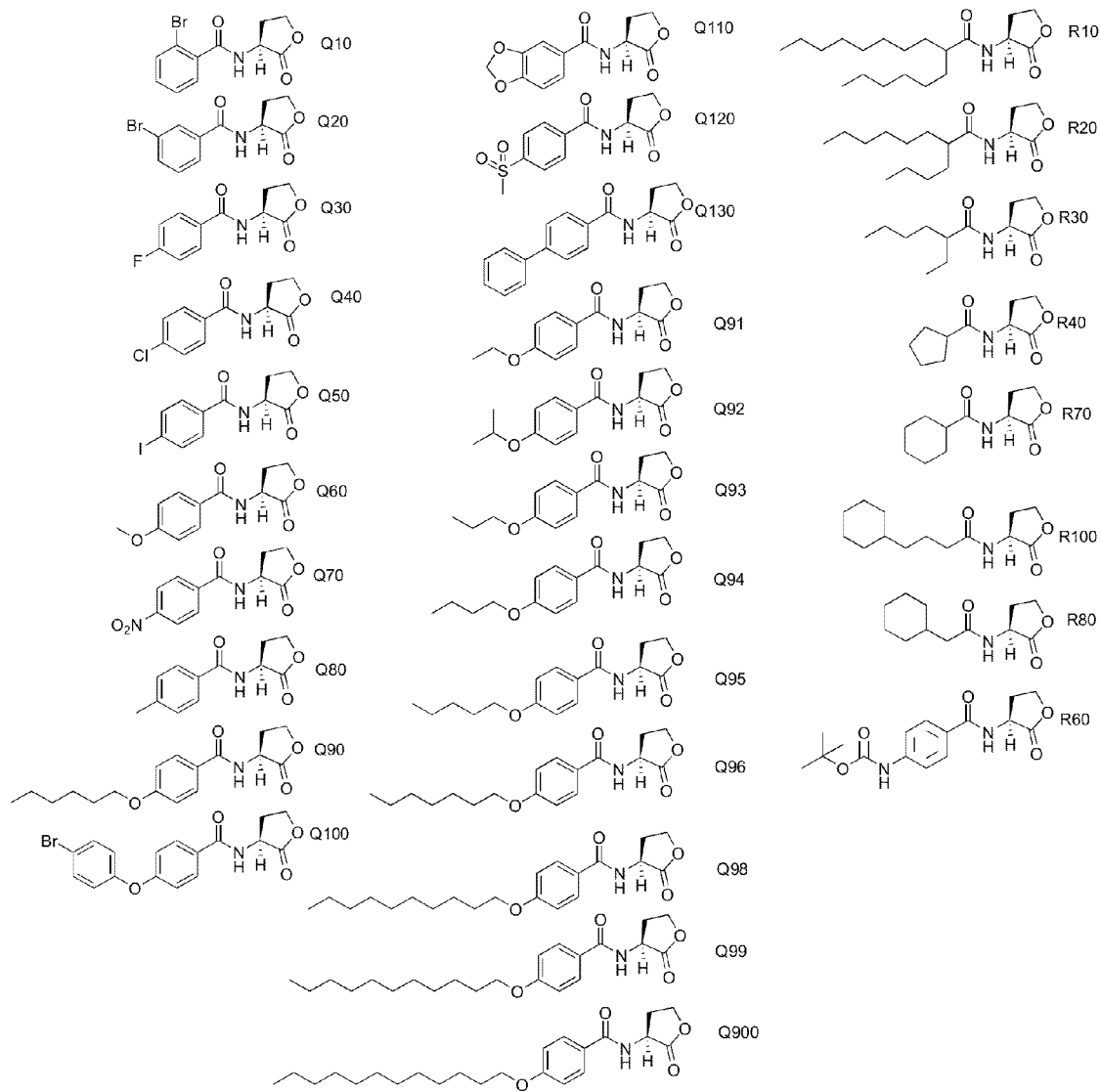
FIG. 34 illustrates structures of Library Q.
Figure 35:
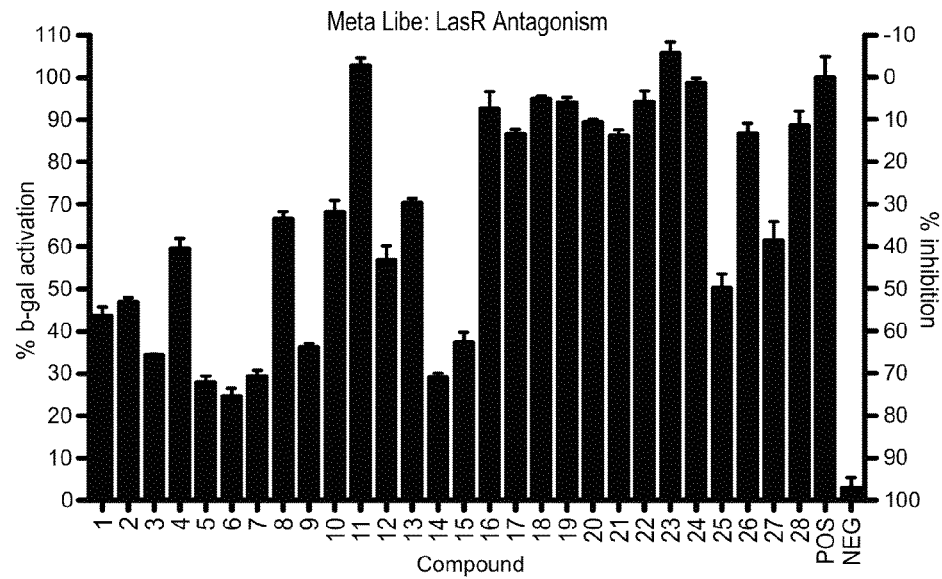
FIG. 35 provides primary antagonism and agonism data for Libraries E and Q screened in *P. aeruginosa*.
Figure 35:
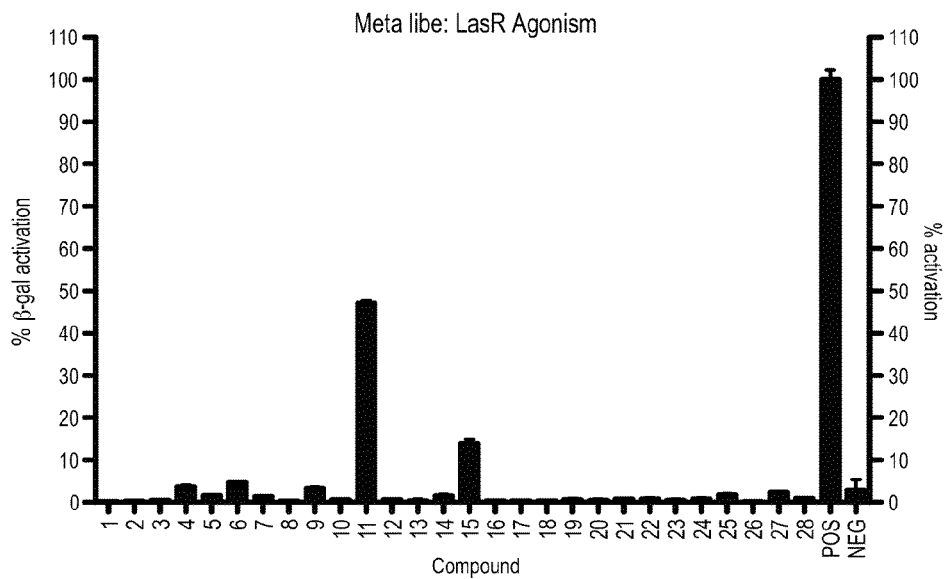
Figure 36:
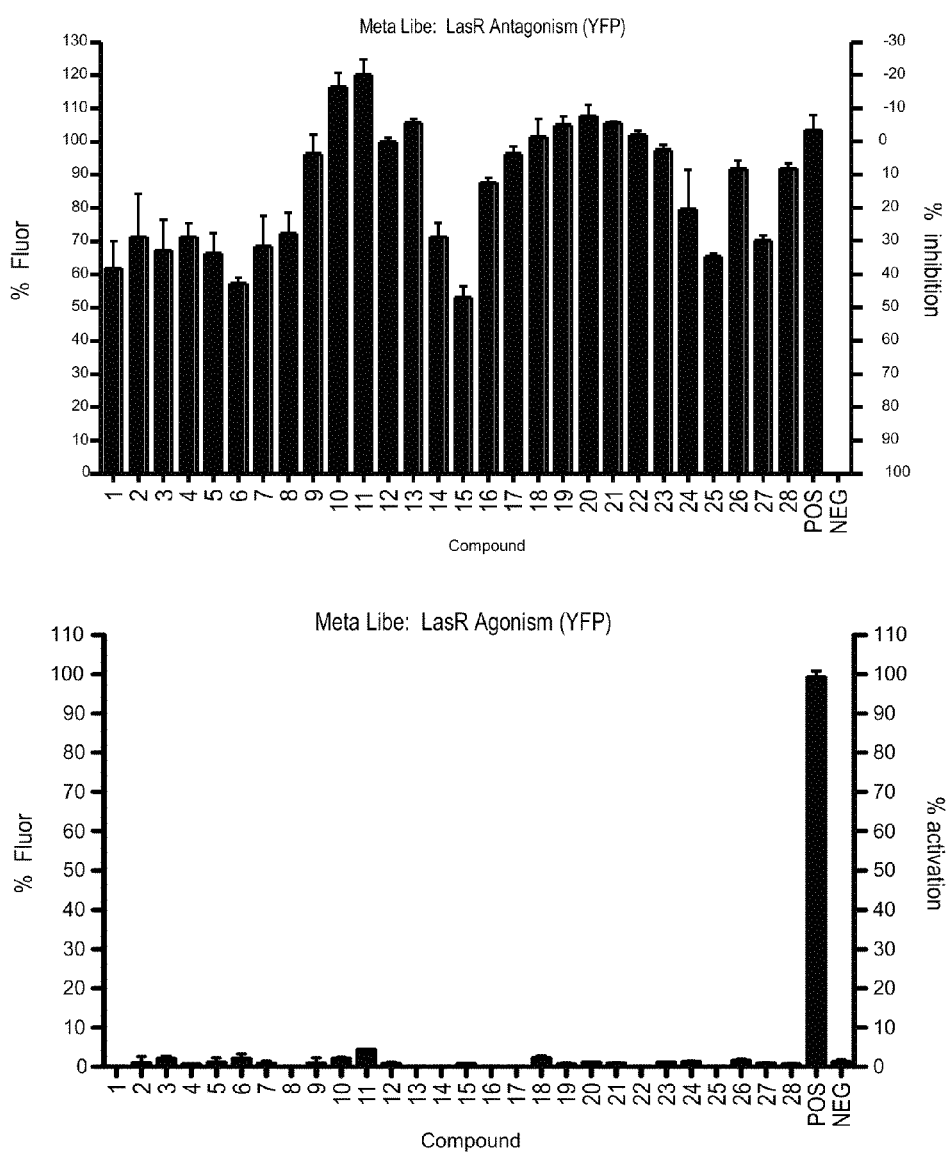
FIG. 36 provides primary antagonism and agonism data for Libraries E and Q screened in *P. aeruginosa*.
Figure 37:
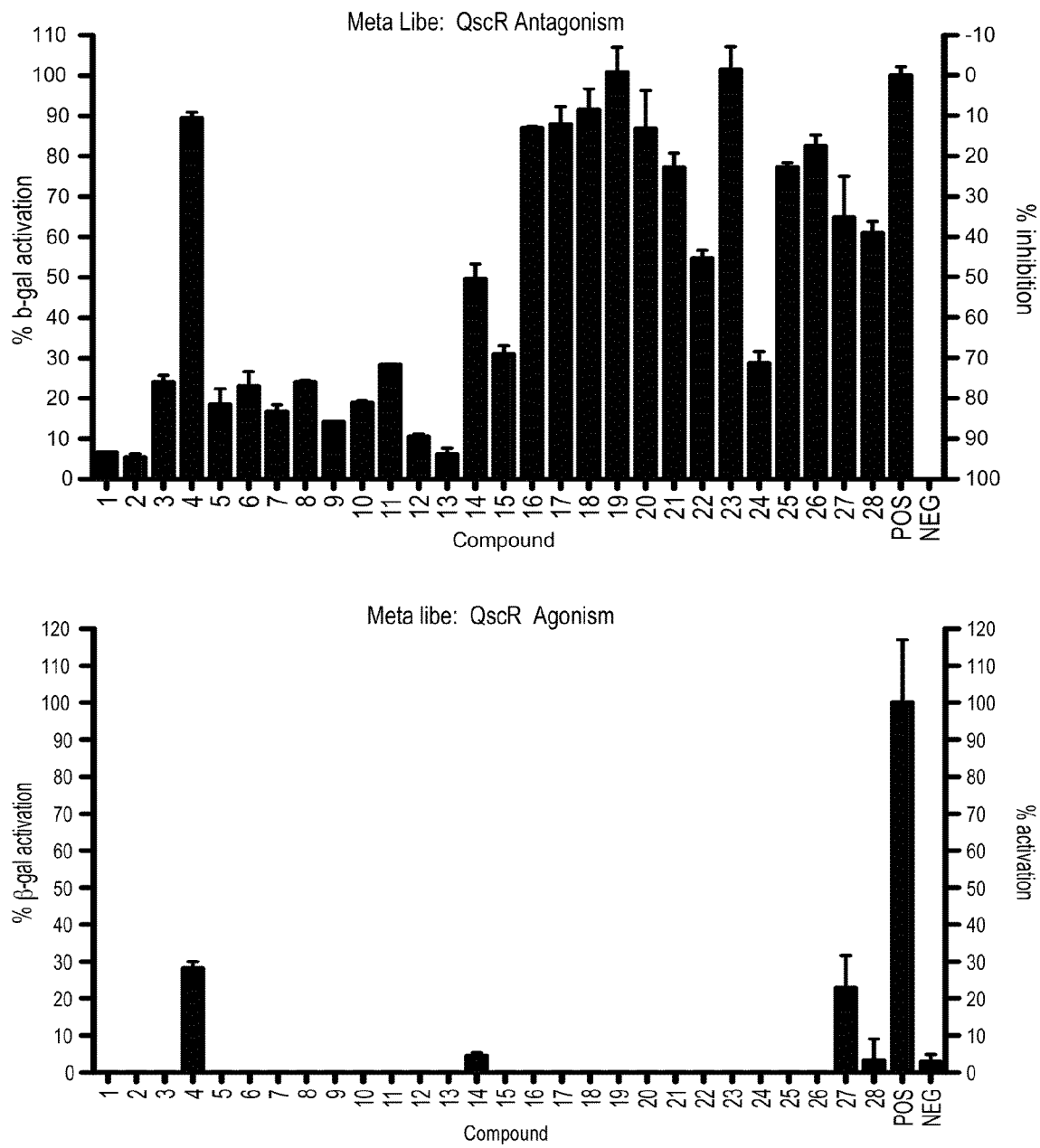
FIG. 37 provides primary antagonism and agonism data for Libraries E and Q screened in *P. aeruginosa*.
Figure 38:
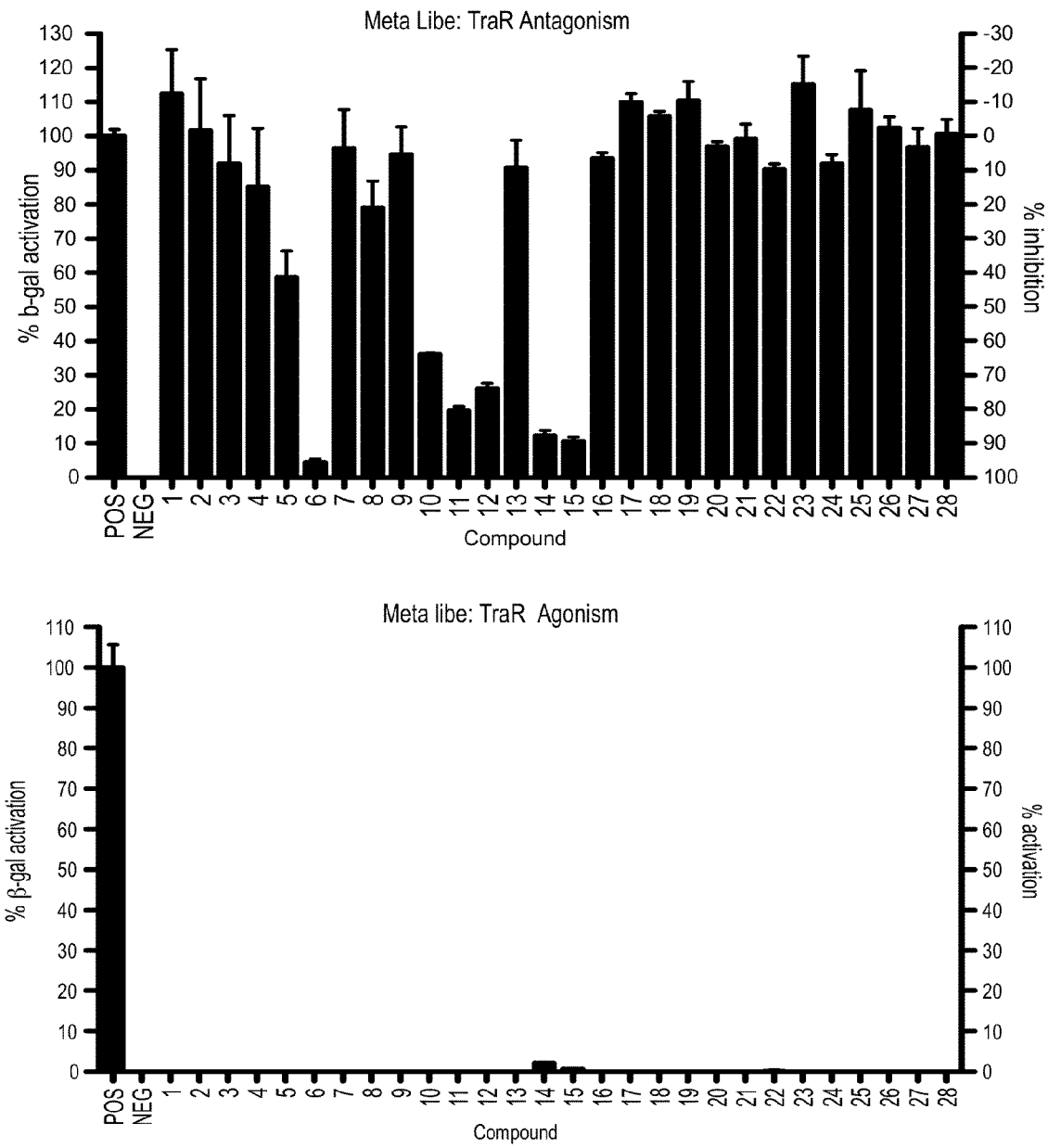
FIG. 38 provides primary antagonism and agonism data for Libraries E and Q screened in *A. tumefaciens*.
Figure 39:
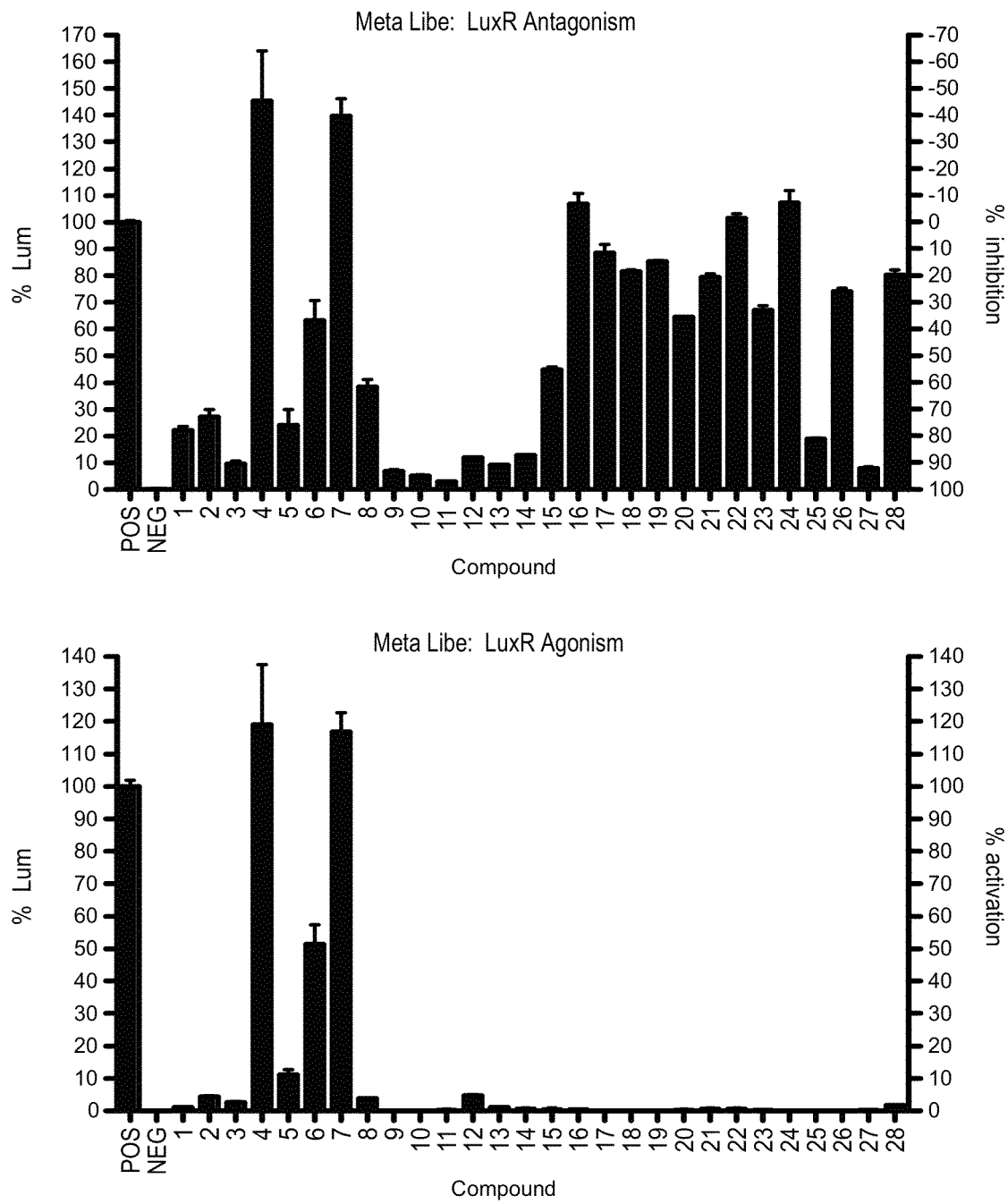
FIG. 39 provides primary antagonism and agonism data for Libraries E and Q screened in *V. fischeri*.
Figure 40:
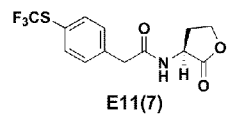
FIG. 40 illustrates compounds of Library E which have show favorable activity as agonists or antagonists.
Figure 40:
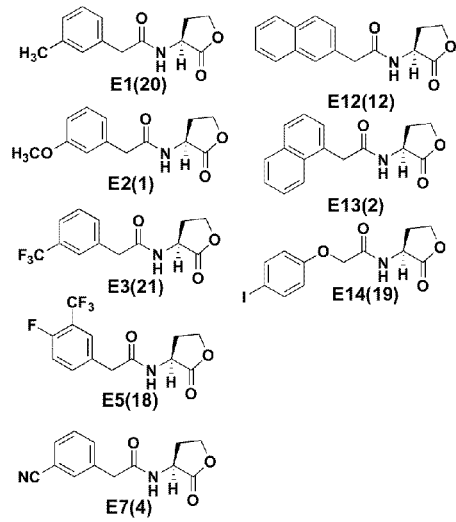
Figure 40:
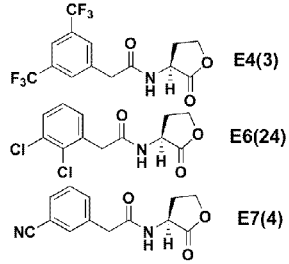
Figure 40:
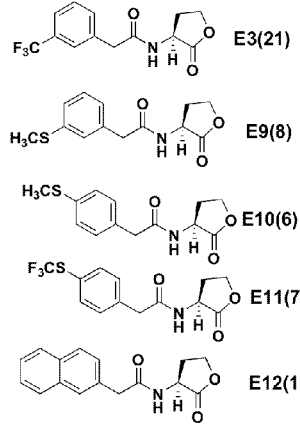
Figure 40:
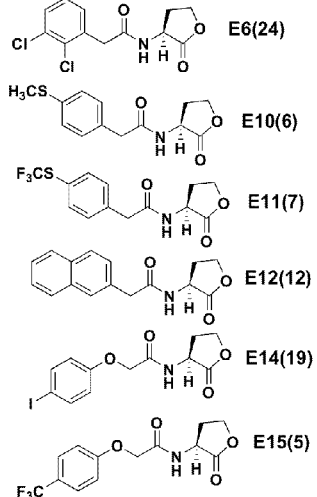
Figure 40:
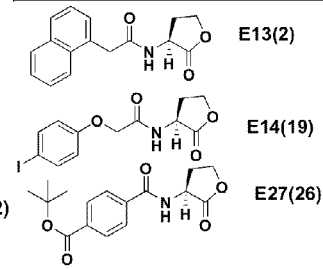
Figure 41:
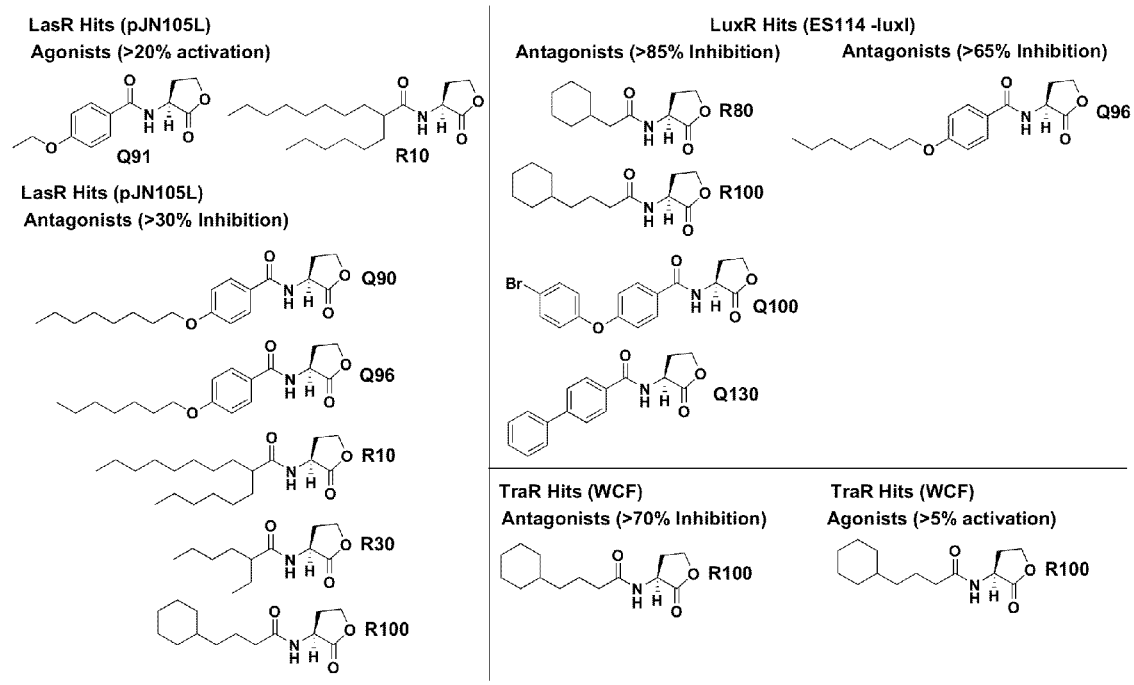
FIG. 41 illustrates compounds of Library Q which have show favorable activity as agonists or antagonists.

FIG. 32. Primary antagonism and agonism data for Library D screened in *V. fischeri*. Top: Antagonism screen performed using 5 μM of synthetic ligand against 5 μM of OHHL (3). Positive (pos) control=5 μM of OHHL (3). Negative control (neg)=no compound. Bottom: Agonism screen performed using 200 μM of synthetic ligand. Positive control (pos)=200 μM of OHHL (3). Error bars, s.d. of the means of triplicate samples.

Computational Methods.

Software.

All molecular modeling experiments were performed using the MOE software suite (v. 2006.08; Chemical Computing Group of Canada). Two-dimensional (2D) chemical structures were generated using ChemDraw (v. 10.0, Std.; CambridgeSoft).

Calculation of Pharmacophore Models for TraR, LasR, and LuxR.

Computational methods to generate pharmacophores using MOE software are well established and were utilized in this study. We provide a brief description of our pharmacophore calculations here. A database containing all of the AHL structures in Libraries A-D was created by importing 2D ChemDraw .sdf files for each ligand into MOE. These compounds then were minimized using the MMFF force field to an energy gradient of <0.01 to create a 3D structural database. After minimization, a conformational import was performed in MOE to create a second database that retained 100 of the lowest energy conformations for each member of Libraries A-D. A field for activity was created in this database, and each ligand was designated as either active (1) or inactive (O). This assignment was based on the primary antagonism and agonism data for the three bacterial species investigated in this study. All of the ligands that showed either ≥50% inhibition or ≥30% activation of TraR, LasR, or LuxR were designated as active (1); those with lower activities were designated inactive (0). Separate pharmacophores (PH4s) were created for each active and inactive ligand using the pharmacophore elucidator in MOE.

Each PH4 was examined for best score of accuracy (acc) in MOE, which was designated acc1 for active compounds and acc0 for inactive compounds. The three PH4s reported in this study were selected based on an acc1 value >0.50 (50%) and an acc0 value >0.50 (50%). This selection was made such that >50% of the active compounds were able to match the PH4, while >50% of the inactive compounds were unable to match the PH4. Based on the overall structural similarity of the compounds in Libraries A-D, this designation allowed for the determination of a PH4 that best describes the overall properties of an active AHL modulator for each R protein.

REFERENCES for Example 4

Bassler, B. L.; Losick, R. Cell 2006, 125, 237-246.
Waters, C. M.; Bassler, B. L. Ann. Rev. Cell Dev. Biol. 2005, 21, 319-346.
Fuqua, C.; Parsek, M. R.; Greenberg, E. P. Annu. Rev. Genet. 2001, 35, 439-468.
de Kievit, T. R.; Iglewski, B. H. Infect. Immun. 2000, 68, 4839-4849.
Hall-Stoodley, L.; Costerton, J. W.; Stoodley, P. Nat. Rev. Microbiol. 2004, 2, 95-108.
Winans, S. C. Trends Microbiol. 1998, 6, 382-383.
Greenberg, E. P., Quorum Sensing in Gram-Negative Bacteria: An Important Signaling Mechanism in Symbiosis and Disease. In Microbial Ecology and Infectious Disease, Rosenberg, E., Ed. American Society for Microbiology: Washington, D.C., 1999; pp 112-122.
Ruby, E. G. Annu. Rev. Microbiol. 1996, 50, 591-624.
Lyon, G. J.; Muir, T. W. Chem. Biol. 2003, 10, 1007-1021.
Gonzalez, J. E.; Keshavan, N. D. Microbiol. Mol. Biol. Rev. 2006, 70, 859-875.
Fuqua, C.; Greenberg, E. P. Nat. Rev. Mol. Cell Biol. 2002, 3, 685-695.
Whitehead, N. A.; Barnard, A. M.; Slater, H.; Simpson, N. J.; Salmond, G. P. FEMS Microbiol. Rev. 2001, 25, 365-404.
Welch, M.; Mikkelsen, H.; Swatton, J. E.; Smith, D.; Thomas, G. L.; Glansdorp, F. G.; Spring, D. R. Molecular Biosystems 2005, 1, 196-202.
Zhu, J.; Oger, P. M.; Schrammeijer, B.; Hooykaas, P. J.; Farrand, S. K.; Winans, S. C. J. Bacteriol. 2000, 182, 3885-3895.
Zhang, R. G.; Pappas, T.; Brace, J. L.; Miller, P. C.; Oulmassov, T.; Molyneaux, J. M.; Anderson, J. C.; Bashkin, J. K.; Winans, S. C.; Joachimiak, A. Nature 2002, 417, 971-974.
Vannini, A.; Volpari, C.; Gargioli, C.; Muraglia, E.; Cortese, R.; De Francesco, R.;
Neddermann, P.; Marco, S. D. EMBO J. 2002, 21, 4393-4401.
Van Delden, C.; Iglewski, B. H. Emerg. Infect. Dis. 1998, 4, 551-560.
Smith, R. S.; Eglevsky, B. H. Cur. Open. Microbiol. 2003, 6, 56-60.
Lycra, J. B.; Canon, C. L.; Pier, G. B. Clin. Microbiol. Rev. 2002, 15, 194-222.
Bottomley, M. J.; Muraglia, E.; Basso, R.; Carmi, A. J. Biol. Chem. 2007, 282, 13592-13600.
Zhu, J.; Winans, S. C. Proc. Natl. Acad. Sci. U.S.A. 2001, 98, 1507-1512.
Schuster, M.; Urbanowski, M. L.; Greenberg, E. P. Proc. Natl. Acad. Sci. U.S.A. 2004, 101, 15833-15839.
Visick, K. L.; Ruby, E. G. Curr. Opin. Microbiol. 2006, 9, 632-638.
Lupp, C.; Urbanowski, M.; Greenberg, E. P.; Ruby, E. G. Mol. Microbiol. 2003, 50, 319-331.
Urbanowski, A. L. Lostroh, C. P.; Greenberg, E. P. J. Bacteriol. 2004, 186, 631-637.
Eberhard, A.; Widrig, C. A.; McBath, P.; Schineller, J. B. Arch. Microbiol. 1986, 146, 35-40.
Schaefer, A. L.; Hanzelka, B. L.; Eberhard, A.; Greenberg, E. P. J. Bacteriol. 1996, 178, 2897-2901.
Passador, L.; Tucker, K. D.; Guertin, K. R.; Journet, M. P.; Kende, A. S.; Iglewski, B. H. J. Bacteriol. 1996, 178, 5995-6000.
Kline, T.; Bowman, J.; Iglewski, B. H.; de Kievit, T.; Kakai, Y.; Passador, L. Bioorg. Med. Chem. Lett. 1999, 9, 3447-3452.
Zhu, J.; Beaber, J. W.; More, M. I.; Fuqua, C.; Eberhard, A.; Winans, S. C. J. Bacteriol. 1998, 180, 5398-5405.
Ikeda, T.; Kajiyama, K.; Kita, T.; Takiguchi, N.; Kuroda, A.; Kato, J.; Ohtake, H. Chem. Lett. 2001, 314-315.
Reverchon, S.; Chantegrel, B.; Deshayes, C.; Doutheau, A.; Cotte-Pattat, N. Bioorg. Med. Chem. Lett. 2002, 12, 1153-1157.
Castang, S.; Chantegrel, B.; Deshayes, C.; Dolmazon, R.; Gouet, P.; Haser, R.; Reverchon, S.; Nasser, W.; Hugouvieux-Cotte-Pattat, N.; Doutheau, A. Bioorg. Med. Chem. Lett. 2004, 14, 5145-5149.
Frezza, M.; Castang, S.; Estephane, J.; Soulere, L.; Deshayes, C.; Chantegrel, B.; Nasser, W.; Queneau, Y.; Reverchon, S.; Doutheau, A. Bioorg. Med. Chem. 2006, 14, 4781-4791.
Hentzer, M., et al. EMBO J. 2003, 22, 3803-3815.
Persson, T.; Hansen, T. H.; Rasmussen, T. B.; Skinderso, M. E.; Givskov, M.; Nielsen, J. Org. Biomol. Chem. 2005, 3, 253-262.
Rasmussen, T. B.; Givskov, M. Microbiology 2006, 152, 895-904.
Smith, K. M.; Bu, Y. G.; Suga, H. Chem. Biol. 2003, 10, 81-89.
Smith, K. M.; Bu, Y.; Suga, H. Chem. Biol. 2003, 10, 563-571.
Jog, G. J.; Igarashi, J.; Suga, H. Chem. Biol. 2006, 13, 123-128.
Glansdorp, F. G.; Thomas, G. L.; Lee, J. J. K.; Dutton, J. M.; Salmond, G. P. C.; Welch, M.; Spring, D. R. Org. Biomol. Chem. 2004, 2, 3329-3336.
Muh, U.; Schuster, M.; Heim, R.; Singh, A.; Olson, E. R.; Greenberg, E. P. Antimicrob. Agents Chemother. 2006, 50, 3674-3679.
Taha, M. O.; Al-Bakri, A. G.; Zalloum, W. A. Bioorg. Med. Chem. Lett. 2006, 16, 5902-5906.

Janssens, J. C.; Metzger, K.; Daniels, R.; Ptacek, D.; Verhoeven, T.; Habel, L. W.; Vanderleyden, J.; De Vos, D. E.; De Keersmaecker, S. C. Appl. Environ. Microbiol. 2007, 73, 535-544.

Muh, U.; Hare, B. J.; Duerkop, B. A.; Schuster, M.; Hanzelka, B. L.; Heim, R.; Olson, E. R.; Greenberg, E. P. Proc. Natl. Acad. Sci. U.S.A. 2006, 103, 16948-16952.

Geske, G. D.; Wezeman, R. J.; Siegel, A. P.; Blackwell, H. E. J. Am. Chem. Soc. 2005, 127, 12762-12763.

Lin, Q.; Blackwell, H. E. Chem. Commun. 2006, 2884-2886.

Gorske, B. C.; Blackwell, H. E. Org. Biomol. Chem. 2006, 4, 1441-1445.

Geske, G. D.; O'Neill, J. C.; Blackwell, H. E. ACS Chem. Biol. 2007, 2, 315-320.

Barnick, J. W. F. K.; van der Baan, J. L.; Bickelhaupt, F. Synthesis 1979, 79, 787-788.

Rathke, M. W.; Nowak, M. A. Synth. Commun. 1985, 15, 1039-1049.

Miller, J. H., Experiments in Molecular Genetics. Cold Spring: 1972; p 352-355.

Lee, J. H.; Lequette, Y.; Greenberg, E. P. Mol. Microbiol. 2006, 59, 602-609.

Stover, C. K., et al. Nature 2000, 406, 959-964.

Silverman, R. B., The Organic Chemistry of Drug Design and Drug Action. Academic Press, Inc.: San Diego, 1992.

Clark, R. B.; Knoll, B. J.; Barber, R. Trends Pharmacol. Sci. 1999, 20, 279-286.

Zhu, B. T. Biomed. Pharmacother. 2005, 59, 76-89.

Fleming, S. A. Tetrahedron 1995, 51, 12479-12520.

Jensen, A. A.; Begum, N.; Vogensen, S. B.; Knapp, K. M.; Gundertofte, K.; Dzyuba, S. V.; Ishii, H.; Nakanishi, K.; Kristiansen, U.; Stromgaard, K. J. Med. Chem. 2007, 50, 1610-1617.

Meagher, K. L.; Lerner, M. G.; Carlson, H. A. J. Med. Chem. 2006, 49, 3478-3484.

Goto, J.; Kataoka, R.; Hirayama, N. J. Med. Chem. 2004, 47, 6804-6811.

Duffy, K. J.; Shaw, A. N.; Delorme, E.; Dillon, S. B.; Erickson-Miller, C.; Giampa, L.; Huang, Y.; Keenan, R. M.; Lamb, P.; Liu, N.; Miller, S. G.; Price, A. T.; Rosen, J.; Smith, H.; Wiggall, K. J.; Zhang, L.; Luengo, J. I. J. Med. Chem. 2002, 45, 3573-3575.

Duffy, K. J.; Price, A. T.; Delorme, E.; Dillon, S. B.; Duquenne, C.; Erickson-Miller, C.; Giampa, L.; Huang, Y.; Keenan, R. M.; Lamb, P.; Liu, N.; Miller, S. G.; Rosen, J.; Shaw, A. N.; Smith, H.; Wiggall, K. J.; Zhang, L.; Luengo, J. I. J. Med. Chem. 2002, 45, 3576-3578.

Example 5

Additional Libraries of Synthetic Quorum Sensing Agonists and Antagonists

FIGS. 62 and 63 illustrate additional libraries, E and Q, respectively, which were screened for agonistic and antagonistic activity. The compounds of the E and Q libraries were synthesized using the methods described in the above examples, and were screened using method similar to those described above.

The bacterial reporter strains used in this study were: *E. coli* pJN105L (*P. aeruginosa*, LasR), *P. aeruginosa* MW1 yfp (LasR), *E. coli* pJN105Q (*P. aeruginosa*, QscR), *A. tumefaciens* WCF (TraR), and *V. fischeri* ES114-luxI (LuxR). Primary screening data is respectively shown in FIGS. 64-68.

FIGS. 69 and 70 illustrate compounds of the E and Q libraries, respectively, which show favorable activity as agonists or antagonists.

Example 6

Synthetic Ligands that Activate and Inhibit a Quorum-Sensing Regulator in *Pseudomonas aeruginosa*

The transcription factor QscR is a regulator of quorum sensing in *Pseudomonas aeruginosa* and plays a role in controlling virulence in this prevalent opportunistic pathogen. This study outlines the discovery of a set of synthetic N-acylated homoserine lactones that are capable of either activating or strongly inhibiting QscR in a cell-based reporter gene assay. We demonstrate that the synthetic antagonists inhibit ligand-dependent QscR binding to DNA. Several of these ligands can selectively modulate QscR instead of LasR, or modulate the activity of both receptors, and represent new chemical tools to study the hierarchy of quorum-sensing signaling in *P. aeruginosa*.

Bacteria use a set of simple signal molecules and their cognate protein receptors to monitor their local population densities in a process termed quorum sensing (QS). Once they reach a sufficiently high population density, many bacteria undergo a lifestyle switch from that of solitary cells to that of a multicellular group. As a group, bacteria initiate processes that benefit the growing colony, and these behaviors can have significant impacts on their eukaryotic hosts. For example, virulence factor production and biofilm formation are under the control of QS in numerous clinically relevant pathogens, including *Pseudomonas aeruginosa* and *Staphylococcus aureus*. Mutants lacking functional QS systems have been shown to exhibit significantly reduced virulence both in vitro and in vivo. Therefore, QS has emerged as an attractive target for the development of new anti-infective therapies. As QS is under the control of low molecular weight molecules and peptides, one strategy to attenuate QS-controlled behaviors is to design non-native molecules or biomacromolecules that can intercept or block native QS signals. Here, we report the discovery of a set of small molecules capable of either activating or inhibiting a key receptor regulating QS in *P. aeruginosa*, QscR.

QS in Proteobacteria relies on LuxI-type proteins that synthesize N-acylated L-homoserine lactone signals, and LuxR-type signal receptors. LuxR-type receptor genes are often genetically linked to their associated LuxI-type synthases. Upon binding their cognate AHL ligand, LuxR-type receptors control the expression of genes involved in bacterial group behaviors. Interception of AHL:LuxR-type receptor binding with a non-native ligand represents an approach to directly modulate QS-controlled processes, and has been the focus of considerable recent research. Much of this work has focused on the LasR QS circuit in *P. aeruginosa*, which is regulated by N-(3-oxo-dodecanoyl)-L-homoserine lactone (OdDHL, 1) and, together with an additional LuxR-type receptor, RhlR, plays a principal role in pathogenesis.

In 2001, Chugani et al. reported the discovery of a gene for a third LuxR-type protein in *P. aeruginosa* that is not genetically linked to an AHL synthase. This "orphan receptor," termed QscR (quorum sensing control repressor), was later shown to respond to the LasR ligand, OdDHL (1), and control a set of genes unique from those controlled by LasR and RhlR. Mutants with inactivated QscR were hypervirulent in an insect infection model. These data suggest that QscR represents a novel target for the modulation of QS-controlled genes in *P. aeruginosa*. To probe this hypothesis, we sought to identify synthetic ligands that either activated or inhibited QscR. Such ligands would represent chemical tools to study the molecular mechanisms of QS gene control by QscR and their role in pathogenesis.

AHLs with aliphatic acyl chain structures closely related to that of OdDHL (1) (e.g., dodecanoyl HL (DDHL, 2)) have previously been shown to activate QscR to similar, if not slightly higher, levels as 1 in cell-based reporter gene assays. This expanded signal specificity has prompted the suggestion that QscR might also respond to AHL signals used by other bacteria that coexist with *P. aeruginosa*. Such hypotheses have been put forth for other orphan LuxR-type receptors, such as SdiA from *Escherichia coli* and *Salmonella enterica*, along with certain LuxR-type receptors that have cognate signals. We reasoned that QscR could be susceptible to modulation by other, non-native AHLs, and therefore focused on this ligand class in the present study.

We recently reported an efficient, solid-phase synthetic route to AHLs and the design and synthesis of several focused libraries of AHLs. These libraries contained AHLs with differing acyl chain length, lactone stereochemistry, and functional groups in the acyl chain. They also included several naturally occurring AHLs, such as 1-4. Evaluation of these ~90 compounds in a range of Gram-negative bacteria (e.g., *P. aeruginosa, Agrobacterium tumefaciens*, and *Vibrio fischeri*) revealed several AHLs with activities ranging from that of potent inhibitors to a super-activator of LuxR-type protein function. Accordingly, these AHL libraries represented a logical set of compounds with which to start our search for synthetic, AHL-derived QscR activators and inhibitors.

We screened our AHL libraries for agonistic and antagonistic activity against QscR using a previously reported, recombinant *E. coli* strain that reports QscR activity via the production of β-galactosidase (β-gal) from a promoter fusion. OdDHL (1) and DDHL (2) served as positive controls for these assays. All AHLs were examined at 5 µM concentrations. Agonism assays contained AHL library member alone, while competitive antagonism assays were performed against DDHL (2, at 10 nM). [DDHL (2) was found to activate QscR at lower concentrations relative to OdDHL (1), and thus provided a more stringent control for these antagonism assays.] We observed that 11% of the AHL library was able to activate QscR to ≥50%. In turn, 6% of the library was capable of inhibiting QscR by ≥75% in these reporter gene assays. Identifying such a large percentage of active compounds further underscores the value of screening these previously validated AHL libraries against LuxR-type receptors. We focused on these most active QscR agonists and antagonists for the remainder of this study. No AHLs were identified in the primary assay with agonistic activities that surpassed that of controls OdDHL (1) or DDHL (2). Not surprisingly, many of these compounds had structures closely related to that of OdDHL (1), e.g., A3, A4, A8, A16, and OOHL (3), corroborating data reported by Lee et al. in this same reporter strain. However, the remaining four AHLs (B2, B7, C22, and D7) had structures that diverged from those of 1 or 2, most notably B2, which had D-stereochemistry. All four AHLs contained aromatic acyl groups. We previously observed that A4, A8, B2, and C22, but not A16 and D7, are also weak to strong activators of LasR. More notably, however, the other three QscR activators, OOHL (3), A3, and B7, are also capable of inhibiting LasR (by ≥50%). These screening data suggest that activation of QscR by AHLs is not restricted to unbranched, aliphatic AHLs. Moreover, they indicate that the development of ligands that specifically modulate QscR instead of LasR, or that activate or inhibit both receptors, will be feasible. A recent report by Müh et al. of a non-AHL ligand (termed TP-1) that activates LasR, yet does not activate QscR, provides further support for these data.

We performed dose response agonism assays on the most active AHLs in this set and OdDHL (1) and DDHL (2) using the β-gal reporter strain, and determined their EC50 values. These assays revealed that the control DDHL (2) and A4 exhibited the lowest EC50 values in this study (i.e., ~5 nM), with OOHL (3) having the next lowest value; these trends were congruent with our primary agonism assay data.

The antagonism assay of the AHL library revealed five non-native AHLs capable of inhibiting QscR by ≥75%. Four phenylacetanoyl HLs (PHLs) were uncovered as slightly weaker QscR antagonists (~70%) and are also included here in our data analysis.

Like the QscR agonists, the acyl chain structures of these QscR antagonists ranged from relatively compact (B6) to long and lipophilic (D13), making the development of specific structure-activity relationships (SARs) for AHL-mediated QscR inhibition challenging. Some trends were clear, however. All of the QscR antagonists contained aromatic acyl groups and native (L) lactone stereochemistry. Three of the most effective inhibitors had benzoyl groups (B6, D12, and D13); potent LuxR-type receptor inhibitors with this type of acyl chain are yet to be reported. PHLs were also strong antagonists of QscR (i.e., the C# AHLs), with C18 the most active QscR antagonist uncovered in this study (IC50=30 nM. This PHL is only a weak LasR inhibitor (20%); however, PHLs C6, C8, C11, and C14 with meta-halogen or nitro groups are also moderate antagonists of LasR (~50%). None of the other QscR antagonists displayed appreciable inhibitory activity against LasR. Interestingly, the other active PHL identified in this study, C22, is an activator of QscR at the concentration tested, and further highlights PHLs as a versatile structure class for the development of both inhibitors and activators of LuxR-type receptors.

We sought to obtain further insights into the mechanism of QscR modulation by non-native AHLs. Previous work has shown that QscR specifically binds the promoter region of the PA1897 gene in the presence of OdDHL (1). In view of the reporter gene assay data outlined above, we reasoned that our QscR antagonists could competitively inhibit the binding of QscR to DNA in the presence of OdDHL (1). We therefore performed electromobility shift assays (EMSA) on purified QscR and radiolabeled PA1897 promoter in the presence of selected QscR antagonists and 1.

The EMSAs revealed that all five AHLs (B6, C18, C25, D12, and D13) were capable of inhibiting OdDHL (1)-dependent QscR:DNA binding. At a 100:1 ratio with OdDHL (1), PHL C18 inhibited OdDHL-dependent binding by 85%, while D12 was 26% inhibitive. This activity trend correlated well with the cell-based reporter assays, where C18 had a six-fold lower IC50 relative to D12. All of the antagonists could further retard QscR:DNA binding at 1000:1 ratios vs. OdDHL (1), with C18 and D13 reducing binding by 100%.

These data suggest that the mechanism of QscR antagonism by these synthetic AHLs is inhibition of OdDHL (1)-dependent QscR:DNA binding. We speculate that these ligands directly bind QscR and/or displace OdDHL (1), yielding a QscR:AHL complex with lowered affinity for the PA1897 promoter sequence. In turn, we hypothesize that our AHL activators bind QscR and promote QscR:DNA binding; EMSAs on selected synthetic QscR agonists are ongoing to probe this model.

In summary, we have identified a series of AHLs that are capable of activating or inhibiting the LuxR-type receptor, QscR, from *P. aeruginosa*. Several of the antagonists were capable of inhibiting OdDHL (1)-dependent QscR:DNA binding. These ligands represent the first non-native small molecule modulators of QscR. We have also discovered synthetic AHLs that either selectively activate or inhibit QscR instead of LasR, or activate or inhibit both receptors. The most interesting non-native ligand in this class is perhaps AHL B7, as it can moderately activate QscR and has previously been shown to strongly inhibit LasR. This bifunctional compound represents a unique tool to probe the role of QscR as a negative regulator of QS pathways in *P. aeruginosa*. Activating QscR, while simultaneously repressing LasR, could have a synergistic effect on virulence inhibition in *P. aeruginosa*. Likewise, synthetic ligands that activate or inhibit both QscR and LasR (e.g., B2 and C11), or modulate QscR specifically (e.g., D7 and C18), could prove valuable in delineating the hierarchy of these two receptors in QS control.

The following reference is expressly incorporated by reference in its entirety to the extent not inconsistent with the disclosure herein: Mattmann, M. E. et al., Bioorg. Med. Chem. Lett. (2008), doi: 10.1016/j.bmcl.2007.11.095.

TABLE 1

| entry | compound | *A. tumefaciens* - TraR[b] | | *E. coli* - LasR[e] | | *V. fischeri* - LuxR[h] | |
|---|---|---|---|---|---|---|---|
| | | Inhibition [%][c] | Activation [%][d] | Inhibition [%][f] | Activation [%][g] | Inhibition [%][i] | Activation [%][j] |
| 1 | A10: OOHL | — | 100 | 50 | 19 | 63 | 24 |
| 2 | A8: OdDHL | 28 | 12 | — | 100 | 86 | 2 |
| 3 | A11: OHHL | 89 | 1 | 15 | 1 | — | 100 |
| 4 | A12 | 93 | 4 | 28 | 0 | 78 | 23 |
| 5 | A13 | 85 | 8 | 18 | 5 | 45 | 2 |
| 6 | A14 | 93 | 2 | 20 | 3 | 70 | 3 |
| 7 | A15 | 9 | 0 | 4 | 18 | 3 | 1 |
| 8 | A17 | 88 | 1 | 28 | 0 | 79 | 3 |
| 9 | A18 | 35 | 0 | 36 | 3 | 72 | 3 |
| 10 | A1 | 0 | 0 | 0 | 0 | 43 | 2 |
| 11 | A2 | 48 | 1 | 11 | 2 | 69 | 25 |
| 12 | A3 | 83 | 7 | 43 | 1 | 86 | 12 |
| 13 | A4 | 92 | 2 | 34 | 44 | 96 | 1 |
| 14 | A5 | 22 | 1 | -10 | 85 | 73 | 2 |
| 15 | A6 | 0 | 0 | 5 | 11 | 27 | 2 |
| 16 | A9 | 14 | 1 | 8 | 1 | 47 | 2 |
| 17 | A7 | 10 | 11 | -18 | 87 | 77 | 2 |
| 18 | C10 | 86 | 7 | 16 | 1 | 5 | 4 |
| 19 | C11 | 59 | 0 | 12 | 0 | 30 | 2 |
| 20 | C12 | 93 | 1 | 10 | 0 | 32 | 2 |
| 21 | C13 | 88 | 1 | 12 | 0 | 60 | 2 |
| 22 | C14 | 44 | 0 | 10 | 0 | 77 | 3 |
| 23 | C15 | 37 | 3 | 15 | 0 | 81 | 2 |
| 24 | C16 | 34 | 0 | 17 | 0 | 80 | 2 |
| 25 | C17 | 29 | 0 | 21 | 0 | 74 | 1 |

TABLE 2

| entry | compound | A. tumefaciens - TraR | | E. coli - LasR | | V. fischeri - LuxR | |
|---|---|---|---|---|---|---|---|
| | | Inhibition (%) | Activation (%) | Inhibition (%) | Activation (%) | Inhibition (%) | Activation (%) |
| 1 | A10: OOHL | — | 100 | 50 | 19 | 63 | 24 |
| 2 | A8: OdDHL | 28 | 12 | — | 100 | 86 | 2 |
| 3 | A11: OHHL | 89 | 1 | 15 | 1 | — | 100 |
| 4 | A13 | 85 | 8 | 18 | 5 | 45 | 2 |
| 5 | A14 | 93 | 2 | 20 | 3 | 70 | 3 |
| 6 | A17 | 88 | 1 | 28 | 0 | 79 | 3 |
| 7 | A18 | 35 | 0 | 36 | 3 | 72 | 3 |
| 8 | A24 | 6 | 4 | 16 | 0 | 7 | 2 |
| 9 | A25 | 50 | 2 | -7 | 84 | 46 | 3 |
| 10 | A26 | 31 | 0 | 16 | 0 | 41 | 3 |
| 11 | A28 | 9 | 0 | 13 | 1 | 34 | 2 |
| 12 | A29 | 9 | 0 | 13 | 0 | 29 | 2 |
| 13 | C2 | 9 | 0 | 13 | 0 | 40 | 2 |
| 14 | C4 | 93 | 2 | 52 | 11 | 80 | 2 |
| 15 | C1 | 8 | 0 | 14 | 1 | 34 | 2 |
| 16 | C3 | 16 | 0 | 21 | 0 | 44 | 3 |
| 17 | A19 | 7 | 3 | 22 | 2 | 48 | 3 |
| 18 | C9 | 25 | 0 | 36 | 0 | 82 | 12 |
| 19 | C8 | 11 | 0 | 19 | 0 | 57 | 3 |
| 20 | C6 | 20 | 0 | 21 | 0 | 42 | 3 |
| 21 | C7 | 21 | 0 | 48 | 1 | 47 | 2 |

TABLE 3

| entry | compound | A. tumefaciens - TraR | | E. coli - LasR | | V. fischeri - LuxR | |
|---|---|---|---|---|---|---|---|
| | | Inhibition (%) | Activation (%) | Inhibition (%) | Activation (%) | Inhibition (%) | Activation (%) |
| 1 | A10: OOHL | — | 100 | 50 | 19 | 63 | 24 |
| 2 | A8: OdDHL | 28 | 12 | — | 100 | 86 | 2 |
| 3 | A11: OHHL | 89 | 1 | 15 | 1 | — | 100 |
| 4 | A17 | 88 | 1 | 28 | 0 | 79 | 3 |
| 5 | B3 | 4 | 0 | 15 | 0 | 14 | 2 |
| 6 | B4 | 25 | 0 | 26 | 1 | 59 | 2 |
| 7 | B5 | 11 | 0 | 27 | 0 | 63 | 8 |

TABLE 3-continued

| 8 | B6 | 4 | 0 | 19 | 0 | 49 | 2 |
|---|---|---|---|---|---|---|---|
| 9 | B7 | 74 | 0 | 29 | 0 | 75 | 3 |
| 10 | B8 | 50 | 0 | 41 | 0 | 65 | 61 |
| 11 | B9 | 6 | 0 | 10 | 0 | 53 | 6 |
| 12 | B10 | 56 | 0 | 45 | 3 | 58 | 70 |
| 13 | B11 | 12 | 0 | 12 | 0 | 38 | 12 |
| 14 | B13 | 93 | 1 | 36 | 0 | 85 | 4 |
| 15 | B14 | 70 | 0 | 57 | 3 | 78 | 28 |
| 16 | B15 | 5 | 0 | 17 | 0 | 63 | 7 |
| 17 | B16 | 88 | 1 | 27 | 0 | 47 | 24 |
| 18 | B17 | 46 | 0 | 54 | 11 | -15 | 129 |
| 19 | B18 | 1 | 0 | 17 | 0 | 23 | 4 |
| 20 | B19 | 2 | 0 | 19 | 2 | 40 | 2 |
| 21 | B20 | 70 | 0 | 19 | 0 | 66 | 5 |
| 22 | B21 | 67 | 0 | 20 | 0 | 79 | 7 |
| 23 | B24 | 21 | 3 | 11 | 0 | 58 | 1 |
| 24 | B23 | 92 | 2 | 26 | 0 | 78 | 3 |
| 25 | B26 | 5 | 0 | 8 | 0 | 12 | 3 |
| 26 | B25 | 11 | 0 | 10 | 27 | 33 | 2 |
| 27 | B27 | 3 | 0 | 7 | 0 | 12 | 2 |
| 28 | B28 | 26 | 0 | 16 | 0 | 57 | 3 |
| 29 | B29 | 35 | 0 | 15 | 0 | 55 | 2 |

TABLE 4

| entry | compound | *A. tumefaciens* - TraR | | *E. coli* - LasR | | *V. fischeri* - LuxR | |
|---|---|---|---|---|---|---|---|
| | | Inhibition (%) | Activation (%) | Inhibition (%) | Activation (%) | Inhibition (%) | Activation (%) |
| 1 | A10: OOHL | — | 100 | 50 | 19 | 63 | 24 |
| 2 | A8: OdDHL | 28 | 12 | — | 100 | 86 | 2 |
| 3 | A11: OHHL | 89 | 1 | 15 | 1 | — | 100 |
| 4 | A12 | 93 | 4 | 28 | 0 | 78 | 23 |
| 5 | A13 | 85 | 8 | 18 | 5 | 45 | 2 |
| 6 | A14 | 93 | 2 | 20 | 3 | 70 | 3 |
| 7 | A15 | 9 | 0 | 4 | 18 | 3 | 1 |
| 8 | A17 | 88 | 1 | 28 | 0 | 79 | 3 |
| 9 | A18 | 35 | 0 | 36 | 3 | 72 | 3 |

TABLE 4-continued

| 10 | A23 | 5 | 0 | 12 | 0 | 18 | 2 |
| --- | --- | --- | --- | --- | --- | --- | --- |
| 11 | D1 | 9 | 0 | 18 | 0 | 15 | 3 |
| 12 | D2 | 8 | 0 | 22 | 0 | 38 | 2 |
| 13 | D3 | 12 | 2 | 18 | 0 | 7 | 2 |
| 14 | A20 | 3 | 0 | 13 | 0 | 37 | 1 |
| 15 | D13 | 90 | 3 | 28 | 0 | 68 | 2 |
| 16 | D12 | 59 | 1 | 13 | 0 | 69 | 2 |
| 17 | A22 | 10 | 0 | 15 | 3 | 47 | 2 |
| 18 | D4 | 8 | 0 | 16 | 4 | 7 | 2 |
| 19 | D5 | 8 | 0 | 9 | 0 | 35 | 2 |
| 20 | D6 | 9 | 0 | 10 | 0 | 56 | 2 |
| 21 | A21 | 13 | 0 | 12 | 0 | 35 | 1 |
| 22 | D11 | 8 | 0 | 27 | 3 | 59 | 1 |
| 23 | D9 | 11 | 0 | 36 | 36 | 45 | 1 |
| 24 | D10 | 90 | 4 | 49 | 30 | 39 | 2 |
| 25 | D14 | 11 | 0 | 18 | 0 | 40 | 1 |
| 26 | D15 | 92 | 1 | 26 | 0 | 50 | 2 |
| 27 | D7 | 16 | 0 | 34 | 32 | 19 | 2 |
| 28 | D8 | 11 | 0 | 17 | 7 | 30 | 1 |
| 29 | C5 | 4 | 0 | 12 | 0 | 46 | 2 |
| 30 | B22 | 9 | 0 | 13 | 1 | 63 | 3 |

TABLE 5

| entry | compound | TraR (μM)[b] | LasR (μM)[c] | LuxR (μM)[d] |
| --- | --- | --- | --- | --- |
| 1 | A10: OOHL | —[e] | 0.11 (2.0)[f] | — |
| 2 | A8: OdDHL | — | — | 0.40 |
| 3 | A12 | 0.69 | — | 1.36 |
| 4 | A13 | 0.83 | — | — |
| 5 | A14 | 1.12 | — | — |
| 6 | A17 | 4.73 | 3.89 | 4.13 |
| 7 | A18 | — | 8.38 | — |
| 8 | A3 | 0.77 | 1.75 | 0.77 |
| 9 | A4 | 1.05 | (2.0)[f] | 0.90 |
| 10 | A7 | — | — | 0.74 |
| 11 | B7 | — | — | 4.13 |
| 12 | B8 | — | 3.97 | — |
| 13 | B10 | — | 4.06 | — |
| 14 | B13 | 1.26 | 1.72 | 0.86 |
| 15 | B14 | — | 4.63 | — |
| 16 | B16 | 2.25 | — | — |
| 17 | B17 | — | 0.61 (2.0)[f] | — |
| 18 | B21 | — | — | 1.06 |
| 19 | B23 | 0.81 | — | 0.61 |
| 20 | C4 | 0.92 | (2.0)[f] | 1.35 |
| 21 | C7 | — | 0.83 (20.0)[f] | — |
| 22 | C9 | — | 1.75 (20.0)[f] | 2.69 |
| 23 | C10 | 0.61 | — | — |
| 24 | C12 | 0.83 | — | — |
| 25 | C13 | 3.49 | — | — |
| 26 | C14 | — | — | 1.43 |
| 27 | C15 | — | — | 1.03 |
| 28 | C16 | — | — | 1.39 |
| 29 | D10 | 0.46 | 4.67 (2.0)[f] | — |
| 30 | D13 | 0.57 | — | — |
| 31 | D15 | 1.40 | — | — |

TABLE 6

| entry | compound | TraR (μM) | LasR (μM) | LuxR (μM) |
| --- | --- | --- | --- | --- |
| 1 | A10: OOHL | 0.25 | — | — |
| 2 | A8: OdDHL | —[b] | 0.01 | — |
| 3 | A11: OHHL | — | — | 3.00 |
| 4 | A4 | — | >200[c] | — |
| 5 | A5 | — | 0.04 | — |

TABLE 6-continued

| entry | compound | TraR (μM) | LasR (μM) | LuxR (μM) |
|---|---|---|---|---|
| 6 | A7 | — | 0.01 | — |
| 7 | A25 | — | 0.54 | — |
| 8 | B8 | — | — | >200$^e$ |
| 9 | B10 | — | — | >50$^e$ |
| 10 | B17 | — | — | 0.35 |
| 11 | B25 | — | >200$^e$ | — |
| 12 | D7 | — | 0.47 (32%)$^d$ | — |
| 13 | D9 | — | 1.62 (36%)$^d$ | — |
| 14 | D10 | — | >200$^e$ | — |

TABLE 7

| entry | compound | *A. tumefaciens* TraR (μM)$^b$ | *P. aeruginosa* LasR (μM)$^c$ | *V. fischeri* LuxR (μM)$^d$ |
|---|---|---|---|---|
| 1 | 1: OOHL | —$^e$ | 0.11$^{f,g}$ | — |
| 2 | 2: OdDHL | — | — | 0.40 |
| 3 | 4 | 0.69$^f$ | — | 1.36$^f$ |
| 4 | 5 | 0.83$^f$ | — | — |
| 5 | 6 | 1.12$^f$ | — | — |
| 6 | 8 | 4.73 | 3.89 | 3.70 |
| 7 | 9 | — | 8.38 | — |
| 8 | A3 | 0.77$^f$ | 1.75$^f$ | 0.77$^f$ |
| 9 | A4 | 1.05 | 0.25$^{f,g}$ | 0.40 |
| 10 | A8 | — | — | 0.74 |
| 11 | A9 | 0.61$^f$ | — | — |
| 12 | A11 | 0.83$^f$ | — | — |
| 13 | A12 | 3.49 | — | — |
| 14 | A13 | — | — | 1.43 |
| 15 | A14 | — | — | 1.03 |
| 16 | A15 | — | — | 1.39 |
| 17 | B7 | 0.92$^f$ | 0.34$^{f,g}$ | 1.35 |
| 18 | B11 | — | 1.75$^{f,g}$ | 2.69$^f$ |
| 19 | B14 | — | 0.83$^{f,g}$ | — |
| 20 | C5 | — | — | 4.13 |
| 21 | C6 | — | 3.97$^{f,g}$ | — |

TABLE 7-continued

| 22 | C8 | — | 4.06$^{f,g}$ | — |
|---|---|---|---|---|
| 23 | C10 | 1.25$^f$ | 1.72$^{f,g}$ | 0.86$^f$ |
| 24 | C11 | — | 4.63 | — |
| 25 | C13 | 2.25$^f$ | — | 0.96$^f$ |
| 26 | C14 | — | 0.61$^{f,g}$ | — |
| 27 | C18 | — | — | 1.06$^f$ |
| 28 | C20 | 0.81$^f$ | — | 0.61 |
| 29 | D6 | 0.57$^f$ | — | — |
| 30 | D15 | 0.46$^f$ | 4.67$^{f,g}$ | — |
| 31 | D17 | 1.40$^f$ | — | — |

TABLE 8

| entry | compound | *A. tumefaciens* TraR (μM) | *P. aeruginosa* LasR (μM) | *V. fischeri* LuxR (μM) |
|---|---|---|---|---|
| 1 | 1: OOHL | 0.20 | — | — |
| 2 | 2: OdDHL | —$^b$ | 0.01 | — |
| 3 | 3: OHHL | — | — | 3.00 |
| 4 | A4 | — | >200$^e$ | — |
| 5 | A5 | — | 0.04 | — |
| 6 | A8 | — | 0.01 | — |
| 7 | B2 | — | 0.54 | — |
| 8 | C6 | — | — | >200$^e$ |
| 9 | C8 | — | — | >50$^e$ |
| 10 | C14 | — | — | 0.35 |
| 11 | C22 | — | >200$^e$ | — |
| 12 | D14 | — | 1.62 (36%)$^d$ | — |
| 13 | D15 | — | 6.28 (30%)$^d$ | — |
| 14 | D18 | — | 0.47 (32%)$^d$ | — |

TABLE 9

| entry | compound | A. tumefaciens - TraR[b] | | E. coli - LasR[e] | | V. fischeri - LuxR[h] | |
|---|---|---|---|---|---|---|---|
| | | Inhibition [%][c] | Activation [%][d] | Inhibition [%][f] | Activation [%][g] | Inhibition [%][i] | Activation [%][j] |
| 1 | 1: OOHL | — | 100 | 50 | 19 | 63 | 24 |
| 2 | 2: OdDHL | 28 | 12 | — | 100 | 86 | 2 |
| 3 | 3: OHHL | 89 | 1 | 15 | 1 | — | 100 |
| 4 | 4 | 93 | 4 | 28 | 0 | 78 | 23 |
| 5 | 5 | 85 | 8 | 18 | 5 | 45 | 2 |
| 6 | 6 | 93 | 2 | 20 | 3 | 70 | 3 |
| 7 | 7 | 9 | 0 | 4 | 18 | 3 | 1 |
| 8 | 8 | 88 | 1 | 28 | 0 | 79 | 3 |
| 9 | 9 | 35 | 0 | 36 | 3 | 72 | 3 |
| 10 | B1 | 6 | 4 | 16 | 0 | 7 | 2 |
| 11 | B2 | 50 | 2 | -7 | 84 | 46 | 3 |
| 12 | B3 | 31 | 0 | 16 | 0 | 41 | 3 |
| 13 | B4 | 9 | 0 | 13 | 1 | 34 | 2 |
| 14 | B5 | 9 | 0 | 13 | 0 | 29 | 2 |
| 15 | C18 | 67 | 0 | 20 | 0 | 79 | 7 |
| 16 | D14 | 11 | 0 | 36 | 36 | 45 | 1 |
| 17 | D15 | 90 | 4 | 49 | 30 | 39 | 2 |
| 18 | D18 | 16 | 0 | 34 | 32 | 19 | 2 |

TABLE 10

| entry | compound | A. tumefaciens - TraR[b] | | E. coli - LasR[e] | | V. fischeri - LuxR[h] | |
|---|---|---|---|---|---|---|---|
| | | Inhibition [%][c] | Activation [%][d] | Inhibition [%][f] | Activation [%][g] | Inhibition [%][i] | Activation [%][j] |
| 1 | 1: OOHL | — | 100 | 50 | 19 | 63 | 24 |
| 2 | 2: OdDHL | 28 | 12 | — | 100 | 86 | 2 |
| 3 | 3: OHHL | 89 | 1 | 15 | 1 | — | 100 |
| 4 | 4 | 93 | 4 | 28 | 0 | 78 | 23 |
| 5 | 5 | 85 | 8 | 18 | 5 | 45 | 2 |
| 6 | 6 | 93 | 2 | 20 | 3 | 70 | 3 |
| 7 | 7 | 9 | 0 | 4 | 18 | 3 | 1 |
| 8 | 8 | 88 | 1 | 28 | 0 | 79 | 3 |
| 9 | 9 | 35 | 0 | 36 | 3 | 72 | 3 |
| 10 | A1 | 0 | 0 | 0 | 0 | 43 | 2 |
| 11 | A2 | 48 | 1 | 11 | 2 | 69 | 25 |
| 12 | A3 | 83 | 7 | 43 | 1 | 86 | 12 |

TABLE 10-continued

| 13 | A4 | 92 | 2 | 34 | 44 | 96 | 1 |
| 14 | A5 | 22 | 1 | -10 | 85 | 73 | 2 |
| 15 | A6 | 0 | 0 | 5 | 11 | 27 | 2 |
| 16 | A7 | 14 | 1 | 8 | 1 | 47 | 2 |
| 17 | A8 | 10 | 11 | -18 | 87 | 77 | 2 |
| 18 | A9 | 86 | 7 | 16 | 1 | 5 | 4 |
| 19 | A10 | 59 | 0 | 12 | 0 | 30 | 2 |
| 20 | A11 | 93 | 1 | 10 | 0 | 32 | 2 |
| 21 | A12 | 88 | 1 | 12 | 0 | 60 | 2 |
| 22 | A13 | 44 | 0 | 10 | 0 | 77 | 3 |
| 23 | A14 | 37 | 3 | 15 | 0 | 81 | 2 |
| 24 | A15 | 34 | 0 | 17 | 0 | 80 | 2 |
| 25 | A16 | 29 | 0 | 21 | 0 | 74 | 1 |

TABLE 11

| entry | compound | *A. tumefaciens* - TraR | | *E. coli* - LasR | | *V. fischeri* - LuxR | |
|---|---|---|---|---|---|---|---|
| | | Inhibition (%) | Activation (%) | Inhibition (%) | Activation (%) | Inhibition (%) | Activation (%) |
| 1 | 1: OOHL | — | 100 | 50 | 19 | 63 | 24 |
| 2 | 2: OdDHL | 28 | 12 | — | 100 | 86 | 2 |
| 3 | 3: OHHL | 89 | 1 | 15 | 1 | — | 100 |
| 4 | 5 | 85 | 8 | 18 | 5 | 45 | 2 |
| 5 | 6 | 93 | 2 | 20 | 3 | 70 | 3 |
| 6 | 8 | 88 | 1 | 28 | 0 | 79 | 3 |
| 7 | 9 | 35 | 0 | 36 | 3 | 72 | 3 |
| 8 | B1 | 6 | 4 | 16 | 0 | 7 | 2 |
| 9 | B2 | 50 | 2 | -7 | 84 | 46 | 3 |
| 10 | B3 | 31 | 0 | 16 | 0 | 41 | 3 |
| 11 | B4 | 9 | 0 | 13 | 1 | 34 | 2 |
| 12 | B5 | 9 | 0 | 13 | 0 | 29 | 2 |
| 13 | B6 | 9 | 0 | 13 | 0 | 40 | 2 |
| 14 | B7 | 93 | 2 | 52 | 11 | 80 | 2 |
| 15 | B8 | 8 | 0 | 14 | 1 | 34 | 2 |
| 16 | B9 | 16 | 0 | 21 | 0 | 44 | 3 |
| 17 | B10 | 7 | 3 | 22 | 2 | 48 | 3 |
| 18 | B11 | 25 | 0 | 36 | 0 | 82 | 12 |
| 19 | B12 | 11 | 0 | 19 | 0 | 57 | 3 |
| 20 | B13 | 20 | 0 | 21 | 0 | 42 | 2 |
| 21 | B14 | 21 | 0 | 48 | 1 | 47 | 2 |

TABLE 12

| entry | compound | A. tumefaciens - TraR | | E. coli - LasR | | V. fischeri - LuxR | |
|---|---|---|---|---|---|---|---|
| | | Inhibition (%) | Activation (%) | Inhibition (%) | Activation (%) | Inhibition (%) | Activation (%) |
| 1 | 1: OOHL | — | 100 | 50 | 19 | 63 | 24 |
| 2 | 2: OdDHL | 28 | 12 | — | 100 | 86 | 2 |
| 3 | 3: OHHL | 89 | 1 | 15 | 1 | — | 100 |
| 4 | 8 | 88 | 1 | 28 | 0 | 79 | 3 |
| 5 | C1 | 4 | 0 | 15 | 0 | 14 | 2 |
| 6 | C2 | 25 | 0 | 26 | 1 | 59 | 2 |
| 7 | C3 | 11 | 0 | 27 | 0 | 63 | 8 |
| 8 | C4 | 4 | 0 | 19 | 0 | 49 | 2 |
| 9 | C5 | 74 | 0 | 29 | 0 | 75 | 3 |
| 10 | C6 | 50 | 0 | 41 | 0 | 65 | 61 |
| 11 | C7 | 6 | 0 | 10 | 0 | 53 | 6 |
| 12 | C8 | 56 | 0 | 45 | 3 | 58 | 70 |
| 13 | C9 | 12 | 0 | 12 | 0 | 38 | 12 |
| 14 | C10 | 93 | 1 | 36 | 0 | 85 | 4 |
| 15 | C11 | 70 | 0 | 57 | 3 | 78 | 28 |
| 16 | C12 | 5 | 0 | 17 | 0 | 63 | 7 |
| 17 | C13 | 88 | 1 | 27 | 0 | 47 | 24 |
| 18 | C14 | 46 | 0 | 54 | 11 | -15 | 129 |
| 19 | C15 | 1 | 0 | 17 | 0 | 23 | 4 |
| 20 | C16 | 2 | 0 | 19 | 2 | 40 | 2 |
| 21 | C17 | 70 | 0 | 19 | 0 | 66 | 5 |
| 22 | C18 | 67 | 0 | 20 | 0 | 79 | 7 |
| 23 | C19 | 21 | 3 | 11 | 0 | 58 | 1 |
| 24 | C20 | 92 | 2 | 26 | 0 | 78 | 3 |
| 25 | C21 | 5 | 0 | 8 | 0 | 12 | 3 |
| 26 | C22 | 11 | 0 | 10 | 27 | 33 | 2 |
| 27 | C23 | 3 | 0 | 7 | 0 | 12 | 2 |
| 28 | C24 | 26 | 0 | 16 | 0 | 57 | 3 |
| 29 | C25 | 35 | 0 | 15 | 0 | 55 | 2 |

TABLE 13

| entry | compound | A. tumefaciens - TraR Inhibition (%) | A. tumefaciens - TraR Activation (%) | E. coli - LasR Inhibition (%) | E. coli - LasR Activation (%) | V. fischeri - LuxR Inhibition (%) | V. fischeri - LuxR Activation (%) |
|---|---|---|---|---|---|---|---|
| 1 | 1: OOHL | — | 100 | 50 | 19 | 63 | 24 |
| 2 | 2: OdDHL | 28 | 12 | — | 100 | 86 | 2 |
| 3 | 3: OHHL | 89 | 1 | 15 | 1 | — | 100 |
| 4 | 4 | 93 | 4 | 28 | 0 | 78 | 23 |
| 5 | 5 | 85 | 8 | 18 | 5 | 45 | 2 |
| 6 | 6 | 93 | 2 | 20 | 3 | 70 | 3 |
| 7 | 7 | 9 | 1 | 4 | 18 | 3 | 1 |
| 8 | 8 | 88 | 0 | 28 | 0 | 79 | 3 |
| 9 | 9 | 35 | 0 | 36 | 3 | 72 | 3 |
| 10 | D1 | 10 | 0 | 15 | 3 | 47 | 2 |
| 11 | D2 | 9 | 0 | 18 | 0 | 15 | 3 |
| 12 | D3 | 8 | 2 | 22 | 0 | 38 | 2 |
| 13 | D4 | 12 | 0 | 18 | 0 | 7 | 2 |
| 14 | D5 | 3 | 3 | 13 | 0 | 37 | 1 |
| 15 | D6 | 90 | 1 | 28 | 0 | 68 | 2 |
| 16 | D7 | 59 | 0 | 13 | 0 | 69 | 2 |
| 17 | D8 | 5 | 0 | 12 | 0 | 18 | 2 |
| 18 | D9 | 8 | 0 | 16 | 4 | 7 | 2 |
| 19 | D10 | 8 | 0 | 9 | 0 | 35 | 2 |
| 20 | D11 | 9 | 0 | 10 | 0 | 56 | 2 |
| 21 | D12 | 13 | 0 | 12 | 0 | 35 | 1 |
| 22 | D13 | 8 | 0 | 27 | 3 | 59 | 1 |
| 23 | D14 | 11 | 0 | 36 | 36 | 45 | 1 |
| 24 | D15 | 90 | 4 | 49 | 30 | 39 | 2 |
| 25 | D16 | 11 | 0 | 18 | 0 | 40 | 1 |
| 26 | D17 | 92 | 1 | 26 | 0 | 50 | 2 |
| 27 | D18 | 16 | 0 | 34 | 32 | 19 | 2 |
| 28 | D19 | 11 | 0 | 17 | 7 | 30 | 1 |
| 29 | D20 | 4 | 0 | 12 | 0 | 46 | 2 |
| 30 | D21 | 9 | 0 | 13 | 1 | 63 | 3 |

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. In particular, each of US published applications 2006-0178430 and US 2008/0027115 is incorporated in its entirety by reference herein. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:
1. A compound represented by the formula FX1:

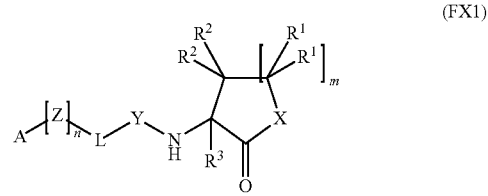

or a pharmaceutically acceptable salt or ester thereof,
wherein m is 1;
each R1, R2, and R3 is hydrogen;
X is —O—;
Y is

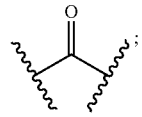

L is —(CH$_2$)$_p$—, wherein p is selected from the range of 1 to 15;
Z is selected from the group consisting of:

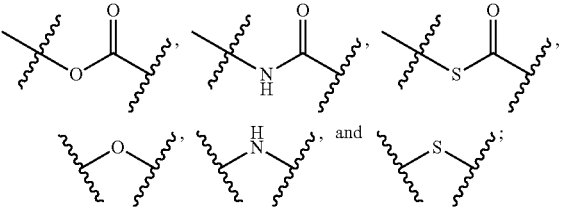

n is 0; and
A is selected from the group consisting of:

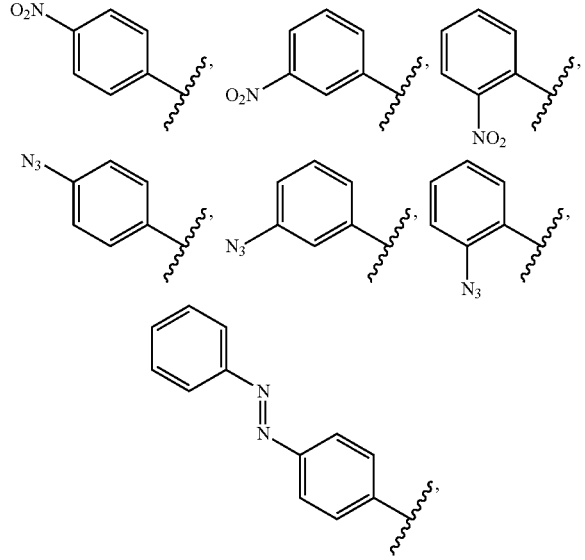

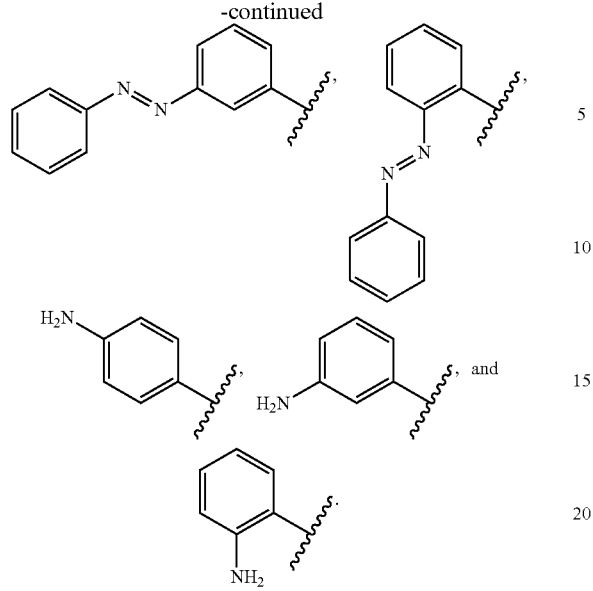
2. The compound of claim 1 wherein p is 1 or 2.
* * * * *

UNITED STATES PATENT AND TRADEMARK OFFICE
CERTIFICATE OF CORRECTION

PATENT NO.       : 8,815,943 B2
APPLICATION NO.  : 13/032036
DATED            : August 26, 2014
INVENTOR(S)      : Helen E. Blackwell, Grant D. Geske and Jennifer C. O'Neill It is certified that error appears in the above-identified patent and that said Letters Patent is hereby corrected as shown below:

In the Claims

In Claim 1, Column 120, lines 33 through 43, replace
"Z is selected from the group consisting of:

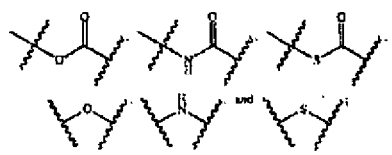

n is 0; and"

with --Z is selected from the group consisting of:

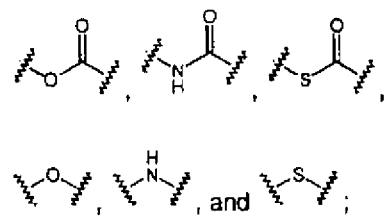

n is 0; and--

Signed and Sealed this
Eleventh Day of November, 2014

Michelle K. Lee
*Deputy Director of the United States Patent and Trademark Office*